US010094827B2

(12) United States Patent
Vinnik et al.

(10) Patent No.: US 10,094,827 B2
(45) Date of Patent: *Oct. 9, 2018

(54) DRUG TARGET SITE WITHIN GP120 OF HIV

(71) Applicant: KFLP BIOTECH, LLC, Denver, CO (US)

(72) Inventors: Andrey Vinnik, Moscow (RU); Peter Fedichev, Dolgoprudny (RU); Maxim Kholin, Moscow (RU); Christopher Molloy, Watford (GB); Aron Katz, Denver, CO (US)

(73) Assignee: KFLP BIOTECH, LLC, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/208,358

(22) Filed: Jul. 12, 2016

(65) Prior Publication Data

US 2016/0313325 A1 Oct. 27, 2016

Related U.S. Application Data

(63) Continuation of application No. 13/881,835, filed as application No. PCT/EP2011/068924 on Oct. 27, 2011, now Pat. No. 9,422,527.

(30) Foreign Application Priority Data

Oct. 27, 2010 (EP) .................................... 10014037

(51) Int. Cl.

| | |
|---|---|
| ***A61K 31/00*** | (2006.01) |
| ***G01N 33/566*** | (2006.01) |
| ***C12Q 1/70*** | (2006.01) |
| ***C40B 30/02*** | (2006.01) |
| ***G01N 33/50*** | (2006.01) |

(Continued)

(52) U.S. Cl.

CPC .......... *G01N 33/566* (2013.01); *A61K 31/00* (2013.01); *C07C 231/12* (2013.01); (Continued)

(58) Field of Classification Search

None

See application file for complete search history.

(56) References Cited

U.S. PATENT DOCUMENTS 9,422,527 B2 * 8/2016 Vinnik .................. A61K 31/00

OTHER PUBLICATIONS

Madani et al. Localized Changes in the gp120 Envelope Glycoprotein Confer Resistance to Human Immunodeficiency Virus Entry Inhibitors BMS-806 and #155. J. Virol., 2004; 78(7): 3742-3752.*

(Continued)

*Primary Examiner* — Janet L Andres

*Assistant Examiner* — Stuart W Snyder

(74) *Attorney, Agent, or Firm* — DT Ward, PC; Donna T. Ward; Lingyun Jia

(57) ABSTRACT

The present invention relates to a method of designing an inhibitor of the binding of HIV (human immunodeficiency virus) glycoprotein (gp)120 to a CD4-receptor or to the integrin alpha4 beta7 (a4b7). The inhibitor interacts with at least two amino acid residues comprised in six motifs within the 3-dimensional structure of gp120. Also provided are compounds, pharmaceutical compositions thereof and uses thereof in the development of an inhibitor of the binding of a HIV gp120 to a CD4-receptor or an integrin alpha4 beta7 (a4b7). The inhibitors are useful for the prevention or treatment of an HIV infection and/or diseases associated with an HIV infection.

3 Claims, 44 Drawing Sheets

Figure 1:
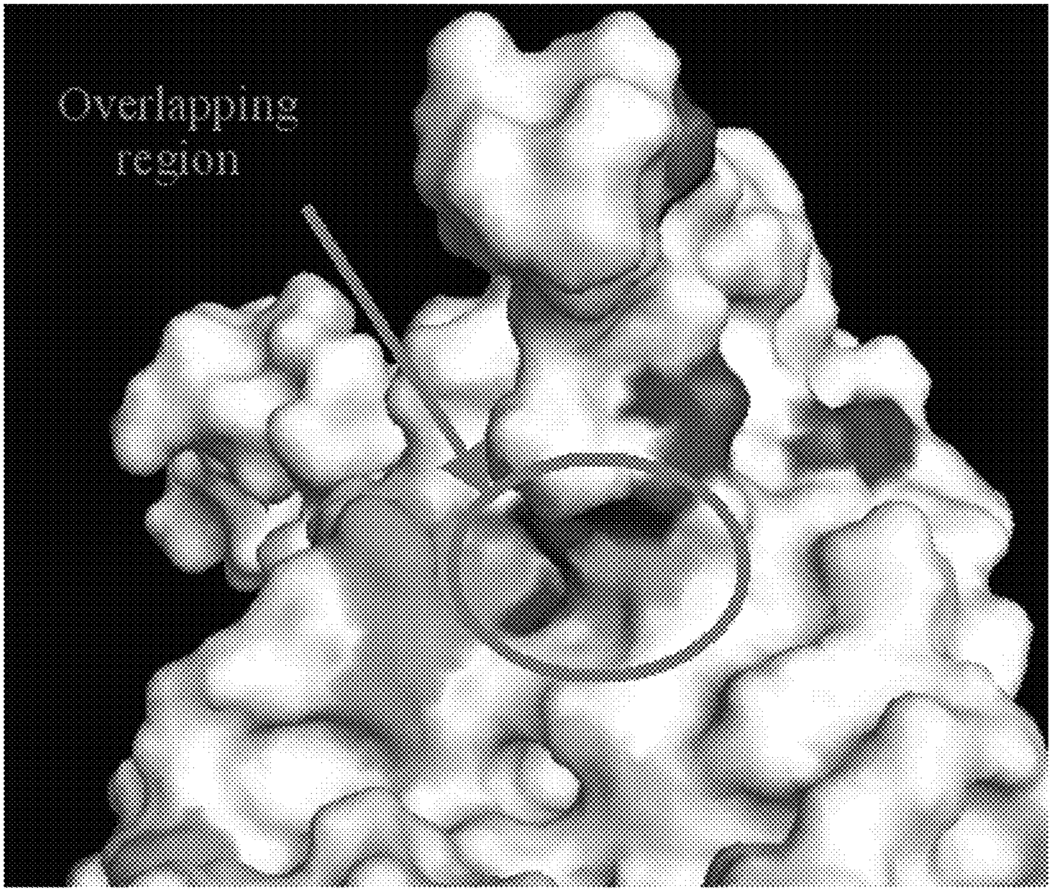

Specification includes a Sequence Listing.

(51) Int. Cl.
*G06F 19/16* (2011.01)
*G06F 19/00* (2018.01)
*C07C 237/40* (2006.01)
*C07K 14/005* (2006.01)
*C12N 7/00* (2006.01)
*C07C 231/12* (2006.01)
*C07C 237/42* (2006.01)
*C07K 16/10* (2006.01)

(52) U.S. Cl.
CPC .......... *C07C 237/40* (2013.01); *C07C 237/42* (2013.01); *C07K 14/005* (2013.01); *C12N 7/00* (2013.01); *C12Q 1/703* (2013.01); *C40B 30/02* (2013.01); *G01N 33/50* (2013.01); *G06F 19/16* (2013.01); *G06F 19/706* (2013.01); *C07C 2601/14* (2017.05); *C07K 16/1063* (2013.01); *C07K 2317/14* (2013.01); *G01N 2333/162* (2013.01); *G01N 2333/70514* (2013.01); *G01N 2500/00* (2013.01); *G01N 2500/02* (2013.01)

(56) References Cited

OTHER PUBLICATIONS

Database pubchem (online) MolPort-005-507-786—Compound Summary. XP-002623049. Sep. 15, 2005, 2 pages.

Database Pubchem (online) MolPort-005-509-145—Compound Summary. XP-002623050. Sep. 17, 2005, 2 pages.

Kwong, et al. "Structure of an HIV gp120 envelope glycoprotein in complex with the CD4 receptor and a neutralizing human antibody." Nature, Nature Publishing Group, London, GB. vol. 393, pp. 649-659. Jan. 1, 1998.

Berchanski, et al. "Prediction of HIV-1 entry inhibitors neomycin-arginine conjugates interaction with the CD-4gp120 binding site by molecular moldeing and multistep docking procedure." Biochimica et Biophysica Acta, vol. 1768, No. 9. Sep. 14, 2007. pp. 2107-2119.

Kong, et al. "Prediction of the binding mode between BMS-378806 and HIV-1 gp120 by docking and molecular dynamics simulation." Biochimica et Biophysica Acta, vol. 1764, No. 4. Apr. 1, 2006. pp. 766-772.

Jhoti, H. et al. "Fragment-based screening using X-ray crystallopraphy and NMR spectroscopy" Current Opinion in Chemical Biology (2007) 11:485-493.

Weislow, O.S. et al., "New Soluble-Formazan Assay for HIV-1 Cytopathic Effects: Application to High-Flux Screening of Synthetic and Natural Products for AIDS-Antiviral Activity" Journal of the National Cancer Institute (1989) 81(8):577-586.

Database pubchem, Database accession No. 4435574, On-line Sep. 15, 2005.

Database pubchem, Database accession No. 4794779, On-line Sep. 17, 2005.

* cited by examiner

Figure 9 continued

| pNL4-3 | | | | | | | | | | | | | |
|---|---|---|---|---|---|---|---|---|---|---|---|---|---|
| T5379534 (nM) | 7500 | 3481 | 1616 | 750 | 348 | 162 | 75 | 35 | 16 | 8 | 3 | 0 | IC50 (nM) | 3199 |
| Av. % Inhibition | 75.3 | 51.1 | 32.2 | 10.8 | 6.1 | 3.0 | 10.3 | 3.6 | 6.3 | 2.0 | 1.2 | 1.2 | IC90 (nM) | 19027 |
| s.d. | 9 | 4 | 9 | 5 | 5 | 7 | 3 | 3 | 2 | 3 | 2 | 2 | Hill's | 1.232 |
| T0520-5895 (nM) | 7500 | 3481 | 1616 | 750 | 348 | 162 | 75 | 35 | 16 | 8 | 3 | 0 | IC50 (nM) | >30000 |
| Av. % Inhibition | 17.3 | 10.4 | 9.0 | 9.5 | 5.6 | 6.0 | 9.2 | 6.9 | 3.6 | -0.9 | -0.5 | -0.5 | IC90 (nM) | >30000 |
| s.d. | 2 | 1 | 4 | 3 | 4 | 2 | 3 | 4 | 3 | 2 | 1 | 1 | Hill's | 0.282 |
| T20 (nM) | 10000 | 4642 | 2155 | 1000 | 464 | 215 | 100 | 46 | 22 | 10 | 5 | 0 | IC50 (nM) | 76 |
| Av. % Inhibition | 105.5 | 103.1 | 102.3 | 101.0 | 98.1 | 84.9 | 63.2 | 28.4 | 11.0 | 2.0 | 2.0 | 2.0 | IC90 (nM) | 258 |
| s.d. | 1 | 1 | 1 | 1 | 2 | 2 | 3 | 3 | 0 | 1 | 1 | 1 | Hill's | 1.790 |
| EFV (nM) | 25 | 12 | 5 | 2.5 | 1.2 | 0.5 | 0.25 | 0.12 | 0.05 | 0.025 | 0.012 | 0 | IC50 (nM) | 9 |
| Av. % Inhibition | 94.8 | 59.5 | 27.4 | 3.4 | -1.2 | -5.2 | -3.7 | -4.2 | -0.6 | -2.0 | -2.0 | -2.0 | IC90 (nM) | 24 |
| s.d. | 1 | 1 | 7 | 6 | 1 | 2 | 5 | 2 | 3 | 4 | 4 | 4 | Hill's | 2.234 |

| pNL-Bal | | | | | | | | | | | | | |
|---|---|---|---|---|---|---|---|---|---|---|---|---|---|
| T5379534 (nM) | 7500 | 3481 | 1616 | 750 | 348 | 162 | 75 | 35 | 16 | 8 | 3 | 0 | IC50 (nM) | 1538 |
| Av. % Inhibition | 88.6 | 68.8 | 38.3 | 35.8 | 34.3 | 8.0 | -4.5 | 6.2 | 0.8 | 0.8 | 0.8 | -0.6 | IC90 (nM) | 16359 |
| s.d. | 0 | 8 | 12 | 11 | 10 | 11 | 12 | 4 | 2 | 2 | 2 | 2 | Hill's | 0.929 |
| T0520-5895 (nM) | 7500 | 3481 | 1616 | 750 | 348 | 162 | 75 | 35 | 16 | 8 | 3 | 0 | IC50 (nM) | 15088 |
| Av. % Inhibition | 32.9 | 22.4 | 24.9 | 19.7 | -7.0 | -6.9 | -9.0 | -13.3 | -1.8 | -0.7 | 6.5 | 6.5 | IC90 (nM) | 245533 |
| s.d. | 4 | 14 | 9 | 19 | 11 | 8 | 14 | 9 | 15 | 13 | 3 | 3 | Hill's | 0.788 |
| T20 (nM) | 10000 | 4642 | 2155 | 1000 | 464 | 215 | 100 | 46 | 22 | 10 | 5 | 0 | IC50 (nM) | 10 |
| Av. % Inhibition | 111.9 | 105.0 | 101.3 | 106.7 | 105.8 | 108.6 | 98.6 | 99.6 | 83.4 | 51.5 | 13.4 | 0.0 | IC90 (nM) | 26 |
| s.d. | 4 | 4 | 2 | 3 | 7 | 1 | 5 | 7 | 11 | 1 | 9 | 3 | Hill's | 2.323 |
| EFV (nM) | 25 | 12 | 5 | 2.5 | 1.2 | 0.5 | 0.25 | 0.12 | 0.05 | 0.025 | 0.012 | 0 | IC50 (nM) | 5 |
| Av. % Inhibition | 100.3 | 73.4 | 50.8 | 23.8 | 3.9 | -8.3 | 19.1 | 4.7 | 5.0 | 0.0 | 0.0 | 0.0 | IC90 (nM) | 19 |
| s.d. | 3 | 7 | 5 | 8 | 19 | 10 | 16 | 9 | 2 | 5 | 5 | 5 | Hill's | 1.716 |

Figure 9 continued

| pNL-AD87 | | | | | | | | | | | | | | |
|---|---|---|---|---|---|---|---|---|---|---|---|---|---|---|
| T5379534 (nM) | 7500 | 3481 | 1616 | 750 | 348 | 162 | 75 | 35 | 16 | 8 | 3 | 0 | IC50 (nM) | 766 |
| Av. % Inhibition | 93.5 | 85.8 | 71.6 | 38.1 | 34.9 | 20.4 | 8.8 | 6.3 | -0.5 | 2.9 | -3.5 | -3.5 | IC90 (nM) | 6470 |
| s.d. | 2 | 5 | 11 | 12 | 11 | 5 | 3 | 7 | 21 | 17 | 6 | 6 | Hill's | 1.030 |
| T0520-5895 (nM) | 7500 | 3481 | 1616 | 750 | 348 | 162 | 75 | 35 | 16 | 8 | 3 | 0 | IC50 (nM) | 249.7 |
| Av. % Inhibition | 72.0 | 68.6 | 71.3 | 58.1 | 51.9 | 50.2 | 14.1 | 10.8 | 0.0 | 5.5 | 0.0 | 0.0 | IC90 (nM) | 18560 |
| s.d. | 5 | 2 | 0 | 6 | 10 | 6 | 5 | 2 | 5 | 12 | 5 | 5 | Hill's | 1.437 |
| T20 (nM) | 10000 | 4642 | 2155 | 1000 | 464 | 215 | 100 | 46 | 22 | 10 | 5 | 0 | IC50 (nM) | 63 |
| Av. % Inhibition | 99.9 | 97.6 | 96.3 | 93.0 | 95.3 | 87.3 | 64.9 | 41.0 | 18.1 | 0.0 | 0.0 | 0.0 | IC90 (nM) | 273 |
| s.d. | 3 | 2 | 1 | 2 | 4 | 6 | 5 | 7 | 9 | 8 | 8 | 8 | Hill's | 1.500 |
| EFV (nM) | 25 | 12 | 5 | 2.5 | 1.2 | 0.5 | 0.25 | 0.12 | 0.05 | 0.025 | 0.012 | 0 | IC50 (nM) | 1 |
| Av. % Inhibition | 99.0 | 91.5 | 84.3 | 75.9 | 48.8 | 19.6 | 36.8 | 26.3 | 32.0 | 0.0 | 0.0 | 0.0 | IC90 (nM) | 14 |
| s.d. | 1 | 1 | 5 | 3 | 14 | 8 | 13 | 7 | 8 | 8 | 8 | 8 | Hill's | 0.819 |

Figure 10 continued

| | pNL4-3 | | | | | | | | | | | | | | |
|---|---|---|---|---|---|---|---|---|---|---|---|---|---|---|---|
| Virus to Cell Infection | T5379534 (nM) | 7500 | 3481 | 1616 | 750 | 348 | 162 | 75 | 35 | 16 | 8 | 3 | 0 | IC50 (nM) | 767 |
| | Av. % Inhibition | 103.8 | 93.2 | 72.3 | 50.8 | 17.7 | 19.4 | -2.3 | 3.5 | 8.7 | 0.0 | 0.0 | 0.0 | IC90 (nM) | 3301 |
| | s.d. | 0 | 4 | 5 | 9 | 14 | 9 | 20 | 9 | 16 | 7 | 7 | 7 | Hill's | 1.505 |
| | T0520-5895 (nM) | 7500 | 3481 | 1616 | 750 | 348 | 162 | 75 | 35 | 16 | 8 | 3 | 0 | IC50 (nM) | n.d. |
| | Av. % Inhibition | 106.0 | -5.4 | -20.6 | -51.9 | -44.2 | -3.2 | -3.9 | 2.7 | 2.4 | 1.1 | 1.2 | 0.0 | IC90 (nM) | n.d. |
| | s.d. | 0 | 6 | 5 | 8 | 14 | 3 | 20 | 7 | 5 | 3 | 3 | 5 | Hill's | n.d. |
| | T20 (nM) | 10000 | 4642 | 2155 | 1000 | 464 | 215 | 100 | 46 | 22 | 10 | 5 | 0 | IC50 (nM) | 48 |
| | Av. % Inhibition | 100.6 | 99.3 | 98.8 | 97.7 | 96.6 | 93.9 | 83.8 | 48.2 | 17.1 | 0.0 | 0.0 | 0.0 | IC90 (nM) | 135 |
| | s.d. | 1 | 2 | 1 | 1 | 2 | 1 | 1 | 5 | 5 | 4 | 4 | 4 | Hill's | 2.111 |
| | EFV (nM) | 25 | 12 | 5 | 2.5 | 1.2 | 0.5 | 0.25 | 0.12 | 0.05 | 0.025 | 0.012 | 0 | IC50 (nM) | 2 |
| | Av. % Inhibition | 99.6 | 90.6 | 77.5 | 53.3 | 21.4 | 14.9 | 12.4 | 11.6 | 4.1 | 3.1 | 0.0 | 0.0 | IC90 (nM) | 12 |
| | s.d. | 1 | 1 | 4 | 1 | 10 | 7 | 5 | 9 | 8 | 7 | 6 | 6 | Hill's | 1.340 |

Figure 11 continued

| "GIA" | | | | | | | | | | | | | | |
|---|---|---|---|---|---|---|---|---|---|---|---|---|---|---|
| T5379534 (nM) | 7500 | 3481 | 1616 | 750 | 348 | 162 | 75 | 35 | 16 | 8 | 3 | 0 | IC50 (nM) | 951 |
| Av. % Inhibition | 82.8 | 85.3 | 63.0 | 35.8 | 30.5 | 16.8 | 14.5 | 1.4 | 5.2 | 0.0 | 0.0 | 0.0 | IC90 (nM) | 10134 |
| s.d. | 3 | 5 | 20 | 19 | 20 | 8 | 2 | 18 | 11 | 8 | 8 | 8 | Hill's | 0.928 |
| T0520-5895 (nM) | 7500 | 3481 | 1616 | 750 | 348 | 162 | 75 | 35 | 16 | 8 | 3 | 0 | IC50 (nM) | 7597.4 |
| Av. % Inhibition | 41.3 | 43.7 | 40.5 | 20.7 | 22.7 | 16.9 | 4.7 | 0.0 | 0.0 | 0.0 | 0.0 | 0.0 | IC90 (nM) | >30000 |
| s.d. | 19 | 15 | 13 | 9 | 6 | 5 | 7 | 4 | 4 | 4 | 4 | 4 | Hill's | 0.496 |
| T20 (nM) | 10000 | 4642 | 2155 | 1000 | 464 | 215 | 100 | 46 | 22 | 10 | 5 | 0 | IC50 (nM) | 127 |
| Av. % Inhibition | 118.0 | 106.9 | 105.3 | 97.0 | 82.4 | 58.4 | 43.9 | 16.5 | 25.4 | 10.6 | 0.0 | 0.0 | IC90 (nM) | 826 |
| s.d. | 7 | 7 | 3 | 2 | 13 | 11 | 14 | 16 | 4 | 10 | 9 | 9 | Hill's | 1.173 |
| EFV (nM) | 25 | 12 | 5 | 2.5 | 1.2 | 0.5 | 0.25 | 0.12 | 0.05 | 0.025 | 0.012 | 0 | IC50 (nM) | 2 |
| Av. % Inhibition | 107.5 | 80.3 | 66.3 | 63.0 | 45.0 | 18.7 | 17.3 | 12.8 | 13.6 | 3.9 | 0.0 | 0.0 | IC90 (nM) | 19 |
| s.d. | 4 | 9 | 10 | 11 | 2 | 5 | 3 | 1 | 1 | 17 | 9 | 9 | Hill's | 0.916 |

Figure 12 continued

| "DIA" | | | | | | | | | | | | | |
|---|---|---|---|---|---|---|---|---|---|---|---|---|---|
| T5379534 (nM) | 7500 | 3481 | 1616 | 750 | 348 | 162 | 75 | 35 | 16 | 8 | 3 | 0 | IC50 (nM) | 2011 |
| Av. % Inhibition | 61.3 | 64.8 | 45.6 | 33.1 | 47.1 | -3.0 | 7.2 | -4.3 | 3.0 | 6.1 | 4.6 | 4.6 | IC90 (nM) | 54286 |
| s.d. | 11 | 13 | 19 | 21 | 23 | 17 | 11 | 5 | 8 | 1 | 6 | 6 | Hill's | 0.667 |
| T0520-5895 (nM) | 7500 | 3481 | 1616 | 750 | 348 | 162 | 75 | 35 | 16 | 8 | 3 | 0 | IC50 (nM) | >30000 |
| Av. % Inhibition | 17.8 | 16.6 | 13.3 | 22.2 | 9.2 | 20.4 | -2.3 | 1.6 | 7.2 | 0.8 | -3.6 | -3.6 | IC90 (nM) | >30000 |
| s.d. | 9 | 16 | 4 | 18 | 10 | 6 | 6 | 13 | 14 | 4 | 12 | 12 | Hill's | 0.291 |
| T20 (nM) | 10000 | 4642 | 2155 | 1000 | 464 | 215 | 100 | 46 | 22 | 10 | 5 | 0 | IC50 (nM) | 2267 |
| Av. % Inhibition | 99.7 | 71.1 | 46.1 | 28.1 | 2.5 | -2.5 | -5.7 | 14.9 | 0.5 | 6.4 | -2.8 | -2.8 | IC90 (nM) | 8766 |
| s.d. | 12 | 7 | 19 | 18 | 23 | 3 | 11 | 18 | 26 | 10 | 15 | 15 | Hill's | 1.625 |
| EFV (nM) | 25 | 12 | 5 | 2.5 | 1.2 | 0.5 | 0.25 | 0.12 | 0.05 | 0.025 | 0.012 | 0 | IC50 (nM) | 3 |
| Av. % Inhibition | 118.7 | 62.2 | 49.1 | 40.2 | 31.7 | 30.0 | 15.6 | 18.9 | 9.0 | 3.1 | 2.8 | 2.8 | IC90 (nM) | 51 |
| s.d. | 18 | 9 | 13 | 9 | 11 | 8 | 5 | 7 | 14 | 8 | 8 | 8 | Hill's | 0.767 |

Residues 9-16 of SEQ ID NO: 3

Residues 6-58 of SEQ ID NO: 2

Consensus disclosed as SEQ ID NO: 31

Residues 3-18 of SEQ ID NO: 8

Residues 252-312 of SEQ ID NO: 2

Consensus disclosed as SEQ ID NO: 34

Figure 23 A

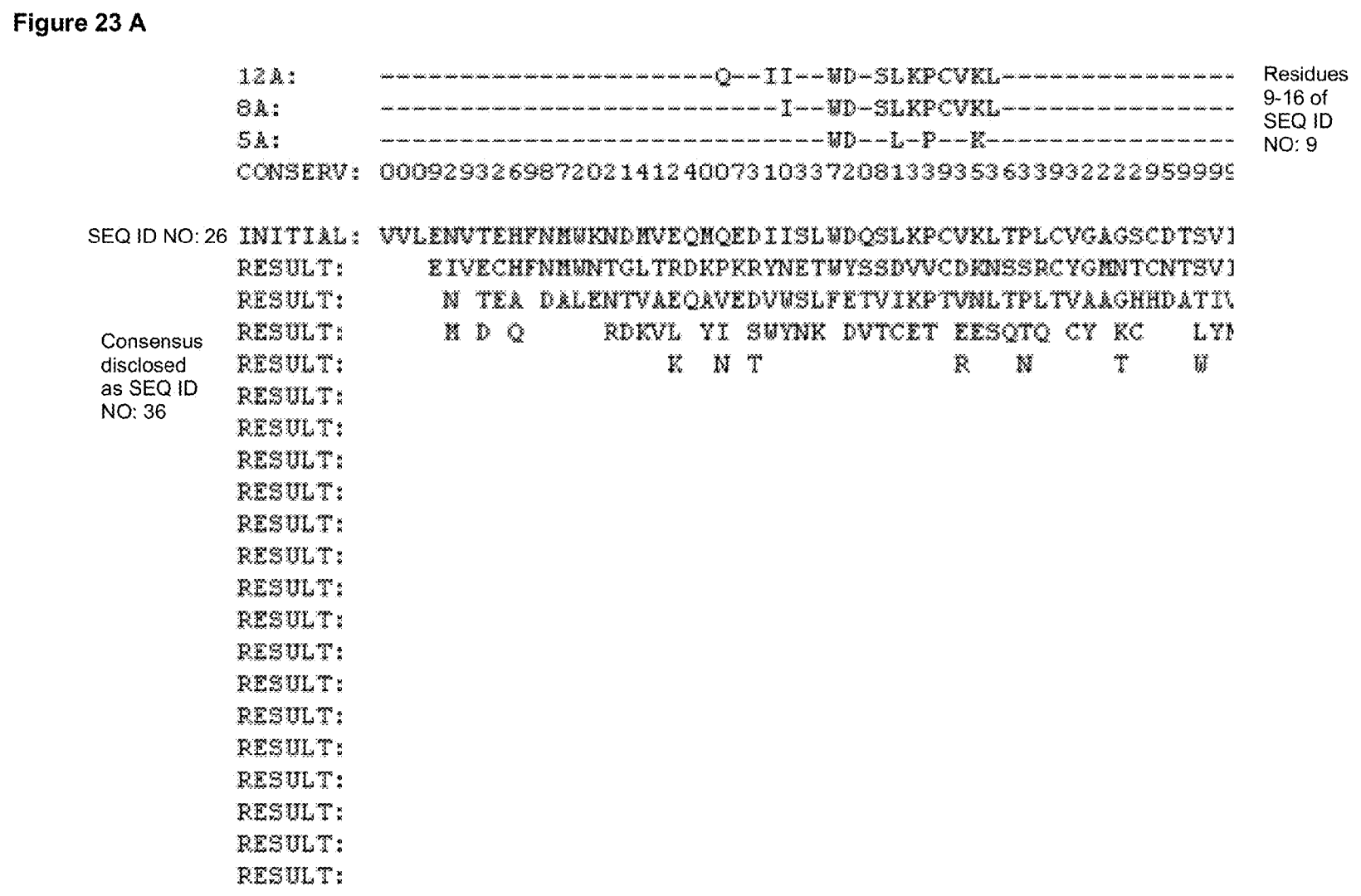

Residues 9-16 of SEQ ID NO: 9

```
12A:      ---------------------Q--II--WD-SLKPCVKL---------------
8A:       -------------------------I--WD-SLKPCVKL---------------
5A:       ----------------------------WD--L-P--K----------------
CONSERV:  000929326987202141240073103372081339353633932222959999
```

SEQ ID NO: 26

```
INITIAL:  VVLENVTEHFNMWKNDMVEQMQEDIISLWDQSLKPCVKLTPLCVGAGSCDTSVI
RESULT:      EIVECHFNMWNTGLTRDKPKRYNETWYSSDVVCDENSSRCYGMNTCNTSVI
RESULT:       N TEA DALENTVAEQAVEDVWSLFETVIKPTVNLTPLTVAAGHHDATIV
RESULT:       M D Q     RDKVL YI SWYNK DVTCET EESQTQ CY KC   LYN
RESULT:                         K  N T            R   N     T    W
RESULT:
RESULT:
RESULT:
RESULT:
RESULT:
RESULT:
RESULT:
RESULT:
RESULT:
RESULT:
RESULT:
RESULT:
RESULT:
RESULT:
RESULT:
RESULT:
```

Consensus disclosed as SEQ ID NO: 36

Figure 23 B

```
                  -------------------VVSTQ----------------   Residues
                  -------------------VVSTQ----------------   14-18 of
                  --------------------VST-----------------   SEQ ID
                                                             NO: 10
                  9009900900009900400009900009950990000900C

SEQ ID NO: 27     GKGPCKNVSTVQCTHGIRPVVSTQLLLNGSLAEEEVVIRSI
                  GFEPCSKVVAATCTRMMETQTSTWFGFNGTRAENRTYIYWH
Consensus          MANNTNIIVSSRAGVIKS S A LALCSSKSGDK FMFCH
disclosed as       SM  PRKFSTALY ERGA A M S  SPA TKKG CV LY
SEQ ID NO:          K  CS    G   LK M P S      I  V T  L  S
37                  S        V   IT                D
                    Q            Q
                    H
                    G
                    D
```

Figure 24 A

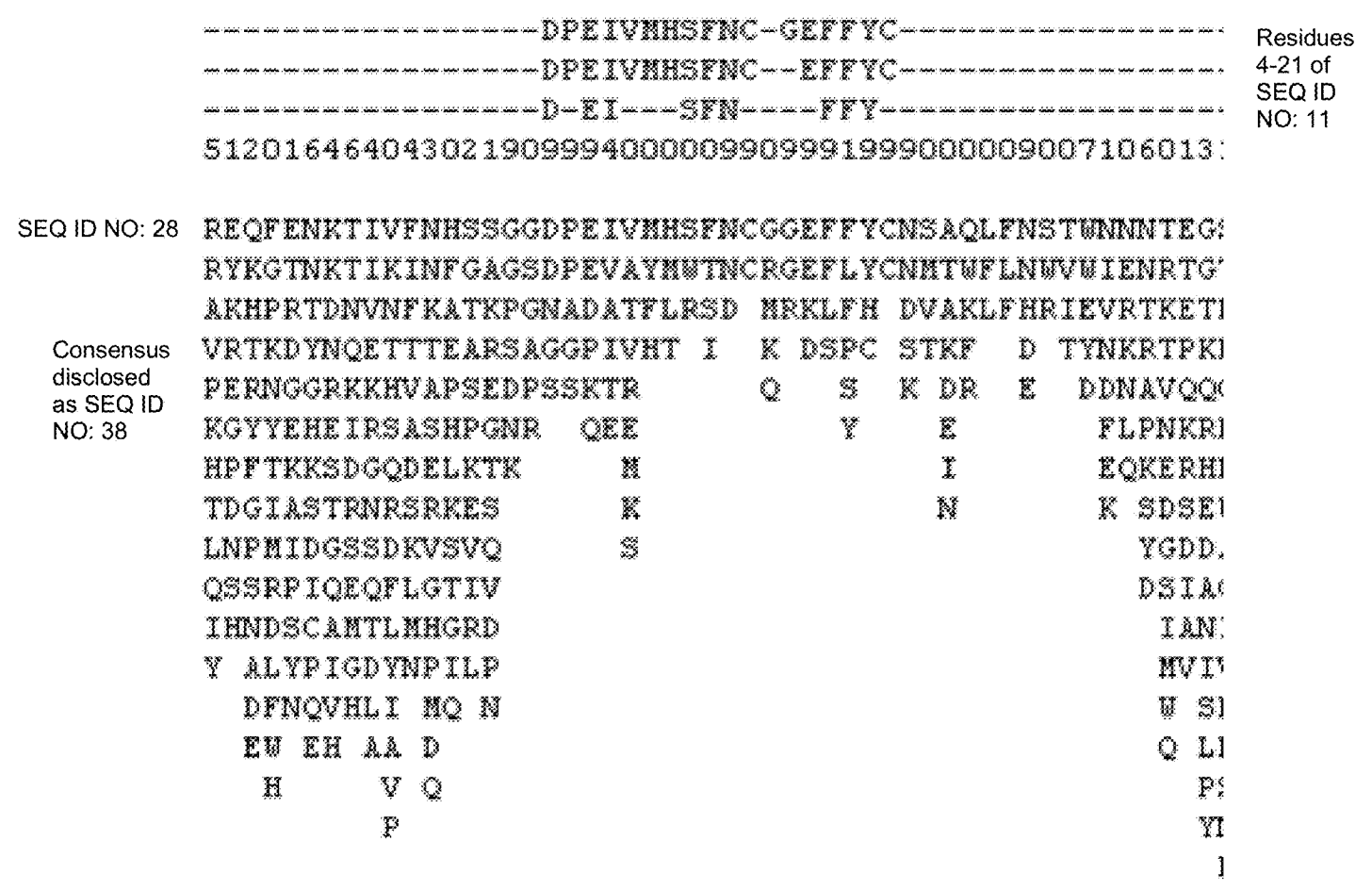

Residues 4-21 of SEQ ID NO: 11

```
-----------------DPEIVMHSFNC-GEFFYC---------------
-----------------DPEIVMHSFNC--EFFYC---------------
-----------------D-EI---SFN----FFY----------------
5120164640430219099940000099099919990000090071060131
```

SEQ ID NO: 28

Consensus disclosed as SEQ ID NO: 38

```
REQFENKTIVFNHSSGGDPEIVMHSFNCGGEFFYCNSAQLFNSTWNNNTEG
RYKGTNKTIKINFGAGSDPEVAYHWTNCRGEFLYCNMTWFLNWVWIENRTG
AKHPRTDNVNFKATKPGNADATFLRSD MRKLFH DVAKLFHRIEVRTKETI
VRTKDYNQETTTEARSAGGPIVHT I  K DSPC STKF  D TYNKRTPKI
PERNGGRKKHVAPSEDPSSKTR      Q   S  K DR  E  DDNAVQQ
KGYYEHEIRSASHPGNR  QEE          Y    E        FLPNKRI
HPFTKKSDGQDELKTK     M               I        EQKERHI
TDGIASTRNRSRKES      K               N        K SDSEI
LNPMIDGSSDKVSVQ      S                          YGDD
QSSRPIQEQFLGTIV                                 DSIA
IHNDSCAMTLMHGRD                                  IAN
Y ALYPIGDYNPILP                                  MVI
  DFNQVHLI MQ N                                  W SI
  EW EH AA D                                     Q LI
   H     V Q                                       P
         P                                         YI
                                                    I
```

Figure 24 B

Residues 3-18 of SEQ ID NO: 13

```
:---------------IKQIINMWQEVGKAMY-----------------:
:----------------KQIINMWQEVGKAMY-----------------:
:-------------------INMWQ-VG-A-Y-----------------:
.3152410401029909999909049980490990094409490590б:
```

SEQ ID NO: 29

```
:GSNNTEGNTITLPCRIKQIINMWQEVGKAMYAPPIRGQIRCSSNITGLI
'GTNQTQHNYVYVPCHIKQIINTWHKVGKNVYLPPREGELTCNSTVTSI:
:TPKRNWRQRAAATRR R VVSARRRAWQHIIFA KGRQFSRTTS SGLI
'KRQHYKAKHNN  YQ P K  I  NIRRYA  L  A L V I N   MT
:QQDNIAPRNRT     E         SEIRL     K K I K A   VI
:RKRTPYKPKY                 VKY        D N D D   F
:HEHGRRLH                  N          V A E
:EWTKANGS                  T          T   V
'DAGEKEV                   L          G
:AGSYQDI                   E          N
.NILDSHT                              H
'IVPADT
 SLWP
 LH W
 PS S
 YN
  M
```

Consensus disclosed as SEQ ID NO: 39

Figure 25

```
                  ------------------GGDMR-N--------------   Residues
                  ------------------GGDM--N--------------   5-9 of
                  ------------------GG-M-----------------   SEQ ID
                  D006112524141320000054040490990099475 7C   NO: 12

SEQ ID NO: 30     LTRDGGINENGTEIFRPGGGDMRDNWRSELYKYKVVKIE
                  ANIDAQINSNTTNTFITFSAEVAELYRLELGDYKLIEIF
                  ITRETNEDTTQNIINSAMVGDLSDMFKVKP   TSVRVF
Consensus         TDQNGGVQEQGIQFSRLGG  MGKKN    S   N
disclosed         LVVYVRNEDSNSTVIMSVA  YKN
as SEQ ID           MIWDDRNDIDSAYT EL  E
NO: 40              W DSTKVRFYDLV  PI
                    Y SWMTQGDAKNR  SN
                    N YEKHIKRKR D
                      IASVKAK E
                      ETASGIS H
                      MYGYAYY M
                      KILGR E
                       FRLL A
                       KYAW V
                        QI  L
                        PP  H
                        HF
```

Figure 26B
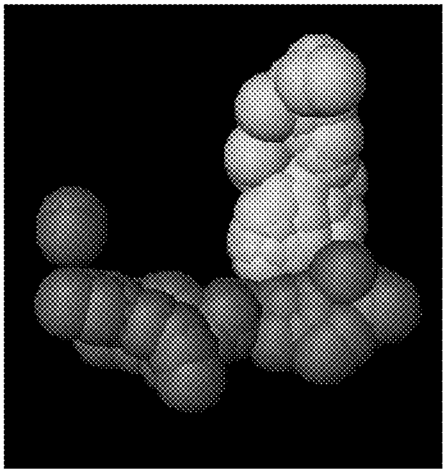
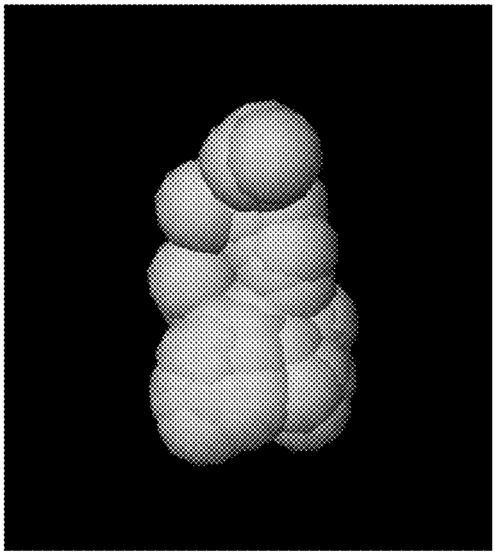
Figure 26A
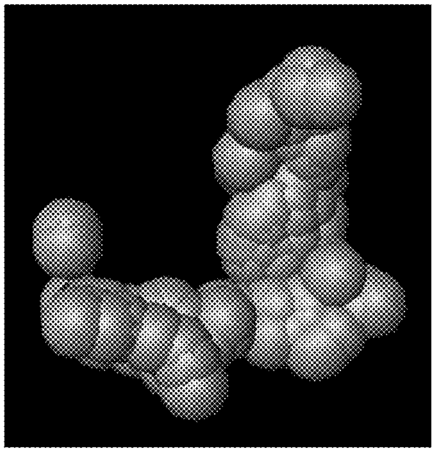
Figure 26C
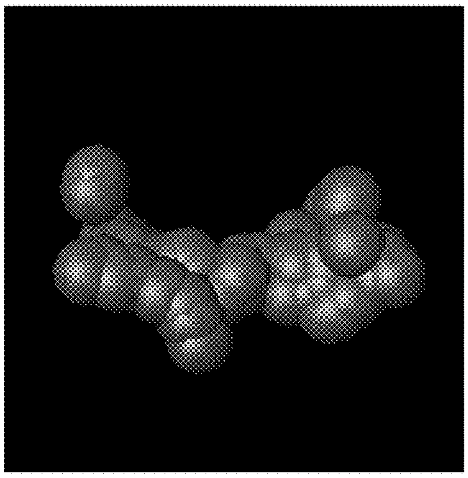

Residues 14-18 of SEQ ID NO: 4
Residues 81-142 of SEQ ID NO: 2
Consensus disclosed as SEQ ID NO: 41

Residues 3-21 of SEQ ID NO: 5
Residues 198-259 of SEQ ID NO: 2
Consensus disclosed as SEQ ID NO: 42

Figures 31A, 31B:
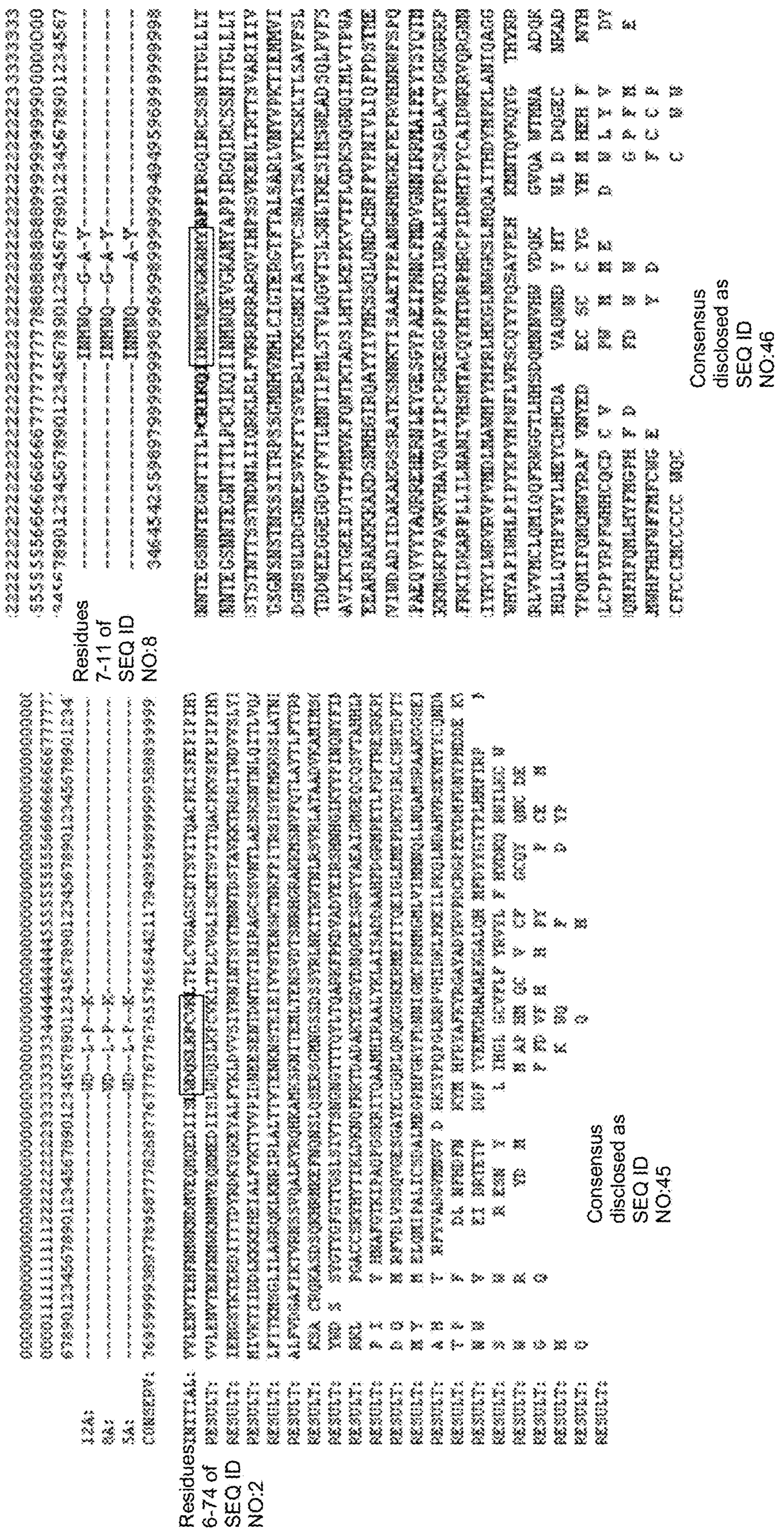

Figure 31A and Figure 31B - sequence alignment figures showing consensus sequences disclosed as SEQ ID NO:45 and SEQ ID NO:46, with residues 6-74 of SEQ ID NO:2 and residues 7-11 of SEQ ID NO:8 indicated.

DRUG TARGET SITE WITHIN GP120 OF HIV

CROSS REFERENCE TO RELATED APPLICATIONS

This application is a Continuation of U.S. patent application Ser. No. 13/881,835 filed on Sep. 16, 2013 which is a 35 U.S.C. § 371 U.S. National Stage Entry of International Application No. PCT/EP2011/068924 filed Oct. 27, 2011, which claims the benefit of priority of European Application No. 10014037.5 filed Oct. 27, 2010, the contents of which are each incorporated herein by reference in its entirety.

REFERENCE TO SEQUENCE LISTING

The present application is being filed along with a Sequence Listing in ASCII format. The Sequence Listing is provided as a file entitled 2052-1000USCON_SL.txt created on Jul. 12, 2016 which is 130,954 bytes in size. The information in electronic format of the sequence listing is incorporated herein by reference in its entirety.

DETAILED DESCRIPTION

The present invention relates to a method of designing an inhibitor of the binding of HIV (human immunodeficiency virus) glycoprotein (gp)120 to a CD4-receptor or to the integrin alpha4 beta7 (a4b7), the method comprising the molecular modelling of a compound such that the modelled compound interacts in silico with at least two amino acid residues comprised in six motifs within the 3-dimensional structure of said gp120 of HIV or within a peptidomimetic reflecting the 3-dimensional structure of said gp120 of HIV, wherein said interaction between said at least two amino acid residues and said compound is characterized by an interatomic distance of less than 8 Angströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said six motifs comprises the amino acid sequence FRPGGGDMRDNWRSELYKYKVV (SEQ ID NO: 7) or a variant thereof; and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (iii) or (iv) comprises or encodes said motifs or variants thereof. Also, the invention relates to a method of identifying an inhibitor of the binding of HIV gp120 to CD4 or the integrin a4b7, compounds that inhibit the binding of HIV gp120 to CD4 or the integrin a4b7, a method of decreasing thermal motion of a tunnel within HIV gp120, compounds for use in preventing or treating a HIV-infection and/or a disease associated with a HIV-infection and a pharmaceutical composition comprising any of the above compounds or inhibitors. Finally, the invention also relates to a tunnel within gp120.

In this specification, a number of documents including manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Human immunodeficiency virus (HIV) is a retrovirus belonging to the primate lentiviruses that can lead upon successful infection to a condition termed acquired immunodeficiency syndrome (AIDS).

Said condition is characterized in that the immune system begins to fail and therefore the patient's body becomes increasingly susceptible to secondary and/or recurring infections. The infection with HIV occurs by, e.g., transfer of blood, semen, vaginal fluid and also breast milk. Due to the presence of unbound infectious virus particles in body fluids the rate of infection is high. In particular, sexual intercourse and transmission from infected mothers to their babies as well as feeding with breast milk account for a majority of new HIV cases.

Since becoming a pandemic in the 1980's HIV has received much attention both in the general public as well as in the scientific community. The World Health Organization (WHO) and the Joint United Nations Programme on HIV/AIDS (UNAIDS) have recently estimated that about 25 million people have died due to AIDS since 1981 making it one of the most destructive pandemics in history. This can be linked back to the unique way of cellular infection, manifestation and persistence of the retrovirus in the body which has not yet been found to be successfully treatable.

Presently, treatment of HIV infected patients relies on combination therapies such as, e.g., highly active antiretroviral therapy (HAART), that may be expensive, cause serious drug-related side effects and may give rise to resistant HIV strains after prolonged progression of the therapy. Conventional combination therapies comprise nucleoside-analogue reverse transcriptase inhibitors (NARTIs or NRTIs), non nucleoside-analogue reverse transcriptase inhibitors (NNRTIs) and/or protease inhibitors.

In addition to reverse transcriptase and protease inhibitors, therapeutic drugs for the treatment or prevention of HIV-related diseases have been and continue to be developed which interfere with the process of binding and entry of HIV into its target cells. The process of HI-viral entry into a target cells represents the first step in the viral infection circle. It is characterized by a complex series of events that are initiated through the binding of the viral surface glycoproteins to specific receptor molecules on the cell's outer membrane. This interaction is thought to trigger a conformational change in the viral glycoprotein, which then mediates fusion of the lipid bilayers of the cell and viral membranes and allows the genetic material of the virus to be introduced into the host-cell cytoplasm.

A more detailed view shows that CD4 is the primary receptor for HIV which is a 60 kD molecule on the surface of certain immune cells such as, e.g., T lymphocytes, cells of the monocyte/macrophage lineage, or dendritic, antigen-presenting cells (Weiss, R. A. (1993), The Retroviridae, 2nd edition (ed. J. A. Levy), pp. 1-108. Plenum Press, New York), and is endogenously involved in T-cell activation (Sweet et al. (1991), Curr. Opin. Biotechnol. 2: 622-633). The virus enters CD4+ cells and after successful amplification and budding of progeny virus particles lyses the infected CD4+ cells. Hence, a hallmark of acquired immunodeficiency syndrome (AIDS) is the depletion of CD4+ cells. The binding of HIV to CD4+ cells involves the formation of a stable complex between CD4 and gp120, the glycoprotein exposed on the envelope of HIV that mediates binding and subsequent entry into the host cell. CD4 has shown to be necessary and sufficient for efficient HIV attachment to target cells. Nevertheless, its presence alone is not sufficient for viral entry and the importance of secondary/fusion receptors could subsequently be established that mediate the fusion of the virus particle and the target cell. This requirement of the presence of a secondary/fusion receptor appears to be so far unique to primate lentiviruses. Several studies identified the CXCR4 and the CCR5 receptor which have been shown to mediate the fusion of virus particles with different tropisms and the respective target cell. The CXCR4 receptor seems to be specific for T-cell tropic HIV strains whereas the CCR5 receptor seems to be specific for M-tropic strains.

In detail, HIV enters macrophages and CD4+ T cells by the adsorption of glycoproteins on the target cell followed by fusion of the viral envelope with the cell membrane and the release of the HIV capsid into the cell (Chan D et Kim P, Cell 93 (5): 681-4 (1998); Wyatt R et Sodroski J, Science 280 (5371): 1884-8 (1998). The first step in fusion involves the high-affinity attachment of the CD4 binding domains of gp120 to CD4. Once gp120 is bound to CD4, the envelope complex undergoes a profound conformational change, exposing the chemokine binding domains of gp120 and allowing them to interact with the target chemokine receptor (generally either CCR5 or CXCR4, but others are known to interact). This results in a more stable two-pronged attachment, which allows the N-terminal fusion peptide gp41 to penetrate the cell membrane.

Thus, the gp120/CD4 interaction in connection with the subsequent interaction with the above-identified coreceptors CXCR4 and CCR5 provides a potential target for intervention in HIV infections. A number of antibodies and small molecules have been developed as blockers or inhibitors of the gp120/CD4 binding by interacting with either gp120 or CD4 (Vermeire et al. (2006), Curr. Med. Chem., 13, 731). Common blockers or inhibitors include but are not limited to antisense molecules, antibodies, antagonists, traps, and their derivatives. However, so far none of these approaches has led to a clinically approved drug. Importantly none of these approaches is designed to target the conformational change undergone by gp120 after binding to CD4. In particular, compounds that are shown to interact with binding sites on the surface of gp120 next to the natural binding site for CD4 could not be shown to inhibit said conformational change (Kong et al., Biochimica et Biophysica Acta—Proteins & Proteomics, Elsevier, Netherlands, vol. 1764, no. 4, April 2006, 766-772, ISSN:1570-9639; Berchanski et al., Biochimica et Biophysica Acta—Biomembranes, Netherlands, vol. 1768, no. 9, September 2007, 2107-2119, ISSN:1570-9639).

Recently, a further receptor was demonstrated to be critically involved in the primary infection of CD4+ cells (Arthos et al., Nature Immunology, vol. 9, no. 3 (2008)). It was shown that the HIV envelope protein gp120 bound to and signalled by means of integrin alpha4 beta7 on CD4+ T lymphocytes. Further, it was shown that gp120 rapidly activated LFA-1, an integrin that facilitates HIV infection, on CD4+ T cells in an alph4 beta7-dependent way. Functioning principally as a homing receptor, alpha4 beta7 mediates the migration of leukocytes to an retention of leukocytes in the lamina propria of the gut. Thus, in the tissue where HIV preferentially replicates, its envelope interacts directly with an adhesion receptor that is specifically linked to the function of CD4+ T cells in that tissue.

As evidenced by the above discussion, the efforts to identify and develop more efficient drugs and therapies to successfully address the increasing rate of new HIV infections, of progression to AIDS and the increasing death toll linked to the latter are intense and ever increasing in view of the rapidly growing knowledge of HIV and its interaction with the human host. Despite said efforts there is still no reported success of therapeutic strategies and their technical implementation to successfully prevent or to treat HIV infection.

The technical problem underlying the present invention was to identify alternative and/or improved means and methods for the prevention or treatment of an HIV infection and/or diseases associated with an HIV infection. The solution to this technical problem is achieved by providing the embodiments characterized in the claims.

Accordingly, the present invention relates in a first embodiment to a method of designing an inhibitor of the binding of HIV (human immunodeficiency virus) glycoprotein (gp)120 to a CD4-receptor or to the integrin alpha4 beta7 (a4b7), the method comprising the molecular modelling of a compound such that the modelled compound interacts, preferably in silico, with at least two amino acid residues comprised in six motifs within the 3-dimensional structure of said gp120 of HIV or within a peptidomimetic reflecting the 3-dimensional structure of said gp120 of HIV, wherein said interaction between said at least two amino acid residues and said compound is characterized by an interatomic distance of less than 8 Angströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said six motifs comprises the amino acid sequence FRPGGGDMRDNWRSELYKYKVV (SEQ ID NO: 7) or a variant thereof; and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (i), (ii), (iii) or (iv) comprises or encodes said motifs or variants thereof.

In accordance with the present invention, the six motifs form a tunnel within the 3-dimensional structure of gp120. The term "tunnel" is used according to its well-known meaning and in accordance with the invention refers to an elongate hollow or water-filled space with an opening on either side within the 3-dimensional structure of gp120. The tunnel's shape is dictated by the position of said six motifs in relation to each other within said 3-dimensional structure of gp120. As will be understood by the skilled person, the six motifs form the (inner) walls of the tunnel. Hence, any modelled compound or test compound or inhibitor according to the invention interacts with the amino acid residues comprised in the six motifs making up the walls of the tunnel as contact/interaction sites. As will be explained herein below, the motifs may vary in sequence and length which does, however, not affect their capability of forming said tunnel. The above is applicable for all embodiments of the invention. The tunnel may also be fragmented to describe shorter versions of said tunnel. For example, a shorter version of the tunnel is made up only of the amino acid residues IISLWDQSLK of the first motif (residues 2-11 of SEQ ID NO: 3); IRPVVSTQLLLN of the second motif (residues 11-22 of SEQ ID NO: 4); VMHSFNCGGEFFYC of the third motif (residues 8-21 of SEQ ID NO: 5); CPKISFEP of the fourth motif (SEQ ID NO: 6); GGDMR of the fifth motif (residues 5-9 of SEQ ID NO: 7); and CSS of the sixth motif. It is understood in accordance with the invention that the definition of a shorter version of the tunnel can replace the definition of the tunnel with six motifs throughout the application.

The tunnel extends through gp120 from the site where gp120 makes contact with CD4 (specifically CD4's Phe43 residue, i.e. the binding site of CD4), i.e. a depression formed by the interface of the outer domain with the inner domain and the bridging sheet of gp120, towards a site that is on the back of said CD4 binding site, where two glycosylated asparagin residues at position 120 and 300 in SEQ ID NO: 2 are found, wherein the latter sites are each on the surface of gp120. Also, said tunnel opens and partially closes as a consequence of thermal motion.

In a further embodiment, the invention relates to a method of designing an inhibitor of the binding of HIV (human immunodeficiency virus) glycoprotein (gp)120 to a CD4-receptor or to the integrin alpha4 beta7 (a4b7), the method comprising the molecular modelling of a compound such that the modelled compound interacts, preferably in silico, with at least two amino acid residues comprised in six motifs forming a tunnel within the 3-dimensional structure of said gp120 of HIV or within a peptidomimetic reflecting the 3-dimensional structure of said gp120 of HIV, wherein said interaction between said at least two amino acid residues and said compound is characterized by an interatomic distance of less than 8 Angströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said six motifs comprises the amino acid sequence FRPGGGDMRDNWRSELYKYKVV (SEQ ID NO: 7) or a variant thereof; and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (i), (ii), (iii) or (iv) comprises or encodes said motifs or variants thereof. The preferred embodiments of the main embodiment described herein below are also preferred embodiments with regard to this embodiment.

An interaction with at least two amino acid residues comprised in six motifs within the 3-dimensional structure of said gp120 of HIV or within a peptidomimetic reflecting the 3-dimensional structure of said gp120 of HIV is indicative that an inhibitor of the binding of HIV (human immunodeficiency virus) glycoprotein (gp)120 to a CD4-receptor and/or to the integrin alpha4 beta7 (a4b7) has been designed.

It is understood that a compound modeled in accordance with the method of the invention functions as an inhibitor of said binding of gp120 to CD4 and/or integrin a4b7. Nevertheless, the method of the invention may comprise the further step (after modeling is completed) of providing the modeled compound; bringing it into contact with a gp120 (isolated or as part of a HI virus) and determining whether binding occurs. Corresponding experimental setups are well-known in the art and can be easily devised by a person skilled in the art. Exemplary methods are shown in the example section (Examples 2 and 3).

The term "designing" refers to devising an inhibitor, preferably by in silico methods, i.e. computer-implemented methods. As regards the in silico methods for designing inhibitors, these are commonly referred to as molecular modeling. Particularly envisaged for the present invention are molecular modeling tools which are also referred to as ligand construction tools. Such methods for rational drug design typically take into account properties including shape, charge distribution, the distribution of hydrophobic groups, ionic groups and groups capable of forming hydrogen bonds at a site of interest of the protein molecule under consideration. Using this information, that can be derived from the high resolution structure of proteins and protein-ligand complexes, these methods either suggest improvements to existing molecules, construct new molecules on their own that are expected to have good binding affinity, screen through virtual compound libraries for such molecules or fragments thereof, or otherwise support interactive design of new drug compounds in silico. Typically, ligand construction makes use of dedicated software and involves interactive sessions in front of a computer display of the three-dimensional structure of the target molecule, i.e., gp120, and of candidate molecules or fragments thereof. Suitable software packages are known in the art and include Chemoffice (CambridgeSoft Corporation), CNS (Acta Cryst. D54, 905-921), CCP4 (Acta Cryst. D50, 760-763), ADF (Computational Chemistry, David Young, Wiley-Interscience, 2001. Appendix A. A.2.1 p. 332) and Gold (G. Jones, P. Willett and R. C. Glen, J. Mol. Biol., 245, 43-53, 1995; G. Jones, P. Willett, R. C. Glen, A. R. Leach and R. Taylor, J. Mol. Biol., 267, 727-748, 1997; M. L. Verdonk, J. C. Cole, M. J. Hartshorn, C. W. Murray and R. D. Taylor, Proteins, 52, 609-623, 2003). Either with or without modifications of candidate or starting molecules, the modeled compound is obtained.

It is understood that said molecular usually modeling makes use of the atomic coordinates of a 3-dimensional structure of said gp120 of HIV. Generally, the coordinates of a target molecule may be experimentally determined, e.g., by NMR spectroscopy and/or X-ray crystallography, or may be obtained by molecular modeling, preferably homology modeling using the high resolution structure of a first target molecule, said high resolution structure being determined by experimental means, to estimate and calculate the structure of a second target molecule which is different but related to the first target molecule and for which an experimentally determined high resolution structure is not yet available. This way it is possible to study, e.g., the structure of allelic variants of one protein without experimentally determining the structure for every allelic variant but only one variant. Suitable software is known in the art and includes, e.g., the GAMESS (US) Quantum Chemistry package. The atomic coordinates of gp120 are accessible for the person skilled in the art and can, e.g., be obtained from databases such as, e.g. the Brookhaven Protein Databank (PDB; www.pdb.org; e.g., accession code 2B4C).

The term "inhibitor" refers to compounds lowering or abolishing the activity of gp120, said activity being defined herein below in detail. Briefly, the activity of gp120 in the context of the present invention means the capability of gp120 to bind to its receptor, i.e. the CD4-receptor or alpha4 beta7, on the surface of the target cell and thereby initiate viral entry. Methods to determine said activity of gp120 are well-known in the art and described herein below. In preferred embodiments, inhibition effected by an inhibitor in accordance with the invention refers to a reduction in activity of at least (for each value) 10, 20, 30, preferred at least 40, 50, 60, 70, 80, 90, 95, 98 and more preferred at least 99%. Most preferred, an inhibitor reduces the activity to less than 10-2, less than 10-3, less than 10-4 or less than 10-5 times as compared to the activity in the absence of the inhibitor. An inhibitor in accordance with the invention is capable of interacting with a novel drug target site, i.e. said tunnel within gp120 that has been surprisingly identified in the course of the invention.

The term "HIV (human immunodeficiency virus) glycoprotein (gp)120" is established in the art (cf. e.g., Coffin, Hughes, Varmus; Retroviruses; Cold Spring Harbor Laboratory Press; ISBN 0-87969-571-4) and has the same meaning in the present application. gp120 is a glycoprotein exposed on the surface of the HIV envelope. The designation "120" stems from its molecular weight of 120 kilodaltons. gp120 is organized with an outer domain, an inner domain with respect to its termini and a bridging sheet. The gp120 gene is around 1.5 kb long and codes for around 500 amino acids (cf. SEQ ID NOs: 2 for HIV-1). It is suggested that three copies of gp120 form into a trimer that caps the end of gp41, another HIV surface glycoprotein that becomes exposed upon conformational change of gp120 as a result of its interaction with the CD4-receptor (cf. Zhu P. et al., Plos Pathogens, 4(11):e1000203 (2008)). The above holds true for HIV-1 and HIV-2 gp120 which represent the gp120 molecules of the two different HIV species of HIV. Both species are well-known and characterized in the art. When referring in this specification only to "gp120" this is meant to refer to the gp120 molecule of both HIV species, i.e. HIV-1 gp120 and HIV-2 gp120; unless it is evident from the context that it is intended to refer to the gp120 of one given HIV species only.

The term "CD4-receptor" is also well-known in the art and has the same meaning in accordance with the invention. Briefly, CD4 (cluster of differentiation 4) is a glycoprotein expressed on the surface of T helper cells, regulatory T cells, monocytes, macrophages and dendritic cells (cf., e.g., C. Janeway, Immunobiology, Garland Science; 6th edition; Part III, Chapter 6; ISBN-10: 0815341016; ISBN-13: 987-0815341017). It is a co-receptor that assists the T cell receptor (TCR) in activating its T cell following an interaction with an antigen presenting cell. CD4 can interact directly with MEW class II molecules on the surface of the antigen presenting cell using its extracellular domain. CD4 is a member of the immunoglobulin superfamily. It has four immunoglobulin domains (D1 to D4) that are exposed on the extracellular surface of the CD4+ cell. D1 and D3 resemble immunoglobulin variable (IgV) domains, D2 and D4 resemble immunoglobulin constant (IgC) domains. As previously described and well-known in the art, CD4 is a primary receptor used by HIV to gain entry into host cells (cf., e.g., Bour S. et al., Microbiol Rev., 59(1):63-93 (1995)) working in concert with co-receptors as described above.

The term "integrin alpha4 beta7" is also termed integrin a4b7 (also known as lymphocyte Peyer patch adhesion molecule (LPAM)) is well-known in the art and has the same meaning in accordance with the invention. Integrin a4b7 is a heteromer receptor (being composed of a4 and b7 receptor subunits) and is expressed on lymphoctyes and is thought to be responsible for T-cell homing into gut-associated lymphoid tissues.

The term "interact" or "interaction" as used herein refers to a relation between at least two molecular entities. This relation may inter alia be described in terms of intermolecular distances and/or free energies of interaction. In the first case, an interaction may be defined by at least one intermolecular distance, preferably by more than one such as two, three, four, five or more intermolecular distances. If an interaction according to the invention is to be described in terms of intermolecular distances only, it is envisaged to use at least three such distances. Typically, intermolecular distances are determined as distances between the centers of atoms of the respective interacting molecular entities. In this case, intermolecular distances according to the invention are referred to as interatomic distances. Preferably, a such determined interatomic distance is equal or less than 8, 7, 6, 5, or 4 Angströms, more preferably in the range from 3.6 and 2.8 Angströms. Preferred values include 3.4, 3.2 and 3.0 Angströms. Alternatively or in addition, an interaction may be defined in terms of free energy. The free energy may be a total free energy determining the strength of an intermolecular interaction in its entirety or a partial free energy, said partial free energy resulting from, for example, one atom-atom interaction within a plurality of atom-atom interactions within the intermolecular interaction under consideration. Preferably, the total free energy of an interaction according to the invention is at least 100 kJ/mol. More preferred are total free energies of an interaction of at least 100, at least 150 or at least 200 kJ/mol.

As an alternative or additional parameter, the IC50 concentration may be used to characterize the strength of an intermolecular interaction between inhibitor and gp120. The IC50 concentration is the concentration of an inhibitor that is required to inhibit 50% of the target's activity, in the present case the activity of gp120. Preferably, the modeled inhibitor interacts with said at least two motifs such that the IC50 concentration is in the two-digit micromolar range, i.e. below 100 μM. More preferred are IC50 concentrations below 50 μM, below 10 μM or below 1 μM. Yet more preferred are nanomolar or even picomolar concentrations, e.g. inhibitors with an IC50 concentration below 100 nM, below 10 nM, below 1 nM or below 100 pM. More generally speaking, and applicable to any inhibitor referred to in this specification, the concentration that is required to achieve an inhibition of 50% of the target's activity may be used. Preferred values of IC50 concentrations as recited above apply also to these concentrations.

An intermolecular interaction may comprise one or more types of interactions. Types of interactions include charge-charge, charge-dipole, and dipole-dipole interactions and furthermore hydrogen bonds and hydrophobic interactions. Dipoles may be permanent, induced or fluctuating. Interactions involving permanent dipoles and hydrogen bonds may be of particular relevance, since they are capable of specifically positioning and orienting a ligand or modulator in a binding pocket or tunnel. Interactions such as, e.g., described above may also be grouped into and referred to as covalent or non-covalent interactions or bonds. A "covalent" interaction is a form of chemical bonding that is characterized by the sharing of pairs of electrons between atoms, or between atoms and other covalent bonds. Covalent bonding includes many kinds of interaction well-known in the art such as, e.g., σ-bonding, π-bonding, metal to non-metal bonding, agostic interactions and three-center two-electron bonds. A "non-covalent" bond is a chemical bond that does not involve the sharing of pairs of electrons. Non-covalent bonds are critical in maintaining the three-dimensional structure of large molecules, such as proteins and nucleic acids, and are involved in many biological processes in which molecules bind specifically but transiently to one another. There are several types of non-covalent bonds: hydrogen bonding, ionic interactions, Van-der-Waals interactions, charge-charge, charge-dipole, dipole-dipole bonds and hydrophobic bonds. Non-covalent interactions often involve several different types of non-covalent bonds working in concert, e.g., to keep a ligand in position on a target binding site. An interaction may occur with a group such as a charge or a dipole, which may be present many times at the surface of the target molecule. Preferably, an interaction is specific, i.e., it occurs at a defined site of the target molecule, i.e. gp120, and goes along with the formation of a network of several distinct and specific interactions. While a specific interaction may occur with hardly any change of the conformation of the molecules involved ("key-in-lock"), in accordance with the present invention it involves conformational changes of one or both of the binding partners ("hand-in-glove" paradigm). The term "binding", for example as used herein below with regard to the binding of CD4 or integrin a4b7 to gp120, is meant to refer to such a specific interaction, i.e. "binding" is a specific form of interaction. Interaction of the modeled compound with the tunnel of gp120 in accordance with the invention may include one or more types of interaction described above (provided that said one or more types of interaction involve interatomic distances of less than 8 Angström) and results in the positioning of the modeled compound partially or fully in the tunnel within gp120 so that it leads to the inhibition of the binding of gp120 to CD4 or integrin a4b7. Said inhibition is due to the inability of gp120—once said modeled/synthesized compound is correspondingly positioned—to undergo a conformational change necessary for binding to CD4 or integrin a4b7. While not wishing to be bound to a specific theory, it is understood in accordance with the present invention that a compound interacting with at least two amino acid residues comprised in the six motifs in a gp120 molecule will be able to inhibit binding to CD4 and at the same time to integrin a4b7. This is because the flexibility of the tunnel within gp120 is considered to be key with regard to the adoption of any conformation of gp120. It is further understood that some combinations of motifs and some combinations of interactions sites in said motifs may prove more potent, i.e. inhibit binding to a higher degree, when in interaction with a suitable modeled/synthesized compound with regard to a either CD4 or integrin a4b7, but are nevertheless expected to have an inhibitory effect on both.

The term "motif" as used in accordance with the present invention is well-known in the art with regard to molecular modelling. For example, in Oliva et al., J Mol Biol 266(4): 814-830 (Mar. 7, 1997) the nature and structural make-up of motifs involved in forming protein loops is extensively discussed; the disclosure content of Oliva et al. is expressly incorporated herein by reference. The term "comprises the amino acid sequence" in accordance with the invention is meant to refer to those amino acids that make up the motif.

Interaction of the modelled compound according to the invention is to occur with an at least two interaction sites comprised in the six motifs or variants thereof defining the 3-dimensional structure of a tunnel within gp120. This includes interaction with at least two interaction sites in one motif or in any combination of motifs, e.g., with interaction sites in the first and second motif; with interaction sites in the first and third motif; with interaction sites in the first and fourth motif; with interaction sites in the first and fifth motif; with interaction sites in the first and sixth motif; with interaction sites in the second and third motif; with interaction sites in the second and fourth motif; with interaction sites in the second and fifth motif; with interaction sites in the second and sixth motif; with interaction sites in the third and fourth motif; with interaction sites in the third and fifth motif; with interaction sites in the third and sixth motif; with interaction sites in the fourth and fifth motif; with interaction sites in the fourth and sixth motif; or with interaction sites in the fifth and sixth motif. Also envisaged are combinations of interactions involving combinations of binding sites in three motifs, four, five or all six motifs. Preferred are combinations of motifs in which at least the second, third or fourth motif is present. For example, preferred is the combination of the second and third motif; the second and fourth motif; the third and fourth motif; or the second, third and fourth motif. In accordance with the invention the modelled/synthesized compound preferably interacts with an interaction site in a motif, wherein said interaction site minimally comprises one amino acid residue, but may also comprises at least (for each value) 30%, 40%, 50%, 60%, 70%, 80% or at least 90% or all amino acid residues of a motif. Thus, referring to an interaction with at least two interaction sites refers to an interaction with at least two amino acid residues comprised within the motifs making up the tunnel. If said at least two amino acid residues that said compound is to interact with are positioned on one motif, in particular if adjacent, they may, however, be considered to represent one interaction site. Said amino acid residues making up an interaction site—when less than 100%—may be a consecutive stretch of amino acid residues or may be an arrangement of amino acid residues dispersed throughout a respective motif or combinations thereof, i.e. an interaction site comprises single amino acid residues and consecutive amino acid residues of a respective motif. The number of amino acid residues interacted with in an interaction site in a motif by the modelled inhibitor may vary for each motif and explicitly comprises any combination of the aforementioned percent values, and may also comprise, e.g., one, at least (for each value) two, three, four, five, six, seven, eight, nine, ten, 11, 12 or 13 amino acid residues as a continuous stretch or separated by amino acid residues that are not interacted with. Preferably, the interaction site of the first motif is located in the amino acid residue stretch made up of or at least partially involves amino acids IISLWDQSLKPCVKL of the first motif (residues 2-16 of SEQ ID NO: 3) or variants thereof; the interaction site for the second motif is located in the amino acid residue stretch made up of or at least partially involves amino acids VVSTQ of the second motif (residues 14-18 of SEQ ID NO: 4) or variants thereof; the interaction site for the third motif is located in the amino acid residue stretch made up of or at least partially involves amino acids DPEIVMHSFNCGGEFFYC of the third motif (residues 4-21 of SEQ ID NO: 5) or variants thereof; the interaction site for the fourth motif is located in the amino acid residue stretch made up of or at least partially involves amino acids CPKISFEP of the fourth motif (SEQ ID NO: 6) or variants thereof; the interaction site for the fifth motif is located in the amino acid residue stretch made up of or at least partially involves amino acids GGGDMRDN of the fifth motif (residues 4-11 of SEQ ID NO: 7) or variants thereof; or the interaction site for the sixth motif is located in the amino acid residue stretch made up of or at least partially involves amino acids CSS of the sixth motif or variants thereof. Hence, it is understood in accordance with the present invention that an interaction site in a motif may exclusively involve amino acids from said preferred amino acid stretch, a combination of amino acids from said preferred amino acid stretch and amino acids chosen from the remaining amino acid residues making up a given motif or only said remaining amino acid residues, i.e. those not defined as belonging to said preferred amino acid stretch in a given motif. Also preferred is that the interaction site comprises or consists of only those amino acid residues that have been shown to be most conserved for HIV-1 and HIV-2. Such as for example, the underlined amino acid residues of the first motif DIISLWDQSLKPCVKLT (SEQ ID NO: 3) for a gp120 of HIV-1 and DIISLWDQSLKPCVKLT (SEQ ID NO: 9) for a gp120 of HIV-2; the underlined amino acid residues of the second motif NVSTVQCTHGIRPVVSTQLLLNGSLAE (SEQ ID NO: 4) for a gp120 of HIV-1 and NVSTVQCTHGIRPVVSTQLLLNGSLAE (SEQ ID NO: 10) for a gp120 of HIV-2; the underlined amino acid residues of the third motif SGGDPEIVMHSFNCGGEFFYCN (SEQ ID NO: 5) for a gp120 of HIV-1 and SGGDPEIVMHSFNCGGEFFYCN (SEQ ID NO: 11) for a gp120 of HIV-2; the underlined amino acid residues of the fourth motif CPKISFEP (SEQ ID NO: 6) for a gp120 of HIV-1 and CPKISFEP (SEQ ID NO: 14) for a gp120 of HIV-2; the underlined amino acid residues of the fifth motif FRPGGGDMRDNWRSELYKYKVV (SEQ ID NO: 7) for a gp120 of HIV-1 and RPGGGDMRDNWRSELYKYKVV (SEQ ID NO: 12) for a gp120 of HIV-2; the underlined amino acid residues of the sixth motif CSS for a gp120 of HIV-1 and CSS for a gp120 of HIV-2. The underlined amino acid residues in motifs of gp120 of HIV-1 have been identified to be conserved throughout various gp120 HIV-1 variants to a degree of at least 70%, at least 80 or at least 90% (cf. FIG. 15A, FIG. 15B to FIG. 19A, FIG. 19B). The underlined amino acid residues in motifs of a gp120 of HIV-2 have been identified to be conserved throughout various HIV-2 variants to a degree of at least 70%, at least 80 or at least 90% (cf. FIG. 23 to FIG. 25). Accordingly, the underlined amino acid residues show a high degree of cross-species conservation. More preferred is that an interaction site of a given motif consists of or comprises the above-defined amino acid residues or a preferred stretch in a motif that belong to the above-defined most conserved amino acids within the respective motif. While not wishing to be bound to a specific scientific theory, it is understood that an inhibitor that interacts with interaction sites involving partially or completely identical amino acid residues for each HIV species is an inhibitor that is expected to act as potent cross species inhibitor. It is, however, equally understood that an inhibitor interacting with an interaction site involving completely or partially different amino acid residues for each HIV species is also expected to act as a potent cross species inhibitor based on the reasoning that it is likely that variant amino acids may have characteristics as the amino acid they replace such as, e.g., their overall or partial electric charge, and hence can substitute each other. Since the replacing amino acids are also capable of forming a tunnel in concert with the other motifs, it can be expected that an inhibitor will not necessarily be affected by the exchange.

The amino acid sequence of the first to sixth motif forming the 3-dimensional structure of a tunnel within gp120 of HIV-1 has been determined with regard to a specific sequence of a specific HIV-1 strain (SEQ ID NO: 2; Protein data bank accession number 2B4C_G). It could be demonstrated by cross population analysis of about 80,000 amino acid sequences of gp120 of HIV-1 variants (taken from the National Institutes of Health databank) that various single or continuous stretches of amino acids in the sequence of the motifs are to a high degree, i.e. at least 90% (corresponding to a conservation index of 9 as will be explained below) of variant motifs, carry the identical amino acid as in the sequence of the motifs mentioned herein above, conserved throughout the analysed population (cf. FIG. 15 to FIG. 17 and FIG. 19 and FIG. 23 to FIG. 24A and FIG. 25). The sequence of some of the motifs identified for gp120 of HIV-1 were subsequently compared to the about 500 available amino acid sequences for gp120 of HIV-2 resulting in the finding that i) also in gp120 of HIV-2 motifs exist that define a similar tunnel as in gp120 of HIV-1 and ii) some amino acids are conserved across the HIV-1 to HIV-2 species border. On the basis of the population analysis, it can be expected that motifs in various HIV-1 strains will be composed of the same or very similar (variants thereof) amino acid sequences as defined for each motif herein above.

It is understood in accordance with the present invention and due to the well-known variant nature of the gp120 molecule in the various strains of the HIV species, that the above described amino acid sequences of each of the five motifs may vary to different extents, i.e. form "variants thereof" that have retained the capability of forming said interaction sites within the 3-dimensional structure of said tunnel within said gp120. Preferably, said variants are natural variants, i.e. motifs that are part of the gp120 sequence of naturally occurring HIV variants. The sequence of said variants can be determined by aligning sequences, wherein methods for sequence alignment are well-known in the art and described herein below. First, the amino acid sequence of a gp120 of a given strain is obtained, e.g., by protein sequencing (e.g., by mass spectrometry or Edman degradation). Next, the identity of the sequence is compared by aligning the sequence to a gp120 amino acid sequence comprising the motifs as specified herein above, e.g. in SEQ ID NO:2. Then, the sequence of the variant strain is determined at a position corresponding the position of the motif within the sequence of SEQ ID NO:2. The determination of said corresponding position may be effected by comparing the aligned sequence next to the motif in SEQ ID NO:2 for the presence of identical sequences. The position of the first motif with regard to SEQ ID NO: 2 is from the amino acid residue at position 29 to 45; of the second motif with regard to SEQ ID NO: 2 is from the amino acid residue at position 99 to 125; of the third motif with regard to SEQ ID NO: 2 is from the amino acid residue at position 221 to 242; of the fourth motif with regard to SEQ ID NO: 2 is from the amino acid residue at position 63 to 70; of the fifth motif with regard to SEQ ID NO: 2 is from the amino acid residue at position 320 to 341; of the sixth motif with regard to SEQ ID NO: 2 is from the amino acid residue at position 297 to 299. Having identified said corresponding position, the identity with regard to amino acid residue and length of the motif can be determined. A sequence variant can be up to (for each value) 3, 2 or up to 1 amino acid residue shorter or longer than the corresponding motif. Hence, a motif variant may in addition to having a sequence variation or alternatively thereto comprise up to (for each value) 1%, 2%, 4%, 6%, 8%, 10%, 15% or up to 20% less amino acid residues as compared to the motifs defined herein above or comprise up to (for each value) 1%, 2%, 4%, 6%, 8%, 10%, 15% or up to 20% more amino acid residues as compared to the motifs defined herein above. Also envisaged is that the variants of motifs as defined herein above may comprise a sequence of a given motif that is only at least (for each value) 20%, 30%, 40%, 50%, 55%, 60%, 65%, 70%, 75%, 80%, 85%, 90%, 95% or 99% identical compared to the sequence of the corresponding motif as defined herein above. While differing with regard to the identity of amino acid residues, it is understood that a given variant motif nevertheless comprises amino acids that are related, preferably, in terms of their structure and charge, to the amino acid residues they replace (in comparison to the herein above defined amino acids) and therefore do not compromise the 3-dimensional integrity of the tunnel within a gp120 molecule. In other words, it must be capable of defining said interaction sites within the 3-dimensional structure of said tunnel within said gp120. Such amino acids may be, e.g., those capable of establishing non-covalent interactions with other parts of a given motif and/or the remaining gp120 molecule so as to maintain the 3-dimensional structure of at least the tunnel. The skilled person is well-aware of amino acids that may be grouped according to their relevant characteristics, such as e.g., their overall or partial charge. Furthermore, the skilled person is in the position to identify suitable amino acid residues in silico that do not influence the 3-dimensional integrity of said tunnel within gp120 of HIV.

In FIGS. 15 to 17 and 19 (HIV-1) and 23 to 24A and 25 (HIV-2) the variant amino acids for each position in a given motif are provided in order of likelihood taking into account the sequences of the available HIV-1 and HIV-2 gp120 sequences for each species. Variants of the first motif for gp120 of HIV-1 (SEQ ID NO: 15) can have the amino acid residue E, T, A, Q, N, V, K, S, G or L at the first position of said motif; the amino acid residue Y, V, L, H, S, T, N, K, A, M or D at the second position of said motif; the amino acid residue A, V, T, K, L, S, N, Q, R, Y or E at the third position of said motif; the amino acid residue L, P, T, A, Q, N, F, I, E, G, R, K or D at the fourth position of said motif; the amino acid residue F, I, V, M, S, G, R, T, C, P, K, Y or D at the fifth position of said motif; the amino acid residue Y, D, T, K, E, N, R, Q, G, H, S, M, F or L at the sixth position of said motif; the amino acid residue K, N, E, S, R, G, T, A, Q, F or Y at the seventh position of said motif; the amino acid residue L, E, N, K, S, T, D, A, R, G, P, H, Y, I, M or F at the eighth position of said motif; the amino acid residue D, E, K, N, G, T, A, M, L, R, Q, F, V or H at the ninth position of said motif; the amino acid residue V, S, N, I, M, T, D, H, Q, Y, P, R, E, G, A, F or K at the 10th position of said motif; the amino acid residue V, E, S, T, N, Q, A, I, R, F, G, Y, M, L, P or D at the 11th position of said motif; the amino acid residue S, N, T, E, G, Y, K, R, Q, D, L, A or V at the 12th position of said motif; the amino acid residue I, T, E, M, S, L, Y, A, K, N, R, F, D, G, H, V, W or Q at the 13th position of said motif; the amino acid residue Y, D, I, L, S, T, E, A, G, N, R, K, H, C, M, F or Q at the 14th position of said motif; the amino acid residue R, N, E, T, D, Q, G, L, S, I, P, Y, A or V at the 15th position of said motif; the amino acid residue N, T, D, I, E, S, A, D, Y, K, G, V, R, M, F, Q or H at the 16th position of said motif; and/or the amino acid residue I, D, V, N, S, R, Y, K, E, M, H, G, A, L or C at the 17th position of said motif, wherein D of the motif takes the first position and T takes the 17th position of the first motif.

Variants of the second motif for gp120 of HIV-1 (SEQ ID NO: 16) can have the amino acid residue K, D, S, P, E, R, T, Q, H, G, I, M, F, Y or V at the first position of said motif; the amino acid residue I, A, G, S, F, T, L, C, K, Y, Q or E at the second position of said motif; the amino acid residue T, G, N, R, C, A, V, I, L, F or K at the third position of said motif; the amino acid residue S, V, I, A, P, H, Q, L, G, M, K or R at the fourth position of said motif; the amino acid residue I, A, L, G, Y, E, R, S, T or F at the fifth position of said motif; the amino acid residue T, L, H, R, P, A, V, I, K, S, N or E at the sixth position of said motif; the amino acid residue R, Y, W, G, F, S, M, A, V, I, P or K at the seventh position of said motif; the amino acid residue A, P, S, Q, I, R, Y, V, G or H at the eighth position of said motif; the amino acid residue Q, R, Y, P, N, L, D, T, G, M, V, W, S or E at the ninth position of said motif; the amino acid residue R, E, S, W, A, V, P or N at the 10th position of said motif; the amino acid residue V, T, L, N, F, M, S, G, A, R or D at the 11th position of said motif; the amino acid residue K, M, S, Q, T, N, G, E, L, A, W, I, P or H at the 12th position of said motif; the amino acid residue A, S, L, Q, T, R, H or E at the 13th position of said motif; the amino acid residue T, A, I, M, L, G, E, S, P, Q, C, W, H or R at the 14th position of said motif; the amino acid residue I, A, L, M, G, T, E, S, P, F, C, W, R, Y or N at the 15th position of said motif; the amino acid residue T, P, L, A, V, Q, I, F, N, H, K or Y at the 16th position of said motif; the amino acid residue S, A, I, N, P, L, H, G, V, R or Q at the 17th position of said motif; the amino acid residue H, R, S, P, K, A, E, L, T, N or M at the 18th position of said motif; the amino acid residue F, P, V, M, S, I, T, A, C, Q, R, Y, W or H at the 19th position of said motif; the amino acid residue I, P, V, A, T, M, S, Q; R, C, F, Y, G, N, W or K at the 20th position of said motif; the amino acid residue V, F, I, S, M, P, W, Y, G, T, Q, C or E at the 21st position of said motif; the amino acid residue D, S, K, P, Y, H, T, I, M, F, A, G, L, W or E at the 22nd position of said motif; the amino acid residue P, S, A, D, C, V, W, R, N, F or E at the 23rd position of said motif; the amino acid residue T, G, R, N, C, I, A, V, Q, L, P, K, M or D at the 24th position of said motif; the amino acid residue I, V, T, R, P, Q, S, F, A, Y, M, G, K or E at the 25th position of said motif; the amino acid residue S, T, V, P, E, G, D, Q, L, R, K, Y, N, C, M or F at the 26th position of said motif; and/or the amino acid residue K, G, A, R, D, T, Q, V, N, S, L, I, H or Y at the 27th position of said motif, wherein N of the motif takes the first position and E takes the 27th position of the second motif.

Variants of the third motif for gp120 of HIV-1 (SEQ ID NO: 17) can have the amino acid residue A, T, P, V, L, I, Q, R, K, N, G, E, H, Y, F, M, W, D or C at the first position of said motif; the amino acid residue E, R, D, S, P, A, K, L, Q, N, V, W, I, H or T at the second position of said motif; the amino acid residue E, R, K, S, W, V, L, A, N, T, I, F, D or Q at the third position of said motif; the amino acid residue G, T, N, A, E, H, V, I, S, R, Y, P, F, Q, L, K or M at the fourth position of said motif; the amino acid residue L, I, V, S, Q, A, M, T, R; E; D, F, H, Y, K, W, N, C or G at the fifth position of said motif; the amino acid residue K, Q, G, D, R, V, N, A, P, S, L, I, H, T or Y at the sixth position of said motif; the amino acid residue V, L, T, F, N, M, S, A, Y, G, P, K, D, C, H or R at the seventh position of said motif; the amino acid residue T, I, E, A, M, K, S, L, R, Q, P, Y, C, G, N, H, F or D at the eighth position of said motif; the amino acid residue T, L, R, K, S, A, H, Q, V, I, F, N, P, Y, E, C, G, D or W at the ninth position of said motif; the amino acid residue L, Y, F, R, I, P, T, S, N, Q, V, D, A, G, M, C, W or E at the 10th position of said motif; the amino acid residue T, H, N, I, M, R, G, F, Y, L, A, Q, K, C, V, P, D, W or E at the 11th position of said motif; the amino acid residue V, L, S, I, C, Y, H, T, R, W, G or N at the 12th position of said motif; the amino acid residue T, I, S, C, D, Y, V, H, K, F, L, M, P, R, G; Q; E or A at the 13th position of said motif; the amino acid residue R, W, Y, S, V, G, L, F, I, H, A, N or Q at the 14th position of said motif; the amino acid residue R, A; K, Q, H, E, M, N, V, S, T, W, Y, C, I, D, L or F at the 15th position of said motif; the amino acid residue E, R, K, W; V, S, A, L, N, D, I, F or Y at the 16th position of said motif; the amino acid residue G, K, D, N, R, V, A, L, F, S, Q, W, H, Y, C, M or T at the 17th position of said motif; the amino acid residue L, S, I, Y, V, C, N, G, M, W or Q at the 18th position of said motif; the amino acid residue L, S, Y, V, P, I, C, D, A, M or N at the 19th position of said motif; the amino acid residue F, N, C, H, S, L, V; I, T, P, G, M, W, K, D or E at the 20th position of said motif; the amino acid residue R, Y, L, S, W, G, A, F, V, I, M, T, P or K at the 21st position of said motif; and/or the amino acid residue D, S, K, Y, T, E, I, H, G, C, Q, R, A; V, P, M or F at the 22nd position of said motif, wherein S of the motif takes the first position and N takes the 22nd position of the third motif.

Variants of the fifth motif for gp120 of HIV-1 (SEQ ID NO: 18) can have the amino acid residue L, V, I, S, T, Y, C, M, A, P, N, W, H, R or D at the first position of said motif; the amino acid residue G, K, T, S, I, Y, Q, L, E, P, V, C, W, D, M, F or N at the second position of said motif; the amino acid residue L, S, A; D, R, H, T, Q, N, G or E at the third position of said motif; the amino acid residue A, E, I, V, T, Q, L, R, S, W, M, P, K or N at the fourth position of said motif; the amino acid residue R, E, S, A, L, K, C, P, N or Q at the fifth position of said motif; the amino acid residue E, R, K, S, A, D, C or N at the sixth position of said motif; the amino acid residue N, E, G, Y, S, I, H, R, A, V, Q, T or K at the seventh position of said motif; the amino acid residue I, T, V, L, R, Y, K, F, G or S at the eighth position of said motif; the amino acid residue K, M, Q, G, E, V, T, N, W, I, F or S at the ninth position of said motif; the amino acid residue N, E, G, V, H, A, L, C, W, R, K, S, T or Y at the 10th position of said motif; the amino acid residue I, S, D; K, L, H, Y, T, Q, G, R, A; C or M at the 11th position of said motif; the amino acid residue S, R, G; N, C, L, F, P or K at the 12th position of said motif; the amino acid residue K, G, A, S, E, T, L or I at the 13th position of said motif; the amino acid residue N, T, G, R, Q, M, D, I, C, K, Y, A, V or H at the 14th position of said motif; the amino acid residue K, Q, G, D, R, A; V, N, H or M at the 15th position of said motif; the amino acid residue I, F, S, V, M, P, K, N, Q or E at the 16th position of said motif; the amino acid residue F, L, H, C, S, D, I, A, V, N or E at the 17th position of said motif; the amino acid residue R, N, Q, E, T, Y, P, G, V, L, I, M, S or D at the 18th position of said motif; the amino acid residue H, C, N, F, S; I or E at the 19th position of said motif; the amino acid residue R, E, N, T, Q, G, I or P at the 20th position of said motif; the amino acid residue I, T, A, L, G, M, S or D at the 21st position of said motif; and/or the amino acid residue I, A, L, E, G, S, M or K at the 22nd position of said motif, wherein F of the motif takes the first position and V takes the 22nd position of the fifth motif.

Variants of the first motif for gp120 of HIV-2 (SEQ ID NO: 19) can have the amino acid residue R, S or T at the first position of said motif; the amino acid residue Y, V or W at the second position of said motif; the amino acid residue N, W or Y at the third position of said motif; the amino acid residue E or N at the fourth position of said motif; the amino acid residue T or K at the fifth position of said motif; the amino acid residue F at the sixth position of said motif; the amino acid residue Y or E at the seventh position of said motif; the amino acid residue S, T or V at the eighth position of said motif; the amino acid residue V or T at the ninth position of said motif; the amino acid residue D, I or C at the 10th position of said motif; the amino acid residue V or E at the 11th position of said motif; the amino acid residue V or T at the 12th position of said motif; the amino acid residue T at the 13th position of said motif; the amino acid residue D, E or R at the 14th position of said motif; the amino acid residue N or E at the 15th position of said motif; the amino acid residue N or S at the 16th position of said motif; and/or the amino acid residue S or Q at the 17th position of said motif, wherein D of the motif takes the first position and T takes the 17th position of the first motif.

Variants of the second motif for gp120 of HIV-2 (SEQ ID NO: 20) can have the amino acid residue K, R or S at the first position of said motif; the amino acid residue I or K at the second position of said motif; the amino acid residue V, I or F at the third position of said motif; the amino acid residue A, V or S at the fourth position of said motif; the amino acid residue A, S, T or G at the fifth position of said motif; the amino acid residue T, S or A at the sixth position of said motif; the amino acid residue R or L at the seventh position of said motif; the amino acid residue A or Y at the eighth position of said motif; the amino acid residue R or G at the ninth position of said motif; the amino acid residue M, V, E, L, I or Q at the 10th position of said motif; the amino acid residue M, R; K or T at the 11th position of said motif; the amino acid residue E, K or G at the 12th position of said motif; the amino acid residue T, S, A or M at the 13th position of said motif; the amino acid residue Q at the 14th position of said motif; the amino acid residue T, S, A, P at the 15th position of said motif; the amino acid residue at the 16th position of said motif is not variant; the amino acid residue A, M or S at the 17th position of said motif; the amino acid residue W at the 18th position of said motif; the amino acid residue F or S at the 19th position of said motif; the amino acid residue G or A at the 20th position of said motif; the amino acid residue F at the 21st position of said motif; the amino acid residue C or S at the 22nd position of said motif; the amino acid residue S or P at the 23rd position of said motif; the amino acid residue T, A or I at the 24th position of said motif; the amino acid residue R or K at the 25th position of said motif; the amino acid residue S at the 26th position of said motif; and/or the amino acid residue G, K, V or D at the 27th position of said motif, wherein N of the motif takes the first position and E takes the 27th position of the second motif.

Variants of the third motif for gp120 of HIV-2 (SEQ ID NO: 21) can have the amino acid residue A, K, R, E, G, T, Q, V, D, P or N at the first position of said motif; the amino acid residue P, S, D; N or K at the second position of said motif; the amino acid residue S, A, P or R at the third position of said motif; the amino acid residue N, G, or S at the fourth position of said motif; the amino acid residue A, G or S at the fifth position of said motif; the amino acid residue D, P, K or Q at the sixth position of said motif; the amino acid residue V, A, T or E at the seventh position of said motif; the amino acid residue A, T, R, E, M, K or S at the eighth position of said motif; the amino acid residue Y, F or H at the ninth position of said motif; the amino acid residue M, L or T at the 10th position of said motif; the amino acid residue W or R at the 11th position of said motif; the amino acid residue T, S or I at the 12th position of said motif; the amino acid residue D at the 13th position of said motif; the amino acid residue at the 14th position of said motif is not variant; the amino acid residue R, M, K or Q at the 15th position of said motif; the amino acid residue R at the 16th position of said motif; the amino acid residue K or D at the 17th position of said motif; the amino acid residue L or S at the 18th position of said motif; the amino acid residue L, P, S or Y at the 19th position of said motif; the amino acid residue H or C at the 20th position of said motif; the amino acid residue at the 21st position of said motif is not variant; and/or the amino acid residue D, S or K at the 22nd position of said motif, wherein S of the motif takes the first position and N takes the 22nd position of the third motif.

Variants of the fifth motif for gp120 of HIV-2 (SEQ ID NO: 22) can have the amino acid residue N, S, I, Y, V, R or D at the first position of said motif; the amino acid residue I, S, M or T at the second position of said motif; the amino acid residue T, A, L or S at the third position of said motif; the amino acid residue F, M, V, E, P or S at the fourth position of said motif; the amino acid residue S, V, A, L, I or N at the fifth position of said motif; the amino acid residue A at the sixth position of said motif; the amino acid residue E at the seventh position of said motif; the amino acid residue V, L, Y or E at the eighth position of said motif; the amino acid residue A, S, G or K at the ninth position of said motif; the amino acid residue E, K or N at the 10th position of said motif; the amino acid residue L, M or K at the 11th position of said motif; the amino acid residue Y, F or N at the 12th position of said motif; the amino acid residue K at the 13th position of said motif; the amino acid residue L or V at the 14th position of said motif; the amino acid residue K at the 15th position of said motif; the amino acid residue P or S at the 16th position of said motif; the amino acid residue G at the 17th position of said motif; the amino acid residue D at the 18th position of said motif; the amino acid residue at the 19th position of said motif is not variant; the amino acid residue T or N at the 20th position of said motif; the amino acid residue L or S at the 21st position of said motif; and/or the amino acid residue I at the 22nd position of said motif, wherein F of the motif takes the first position and V takes the 22nd position of the fifth motif.

The amino acid residues are arranged in the order of likelihood. In other words, the first mentioned amino acid residue for a given position within a given motif is the amino acid residue most likely to replace the amino acid at the corresponding position of said given motif in a variant motif based on a population analysis as described herein above. While the above covers sequence variants, the additional information of the likelihood of a given amino acid variation occurring will be appreciated by the person skilled in the art since it will be possible to thereby design inhibitors which will interact with the most frequently occurring and/or rarely occurring HIV strains. Any of the above described sequence variants is understood to be capable of forming a tunnel within said 3-dimensional structure of said gp120. The sequence of said sequence variants is depicted in FIGS. 15 to 17 and 19 for HIV-1 and in FIG. 23 to FIG. 24A and FIG. 25 for HIV-2. In case of a discrepancy of the amino acid sequence information for the variants given in the description herein above and the sequence listing in comparison to said Figures, the authoritative sequence is that given in said Figures.

The term "binding" as used in accordance with the present invention with respect to the association of CD4 or integrin a4b7 and gp120 refers to the specific interaction of CD4 or integrin a4b7 to gp120 when brought into contact. Said specific interaction is characterized by a substantial conformational change of the core and periphery of gp120 accompanying said interaction. Furthermore, due to the structural adaptation of gp120 the kinetics of the interaction are slow (cf. Myszka D. et al., Proc Natl Acad Sci U.S.A., 97(16): 9026-9031 (2000); regarding CD4).

The term "peptidomimetic" as used in accordance with the invention refers to a compound that mimics the biological action of a natural (poly)peptide, i.e. gp120. Said compound may be a protein-like chain containing non-peptidic elements designed to mimic a (poly)peptide. Accordingly, a peptidomimetic in accordance with the present invention may be a compound that mimics the three-dimensional structure of a gp120 as defined herein, and also mimicks its function. Specifically encompassed are peptidomimetics that at least structurally and functionally mimic the part of gp120 that makes up the novel tunnel binding site as described herein. The term "peptide" as used herein describes a group of molecules consisting of up to 30 amino acids, whereas "proteins" consist of more than 30 amino acids. Peptides and proteins may further form dimers, trimers and higher oligomers, i.e. consisting of more than one molecule which may be identical or non-identical. The corresponding higher order structures are, consequently, termed homo- or heterodimers, homo- or heterotrimers etc. The terms "peptide" and "polypeptide" (wherein "polypeptide" is interchangeably used with "protein") also refer to naturally modified peptides/proteins wherein the modification is effected e.g. by glycosylation, acetylation, phosphorylation and the like. Such modifications are well-known in the art.

The amino acid residues of the motifs of the main embodiment provide a structural description of a novel drug target site of gp120. Said novel drug target site takes the form of a tunnel that is formed by said six sequence motifs within gp120 that was identified by the inventors. In other words, a "tunnel" in accordance with the invention consists of said six motifs or variants thereof. Preferably, the motifs have a sequence that has the same length as the specific sequence of the motifs recited herein above. It is understood that the presence of all of the motifs or variants thereof is sufficient to form said tunnel within the 3-dimensional structure of gp120. In other words, the tunnel is an inherent feature of the HIV strains analyzed.

Since at least two amino acid residues comprised in six motifs forming the 3-dimensional structure of the tunnel interact with the compound to be modeled, the present invention also provides an implicit definition of pharmacophores capable of binding to said tunnel. The term "pharmacophore" is known in the art and refers to the molecular framework responsible for the biological or pharmacological activity of a compound (Güner (2000), Pharmacophore Perception, Development, and use in Drug Design, ISBN 0-9636817-6-1; Langer and Hoffmann (2006), Pharmacophores and Pharmacophore Searches, ISBN 3-527-31250-1). Typical pharmacophore features include hydrogen bond donors, hydrogen bond acceptors, dipoles, charges, ions and hydrophobic moieties. The pharmacophore furthermore includes information on the spatial arrangement of one or more of such moieties.

The amino acid sequence of the motifs or variants thereof of the main embodiment constitute the structural elements that form the three-dimensional structure of a tunnel within gp120 which has surprisingly not been identified prior to this invention despite extensive research in the HIV research field. As shown in the enclosed figures, these structural elements form a previously unknown interaction area, i.e. said tunnel, of gp120. More surprisingly, this tunnel was found by the present inventors to be an allosteric interaction area. The term “allosteric” is known in the art and refers to an alteration of conformation in response to ligand interaction. Ligand interaction occurs at a site which is not the active site or one of the active sites of the target (here gp120), but exerts a modulating effect on the active site(s). This modulation involves structural changes which in turn frequently entail functional changes. In other words, interaction of ligands with this tunnel reduces the ability of gp120 to undergo conformational changes required for its physiological action: it locks a conformation of gp120 that cannot mediate viral entry. The locked conformation is an inactive conformation of gp120.

Sequence identity levels as recited above may be determined by methods well known in the art. Two nucleotide or protein sequences can be aligned electronically using suitable computer programs known in the art. Such programs comprise BLAST (Altschul et al. (1990), J. Mol. Biol. 215, 403-410), variants thereof such as WU-BLAST (Altschul & Gish (1996), Methods Enzymol. 266, 460-480), FASTA (Pearson & Lipman (1988), Proc. Natl. Acad. Sci. USA 85, 2444-2448), CLUSTALW (Higgins et al. (1994), Nucleic Acids Res. 22, 4673-4680) or implementations of the Smith-Waterman algorithm (SSEARCH, Smith & Waterman (1981), J. Mol. Biol. 147, 195-197). These programs, in addition to providing a pairwise sequence alignment (multiple sequence alignment in case of CLUSTALW), also report the sequence identity level (usually in percent identity) and the probability for the occurrence of the alignment by chance (P-value). Preferably, the BLAST program is employed to determine sequence identity levels.

Preferably the sequence identity at the amino acid sequence level of gp120 is at least (for each value) 85%, 90%, more preferred at least 95%, 96%, 97%, 98% and most preferred at least 99%. Preferred sequence identities at the nucleic acid sequence level are at least (for each value) 85%, 90%, 92%, 94%, more preferred at least 95%, 96%, 97%, 98% and most preferred at least 99%. Nevertheless, sequence identities (for protein and DNA sequences) of less than 80% such as e.g., at least (for each value) 75%, 70%, 65%, 60%, 55%, 50%, 45%, or at least 40% are envisaged. It is understood in accordance with the invention that the variations in the amino acid sequence of said five sequence motifs, i.e. the amino acid sequence of the variants, is encompassed by said aforementioned sequence identity levels.

The above definitions apply mutatis mutandis to other embodiments described herein below unless it is expressly stated otherwise.

The inventors have been able to identify a novel target site on gp120 that provides the means to inhibit the binding of gp120 to CD4 or integrin a4b7 resulting in the prevention of viral entry. The finding is particularly surprising since gp120 has been the subject of intense studies by research groups throughout the world for many years and is generally considered to be a structurally well defined molecule. In this regard, many crystallization structures have been generated of gp120 over the years and used in various studies to identify potential drug targets on gp120. However, none of the prior art studies was able to identify the tunnel as defined herein above constituting a novel drug target site on gp120.

Some prior art compounds have been shown to prevent the binding of HIV-1 envelope gp120 protein to cellular CD4 receptors via a specific and competitive mechanism by binding to a binding site on the surface of gp120 termed herein binding site I (Guo Q. et al., Journal of Virology, 77(19):10582-10536 (2003)). Another group of inhibitors was found to prevent certain minimal conformational changes in gp120 upon gp120/CD4 binding (Si Z. et al. Proceedings of the National Academy of Sciences, 101(14): 5036 (2004)). It was suggested that in this case an inhibitor binds to another binding site on the surface of gp120 termed herein binding site II. The surface areas of the above-mentioned different two binding sites have been shown to partially overlap in the region of a small hydrophobic pocket (cf. FIG. 1). Although said binding sites have been studied extensively, the novel tunnel was not identified in any of the prior art studies regarding the structure of gp120 and compounds binding thereto. Without whishing to be bound by any specific theory, one reason for this may be that this tunnel opens and closes thermodynamically and therefore may only be visualized using, e.g., computerised models which allow the protein to thermodynamically flex. The residues of binding site I are located in a large cavity which is penetrated by the phenyl residue of CD4 and hence is responsible for gp120-CD4 interaction (cf. FIG. 2). A three-dimensional structure of gp120 interacting with CD4 is presented in FIG. 3 (1G9N from the Protein Data Bank (Wang R. et al., J. Med. Chem., 48(12):4111-4119(2005); Westbrook J. et al., Nucleic Acids Res., 31(1):489-491 (2003)). FIG. 3 shows the Phe43 residue of CD4 entering deep into a hydrophobic pocket within the gp120 structure around binding site I. Said pocket is naturally responsible for specific recognition of the Phe43 residue of CD4.

Figure 4:
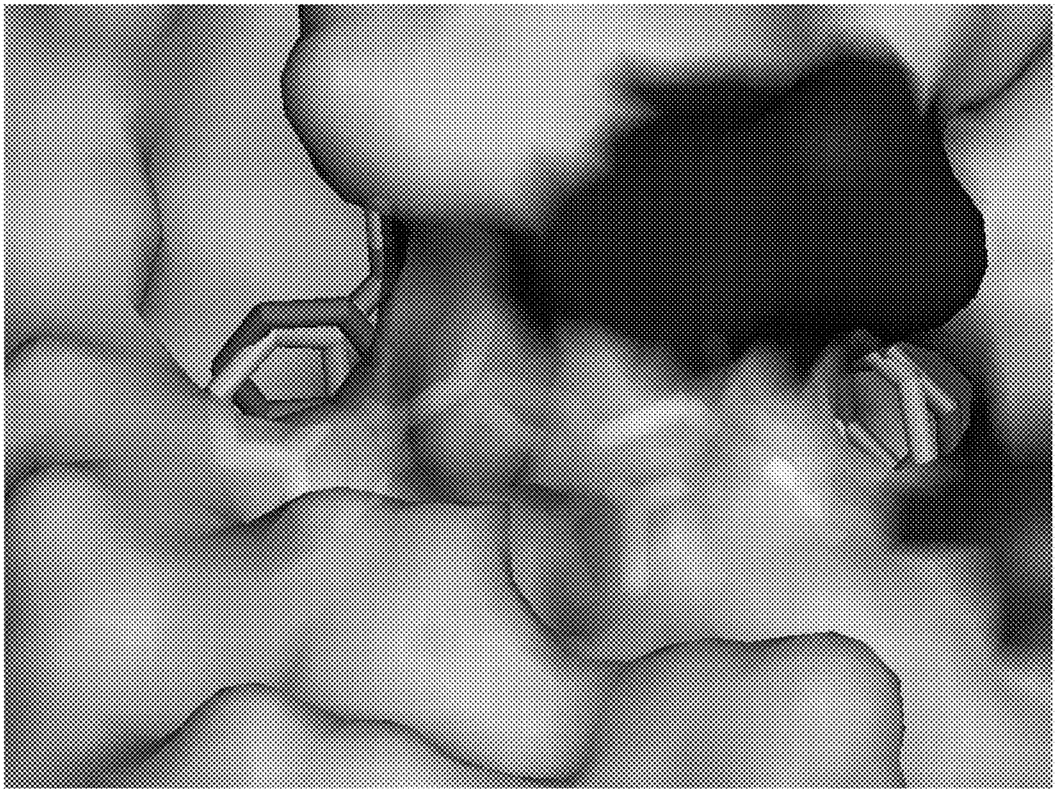

While employing molecular dynamics simulations to study various gp120 conformations the inventors identified a water filled tunnel connecting the hydrophobic pocket of binding site I with the hydrophobic pocket of binding site II. The tunnel has not been identified previously and is hence not present in any of the X-ray structures available in the Protein Data Bank. FIGS. 4 and 5 show that the binding sites I and II are closely placed within the gp120 three-dimensional structure.

When targeting the tunnel with compounds that interact with, e.g. enter, the tunnel the inventors could show that said compounds reduce the flexibility of gp120 to the extent that a conformational change necessary for binding to CD4 and to integrin a4b7 does not occur. As a result the initiation of viral entry into the target cells is inhibited (see Examples 2 and 3).

Interestingly and supporting the functional principle of the present invention, the tunnel structure is to a significant degree conserved within the various HIV species and subspecies. This is evidenced by the structural similarity of the HIV-1 and HIV-2 gp120 molecules which each feature the same tunnel elements, i.e. the motifs belonging to the tunnel as shown in the figures below (see also FIG. 22A and FIG. 22B). While the amino acids may vary to some extent from species to species or subspecies to subspecies, the overall structure, i.e. presence of six motifs defining the 3-dimensional structure of gp120, within one species including any subspecies could be shown to be highly conserved (see FIG. 22A and FIG. 22B). Without wishing to be bound by any specific scientific theory, the inventors believe that the reason for the highly conserved structure within the gp120 molecule, viz. the tunnel, of various HIV strains and subtypes is that it reflects an essential element of a universal, i.e. shared by all HIV strains and subtypes, mode of infection. In other words, disruption of said tunnel by mutation appears to have inescapably led to an evolutionary dead end. Taking advantage of said evolutionary conserved feature, the disruption of the functionality of the tunnel within gp120 results in the prevention of interaction with CD4 and integrin a4b7.

As will immediately be appreciated by the person skilled in the art, the identification of the above-described novel drug target on gp120 enables the development of novel compounds and their use as drugs in the treatment of HIV infections and HIV-associated diseases as will be described below. Corresponding compounds could overcome the problem of development of resistant strains that is due to the known hypervariability of existing drug target sites and would further affect gp120 without mechanism-related impacts on the immune system which are implicit in the treatments targeting, e.g., CXCR4 and CCR5 co-receptors. In this regard, the inventors have conducted tests of antiviral activity of compounds interacting with the tunnel as described herein on different HIV strains (see example 4) that demonstrated that the tested compounds exhibit antiviral activity in different viral strains. This corroborates the above hypothesis that the tunnel structure is a highly conserved feature and as such a valuable cross-species and -strain pharmaceutical target.

In a preferred embodiment of the invention, the method further comprises synthetically producing said designed inhibitor.

Accordingly, the invention also relates to a method of producing an inhibitor of the binding of HIV (human immunodeficiency virus) glycoprotein (gp)120 to a CD4-receptor or to the integrin alpha4 beta7 (a4b7), the method comprising (a) the molecular modelling of a compound such that the modelled compound interacts in silico with at least two amino acid residues comprised in six motifs within the 3-dimensional structure of said gp120 of HIV or within a peptidomimetic reflecting the 3-dimensional structure of said gp120 of HIV, wherein said interaction between said at least two amino acid residues and said compound is characterized by an interatomic distance of less than 8 Ångströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said six motifs comprises the amino acid sequence FRPGGGDMRDNWRSELYKYKVV (SEQ ID NO: 7) or a variant thereof; and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (i), (ii), (iii) or (iv) comprises or encodes said motifs or variants thereof; and (b) synthesizing said compound that interacts with said at least two amino acid residues comprise in said six motifs within the 3-dimensional structure of gp120.

These embodiments are particularly, but not exclusively, envisaged for those cases where the inhibitor is a small organic molecule, a peptide or polypeptide. Means and methods for synthesizing peptides or polypeptides are well known in the art and may involve organic synthesis and/or the recombinant production using the methods of molecular biology and protein biochemistry. A large number of suitable methods exist in the art to produce peptides or polypeptides in appropriate hosts. If the host is a unicellular organism such as a prokaryote, a mammalian or insect cell, the person skilled in the art can revert to a variety of culture conditions. Conveniently, the produced protein is harvested from the culture medium, lysates of the cultured organisms or from isolated (biological) membranes by established techniques. In the case of a multicellular organism, the host may be a cell which is part of or derived from a part of the organism, for example said host cell may be the harvestable part of a plant. A preferred method involves the recombinant production of protein in hosts as indicated above. For example, nucleic acid sequences comprising a (poly)nucleotide can be synthesized by PCR, and inserted into an expression vector. Subsequently a suitable host may be transformed with the expression vector. Thereafter, the host is cultured to produce the desired peptide(s) or polypeptide(s), which is/are isolated and purified.

An alternative method for producing peptides or polypeptides is in vitro translation of mRNA. Suitable cell-free expression systems for use in accordance with the present invention include rabbit reticulocyte lysate, wheat germ extract, canine pancreatic microsomal membranes, *E. coli* S30 extract, and coupled transcription/translation systems such as the TNT-system (Promega).

These systems allow the expression of recombinant peptides or polypeptides upon the addition of cloning vectors, DNA fragments, or RNA sequences containing coding regions and appropriate promoter elements.

In addition to recombinant production, the peptide or polypeptide may be produced synthetically, e.g. by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154).

Synthetic peptide or polypeptide synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by Houghton Proc. Natl. Acad. Sci. USA (82) (1985), 5131-5135, can be used. Furthermore, (poly)peptides may be produced semi-synthetically, for example by a combination of recombinant and synthetic production.

Peptide or polypeptide isolation and purification can be achieved by any one of several known techniques; for example and without limitation, ion exchange chromatography, gel filtration chromatography and affinity chromatography, high pressure liquid chromatography (HPLC), reversed phase HPLC, and preparative disc gel electrophoresis. (Poly)peptide isolation/purification techniques may require modification of the proteins of the present invention using conventional methods. For example, a histidine tag can be added to the protein to allow purification on a nickel column. Other modifications may cause higher or lower activity, permit higher levels of protein production, or simplify purification of the protein.

As regards small organic molecules, reference is made to the Beilstein database available from MDL Information Systems as an example.

In another preferred embodiment of the method of the invention, said molecular modelling comprises (a) measuring at least one intermolecular distance; (b) calculating at least one free energy of interaction; and/or determining the accessibility to the tunnel.

Accessibility of the tunnel limits the size of the allosteric effector, i.e. the inhibitor, and thereby the maximal intermolecular interaction energy. Tools for molecular modeling as described above typically provide the option of measuring one or more intermolecular distances. Preferably, the intermolecular distances are determined as distances between the centers of atoms. Tools for molecular modeling also generally provide the option of calculating free energies of interaction. The term "free energy" in relation to an interaction is well known in the art and is related to the equilibrium binding constant by the equation $\Delta G=-RT \ln K$, wherein $\Delta G$ is the change in free energy upon binding, K is the binding constant, T is the temperature and R is the universal gas constant. Free energies to be calculated may be, as described above, total free energies and/or partial free energies.

Another embodiment of the invention relates to a method of identifying an inhibitor of the binding of HIV (human immunodeficiency virus) glycoprotein (gp)120 to a CD4-receptor or to the integrin alpha4 beta7 (a4b7), the method comprising (a) bringing into contact a HIV gp120 or a peptidomimetic reflecting the three-dimensional structure of said gp120 and a test compound; (b) determining whether said test compound interacts with at least two amino acid residues comprised in six motifs within the 3-dimensional structure of said gp120 or within a peptidomimetic reflecting the 3-dimensional structure of said gp120, wherein said interaction between said at least two amino acid residues and said compound is characterized by an interatomic distance of less than 8 Angströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said six motifs comprises the amino acid sequence FRPGGGDMRDNWRSELYKYKVV (SEQ ID NO: 7) or a variant thereof; and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (iii) or (iv) comprises or encodes said motifs or variants thereof; and (c) identifying those compounds which interact with at least two amino acid residues comprised in said six motifs within the 3-dimensional structure of said gp120 in (b).

An interaction with at least two amino acid residues comprised in six motifs within the 3-dimensional structure of said gp120 of HIV or within a peptidomimetic reflecting the 3-dimensional structure of said gp120 of HIV is indicative that an inhibitor of the binding of HIV (human immunodeficiency virus) glycoprotein (gp)120 to a CD4-receptor or to the integrin alpha4 beta7 (a4b7) has been identified.

In a further embodiment, the invention relates to a method of identifying an inhibitor of the binding of HIV (human immunodeficiency virus) glycoprotein (gp)120 to a CD4-receptor or to the integrin alpha4 beta7 (a4b7), the method comprising (a) bringing into contact a HIV gp120 or a peptidomimetic reflecting the three-dimensional structure of said gp120 and a test compound; (b) determining whether said test compound interacts with at least two amino acid residues comprised in six motifs forming a tunnel within the 3-dimensional structure of said gp120 or within a peptidomimetic reflecting the 3-dimensional structure of said gp120, wherein said interaction between said at least two amino acid residues and said compound is characterized by an interatomic distance of less than 8 Angströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said six motifs comprises the amino acid sequence FRPGGGDMRDNWRSELYKYKVV (SEQ ID NO: 7) or a variant thereof; and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (iii) or (iv) comprises or encodes said motifs or variants thereof; and (c) identifying those compounds which interact with at least two amino acid residues comprised in said six motifs forming a tunnel within the 3-dimensional structure of said gp120 in (b). The preferred embodiments described herein below are also preferred embodiments with regard to this embodiment.

These embodiments relate to a screen for the identification of HIV gp120 inhibitors which in turn are suitable as medicaments or lead compounds for the development of a medicament. The screen may be implemented in various ways such as a biochemical screen or a cellular screen. In case of a cellular screen said "bringing into contact a HIV gp120 or a peptidomimetic reflecting the three-dimensional structure of said gp120 and a test compound" may be effected, e.g., by bringing into contact an HIV or a cell producing said virus or said peptidomimetic with a test compound. Alternatively or additionally, also isolated (recombinantly produced) gp120 molecules may be brought into contact with the test compound. The bringing into contact is performed under conditions which allow interaction of the test compound to gp120, in case the test compound is in principle capable of binding as required. Suitable conditions include conditions in liquid phase such as aqueous solutions, preferably buffered solutions. Furthermore, ionic strength may be adjusted, e.g., by the addition of sodium chloride. The concentration of sodium chloride may be between 0 and 2 M, preferably between 100 and 200 mM. Alternatively, sodium chloride is absent from the assay. For biological assays in many cases the presence of one or more further substances, including other salts than sodium chloride, trace elements, anti-oxidants, amino acids, vitamins, growth factors, ubiquitous co-factors such as ATP or GTP, is required. Said further substances may either be added individually or provided in complex mixtures such as, e.g., serum. These and further accessory substances are well known in the art as are concentrations suitable for biological assays. The skilled person is aware of suitable conditions in dependency of the particular assay format to be used in the method of screening according to the invention.

In a further embodiment, the screen may be implemented as a virtual screen, i.e., the screen may be performed in silico. Virtual screens may be implemented by computer-based docking of one test compound at a time into the allosteric interaction site, preferably binding site, i.e. the tunnel defined above, wherein both the test compound and the interaction site are represented in silico. Thereby, the interaction position and conformation is calculated. The interaction site may, for example, be comprised in a representation of the entire gp120 molecule or, alternatively, of those parts only which make up the tunnel as defined herein above. Upon completion of docking, the interaction affinity involving determining interatomic distances (or equivalently the free energy of interaction as defined herein above) is determined based on the parameters of the computer representation of the involved molecules. A threshold may be chosen such as to select those test compounds which are candidate high affinity binders. Suitable software packages are known in the art and include Chemoffice, CNS, CCP4, ADF and Gold (see above).

In a preferred embodiment of the method of the invention, said determining in step (b) is effected by X-ray crystallography and/or NMR spectroscopy.

In this embodiment of the invention, the occurrence of an interaction involving one or more residues of gp120 is determined by assessing structural parameters using NMR spectroscopy or X-ray crystallography. These structural parameters may comprise the coordinates of the complex between said test compound and gp120. Alternatively, structural parameters may be determined only to the extent necessary to determine whether interaction/binding according to the invention, in particular interaction with one or more residues of gp120 occurs. Examples of the latter, more selective methods include NMR spectroscopic methods exploiting the nuclear Overhauser effect or saturation transfer difference (STD). Suitable methods include the recording of NOESY and/or ROESY spectra. The required NMR spectra can be obtained in medium to high throughput manner, wherein throughput may be further increased by assessing a mixture of ligands, for example 10, 20 or 100 ligands at a time and further analyzing only those mixtures which are found to comprise one or more binding molecules. Also, means and methods for high throughput crystallization are available; see, for example, Stevens (Current Opinion in Structural Biology 2000, 10: 558-564) and Kuhn et al. (Current Opinion in Chemical Biology 2002, 6: 704-710).

In a more preferred embodiment, X-ray crystallography comprises (a) generating a crystal of a complex formed by said test compound bound to gp120; (b) generating and recording x-ray diffraction data; (c) digitising the data; (d) calculating an electron density map; (e) determining the three-dimensional structure of the crystal components; and (f) storing the crystal coordinates generated on a data carrier.

X-ray diffraction may be performed on a beamline such as the ID29 beamline of ESRF, Grenoble or using in-house devices such as a Bruker X8PROTEUM. Data may be further processed with XDS (W. Kabsch, *J. Appl. Cryst.* 21, 67 (1988)) and refined with CNS (A. T. Brünger et al. *Acta Cryst. D* 54, 905 (1998)). In one alternative, the PROTEUM2 software (Bruker) may be used. Structure can further be solved with, for example, AmoRe (J. Navaza, *Acta Crystallogr.* A 50, 157 (1994)) and analysed with Xfit (D. E. McRee, J. Struct. Biol. 125, 156 (1999)) while structure validation may be performed with PROCHECK (R. A. Laskowski, M. W. MacArthur, *J. Appl. Crystallogr.* 26, 283 (1993)) and WHATCHECK (R. W. W. Hooft, G. Vriend, C. Sander, E. E. Abola, *Nature* 381, 272 (1996)). The final map containing the atomic coordinates of the constituents of the crystal may be stored on a data carrier; typically, the data is stored in PDB format or in X_PLOR format, both of which are known to the person skilled in the art. However, crystal coordinates may as well be stored in simple tables or text files.

In another preferred embodiment of the invention, the method further comprises the step of (a') (i) determining whether said test compound forms a complex with said gp120; and/or (ii) determining whether said test compound modulates the activity and/or conformation of said gp120; and/or (iii) determining the cytotoxicity of said test compound; wherein step (a') is to be effected after step (a) and prior to step (b), and wherein said determining in step (b) is performed with test compounds determined to bind, to modulate, and/or to be non-cytotoxic in step (a').

This embodiment provides for filtering a subset of test compounds testing positive in one or more of the assays of (a') (i) to (iii). The advantage of such filtering is that the subsequent determining whether the test compound interacts with one or more residues of gp120 has to be done only with said test compounds testing positive. Assaying for test compounds that form complexes with HIV gp120 filter may be advantageous when large libraries of compounds are screened for potential inhibitors. Applying the step of filtering out only those test compounds that form a complex with HIV gp120, limits interaction studies only to those compounds instead of the entire library.

Means and methods for identifying complexes formed by interaction partners, e.g. between a test compound and HIV-1 and/or HIV-2 gp120, are well known in the art and include assays based on fluorescence such as fluorescence resonance energy transfer (FRET) assays and fluorescence polarization (FP) assays, immunological assays such as ELISA, surface plasmon resonance, isothermal titration calorimetry and Fourier Transformed Infrared Spectroscopy (FTIR).

The term “activity of gp120” is meant to refer to the capability of gp120 to bind to CD4 and/or integrin a4b7 which results in the initiation of viral entry. Also encompassed is the binding to co-receptors such as, e.g., CXCR5 and CCR5. Assays for assessing gp120 activity are discussed further below.

Since the method of identifying an inhibitor according to the invention is designed to identify compounds binding to the allosteric tunnel of gp120, an additional or alternative filtering step involves the determining whether the test compound modulates or changes the conformation of said gp120. A change in conformation may be determined by using methods known in the art including the determination of electrophoretic or chromatographic mobility and fluorescence-based methods. In the latter case, changes in intramolecular distances between fluorophors arising from a change of conformation may be determined.

Cytotoxicity may, e.g., be assayed in a cellular assay by determining the cellular uptake of neutral red. Only living cells are capable of neutral red uptake via an active transport mechanism. Hence when applying a target compound to cells preferably in varying concentrations the cytotoxicity of said target compound may be assessed.

In a more preferred embodiment of the method of the invention, said activity is the capability of said gp120 to initiate viral entry of HIV into mammalian cells. Preferably, the mammalian cell is a human cell. As described above, activity of gp120 is defined to be its capability to bind to CD4 and the relevant co-receptors as well as integrin a4b7 and initiate viral entry. Said binding results in a conformational change of each of the three gp120 molecules making up the gp120 trimer shielding gp41. Thereby subsequently an interaction of gp41 with the membrane of the target cell is allowed. In other words, the interplay of gp120 and CD4 or integrin a4b7 resulting in the initiation of viral entry is referred to as activity of gp120. Methods to determine said activity are well-known in the art and comprise, e.g., the assays described in Example 2 (cell-cell and viruscell infection assay) determining whether cells have been infected or not.

In another preferred embodiment of the method of the invention, the modelled compound additionally interacts with or the test compound is determined to additionally interact with a further motif of HIV gp120 or corresponding motifs in a peptidomimetic reflecting the three-dimensional structure of said gp120 molecule.

In accordance with the invention it is preferred that the modelled compound or the test compound interacts additionally with parts, i.e motifs, of gp120 which are not part of the tunnel. Preferably, said parts are in the direct vicinity of the tunnel such as, e.g. the binding site I of HIV gp120 that has been described herein previously. In other words, a compound interacting with the tunnel of gp120 in accordance with the invention may be (i) one entity that interacts exclusively with the tunnel or interacts with the tunnel and a part of gp120 other than the tunnel. A preferred exemplary motif that can be interacted with by a modelled compound or a test compound in addition to said at least two amino acid residues comprised in said six motifs, is a motif (external motif) comprising the amino acid sequence CRIKQIINMWQEVGKAMYAPPI (SEQ ID NO: 8) of SEQ ID NO: 2 or a variant thereof. Said external motif is located at an end of the tunnel and as such interaction of a compound with said external alone does not result in an inhibition of gp120's ability to change its conformation and as a result inhibit binding to CD4 and/or a4b7. The definitions of "interaction", "interaction sites" and other definitions relating to motifs described herein also apply to the interaction of a modelled compound or a test compound with said external motif and to said external motif itself. Preferably, the interaction site for the external motif is located in the amino acid residue stretch made up of or at least partially involves amino acids IKQIINMWQEVGKAMY of the external motif (residues 3-18 of SEQ ID NO: 8) or variants thereof. Also preferred is that the interaction site of the external motif comprises or consists of only those amino acid residues that have been shown to be most conserved for HIV-1 and HIV-2, such as the underlined amino acid residues of the external motif CRIKQIINMWQEVGKAMYAPPI (SEQ ID NO: 8) for a gp120 of HIV-1 and CRIKQIINMWQEVGKAMYAPPI (SEQ ID NO: 13) for a gp120 of HIV-2.

Variants of the external motif for gp120 of HIV-1 (SEQ ID NO: 23) can have the amino acid residue R, S, Y, M, F, G, A, L, I, V, W, P, T, H or N at the first position of said motif; the amino acid residue K, G, S, N, Q, I, T, E, P, H, M, W, L, C, Y, V or D at the second position of said motif; the amino acid residue L, M, V; T, N, R, K, Y, C, S, P, F, H, D or E at the third position of said motif; the amino acid residue R, N, E; I, T, Q, S, G, P, M, Y, L, H, A or D at the fourth position of said motif; the amino acid residue L, H, R, P, K, A, N, E, G, T, M, V or S at the fifth position of said motif; the amino acid residue F, V, L, M, T, Y, N, S, K, A, P, R or D at the sixth position of said motif; the amino acid residue V, M, T, L, A, Y, K, G, E, C, R, S or Q at the seventh position of said motif; the amino acid residue R, H, K, S, D, I, T, Y, G, Q, L, C, M, V, E, P or F at the eighth position of said motif; the amino acid residue R, L, K, T, S, V, I, P, G, Y, H, Q, N, A, C, W or D at the ninth position of said motif; the amino acid residue R, C, G, V, L, M, S, A, P, H, K, Y, N or Q at the $10^{th}$ position of said motif; the amino acid residue R, I, M, L, H, K, A, E, P, T, G, Y, V, W or S at the $11^{th}$ position of said motif; the amino acid residue R, G, K, Q, T, S; A, I, V, D, L, P, H, N, C, M, W or Y at the $12^{th}$ position of said motif; the amino acid residue A, T, I, G, L, S, E, P, K, R, N, Q, W or D at the $13^{th}$ position of said motif; the amino acid residue R, E, A; V, K, Q, T, N, D, P, W or S at the $14^{th}$ position of said motif; the amino acid residue Q, R, S, T, E, L, P, N, I, H, G, A, V, Y, C, M, W or D at the $15^{th}$ position of said motif; the amino acid residue V, G, T, S, P, Q, E, C, W, R, K, Y or E at the $16^{th}$ position of said motif; the amino acid residue I, T, V, L, K, N, A, F, R, C, S, P, Q, H, Y or E at the $17^{th}$ position of said motif; the amino acid residue H, F, C, S, V, D, N, M, A, P, L, E, K, T or G at the $18^{th}$ position of said motif; the amino acid residue P, T, S, N, V, C, G, D, L, I, M or H at the $19^{th}$ position of said motif; the amino acid residue S, A, N, L, T, H, R, V, K, D or Q at the $20^{th}$ position of said motif; the amino acid residue S, L, A, T, F, R, H, G, Y, N or Q at the $21^{st}$ position of said motif; and/or the amino acid residue V, T, R, L, F, M, N, P, H, A, K, G, W, Y or D at the $22^{nd}$ position of said motif, wherein C of said motif takes the first position and I takes the $22^{nd}$ position of the external motif.

Variants of the external motif for gp120 of HIV-2 (SEQ ID NO: 24) can have the amino acid residue R or Y at the first position of said motif; the amino acid residue H or Q at the second position of said motif; the amino acid residue at the third position of said motif is not variant; the amino acid residue R, P or E at the fourth position of said motif; the amino acid residue at the fifth position of said motif is not variant; the amino acid residue V or K at the sixth position of said motif; the amino acid residue V at the seventh position of said motif; the amino acid residue S at the eighth position of said motif; the amino acid residue T, A or I at the ninth position of said motif; the amino acid residue R at the $10^{th}$ position of said motif; the amino acid residue H or R at the $11^{th}$ position of said motif; the amino acid residue K, R or N at the $12^{th}$ position of said motif; the amino acid residue A, I or S at the $13^{th}$ position of said motif; the amino acid residue W, R, E at the $14^{th}$ position of said motif; the amino acid residue Q, R, I, V, N, T, L or E at the $15^{th}$ position of said motif; the amino acid residue N, H, Y, R or K at the $16^{th}$ position of said motif; the amino acid residue V, I, A, L or Y at the $17^{th}$ position of said motif; the amino acid residue I at the $18^{th}$ position of said motif; the amino acid residue L or F at the $19^{th}$ position of said motif; the amino acid residue A or L at the $20^{th}$ position of said motif; the amino acid residue at the $21^{st}$ position of said motif is not variant; and/or the amino acid residue R or K at the $22^{nd}$ position of said motif, wherein C of said motif takes the first position and I takes the $22^{nd}$ position of the external motif.

Also envisaged is linking of a modeled/synthesized compound or a test compound once designed/synthesized or identified in accordance with the method of the invention to a known gp120 binding compound not interacting with the tunnel or alternatively to a modelled compound or a test compound that interacts with gp120 other than to the tunnel. In other words, such compounds interacting with the tunnel of gp120 may be composed of two entities linked to each other, wherein one entity interacts with the tunnel and the other entity interacts with said other motif or part of gp120. A corresponding compound may be a bipartite compound or one of the two entities can correspond to a discrete compound that is linked to another compound, i.e. the second entity. The combination of interaction with the tunnel and other parts of gp120 in contrast to exclusively interacting with the tunnel provides the advantage of more flexibility as regards designing modelled compounds or identifying test compounds in view of increasing binding affinities and likelihood of said compounds at least partially entering the tunnel.

In a further preferred embodiment of the method of the invention, molecular modeling starts from a compound selected from a compound of the formula (1) and (2) or a salt or solvate thereof, or the test compound to be screened in accordance with the method of the invention described herein is selected from a compound of the formula (1) and (2) or a salt or solvate thereof:

(1)

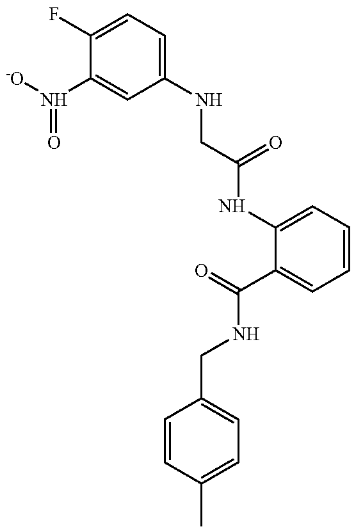

(2)

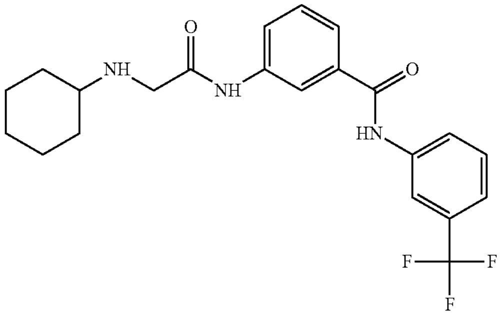

As demonstrated in the Example section the above compounds of formula (1) and (2) have been shown to be capable of inhibiting the binding of CD4 or integrin a4b7 to gp120 through interaction with the novel targeting site, i.e. the tunnel. Accordingly, molecular modeling may be based on the structural information of the compounds of formula (1) and (2). Such molecular modeling starting from said compounds may lead to improved compounds as described below. The compound of formula (1) corresponds to the compound termed “T5379534” in example 2 and 3 (and FIG. 35A to FIG. 35D and FIG. 37A and FIG. 37B) while the compound of formula (2) corresponds to the compound termed “T0520-5895” in example 2 and 3 (and FIG. 34A and FIG. 34B, and FIG. 37A and FIG. 37B).

The compound of formula (1) interacts with sequence motifs 1, 2, 3, 5 within the 3-dimensional structure of the gp120 used for experimentation and with the external motif described herein above. Specifically, said compound has been demonstrated to interact with the second “I”, “W” and “KLT” of said first motif (residues 15-17 of SEQ ID NO: 3) at 12 Angström, with the second “I” and “W” of said first motif at 8 Angström; with “VVSTQ” of the second motif (residues 14-18 of SEQ ID NO: 4) at 12 Angström, with “VST” of the second motif (residues 15-17 of SEQ ID NO: 4) at 8 Angström and “T” of said interaction site “VVSTQ” of the second motif (residues 14-18 of SEQ ID NO: 4) at 5 Angström; with “GGDPEIVMHSFN” (residues 2-13 of SEQ ID NO: 5) and the first “F” and the “Y” within the sequence “GGEFFYCN” of the third motif (residues 15-22 of SEQ ID NO: 5) at 12 Angström; with “GDPEIVMHSFN” (residues 3-13 of SEQ ID NO: 5) and the first “F” and the “Y” within the sequence “GGEFFYCN” of the third motif (residues 15-22 of SEQ ID NO: 5) at 8 Angström; with “D”, “EI” and “SFN” within the sequence of “GGDPEIVMHSFN” (residues 2-13 of SEQ ID NO: 5) and the first “F” and the “Y” within the sequence “GGEFFYCN” of the third motif (residues 15-22 of SEQ ID NO: 5) at 5 Angström; with “IINMWQEVGKA” within the external motif (residues 6-16 of SEQ ID NO: 8) at 12 Angström; with “IINMWQEVGK” within the external motif (residues 6-15 of SEQ ID NO: 8) at 8 Angström; with “INMWQEV” within the external motif (residues 7-13 of SEQ ID NO: 8) at 5 Angström; with “GGGDMRDNW” within the fifth motif (residues 4-12 of SEQ ID NO: 7) at 12 Angström, with “GGDMR” within the fifth motif (residues 5-9 of SEQ ID NO: 7) at 8 Angström, and with “GDMR” within the fifth motif (residues 6-9 of SEQ ID NO: 7) at 5 Angström.

The compound of formula (2) interacts with the same sequence motifs as the above compound within the 3-dimensional structure of the gp120 used for experimentation. Specifically, said compound has been demonstrated to interact with the second “I” and “W” of said first motif (SEQ ID NO: 3) at 12 Angström, with the second “I” and “W” of said first motif (SEQ ID NO: 3) at 8 Angström; with the “W” of said first motif at 5 Angström; with “VVSTQ” of the second motif (residues 14-18 of SEQ ID NO: 4) at 12 Angström, with “VST” of the second motif (residues 15-17 of SEQ ID NO: 4) at 8 Angström, “V” and “T” of said interaction site “VVSTQ” of the second motif (residues 14-18 of SEQ ID NO: 4) at 5 Angström; with “GGDPEIVMHSFN” (residues 2-13 of SEQ ID NO: 5) and the first “F” and the “Y” within the sequence “GGEFFYCN” of the third motif (residues 15-22 of SEQ ID NO: 5) at 12 Angström; with “GDPEIVMHSFN” (residues 3-15 of SEQ ID NO: 5) and the first “F” and the “Y” within the sequence “GGEFFYCN” of the third motif (residues 15-22 of SEQ ID NO: 5) at 8 Angström; with “D”, “EI” and “SFN” within the sequence of “GGDPEIVMHSFN” (residues 2-13 of SEQ ID NO: 5) and the first “F” and the “Y” within the sequence “GGEFFYCN” of the third motif (residues 15-22 of SEQ ID NO: 5) at 5 Angström; with “IINMWQEVGKA” within the external motif (residues 6-16 of SEQ ID NO: 8) at 12 Angström; with “IINMWQEVGK” within the external motif (residues 6-15 of SEQ ID NO: 8) at 8 Angström; with “INMWQEV” within the external motif (residues 7-13 of SEQ ID NO: 8) at 5 Angström; with “GGGDMRDNW” within the fifth motif (residues 4-12 of SEQ ID NO: 7) at 12 Angström, with "GGDMR" (residues 5-9 of SEQ ID NO: 7) and "N" in the sequence of "GGGDMRDNW" within the fifth motif (residues 4-12 of SEQ ID NO: 7) at 8 Angström, and with "GDMR" within the fifth motif (residues 6-9 of SEQ ID NO: 7) at 5 Angström. In the case of variant motifs forming a tunnel within the 3-dimensional structure of gp120 molecule, said compounds of formula (1) and (2) may interact with less than motifs 1, 2, 3, 5 and the external motif and/or with different amino acid residues within said motifs and still be considered an inhibitor in accordance with the invention, provided that the inhibitor binds to at least two amino acid residues comprised in said motifs forming the tunnel.

A further embodiment of the invention relates to a compound according to formula (1) or (2) as defined herein above. Preferably, the compound according to formula (1) or (2) is used as a medicament and/or as a lead compound to further improve the pharmaceutical characteristics of the compound. The skilled person is well-aware of the different formulations a medicament may be made of such as, e.g., the formulations as described herein below.

In another embodiment the invention relates to a method of decreasing thermal motion of a tunnel within gp120 comprising contacting said gp120 with a compound that interacts with at least two amino acid residues comprised in six motifs within the 3-dimensional structure of said gp120 of HIV or within a peptidomimetic reflecting the 3-dimensional structure of said gp120 of HIV, wherein said interaction between said at least two amino acid residues and said compound is characterized by an interatomic distance of less than 8 Angströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said five motifs comprises the amino acid sequence FRPGGGDMRDNWRSELYKYKVV (SEQ ID NO: 7) or a variant thereof and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (iii) or (iv) comprises or encodes said motifs or variants thereof.

An interaction with at least two amino acid residues comprised in six motifs within the 3-dimensional structure of said gp120 of HIV or within a peptidomimetic reflecting the 3-dimensional structure of said gp120 of HIV is indicative that a decrease of the thermal motion of said tunnel within gp120 has been achieved.

In a further embodiment, the invention relates to a method of decreasing thermal motion of a tunnel within gp120 comprising contacting said gp120 with a compound that interacts with at least two amino acid residues comprised in six motifs forming a tunnel within the 3-dimensional structure of said gp120 of HIV or within a peptidomimetic reflecting the 3-dimensional structure of said gp120 of HIV, wherein said interaction between said at least two amino acid residues and said compound is characterized by an interatomic distance of less than 8 Angströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said five motifs comprises the amino acid sequence FRPGGGDMRDNWRSELYKYKVV (SEQ ID NO: 7) or a variant thereof; and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (iii) or (iv) comprises or encodes said motifs or variants thereof.

The term "thermal motion" is well-known in the art and has the same meaning in accordance with the invention. Briefly, thermal motion relates to the random motion of molecules that results from their being in thermal equilibrium at a particular temperature. In general, thermal motions are faster at higher temperatures and for lower mass particles. In accordance with the present invention, decreasing thermal motion of the tunnel will inhibit the flexibility of gp120 which results in the incapability of changing the conformation of gp120 required for binding to CD4 or to the integrin a4b7. In other words, the capability of gp120 to undergo a conformational change is dependent on the degree of thermal motion of said tunnel within gp120 as defined herein. The term "decreasing" means in accordance with the present invention lowering or completely abolishing said thermal motion. In preferred embodiments, a decrease refers to a reduction in thermal motion of at least (for each value) 10, 20, 30, 40, more preferred at least 50, 60, 70, 80, 90, 95, 98 and most preferred at least 99% as well as a reduction of 100%, i.e. completely abolishing thermal motion. Also preferred, thermal motion drops to less than $10^{-2}$, less than $10^{-3}$, less than $10^{-4}$ or less than $10^{-5}$ times the activity compared to the activity in the absence of the compound.

In another embodiment, the invention relates to a compound capable of interacting with at least two amino acid residues comprised in six motifs within the 3-dimensional structure of said gp120 of HIV or within a peptidomimetic reflecting the 3-dimensional structure of said gp120 of HIV, wherein said interaction between said at least two amino acid residues and said compound is characterized by an interatomic distance of less than 8 Angströms, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; wherein a fifth motif of said five motifs comprises the amino acid sequence FRPGGGDMRDNWRSELYKYKVV (SEQ ID NO: 7) or a variant thereof and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (iii) or (iv) comprises or encodes said motifs or variants thereof.

The skilled person is in the position to identify compounds that can interact with said at least two amino acid residues comprised insix sequence motifs within the three-dimensional structure of said gp120 of HIV, for example in accordance with methods described herein above, i.e. in silico methods such as used in molecular modeling. Briefly, the tertiary structure of a compound is determined by methods well-known in the art or obtained otherwise, e.g. from a database comprising data of the tertiary structure of compounds, and then used in an in silico method as described above that enable the analysis whether the compound to be analysed can interact with said at least two amino acid residue comprised in six motifs within the 3-dimensional structure of gp120 of HIV. It is understood in accordance with the invention that a compound as defined herein above can be used as an inhibitor of the binding of CD4-receptor or integrin a4b7 to gp120 of HIV. Therefore, it is also understood that a compound as defined herein can be used for the prevention and/or treatment of a HIV-infection and/or a disease associated with a HIV-infection as detailed below.

In another embodiment, the invention relates a method of inhibiting the binding of HIV (human immunodeficiency virus) glycoprotein (gp)120 to the integrin alpha4 beta7 (a4b7), the method comprising the step of inhibiting a conformational change of said gp120 taking place upon binding to said integrin a4b7, wherein inhibition of said conformational change inhibits the binding of HIV-1 or HIV-2 gp120 to said integrin.

Without wishing to be bound by specific theory and as explained herein above, it is expected on the basis of experimental evidence (see example 3) that gp120 undergoes a conformational change to be able to bind to the integrin a4b7. Therefore, inhibiting the conformational change that gp120 must undergo to be able to bind to said integrin will lead to the inhibition of said binding of gp120 to integrin a4b7.

In a preferred embodiment of the invention, the inhibition is effected by decreasing the thermal motion of a tunnel within said gp120, and wherein the 3-dimensional structure of said tunnel within the 3-dimensional structure of said gp120 is formed by six motifs, wherein a first motif of said six motifs comprises the amino acid sequence DIISLWDQSLKPCVKLT (SEQ ID NO: 3) or a variant thereof; wherein a second motif of said six motifs comprises the amino acid sequence NVSTVQCTHGIRPVVSTQLLLNGSLAE (SEQ ID NO: 4) or a variant thereof; wherein a third motif of said six motifs comprises the amino acid sequence SGGDPEIVMHSFNCGGEFFYCN (SEQ ID NO: 5) or a variant thereof; wherein a fourth motif of said six motifs comprises the amino acid sequence CPKISFEP (SEQ ID NO: 6) or a variant thereof; and wherein a fifth motif of said six motifs comprises the amino acid sequence FRPGGGDMRDNWRSELYKYKVV (SEQ ID NO: 7) or a variant thereof; and wherein a sixth motif of said six motifs comprises the amino acid sequence CSS or a variant thereof, said gp120 of HIV comprising or consisting of (i) the sequence of SEQ ID NO: 2; (ii) the sequence encoded by the sequence of SEQ ID NO: 1; (iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, wherein said sequence of (iii) or (iv) comprises or encodes said motifs or variants thereof.

In a more preferred embodiment of the method of the invention, the decrease in thermal motion is effected according to the method of decreasing thermal motion of a tunnel within gp120 of HIV defined herein above.

In another more preferred embodiment of the invention, the method is further effecting the inhibition of the binding of HIV gp120 to a CD4-receptor.

As has been described herein above in detail before, the capability of gp120 to bind to CD4 depends on the structural flexibility of gp120 which in turn depends on the flexibility of the tunnel. Said flexibility of the tunnel is dependent from the thermal motion of the tunnel. Hence, decreasing the thermal motion of said tunnel within gp120 of HIV will lead to the inhibition of the conformational change necessary for gp120 to bind to CD4.

In a further embodiment, the invention relates to the use of a compound selected from compounds of the formula (1) or (2) as defined herein above or a salt or solvate thereof as a lead compound in the development of an inhibitor of the binding of a HIV gp120 to a CD4-receptor or integrin alpha4 beta7 (a4b7).

The term "lead compound" is known in the art and refers to a compound providing a starting point for developing a pharmaceutically active agent. Generally, said pharmaceutically active agent is different from, preferably optimized as compared to the lead compound. In other words, the development of a lead compound preferably involves the optimization of the pharmacological properties of said lead compound. The term "lead compound" therefore refers also to a compound that is analyzed only with regard to the parts of the compound that are capable of interacting with at least two amino acid residues comprised in said six motifs within the 3-dimensional structure of gp120. In other words, one can devise other compounds on the basis of lead compounds that may not or may only partially be structurally related to the lead compound but that are functionally related, i.e. show the desired activity. In accordance with the present invention a functionally related compound is a compound that interacts with at least two amino acid residues comprised in said six motifs or variants thereof within the 3-dimensional structure of gp120. It is understood that said functional relationship includes the capability of inhibiting the binding of gp120 to CD4 and/or integrin a4b7.

Methods for the optimization of the pharmacological properties of compounds identified in screens, generally referred to as lead compounds, are known in the art and comprise a method of modifying a compound identified as a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiazolidines or combinations thereof.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

Another embodiment of the invention relates to a pharmaceutical composition comprising one or more of the compounds selected from the formula (1) or (2) as defined herein above or salts or solvates or functional derivatives thereof or a compound as defined herein above. While said compounds of formula (1) or (2) may be used as a lead compound, which includes as mentioned previously optimizing the compound (e.g., to increase its bioavailability), said compounds have shown such effectiveness against HIV infection in tests that they can be formulated into a pharmaceutical composition to be used in a treatment regimen of, e.g., an HIV-infection and/or a disease associated with an HIV-infection, optionally with further active ingredients to this end.

Equally envisaged is a pharmaceutical composition comprising one or more of the inhibitors or salts or solvates or functional derivatives thereof designed or identified according to the methods described herein above.

The pharmaceutical composition may further comprise pharmaceutically excipients. Pharmaceutically acceptable excipients that may be used in the formulation of the pharmaceutical compositions may comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintegrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins. Other suitable pharmaceutically acceptable excipients are described in Remington's Pharmaceutical Sciences, 15th Ed., Mack Publishing Co., New Jersey (1991). Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in the pancreas or into a brain artery or directly into brain tissue. The compositions may also be administered directly to the target site, e.g., by biolistic delivery to an external or internal target site, like the pancreas or brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, individual response of the patient to be treated, severity of the disease to be treated, the activity and bioavailability of the particular compound applied and other drugs being administered concurrently. Pharmaceutically active matter may be present in amounts between 1 ng and 10 mg/kg body weight per dose; however, doses below or above this exemplary range are envisioned, especially considering the aforementioned factors. If the regimen is a continuous infusion, it is preferably in the range of 1 μg to 10 mg units per kilogram of body weight per minute.

The pharmaceutical compositions of the invention can be produced in a manner known per se to the skilled person or as described, for example, in Remington's Pharmaceutical Sciences, 15th Ed., Mack Publishing Co., New Jersey (1991).

A further embodiment of the invention relates to a compound selected from the formula (1) or (2) as defined herein above or salts or solvates or functional derivatives thereof or a compound as defined herein above for use in preventing or treating a HIV-infection and/or a disease associated with a HIV-infection.

As used herein, the term "HIV-infection" generally encompasses infection of a host, particularly a human host, by the human immunodeficiency virus (HIV) family of retroviruses including, but not limited to, HIV-1, HIV-2 (previously also known as HTLV-III/LAV/ARV, LAV-1, LAV-2). "HIV" can be used herein to refer to any strains, forms, subtypes, classes and variations in the HIV family. Thus, "treatment" of a HIV-infection and/or a disease associated with a HIV-infection will encompass the treatment of a person who is a carrier of any of the HIV family of retroviruses or a person who is diagnosed of active AIDS, as well as the treatment or prophylaxis of AIDS-related conditions in such persons. AIDS is also an example of a disease associated with an HIV-infection. The skilled person is well-aware of the pathology of AIDS including initiation, progression and clinical outcomes. A carrier of HIV may be identified by any method known in the art. For example, a person can be identified as an HIV carrier on the basis that the person is anti-HIV antibody positive, or is HIV-positive, or has symptoms of AIDS. That is, "treating HIV-infection" should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating CD4 positive T cells), and AIDS (which is defined by more serious AIDS-defining illnesses and/or a decline in the circulating CD4 cell count to below a level that is compatible with effective immune function). In addition, "preventing or treating of a disease associated with an HIV-infection" will also encompass treating suspected infection by HIV after suspected past exposure to HIV by e.g., contact with HIV-contaminated blood, as a result of blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "preventing" also encompasses treating a person who has not been diagnosed as having a HIV infection but is believed to be at risk of infection by HIV. Diseases associated with an HIV-infection can generally be treated by eradicating the primary cause thereof, optionally in conjunction with medicaments known in the art that are registered for the treatment of such secondary causes.

The skilled person is well-aware of the pathology of a HIV-infection and diseases associated with a HIV-infection and hence is in the position to devise a therapy according to general principles known in the art and described, for example, elsewhere herein.

The impact of a drug that inhibits new infection of $CD4^+$ cells will lead to a recuperation of said cell population and hence restore the patient's immune system, i.e. treat AIDS or prevent the outbreak of AIDS. The same is, of course, also true for a HIV infection that has not yet resulted in AIDS. As mentioned, said recuperation of the $CD4^+$ cell population has a beneficial effect also on the fight against secondary infections like, e.g., recurring viral infections and bacterial infections, that characterize the medical condition AIDS and are mostly responsible for the death of AIDS patients. The same applies to other embodiments relating to HIV infection and HIV-associated diseases in this specification. The usefulness to inhibit gp120 to CD4 binding has been described and discussed herein above. In particular, Example 2 demonstrates the potent effect of compounds that act as inhibitors of the binding of gp120 to CD4 in accordance with the invention. Equally envisaged is an inhibitor or salts or solvates or functional derivatives thereof designed or identified according to the methods described herein above for use in preventing or treating a HIV-infection and/or a disease associated with a HIV-infection.

Examples 2 and 3 provide proof of the in vitro activity of said exemplary compounds of formula (1) and (2) as defined herein above of the invention in the inhibition of viral entry and thereby of HIV replication. As shown in FIGS. 34A and 34B and FIGS. 35A to 35D said compounds interact with motifs in the tunnel.

Accordingly, the invention also relates in an embodiment to a method of preventing or treating a HIV-infection and/or a disease associated with a HIV-infection by administering an effective dose of a compound selected from the formula (1) and/or (2) or inhibitors designed or identified according to the methods described herein above or salts or solvates or functional derivatives thereof to a patient in need thereof.

The figures show:

FIG. 1: Overlap of the residue sets of binding site I and binding site II.

Figure 2:
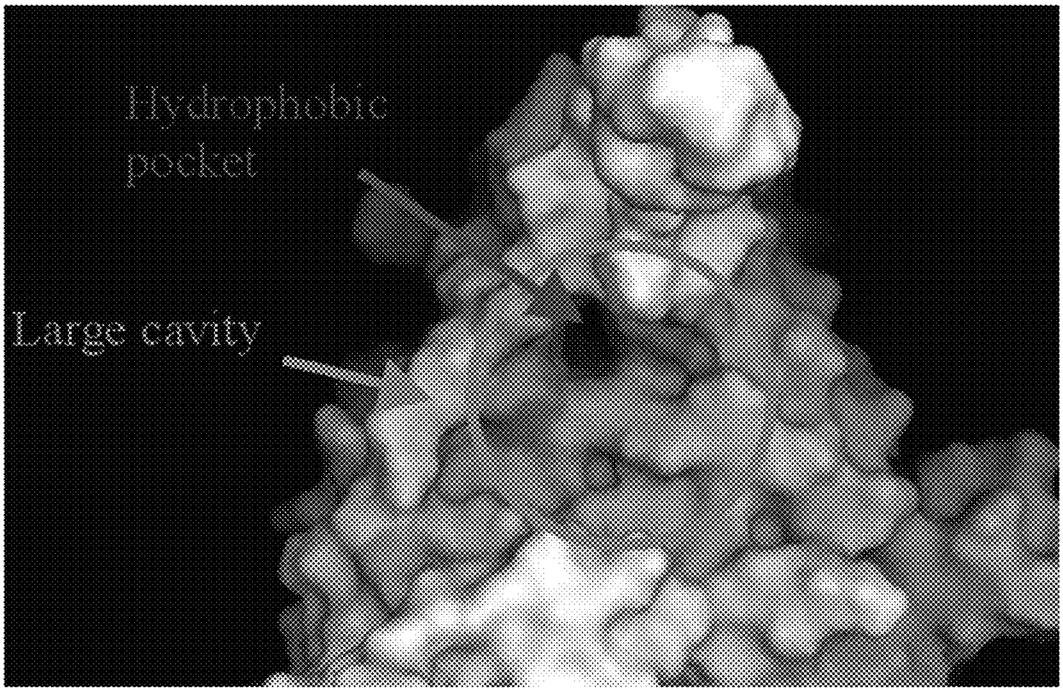
Figure 3:
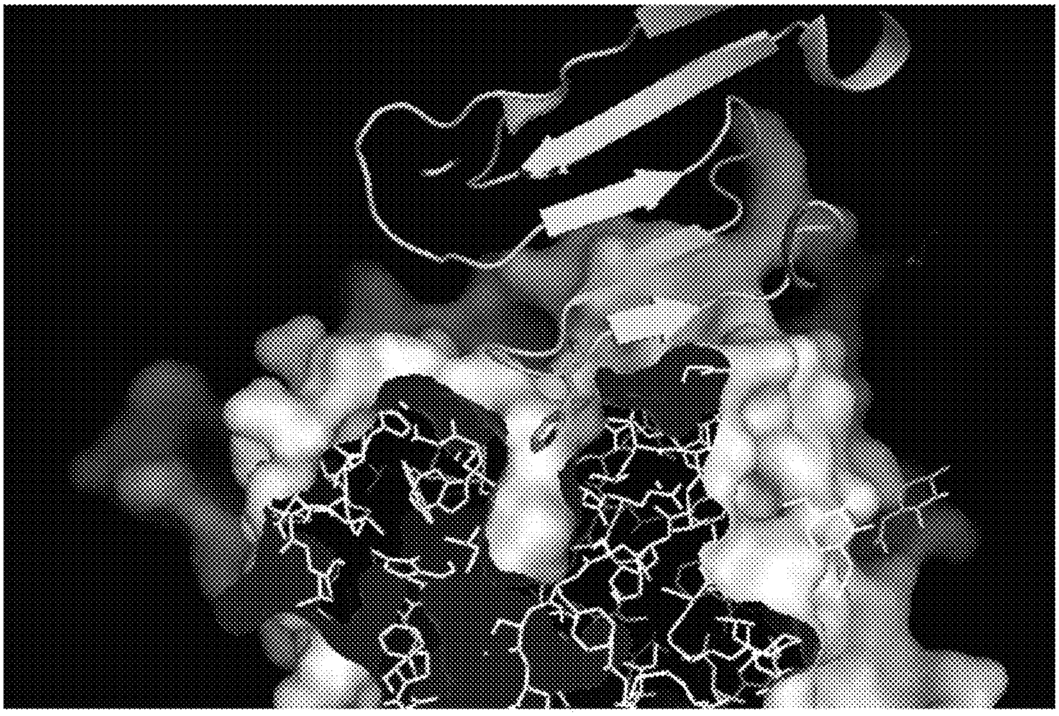

FIG. 2: Residues of binding site I are located in a large cavity.

FIG. 3: PHE43 binding pocket. CD4 is depicted as a ribbon model with the PHE43 residue differently designed reaching into the pocket.

FIG. 4: The tunnel connecting the two binding sites I and II. The figure shows that binding site I and binding site II are the two sides of a further active site buried within gp120.

Figure 5A:
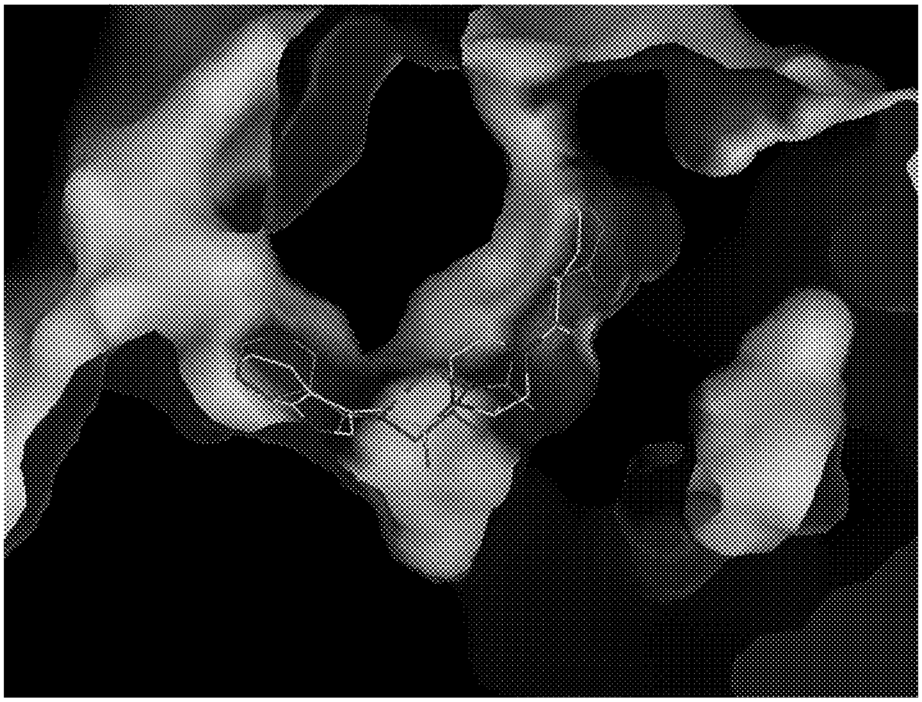
Figure 5B:
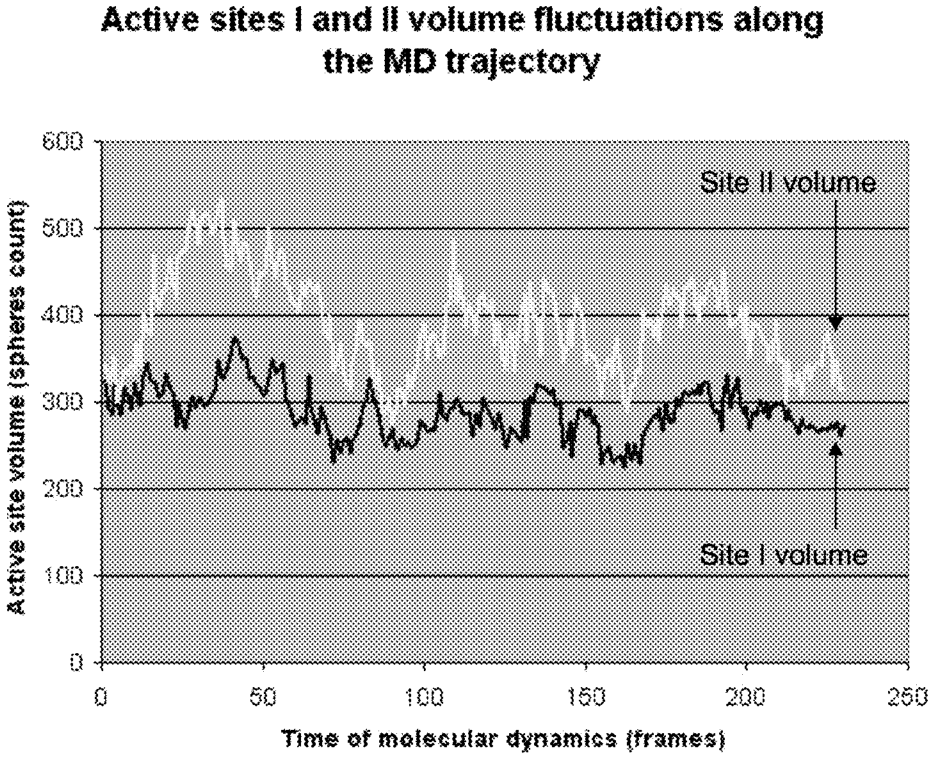

FIG. 5A: This figure represents the cut-in view inside the gp120 protein of the tunnel connecting the binding sites I and II with a model ligand resting in the tunnel. FIG. 5B: Active sites I and II volume fluctuations along the MD trajectory. To calculate the active site volume the active site was filled by spheres generated by Ligand module of QUANTUM software and calculated the number of spheres in each protein conformation (frame) The volume of Site I is indicated by the lower line and the volume of Site II is indicated by the upper line (both are labeled).

Figure 6:
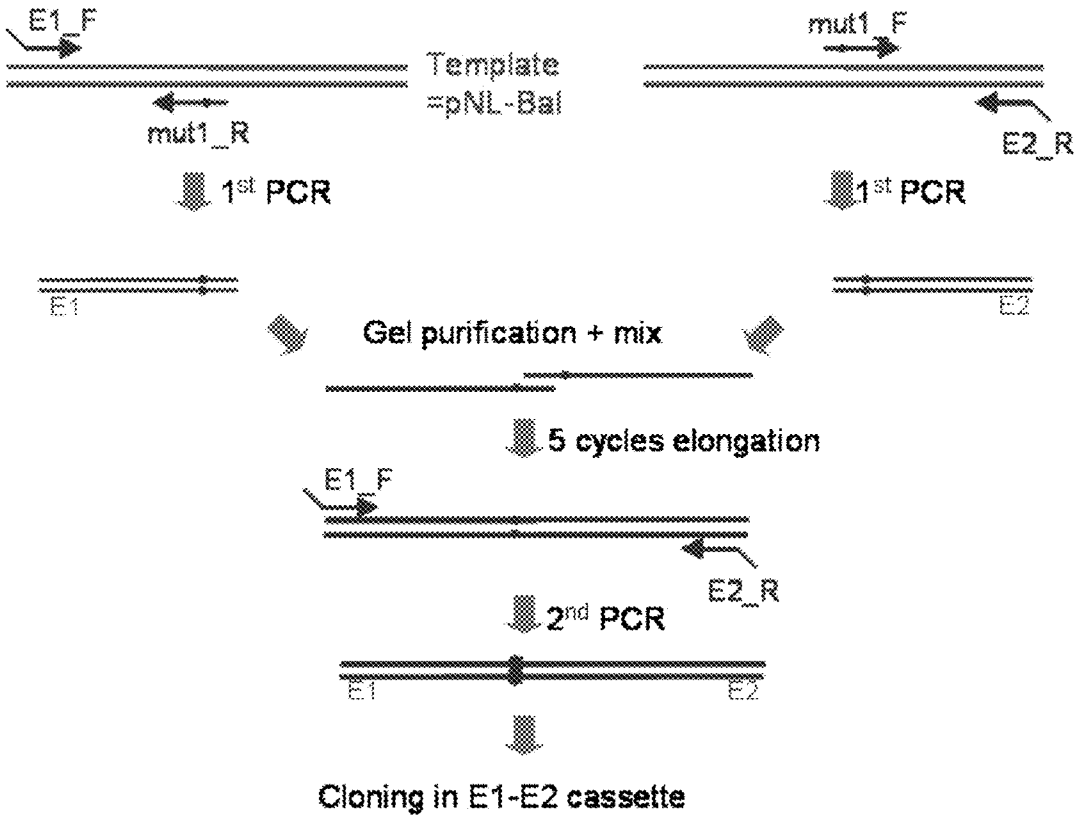

FIG. 6: Overlapping-PCR strategy utilized for generating each one of the two mutants of example 2.

Figure 7:
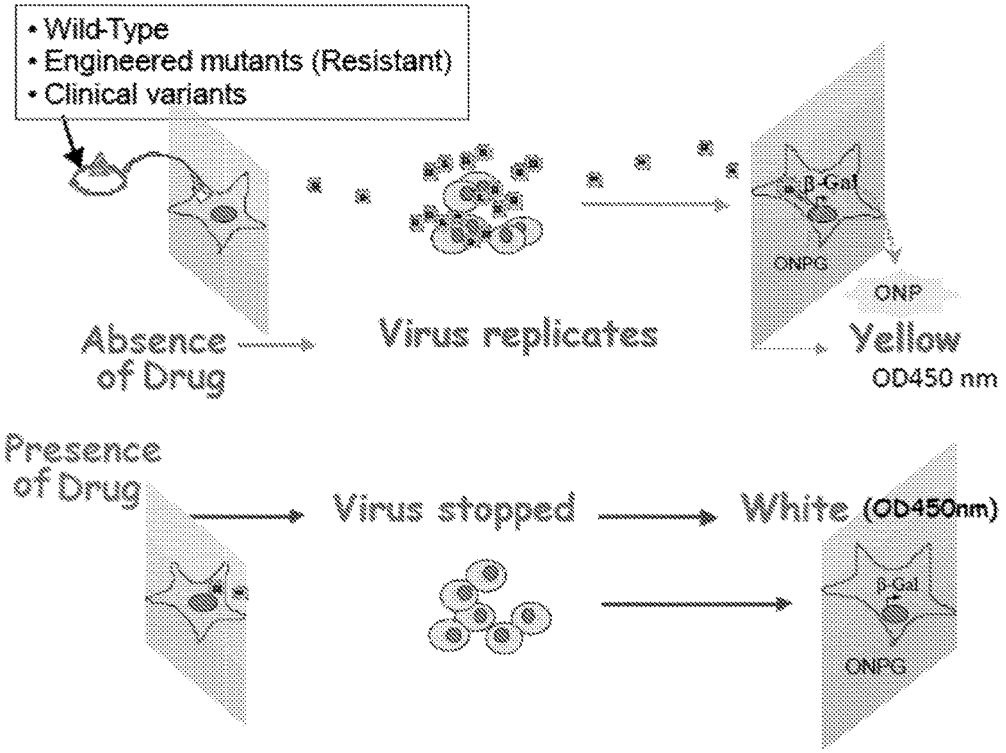

FIG. 7: Principle of dual-enhancement of Cell-infection for Phenotyping resistance (deCIPhR) as used in example 2.

Figure 8:
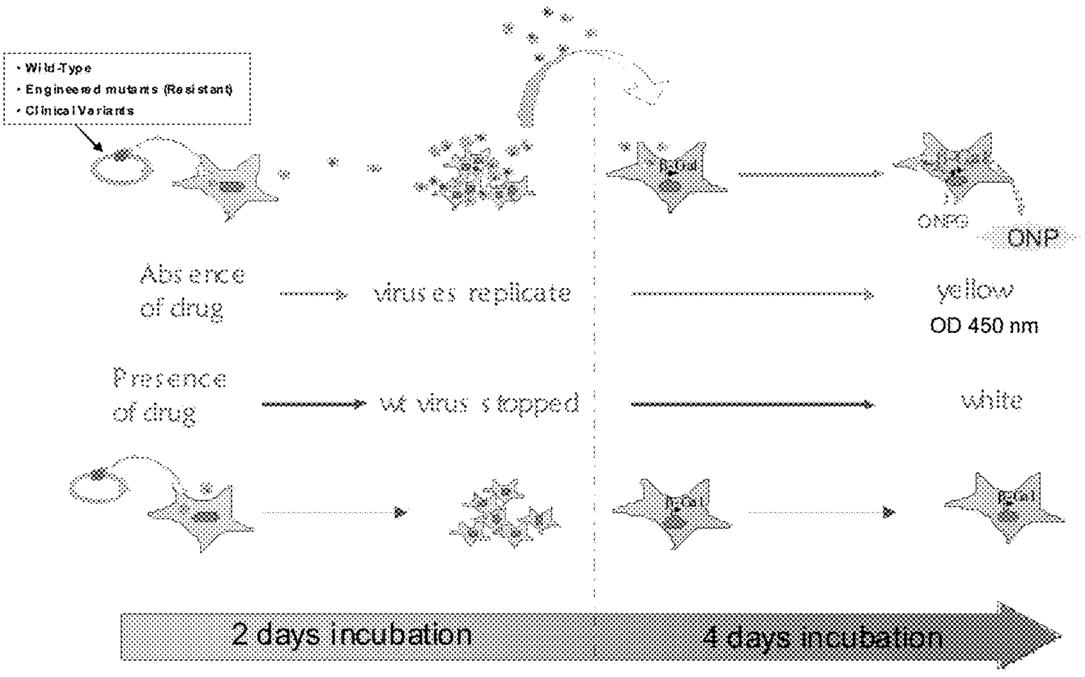

FIG. 8: Principle of a Virus to Cell-infection system as used, e.g., in example 2.

Figure 9:
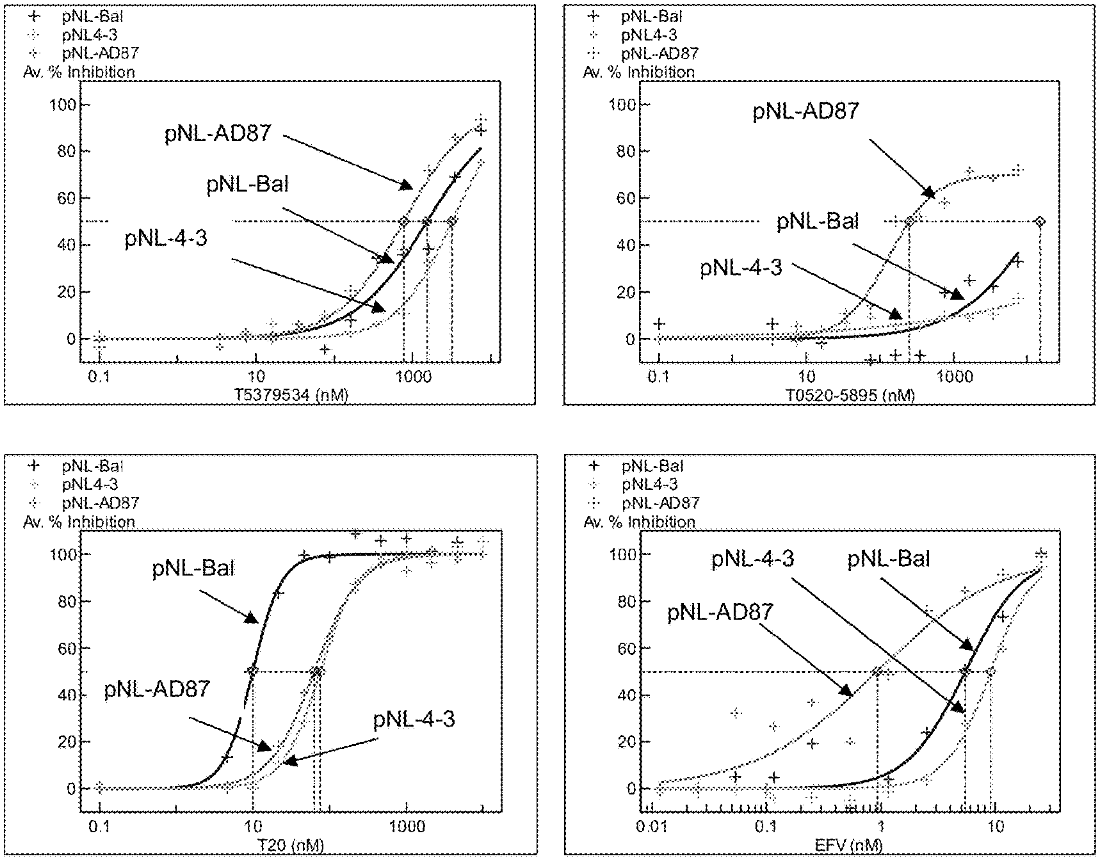

FIG. 9: Complete dose-response curves for T5379534 and T0520-5895 and references T20 and EFV on pNL4-3, pNL-Bal and pNL-AD87 HIV-1 viruses. Percentage inhibition of viral replication (average of triplicate) are plotted as a function of compound concentration (log scale). Each curve is identified by an arrow. Tables below graphs report observed values and calculated inhibition parameters (see paragraph 4 of example 2). Error bars are omitted for clarity.

Figure 10:
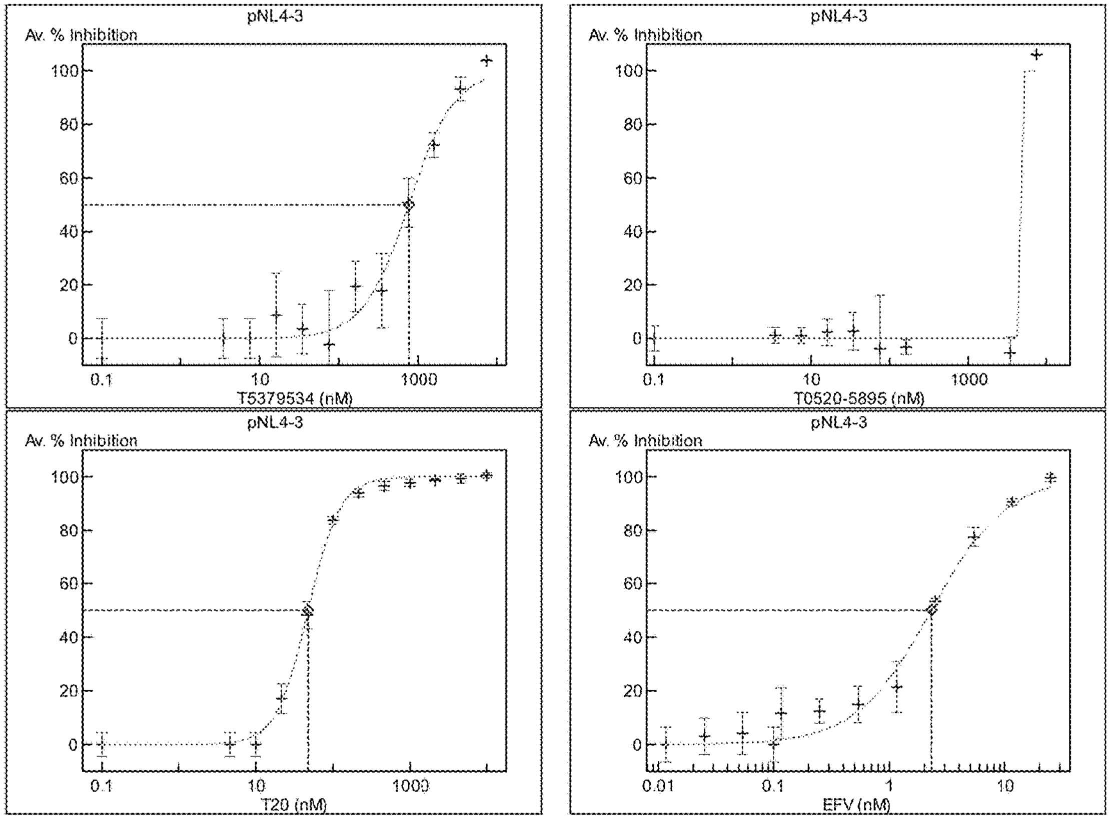

FIG. 10: Complete dose-response curves for T5379534 and T0520-5895 and references T20 and EFV on pNL4-3 HIV-1 virus in virus-to-cell infection format. Percentage inhibition of viral replication (average of triplicate) are plotted as a function of compound concentration (log scale). Tables below graphs report observed values and calculated inhibition parameters (see paragraph 4 of example 2). Error bars are omitted for clarity.

Figure 11:
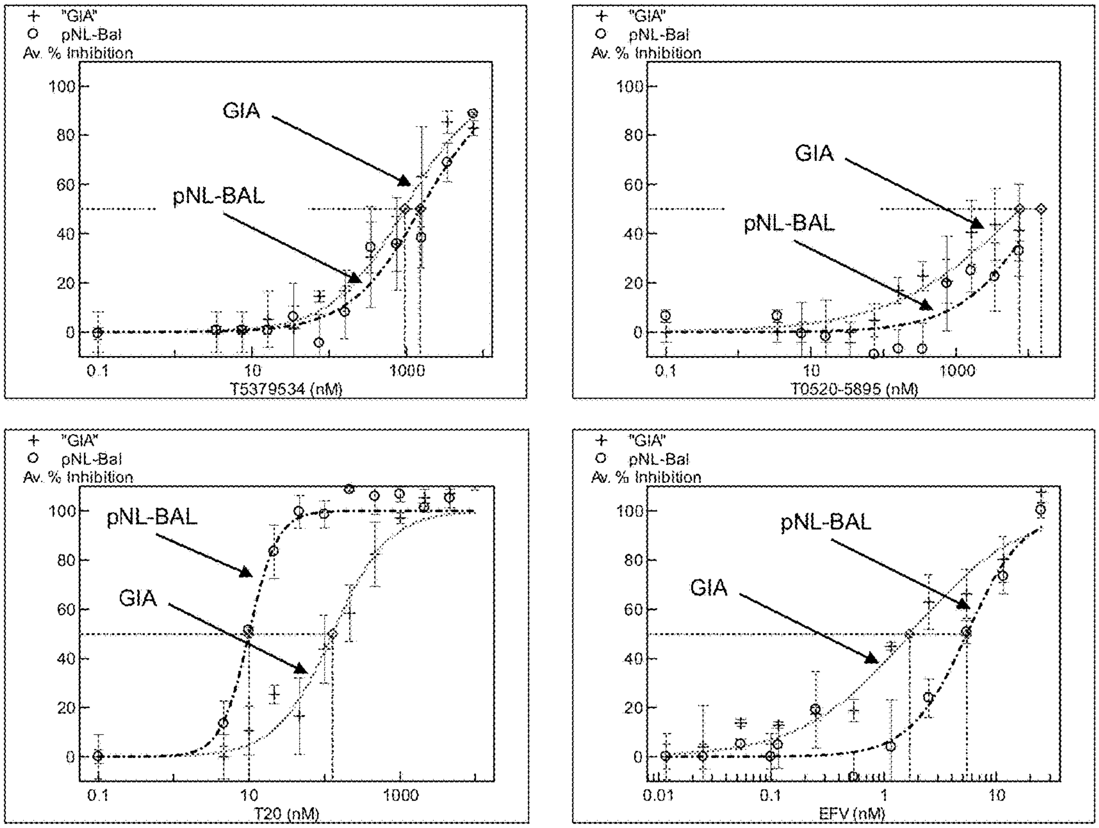

FIG. 11: Complete dose-response curves for T5379534 and T0520-5895 and references T20 and EFV on "G-I-A" mutant. Percentage inhibition of viral replication (average of triplicate) are plotted as a function of compound concentration (log scale). Tables below graphs report observed values and calculated inhibition parameters (see paragraph 4 of example 2).

Figure 12:
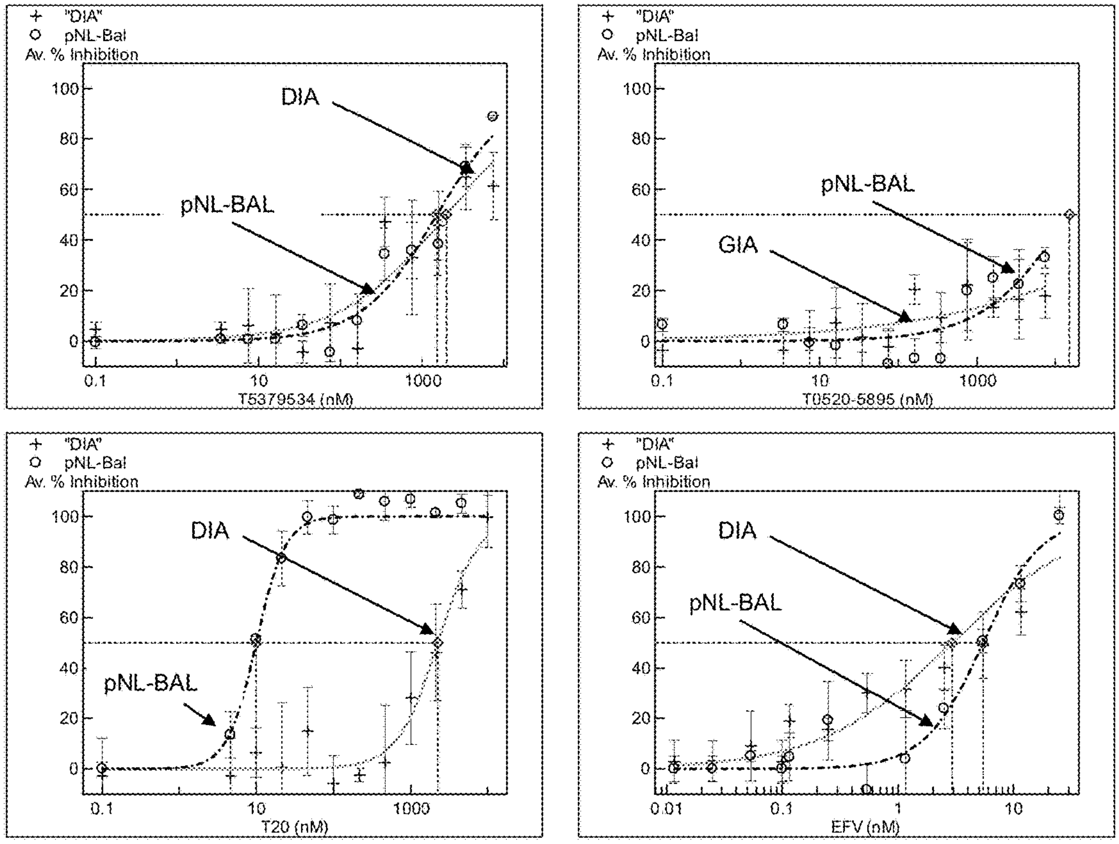

FIG. 12: Complete dose-response curves for T5379534 & T0520-5895 and references T20 and EFV on "D-I-A" mutant. Percentage inhibition of viral replication (average of triplicate) are plotted as a function of compound concentration (log scale). Tables below graphs report observed values and calculated inhibition parameters (see paragraph 4 of example 2).

Figure 13A:
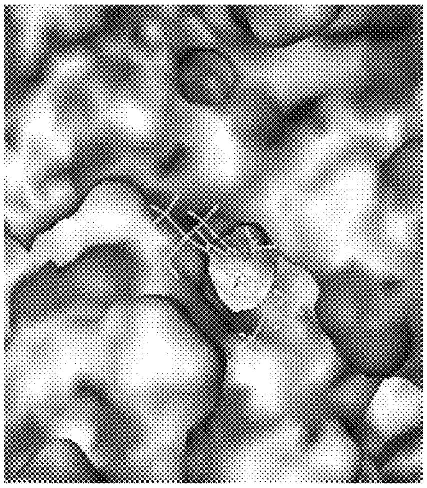
Figure 13B:
Figure 13C:
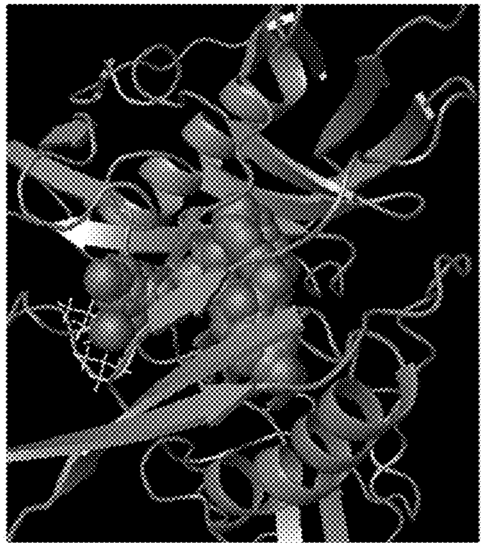
Figure 13D:
Figure 14A:
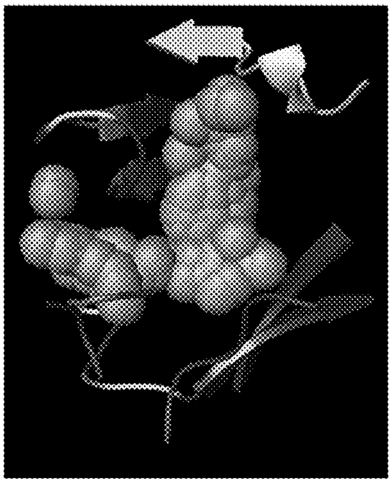
Figure 14B:
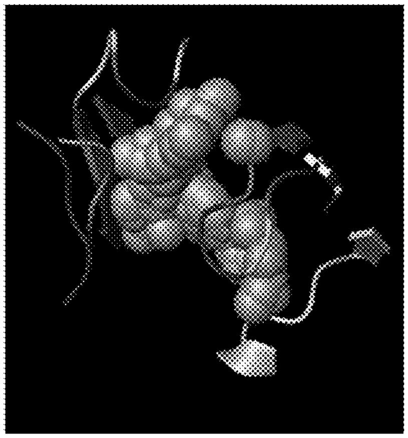
Figure 14C:
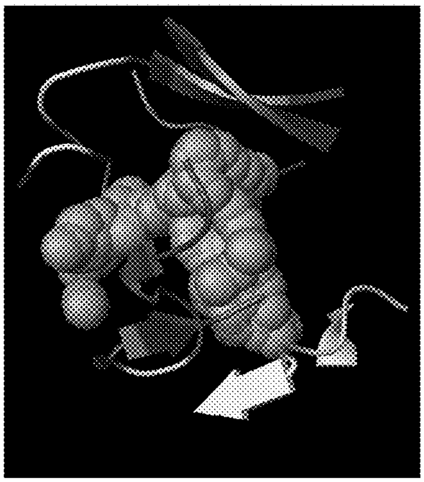
Figure 14D:
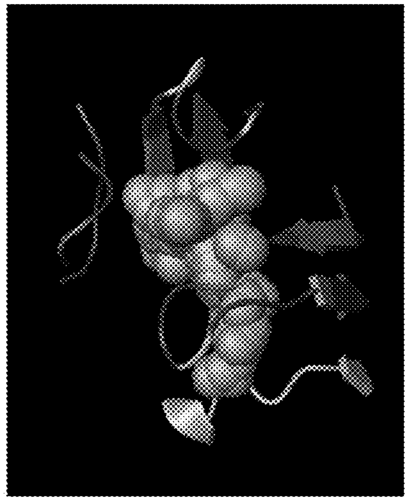
Figure 14:
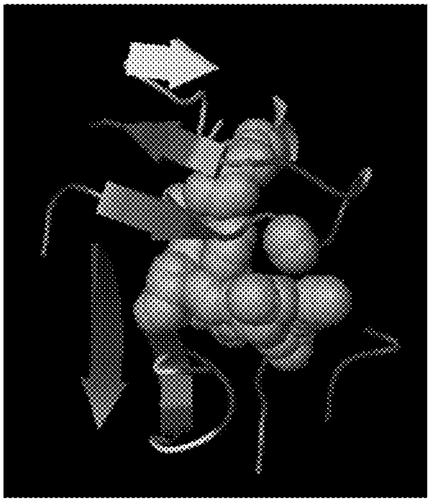
Figure 14F:
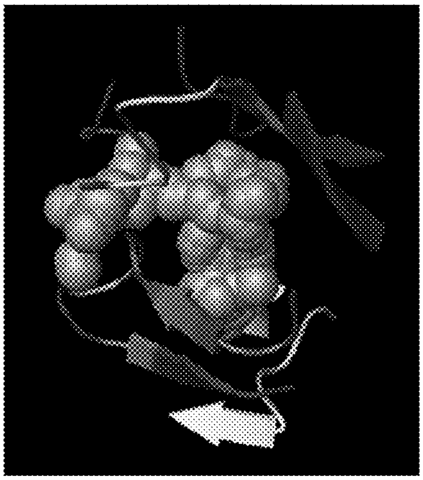

FIG. 13A to FIG. 13D: Structure of gp120 and location of the tunnel. FIG. 13A Model ligand placed in a tunnel gate. To the right of said tunnel gate is the other tunnel gate. FIG. 13B to FIG. 13D Alternate views of gp120 and the tunnel within gp120, wherein the model ligand in the tunnel.

FIG. 14A to FIG. 14F: Alternate views of the tunnel with the motifs 1, 2, 3 and 5 of the tunnel and the external motif.

Figure 15B:
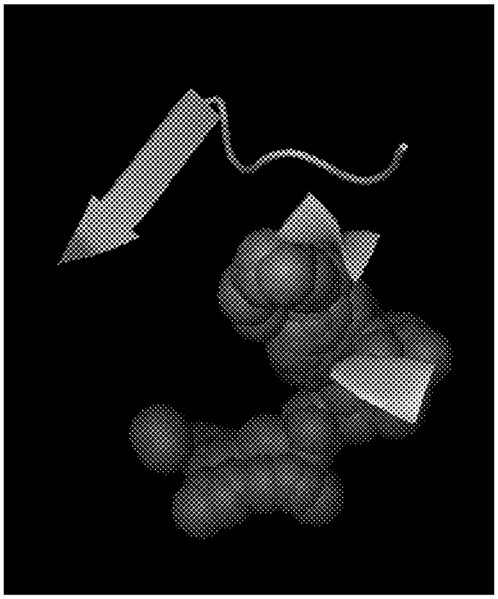
Figure 15A:
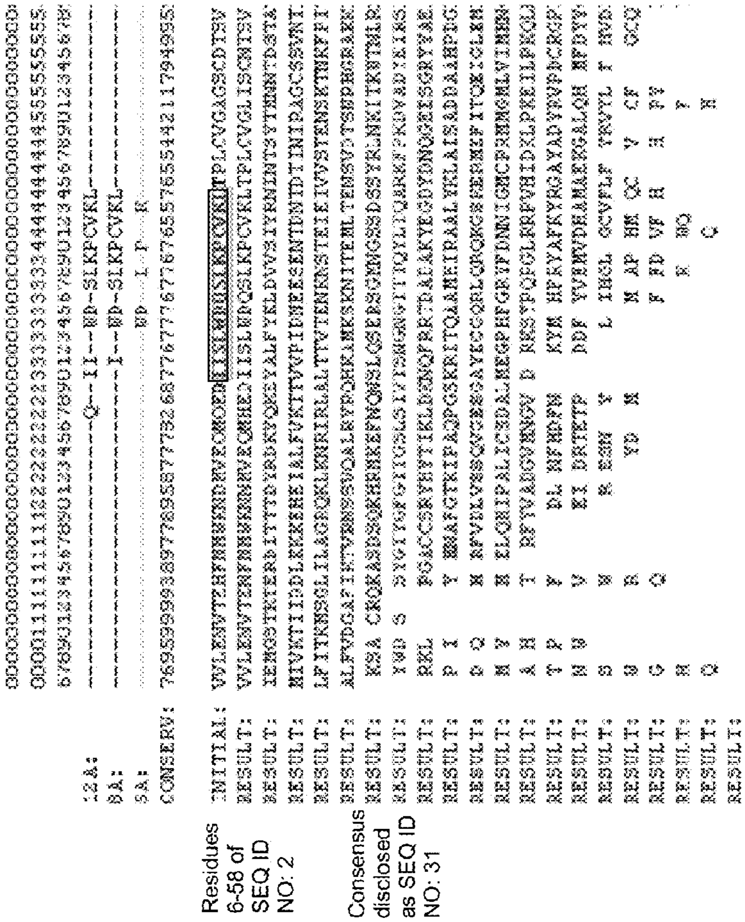

FIG. 15A and FIG. 15B: A Amino acid sequence of gp120 of HIV-1 (residues 6-58 of SEQ ID NO: 2) comprised in a first motif (Bold amino acid residues and sequence that is flanked by said bold residues). "Conserv" describes the conservation index of the amino acid at said position. A conservation index of 9 means that 90% to 99.99%, and index of 8 means that 80% to 89.99% (and so forth for an index of 7, 6, 5, 4, 3, 2, 1 or 0) of the HIV-1 variants have the amino acid residue specified in the sequence "initial" at this position in the motif, wherein "initial" is the amino acid sequence of the HIV-1 strain taken for analysis (SEQ ID NO: 2). The first line "Result" (from top to bottom) depicts the consensus sequence of all HIV-1 variants analysed (~80,000). The remaining "Result" lines show the likelihood of variant amino acids replacing the amino acids of the motif from top to bottom (top: most likely, bottom: least likely). The same holds true for FIG. 16A and FIG. 16B to FIG. 19A and FIG. 19B for HIV-1 and FIGS. 23 to 25 for HIV-2, mutatis mutandis. FIG. 15A discloses "SLKPCVKL" as residues 9-16 of SEQ ID NO: 3. B Model showing the tunnel in relation to the motif (ribbon model).

Figure 16B:
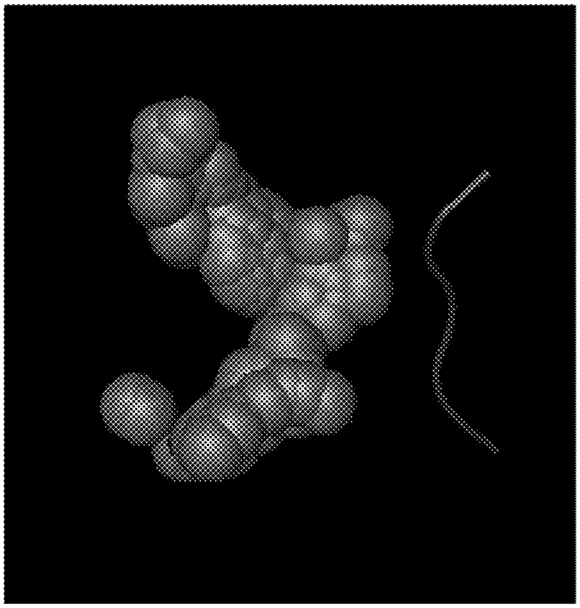
Figure 16A:
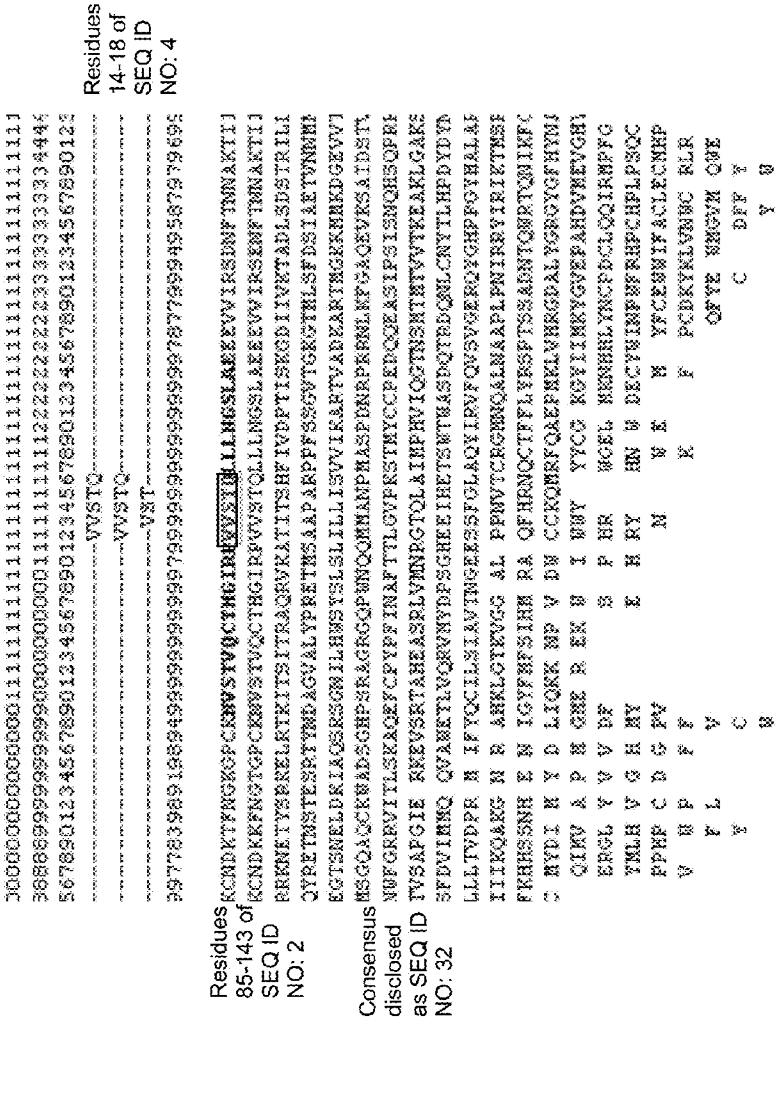

FIG. 16A and FIG. 16B: A Amino acid sequence of gp120 of HIV-1 (residues 85-143 of SEQ ID NO: 2) comprised in a second motif. FIG. 16A discloses "VVSTQ" as residues 14-18 of SEQ ID NO: 4. B Model showing the tunnel in relation to the motif (ribbon model).

Figure 17A:
Figure 17B:
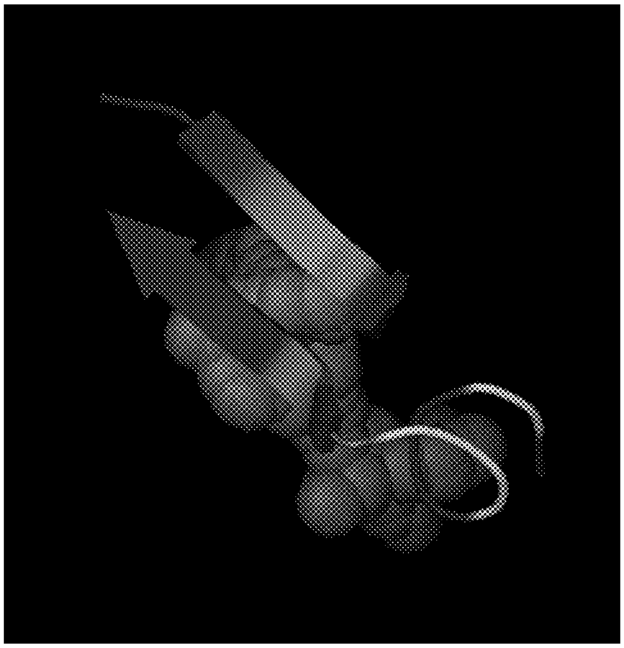

FIG. 17A and FIG. 17B: A Amino acid sequence of gp120 of HIV-1 (residues 205-262 of SEQ ID NO: 2) comprised in a third motif. FIG. 17A discloses "DPEIVMHSFNC" as residues 4-14 of SEQ ID NO: 5, "GEFFYC" as residues 16-21 of SEQ ID NO: 5 and "EFFYC" as residues 17-21 of SEQ ID NO: 5. B Model showing the tunnel in relation to the motif (ribbon model).

Figure 18A:
Figure 18B:
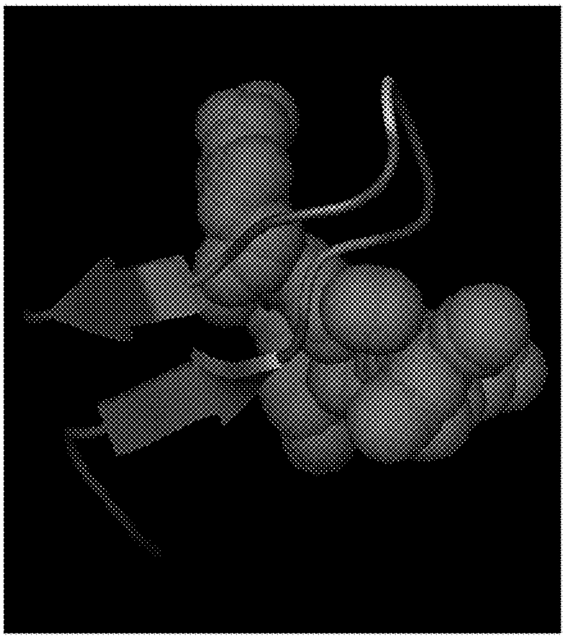

FIG. 18A and FIG. 18B: A Amino acid sequence of gp120 of HIV-1 (residues 252-312 of SEQ ID NO: 2) comprised in the external motif. FIG. 18A and FIG. 18B disclose "IKQIINMWQEVGKAMY" as residues 3-18 of SEQ ID NO: 8, "KQIINMWQEVGKAMY" as residues 4-18 of SEQ ID NO: 8 and "INMWQ" as residues 7-11 of SEQ ID NO: 8. B Model showing the tunnel in relation to the motif (ribbon model).

Figure 19A:
Figure 19B:
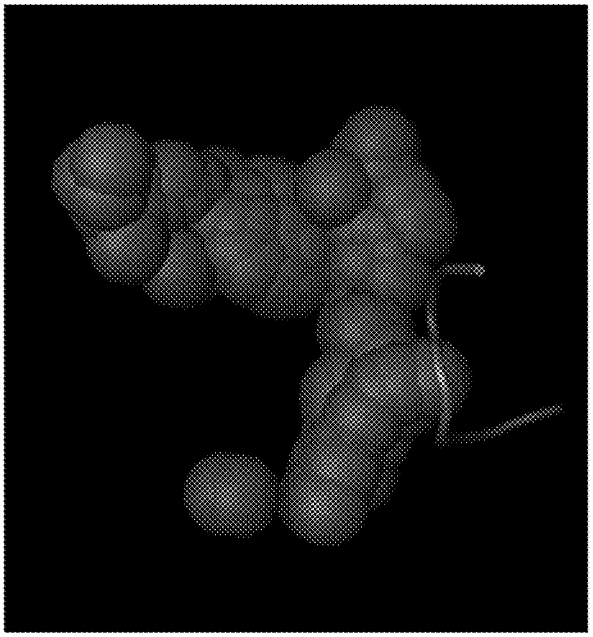

FIG. 19A and FIG. 19B: A Amino acid sequence of gp120 of HIV-1 (residues 296-344 of SEQ ID NO: 2) comprised in a fifth motif. FIG. 19A and FIG. 19B disclose "GGDMR" as residues 5-9 of SEQ ID NO: 7 and "GGDM" as residues 5-8 of SEQ ID NO: 7. B Model showing the tunnel in relation to the motif (ribbon model).

Figure 20:
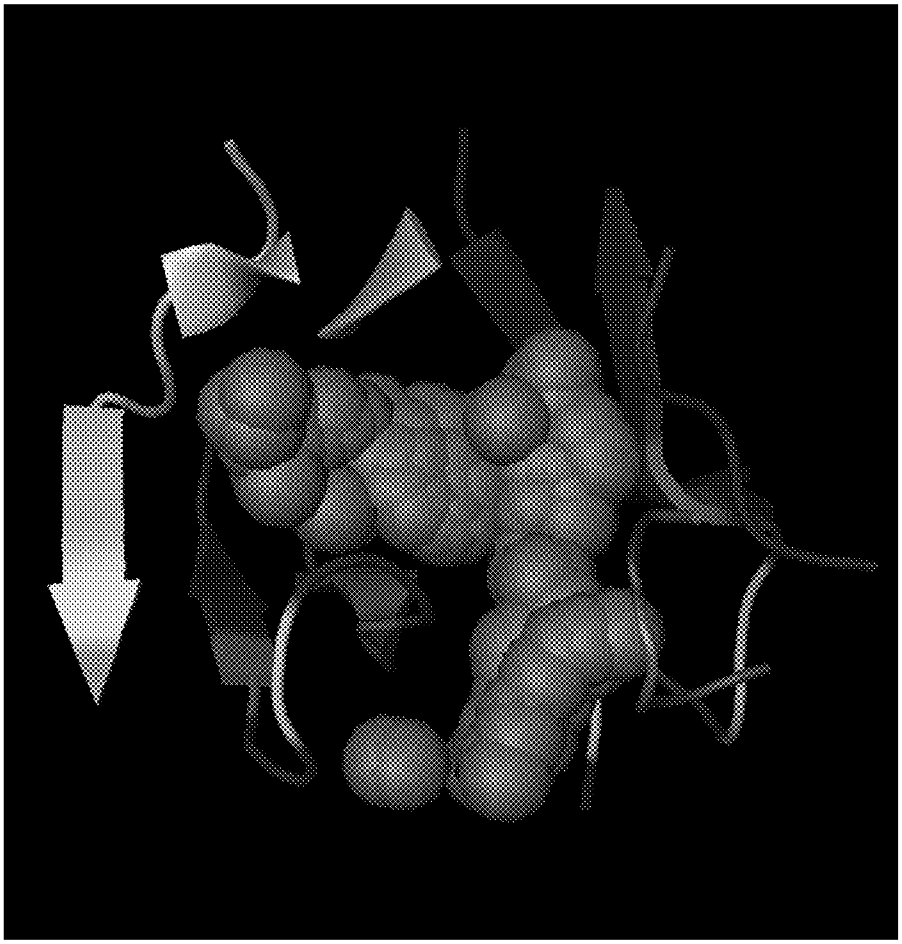

FIG. 20: Model of the tunnel within HIV-1 gp120 with motifs 1, 2, 3, 5 and the external motif as ribbon model.

Figure 21B:
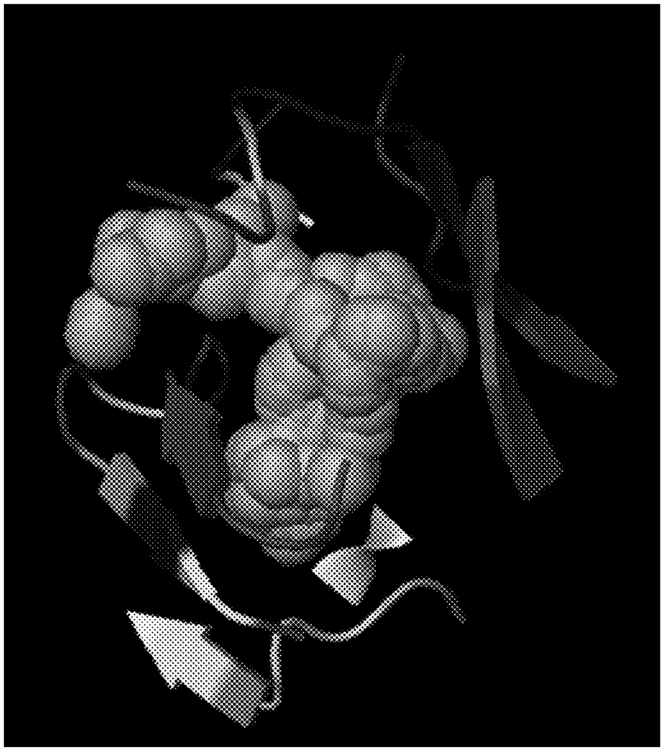
Figure 21A:

FIG. 21A and FIG. 21B: Alternate views of the tunnel and the motifs 1, 2, 3, 5 and the external motif making up the tunnel (ribbon model).

Figure 22A:
Figure 22B:
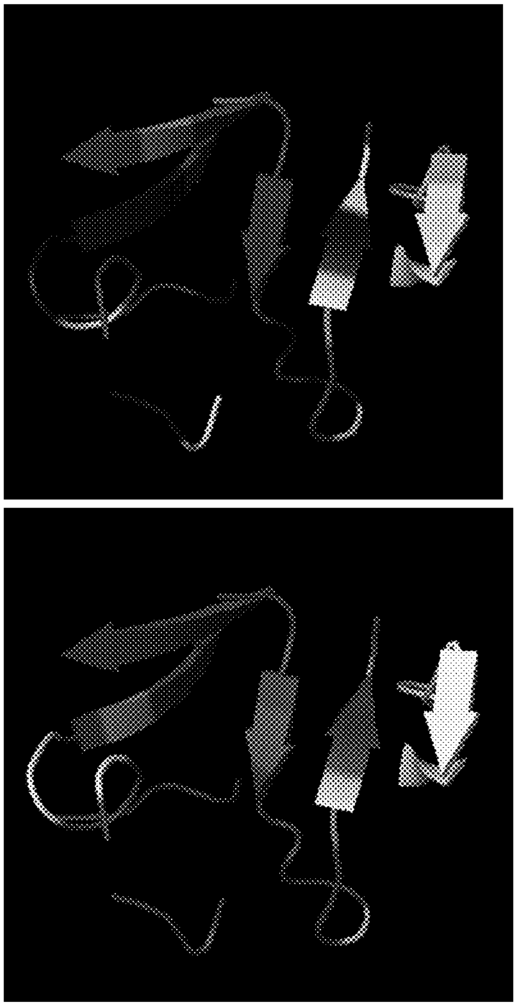

FIG. 22A and FIG. 22B: Comparison of motifs 1, 2, 3, and 5 forming the tunnel within gp120 and the external motif of HIV-1 (A: left picture) and HIV_2 (A: right picture). Alternate views of said comparison are shown in FIG. 22B (left picture motifs of HIV-1 and right picture motifs of HIV-2)

FIG. 23A and FIG. 23B: A Amino acid sequence of gp120 of HIV-2 (SEQ ID NO: 26) comprised in a first motif (for sequence of said motif see description herein above). FIG. 23 A discloses "SLKPCVKL" as residues 9-16 of SEQ ID NO: 9. B Amino acid sequence of gp120 of HIV-2 (SEQ ID NO: 27). comprised in a second motif (for sequence of said motif see description herein above). FIG. 23 B discloses "VVSTQ" as residues 14-18 of SEQ ID NO: 10.

FIG. 24A and FIG. 24 B: A Amino acid sequence of gp120 of HIV-2 (SEQ ID NO: 28) comprised in a third motif (for sequence of said motif see description herein above). FIG. 24A discloses "DPEIVMHSFNC" as residues 4-14 of SEQ ID NO: 11, "GEFFYC" as residues 16-21 of SEQ ID NO: 11 and residues "EFFYC" as residues 17-21 of SEQ ID NO: 11. B Amino acid sequence of gp120 of HIV-2 (SEQ ID NO: 29). comprised in the external motif (for sequence of said motif see description herein above). FIG. 24B discloses "IKQIINMWQEVGKAMY" as residues 3-18 of SEQ ID NO: 13, "KQIINMWQEVGKAMY" as residues 4-18 of SEQ ID NO: 13 and "INMWQ" as residues 7-11 of SEQ ID NO: 13.

FIG. 25: Amino acid sequence of gp120 of HIV-2 (SEQ ID NO: 30) comprised in a fifth motif (for sequence of said motif see description herein above). FIG. 25 discloses "GGDMR" as residues 5-9 of SEQ ID NO: 12 and "GGDM" as residues 5-8 of SEQ ID NO: 12.

FIG. 26A, FIG. 26B and FIG. 26C: Model of the tunnel structure in A and B, wherein in B the darker shaded, horizontal section may be termed Site 1 of the tunnel and includes external motif 4 and the lighter shaded horizontal section is termed Site 2 of the tunnel. C (Site 1) and D (Site 2) show models of the isolated sections of the tunnel and the adjacent external motif (for Site 1).

Figure 27A:
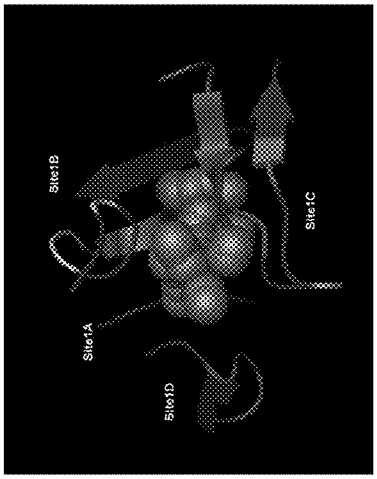
Figure 27B:
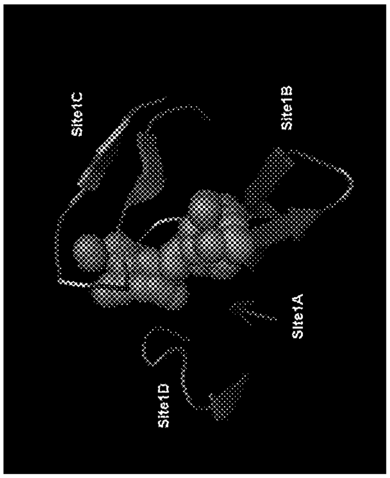
Figure 27C:
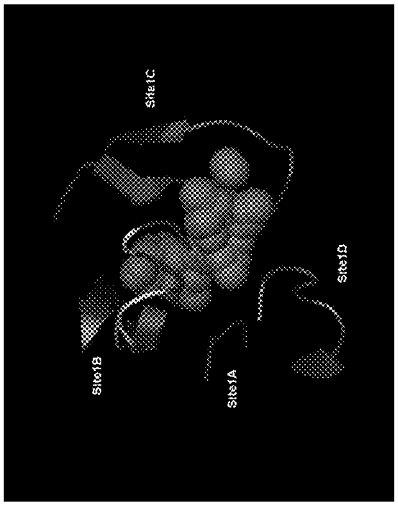

FIG. 27A, FIG. 27B and FIG. 27C: A Alternate views of Site 1 and resolution of those parts of said motifs 1, 2, 3 and 5 (partially making up the whole tunnel) and the external motif involved in forming Site 1.

Figures 28A, 28B:

FIG. 28A and FIG. 28B: A Amino acid sequence of Site 1A (residues 81-142 of SEQ ID NO: 2) (Bold amino acid residues (second motif) and sequence that is flanked by said bold residues). FIG. 28A discloses "VVSTQ" as residues 14-18 of SEQ ID NO: 4. B Amino acid sequence of Site 1B (residues 198-259 of SEQ ID NO: 2) (Bold amino acid residues (third motif) and sequence that is flanked by said bold residues). FIG. 28B discloses "GDPEIVMHSFN" as residues 3-13 of SEQ ID NO: 5 and "FFYC" as residues 18-21 of SEQ ID NO: 5.

Figure 29B:
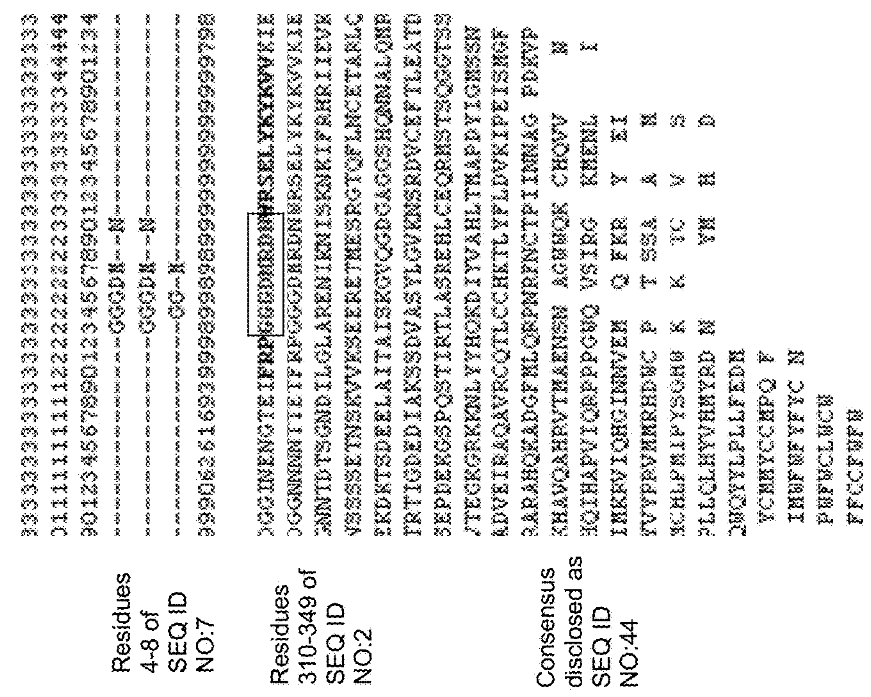
Figure 29A:
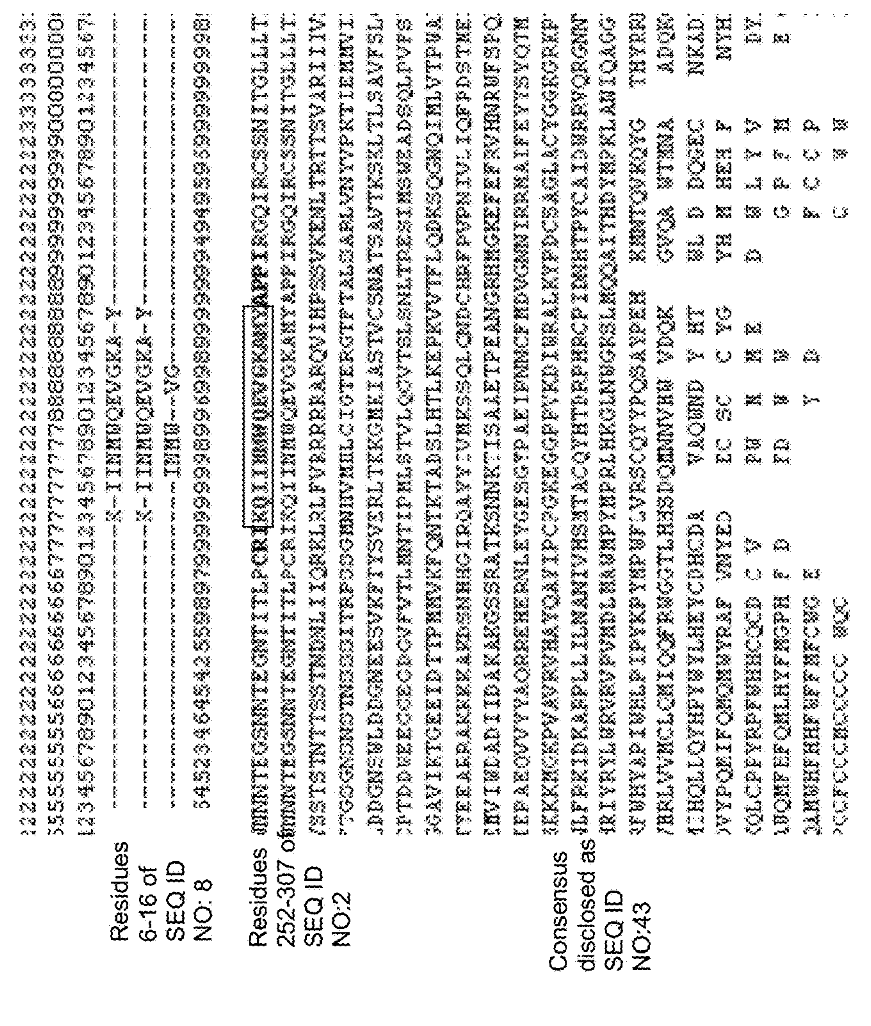

FIG. 29A: Amino acid sequence of Site 1C (residues 252-307 of SEQ ID NO: 2) (Bold amino acid residues (external motif) and sequence that is flanked by said bold residues). FIG. 29A discloses "IINMWQEVGKA" as residues 6-16 of SEQ ID NO: 8 and "INMW" as residues 7-10 of SEQ ID NO: 8. FIG. 29B: Amino acid sequence of Site 1D (residues 310-344 of SEQ ID NO: 8) (Bold amino acid residues (fifth motif) and sequence that is flanked by said bold residues). FIG. 29B discloses "GGGDM" as residues 4-8 of SEQ ID NO: 7.

Figure 30A:
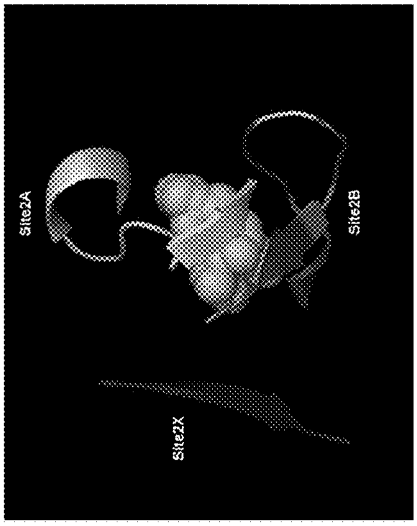
Figure 30B:
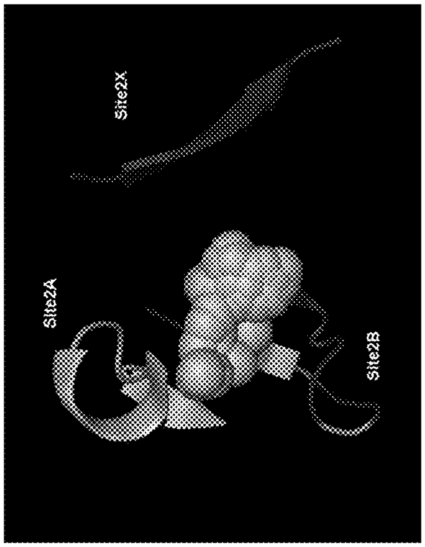
Figure 30C:
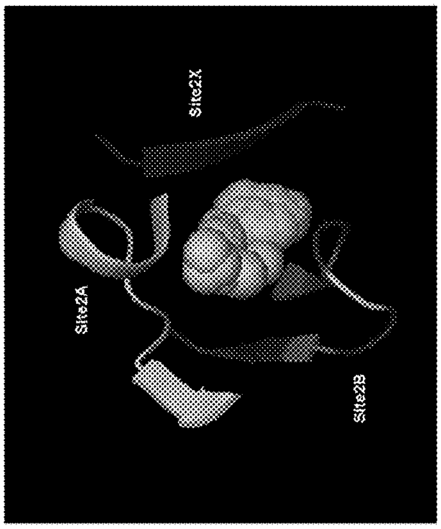

FIG. 30A, FIG. 30B and FIG. 30C: A Alternate views of Site 2 and resolution of those parts of said motifs 1, 2, 3 and 5 (partially making up the whole tunnel) and the external motif involved in forming Site 2.

FIG. 31A: Amino acid sequence of Site 2A (residues 6-74 of SEQ ID NO: 2) (Bold amino acid residues (first motif, partially) and sequence that is flanked by said bold residues). FIG. 31B: Amino acid sequence of Site 2B (residues 253-307 of SEQ ID NO: 2) (Bold amino acid residues (external motif) and sequence that is flanked by said bold residues). FIG. 31B discloses "INMWQ" as residues 7-11 of SEQ ID NO: 8.

Figure 32:

FIG. 32: Amino acid sequence of Site 2X (residues 213-263 of SEQ ID NO: 2) (Bold amino acid residues (third motif, partially) and sequence that is flanked by said bold residues).

Figure 33A:
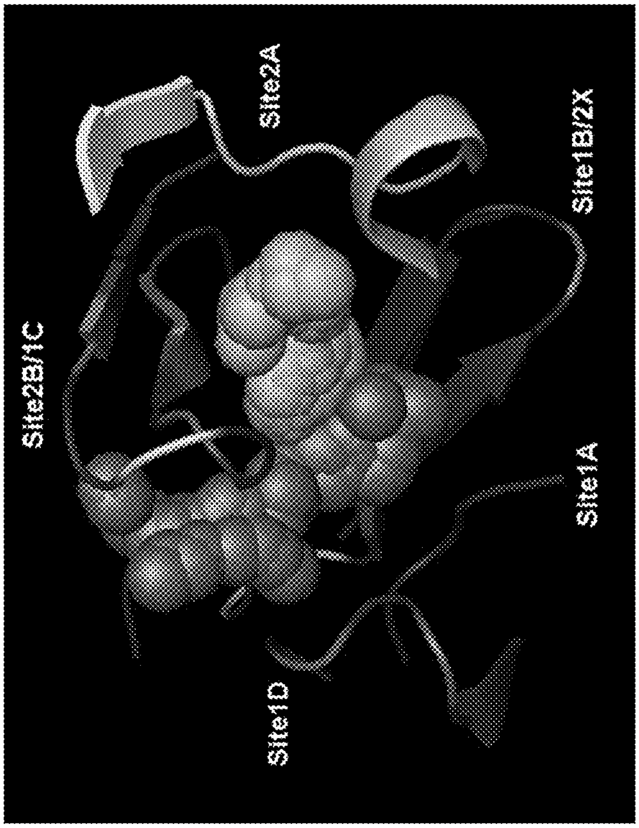
Figure 33B:
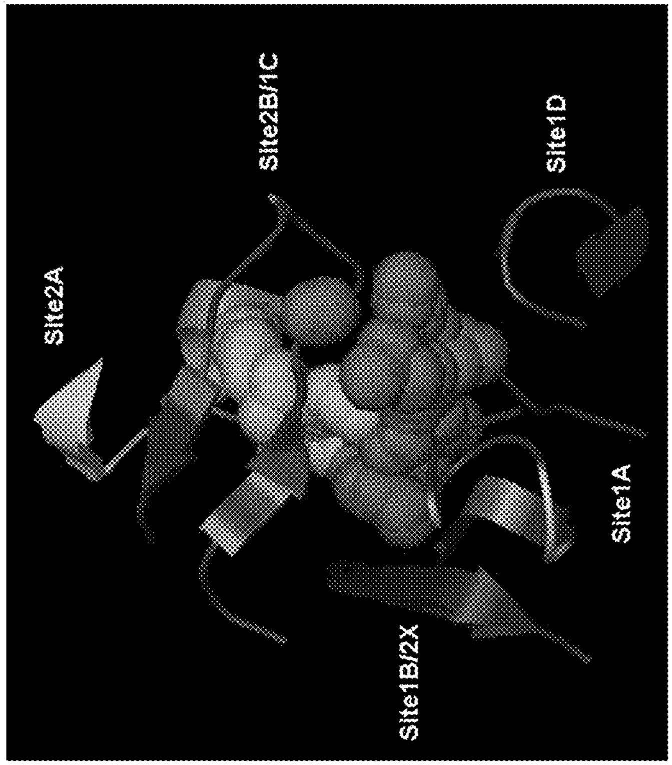

FIG. 33A and FIG. 33B: Alternate views of the relation of the parts 1A, B, C and D and 2A, B and X in making up motifs 1, 2, 3 and 5 that partially form the tunnel within HIV and the external motif.

Figure 34B:
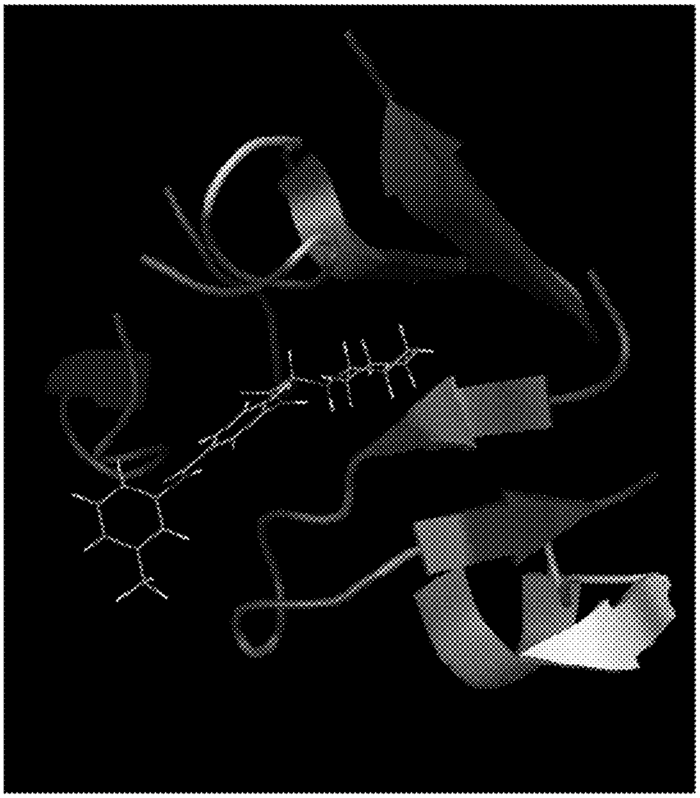
Figure 34A:
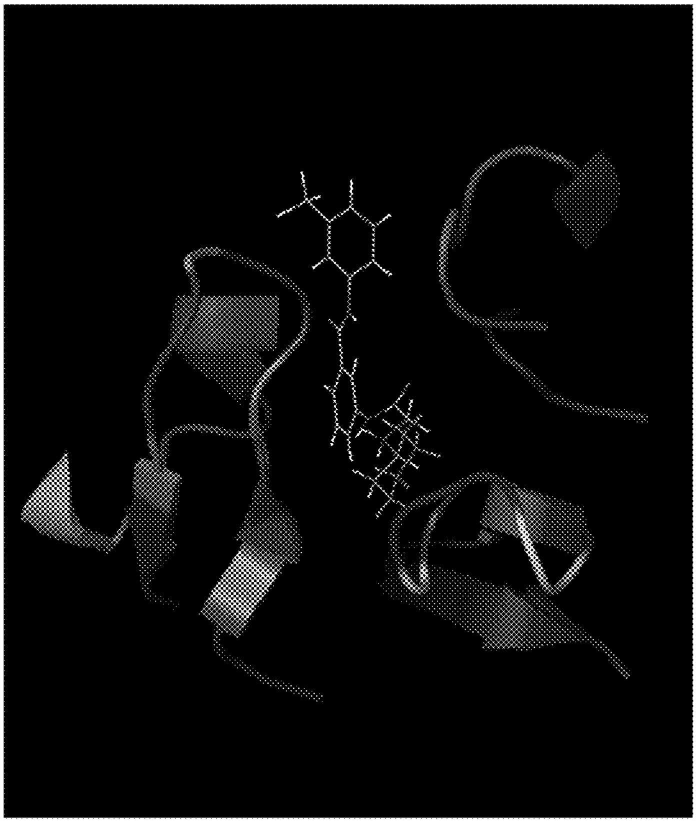

FIG. 34A and FIG. 34B: FIG. 34A Model of compound T0520-5895 interacting with the motifs 1, 2, 3, 5 and the external motif. FIG. 34B Alternate view of compound T0520-5895 interacting with the motifs 1, 2, 3, 5 and the external motif.

Figure 35B:
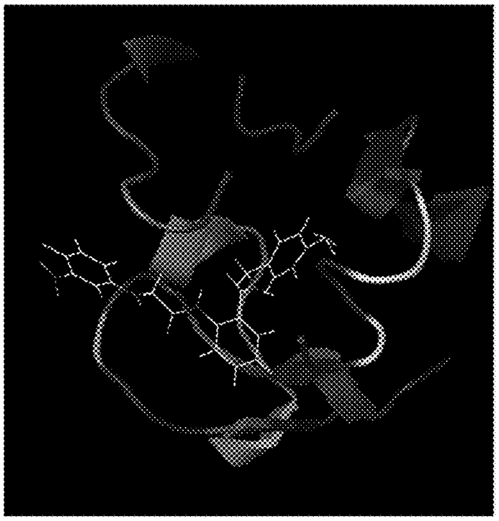
Figure 35D:
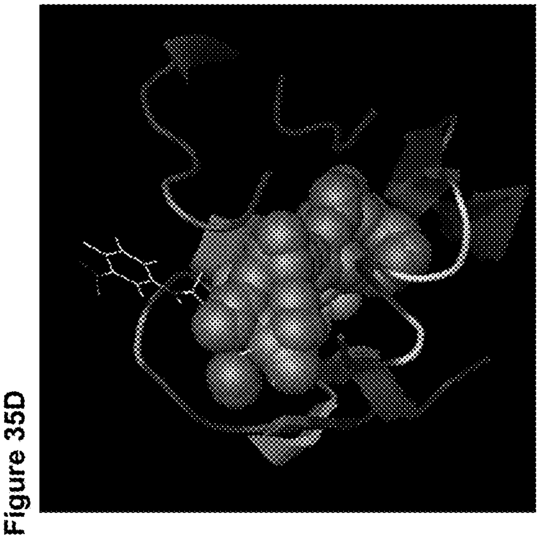
Figure 35A:
Figure 35C:
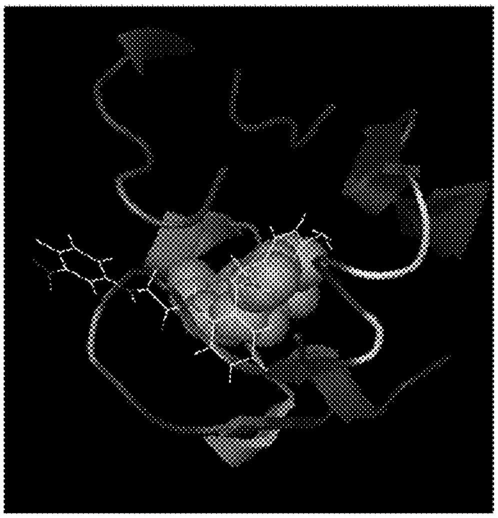

FIG. 35A to FIG. 35D: FIG. 35A Model of compound T5375934 interacting with the motifs 1, 2, 3, 5 and the external motif and alternate view (FIG. 35B). FIG. 35C Model of compound T0520-5895 interacting with the motifs 1, 2, 3, 5 and the external motif and its relation to Site 2. FIG. 35D Model of compound 70520-5895 interacting with the motifs 1, 2, 3, 5 and the external motif and its relation to Site 1 and 2.

Figure 36:
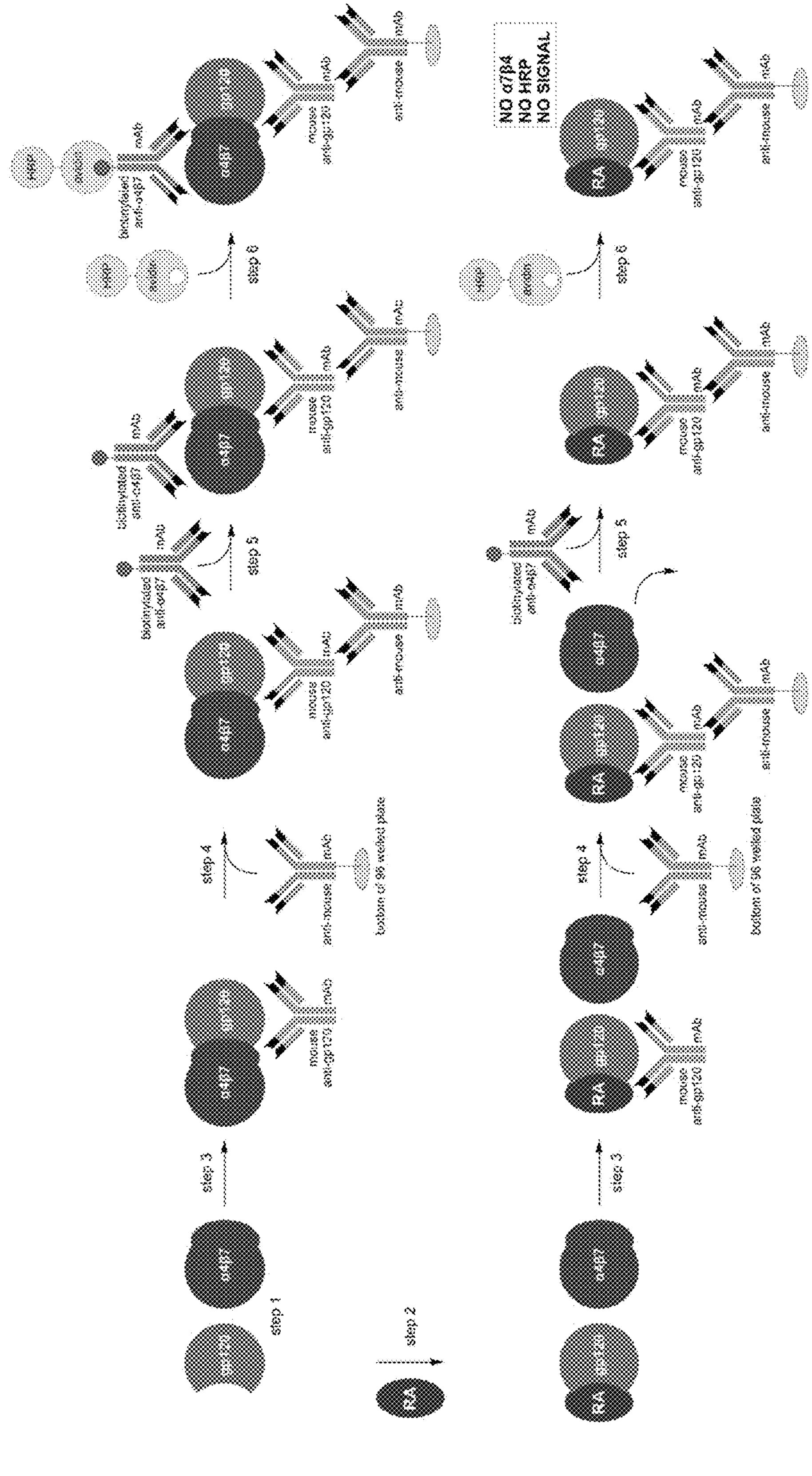

FIG. 36: ELISA Assay. A sandwich assay was developed to screen for compounds that inhibit the binding of a4b7 to gp120. Without inhibitors, gp120 and a4b7 bind and this complex can be identified by addition of a mouse anti-gp120 mAb (step 3). This a4b7.gp120.anti-gp120 mAb complex is then sequestered on the bottom surface of a 96 welled-plate coated with an anti-mouse secondary mAb (step 4). The complex is then detected by addition of a biotinylated primary mAb against a4b7 (step 5) and detected using an HRP-avidin (step 6). A positive binding event is identified by the presence of HPR activity within each well. The addition of an inhibitor (step 2) blocks the binding between gp120 and a4b7 leading to a lack or reduction of HRP activity as shown in steps 2-5 at the bottom of the figure.

Figure 37B:
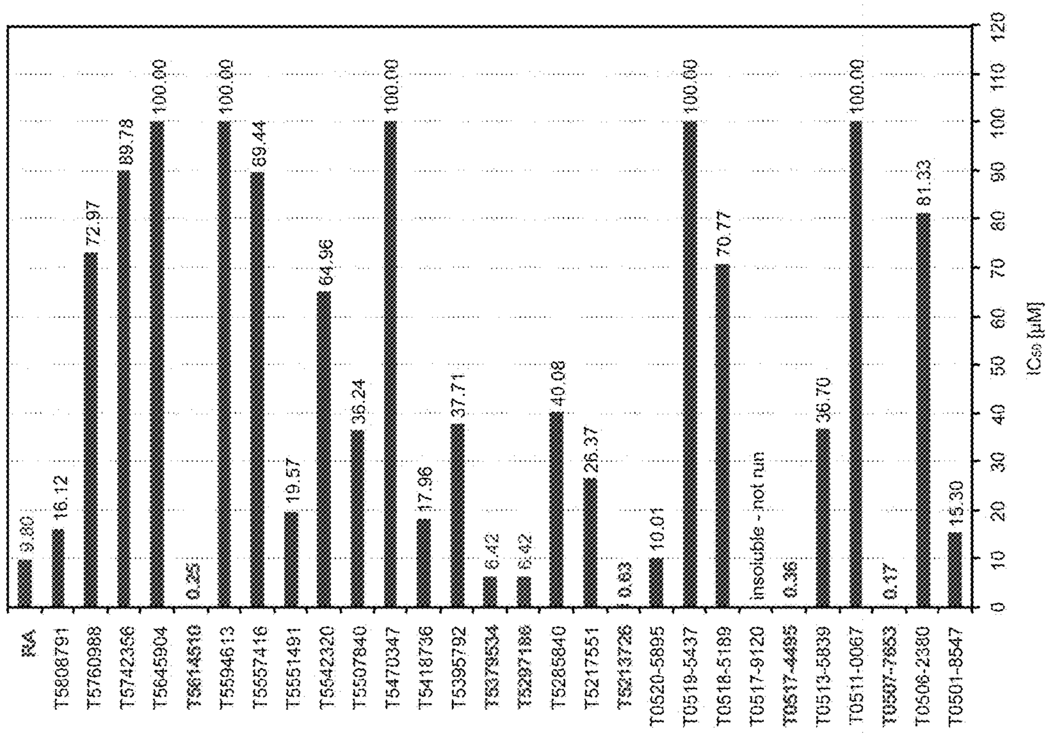
Figure 37A:
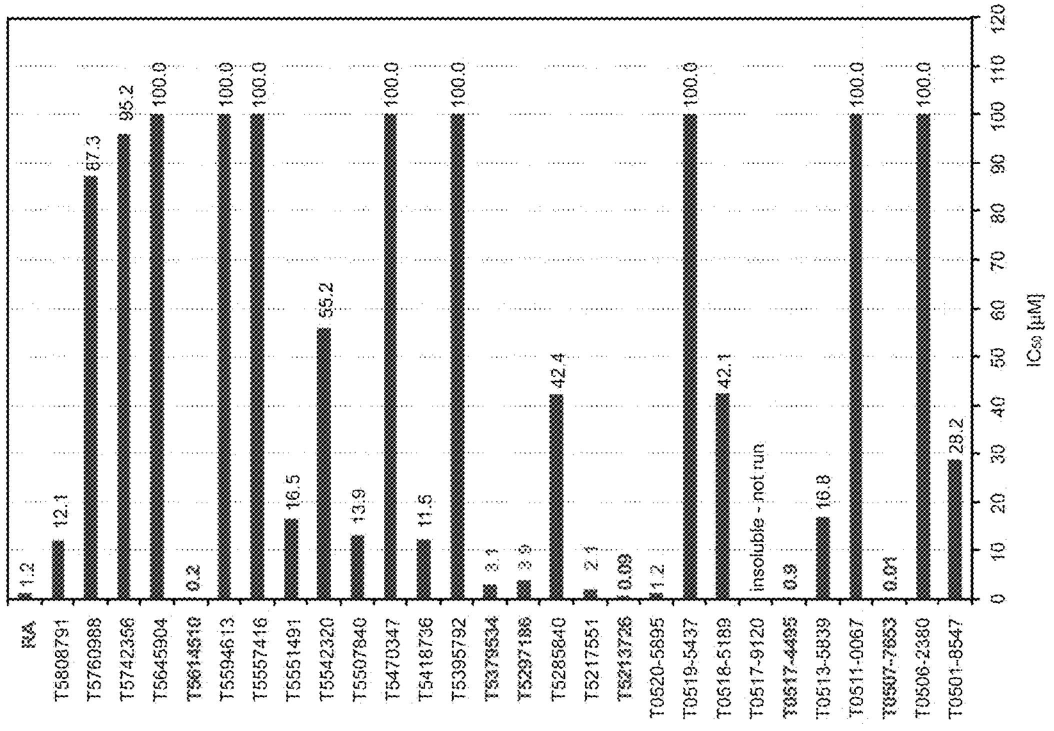

FIG. 37A and FIG. 37B: Activity of a panel of inhibitors in blocking the binding of gp120 to a4b7. (FIG. 37a) The left chart depicts data collected in example 3 using ELISA assay. (FIG. 37b) The right chart depicts data collected by screening cell extracts. Bold letters used for a compound denote active compounds. The remaining compounds are weak or non-inhibitors. All assays were repeated six times (three times for each anti-gp120 mAb used in the case of the ELISA data) and an average was presented. All values were obtained within 5% deviation.

The examples illustrate the invention:

EXAMPLE 1: BINDING SITE OF GP120. MODEL VALIDATION AND PHARMACOPHORE HYPOTHESIS

A 3D structure of gp120 protein interacting with CD4 is presented in FIG. 3 (1G9N from the Protein Data Bank (Wang et al., J. Med. Chem. 48(12):4111, 4119 (2005))). As can be seen, Phe43 of CD4 enters into hydrophobic pocket within gp120 structure. The pocket is naturally responsible for specific recognition of the Phe43 residue of CD4. The small size of the binding pocket is a significant obstacle for successful docking of potential ligands. Since the protein structure in the PDB Data Bank is only a single snapshot of the actual protein conformational space, docking of any reasonably large or flexible molecule may fail and the correct orientation of ligand in the binding site may not be found. In what follows we outline a docking strategy designed to overcome this difficulty.

Docking Procedure

Several 3D structures of gp120 protein from RSCB Protein Data Bank were selected for docking (1G9M, 1G9N, 2B4C and 1GC1). To obtain more protein conformations Molecular Dynamics simulation was performed starting from the 1G9M structure. The active sites volume in the protein conformations along the trajectory generated by the Molecular Dynamics was followed aiming to identify the conformations with largest binding pocket volume (see FIG. 5B).

Finally ~60 protein conformations, both taken from PDB Data Bank and those generated by Molecular Dynamics and corresponding to the largest volumes of the binding sites, were selected and prepared for docking. Such a large number of different protein conformations used in the docking study represents a reasonable portion of the protein conformational ensemble, rather than a single snapshot made available in a ray experiment. Docking of a specific ligand to a single protein structure may not succeed; however docking of the same small molecule to multiple conformations usually helps to identify the right binding mode. If a sufficiently large number of the protein conformations is used, the maximal value of the predicted binding affinity provides a good indication of the actual ligand activity. This approach has been proved to be useful in various docking studies.

All small gp120 inhibitors with known chemical structure and experimentally determined biological activity where included in the research. Both the proteins and small molecules typization, and in silico screening were carried out by the molecular processing and docking tools taken from the QUANTUM drug discovery software suite [QUANTUM]. The software predicts the binding affinities of small molecules to resolved protein targets using a set of principles based on molecular simulations with an advanced continuous water model (P. O. Fedichev and L. I. Men'shikov. Long-range order and interactions of macroscopic objects in polar liquids, 2006.). The approach provides the logarithmic values of the binding constant, pKd (−1gKd), with the accuracy of about one pKd unit.

Docking of the molecules was performed on refined gp120 protein structures. The docking box 12×18×20 covers all the residues important for ligand binding, see FIG. 1. After the docking all the ligand-protein complexes were sent to Molecular Dynamics calculations for refinement.

The Nature of the Binding Site

Molecular dynamics simulations provide an important insight into the nature of the gp120 protein ligand binding site. To visualize the consequences of the protein thermal motion the volume of the docking space associated with certain binding areas of Site 1 (residues 368, 370, 371, 427, 457, 357 of gp120) and of Site 2 (112, 113, 382, 426, 125, 429, 433, 475 of gp120) was monitored, see FIG. 5B. As it is clear from the graphs, the volumes of the active sites associated with both of the residues sets undergo distinct low frequency oscillations on top of the random thermal noise. Such long period movements are often associated with important structural changes.

A closer look at the structural transition reveals the opening of a water filled "tunnel" connecting the two pockets in the binding areas of Sites 1 and 2. The opening volume is fairly large and can accommodate a narrow and long ligand molecules, as shown in FIG. 4, FIG. 5A and FIG. 5B. The tunnel is not present in any of the ray structures available in the PDB Data Bank. The Figures show that apparently unrelated binding areas I and II are indeed closely placed within the protein 3D structure. The overlap extends deeply inside the discovered tunnel, which means that the suggested theory of the gp120 binding site provides a novel unified concept bridging together different pieces of biological knowledge.

Moreover, as can be seen from our docking results, none of the publicly accessible gp120 PDB structures can be used for binding area Site 2 binders docking.

EXAMPLE 2: PROFILING OF ANTI-HIV ACTIVITY

Two compounds were evaluated for their activity as inhibitor of HIV replication on three different lab strains using the deCIPhR cellular format. The two compounds were also tested for inhibition of replication of the lab strain pNL4-3 in a virus-to-cell infection format. The results are reported in the table below as IC50 values (concentration of compounds inhibiting 50% of viral replication).

| Infection Type | Virus Strain | Tropism | IC50 (nM) | | | |
|---|---|---|---|---|---|---|
| | | | T5379534 | T0520-5895 | T20 | EFV |
| Cell to Cell | pNL-Bal | R5 | 1538 | 15088* | 10 | 5 |
| | pNL-AD87 | R5 | 766 | 250** | 63 | 1 |
| | pNL4-3 | X4 | 3199 | >30000 | 76 | 9 |
| Virus to Cell | pNL4-3 | X4 | 767 | inactive | 48 | 2 |

*extrapolated values
**plateau of activity at ~70%

Results indicate that the two compounds T5379534 which corresponds to the compound of formula (1) and T0520-5895 which corresponds to the compound of formula (2) did show significant anti-HIV activity without signs of cytotoxicity.

These two compounds were further tested on the replication of two engineered viruses ("GIA" and "DIA" resistant to the fusion inhibitor T-20 (Enfuvirtide, Fuzeon). Results are reported in the table below as $IC_{50}$ values and as "resistance factor" (ratio between $IC_{50}$ value on mutant virus and $IC_{50}$ value on reference strain).

| Virus Type | Tropism | T5379534 | | T0520-5895 | | T20 | | EFV | |
|---|---|---|---|---|---|---|---|---|---|
| | | IC50 (nM) | Rf | IC50 (nM) | Rf | IC50 (nM) | Rf | IC50 (nM) | Rf |
| pNL-Bal | R5 | 1538 | 1 | 15088* | 1 | 10 | 1 | 5 | 1 |
| "G-I-A" | R5 | 951 | 0.6 | 7597 | 0.5 | 127 | 12.7 | 1.7 | 0.3 |
| "D-I-A" | R5 | 2011 | 1 | >30000 | >40 | 2267 | 227 | 3 | 0.6 |

*extrapolated values
cross-resistance to both compounds T5379534 and T0520-5895.

B. Comments

The compounds T5379534 and T0520-5895 do show activity on reference strains of HIV and variants resistant to T20.

C. Experimental Section

Preparation of Compounds

The compounds T5379534 (MW=436.15) and T0520-5895 (MW=491.18) were provided by Xenobe organization (Dr. James laClair) as aliquots of 1 mg/mL solution. All other drugs used in the study were obtained from the respective pharmaceutical manufacturer.

Compound stocks were prepared as 1.5 mM solution in 100% DMSO and vials were agitated for two hours at 50° C. Stock solutions were kept at −20° C., light protected as aliquots. Working dilutions (⅓ log) were prepared extemporaneously by serial dilutions in H₂O/DMSO (95/5). Ten μL of working dilutions were then pipetted and directly tested for anti-HIV activity in the 200 μL final volume of the deCIPhR cellular assay format, yielding final concentrations of 7,500, 3,481, 1,616, 750, 348, 162, 75, 35, 16, 8 and 3 nM.

1. Wild-Type Viruses

The activity of the compounds was profiled on three different viruses that were chosen as reference for distinct co-receptor usage. Their characteristics are summarized for each virus in Table I.

TABLE I

Characteristics of viruses selected for the study

| Virus | pNL4-3 | pNL-Bal | pNL-AD87 |
|---|---|---|---|
| Origin | USA | USA | USA |
| Subtype | B | B | B |
| Co-receptor Tropism | CXCR4 | CCR5 | CCR5 |

1.1. pNL4-3

The proviral DNA pNL4-3 was obtained from the AIDS reagent center (Genbank accession number #AF324493). After transfection, pNL4-3 produces a full-length infectious virus often used as reference for a B-Subtype, CXCR4-tropic strain (Adachi et al., 1986).

1.2. pNL-Bal

The DNA sequence coding for Vpu, Tat, Rev, Env, and Nef from the CCR5-tropic clone BAL2 (HIVBAL2A, Genbank accession number #M68894) was introduced by PCR-cloning into the reference proviral strain pNL4-3 (Genbank accession number #AF324493), where it replaced the corresponding region. Presence of insert was ascertained by restriction digest analysis and double sequencing on ABI 310 prism sequencer. After transfection, pNL-BaL produces a full-length infectious virus often used as reference for a B-Subtype, CCR5-tropic strain (Donaldson et al., 1994).

1.3. pNL-AD87

The DNA sequence coding for Vpu, Tat, Rev, Env, and Nef from the CCR5-tropic clone AD87 (HIV strain ADB, Genbank accession number #AF004394) was introduced by PCR-cloning into the reference proviral strain pNL4-3 (Genbank accession number #AF324493), where it replaced the corresponding region. Presence of insert was ascertained by restriction digest analysis and double sequencing on ABI 310 prism sequencer. After transfection, pNL-AD87 produces a full-length infectious virus often used as reference for a B-Subtype, CCR5-tropic strain (Theodore et al., 1996).

2. Generation of ENV-Mutants

The two compounds were evaluated for possible cross-resistance to fusion inhibitors by testing activity on engineered proviruses carrying mutations described to lead to decreased susceptibility to T-20. The three amino-acids motif G36-I37-V38 (GIV) is part of a highly conserved region within the Env gene (HR1) and was found to be mutated in patients failing T-20 treatment during Phase III clinical trials (Wei, X. et al., Antimicrobial Agents and Chemotherapy, 46, 1896 (2002)).

Two distinct mutants with alterations within the gp41 sequence of their Env-gene were to be generated.

Mutant "G-I-A": substitution from Valine to Alanine at amino-acid position 38 of HIV gp41 (numbering according to reference lab strain pNL4-3, GenBank accession number #AF324493). This single mutation has been described to lead to intermediate degree of resistance to the compound T20 (Enfuvirtide, Fuzeon®).

Mutant "D-I-A": substitutions from Glycine to Aspartic Acid at amino-acid position 36 and from Valine to Alanine at amino-acid position 38 of HIV gp41 (numbering according to reference lab strain pNL4-3, GenBank accession number #AF324493). This single mutation has been described to lead to high degree of resistance to the compound T20 (Enfuvirtide, Fuzeon®).

The two mutants included in the present study were generated using an overlapping-PCR strategy as schematically depicted in FIG. 6.

A first PCR step was performed using purified proviral DNA of pNL-Bal as template along with either the primer pair E1_F/mut1_R or the primer pair mut_1F/E2_R. Oligonucleotidic primers were as follows:

- E1_F: forward primer corresponding to the sequence located downstream from V2 (Nt 6942, numbering according to HxB2); this primer contains the sequence for a restriction site of restriction endonuclease E1;
- mut1_R: this reverse primer containing the targeted mutation(s) was designed to have at least 12-15 nucleotides complementary to the 3' end of primer mut1_F (see annex);
- mut1_F: this forward primer containing the targeted mutation(s) was designed to have at least 12-15 nucleotides complementary to the 3' end of primer mut1_R (see annex);
- E2_R: reverse primer corresponding to the sequence located near the middle of the gp41 sequence (Nt 8043, numbering according to HxB2); it also contains the sequence of a restriction site for restriction endonuclease E2.

All PCR-products generated by this first step were gel-purified, quantified using a nanodrop densitometer and combined at a 1:1 ratio. An elongation step was then performed through 5 cycles in the absence of primers; primers E1_F and E2_R were then added, and a second step PCR reaction was performed.

Parameters of PCR reactions were as follows:

1$^{st}$ Step PCR:

| | |
|---|---|
| 2 min denaturation/enzyme activation at 98° C. | |
| 10 sec denaturation at 98° C. | \| |
| 10 sec annealing at 55° C. | \| |
| 15 sec extension at 72° C. | \| → 25 cycles |
| 10 min final extension at 72° C. | |

Intermediate Elongation:

| | |
|---|---|
| 2 min denaturation/enzyme activation at 98° C. | |
| 10 sec denaturation at 98° C. | \| |
| 10 sec annealing at 55° C. | \| |
| 20 sec extension at 72° C. | \| → 5 cycles |

2$^{nd}$ Step PCR

| | |
|---|---|
| 2 min denaturation/enzyme activation at 98° C. | |
| 10 sec denaturation at 98° C. | \| |
| 10 sec annealing at 55° C. | \| |
| 30 sec extension at 72° C. | \| → 30 cycles |
| 10 min final extension at 72° C. | |

Next, 1.1 Kb PCR products were gel-purified through electrophoresis on a 0.8% agarose gel/Tris-Borate EDTA. Fragments were excised and eluted using ion exchange columns (Macherey-Nagel). Purified DNA fragments were subsequently digested with restriction enzymes E1 and E2 and ligated into a cloning cassette previously prepared by digestion with restriction endonucleases E1 and E2. Ligated recombinant proviral DNA was transformed into *E. coli* bacteria (HB110/λ) and grown on LB-Agar containing 200 μg/mL ampicillin as resistance marker. Single colonies were picked and grown overnight in LB medium containing 200 μg/mL ampicillin. Amplified plasmid was prepared using a miniprep extraction kit (Macherey-Nagel) and sequenced using a dideoxy sequencing kit (Applied Biosystems).

3. Infection Experiments 3.1 Principle of Decipher

Principle of Dual-Enhancement of Cell-Infection to Phenotype Resistance (deCIPhR™): deCIPhR test is a proprietary assay system developed by InPheno AG (FIG. 7):

Fully infectious HIV-1 is produced from a proviral reference DNA reflecting a reference HIV-1 virus. Recombinants carrying an exchanged specific-sequence (e.g. mutants resistant to existing HIV-1 inhibitors or sequences issued from clinical situations) can easily be engineered by PCR-based amplification/ligation (see paragraph 3). The unique test format allows 3 to 5 rounds of viral replication and permits a dynamic parallel read-out of viral fitness and resistance to the respective drugs under investigation. Colorimetric readout (405 nm) is translated in percent viral inhibition through normalization with positive and negative control wells included in each 96 well-plate.

The format of deCIPhR includes characteristics essential for optimal assessment of parameters of viral replication:

- Generation of restriction-recombinant virus is more rapid and efficient, and position-defined and thus proves to be superior to pseudotypes;
- Cell to cell infection most closely mimics viral behavior within the host;
- A replicative system bests reflects viral dynamics.

Each mutated proviral DNA is transfected into a human epitheloid cell line using lipofectant agent (lipofectamine 2000, Invitrogen) following the manufacturer's instructions. Cell to cell spread and replication of recombinant viruses is allowed for but also restricted to a period of four days in the absence or presence of specific drugs by co-culture with a second cell line expressing both chemokine receptors CXCR4 and CCR5. Finally, culture supernatants are transferred to a third reporter cell line also expressing both kinds of co-receptors. The infection is incubated for another 48 hours period, after which cells are fixed (formaldehyde/glutaraldehyde) prior to incubation with a chromogenic substrate for beta-galactosidase, typically ortho-nitrophenyl-galactopyranoside.

3.2 Principle of Virus to Cell Infection (FIG. 8)

Fully infectious HIV-1 is produced from proviral reference DNA reflecting a reference wild-type HIV-1 virus (pNL4-3, Genbank #AF003888). The unique test format allows direct viral infection and replication and permits a dynamic parallel read-out of viral fitness and resistance to the respective drugs under investigation.

Format for virus to cell infection: Briefly, the assay was performed in 6 well tissue culture plates and included 50,000 HIV-producing cells (HeLa) in a final volume of 2 mL DMEM medium (Gibco, Parsley, UK). After 2 days of incubation, 4 μL of viral supernatant was added to 5,000 pre-incubated HIV-reporter cells (HeLaCCR5) in a final volume of 200 μL of RPMI medium (Gibco, Parsley, UK) including 10 μL of substances to be tested.

3.3 Data-Processing for Activity Determination

A range of twelve concentrations of each compound was tested in triplicates in the deCIPhR format on each mutated provirus. The colorimetric readout obtained at the end of the deCIPhR experiment (optical density at 405 nm) was translated into a percentage of viral inhibition as function of compound concentration and processed by a statistical curve fitting software (XLfit v 4.0.1, IDbusiness solutions, Guilford, UK) yielding the selection of a best-modeled curve according to the following equation (equation 205: one-site pharmacological dose-response):

$$y_1 = \int_A^B A + \frac{B-A}{1+\left(\frac{C_1}{x_1}\right)^{D_1}}$$

Where:

$y_1$ is the modeled effect (% viral inhibition) of drug 1 at concentration x1

$x_1$ is the concentration of drug 1 yielding the modeled effect y1

A is a constant fixed to 0

B is a constant fixed to 100

$C_1$ is the concentration required to obtain 50% of the modeled effect (IC50) for drug 1

$D_1$ is the slope of the modeled curve (Hill's coefficient) for drug 1.

This algorithm used integral calculations to model inhibition curves for each compound, taking into account values of the triplicates and the observed standard deviations and allows to directly extract $IC_{50}$ and $IC_{90}$ values.

3.4 Replication Capacity Determination

The cellular system deCIPhR allows the rapid evaluation of drug activity on any variant/mutant of HIV-1. Viruses produced from a proviral DNA are allowed to replicate through 3 to 5 cycles in the cell system thereby allowing to observe dynamics of the viral replication. The enzymatic reporter read-out has been demonstrated to be strictly proportional to the production of viral particles as measured by quantitative RT-PCR of viral RNA, Reverse-transcriptase activity, and the concentration of p24 antigen in the culture supernatant. Mutated viruses engineered in the present study differ by mutations in Env gene (HR1). The remaining part of the proviral genomic DNA outside this region stems from the clonal reference provirus NL-Bal thus providing an isogenic background. Therefore, whereas the relative susceptibility of mutated viruses to fusion inhibitors such as the two test compounds is not known a-priori, the susceptibility to Reverse transcriptase inhibitors (RTIs) is expected to be identical. Concentrations of RTIs inhibiting 100% of viral growth without signs of cytotoxicity (hereafter termed $IC_{100}$) have previously been determined. The viral "fitness" or "replication capacity" was measured as a percentage of the respective replication capacity of the reference virus, calculated as follows:

$$RC(\%) = \frac{\text{Readout}_{100\%}(\text{sample}) - \text{Readout}_{0\%}(\text{sample})}{\text{Readout}_{100\%}(ref) - \text{Readout}_{0\%}(ref)} \times 100$$

Whereby:

RC (%)=Replication capacity of the recombinant virus under investigation $\text{Readout}_{100\%}$(sample)=enzymatic reporter readout of the mutated virus under investigation (average of 6 values) in the absence of inhibitor.

$\text{Readout}_{0\%}$(sample)=enzymatic reporter readout of the mutated virus under investigation (average of 6 values) in the presence of $IC_{100}$ concentration of 10 μM Efavirenz as RTI.

$\text{Readout}_{100\%}$(ref)=enzymatic reporter readout of the reference virus (pNL-Bal) (average of 6 values) in the absence of inhibitor.

$\text{Readout}_{0\%}$(ref)=enzymatic reporter readout of reference virus (pNL-Bal) (average of 6 values) in the presence of $IC_{100}$ concentration of 10 μM Efavirenz as RTI.

4. Results 4.1 Activity of Two Compounds on Replication of Wild-Type Viruses

The two compounds under investigation were tested along with reference compounds T20 and EFV on three wild-type viruses (pNL4-3, green curves; pNL-Bal, blue curves and pNL-AD87, orange curves) using the deCIPhR cellular system (see paragraph 4.1). The results of the inhibition of HIV-replication by the four compounds are reported in FIG. 9 as inhibition curves where the percentage of inhibition of HIV-replication is plotted as a function of compound concentration (described in paragraph 4). Tables below the graphs report the inhibition observed at each concentration as well as derived parameters for compounds under investigation and also for reference compounds.

Of note is that no signs of cytotoxicity was microscopically observed for the all compounds at tested concentrations.

Next, the two compounds were assessed for inhibition of viral replication in a virus-to-cell infection format along with reference compounds T20 and EFV. In this experiment only pNL4-3 reference HIV strain was used.

Graphs in FIG. 10 show the inhibition curves as percent of virus inhibition as a function of increasing concentrations of each compound. The table in FIG. 10 reports the calculated parameters of HIV inhibition (IC50, IC90 and Hill's coefficient).

Of note is that signs of cytotoxicity were microscopically observed for the highest concentration of compounds T5379534 and T0520-5895.

4.1 Activity of the Compounds on Replication of Engineered Viruses Resistant to the Fusion Inhibitor T20 (Fusion Inhibitor)

In this subsection of the study the compounds T5379534 and T0520-5895 were tested on the mutated viruses "G-I-A" and "D-I-A".

4.2.1 Activity of T5379534 and T0520-5895 on "G-I-A" Mutant

The two compounds under investigation were tested along with reference compounds T20 and EFV on the mutated virus "G-I-A" in which the Valine at position 38 of gp41 from pNL-Bal is substituted with an Alanine. The results of the inhibition of HIV-replication by the four compounds are reported in FIG. 11 as inhibition curves where the percentage of inhibition of HIV-replication is plotted as a function of compound concentration (described in paragraph 4). Tables below the graphs report the inhibition observed at each concentration as well as derived parameters for compounds under investigation and also for reference compounds.

4.2.2 Activity of T5379534 and T0520-5895 on "D-I-A" Mutant

The two compounds under investigation were tested along with reference compounds T20 and EFV on the mutated virus "D-I-A" in which the Glycine at position 36 of gp41 from pNL-Bal is substituted with an Aspartic Acid and the Valine at position 38 with an Alanine. The results of the inhibition of HIV-replication by the four compounds are reported in FIG. 12 as inhibition curves where the percentage of inhibition of HIV-replication is plotted as a function of compound concentration (described in paragraph 4). Tables below the graphs report the inhibition observed at each concentration as well as derived parameters for compounds under investigation and also for reference compounds.

4.3 Calculation of Resistance Factor

In order to be able to assess possible cross-resistance of mutants to the two evaluated compounds a Resistance factor was calculated for each compound on each mutant following the equation:

$$\text{Resistance factor}_{x,m} = \frac{IC_{50x,m}}{IC_{50x,wt}}$$

Where:

- Resistance $\text{factor}_{x,m}$: Resistance factor of compound x on mutant m
- $IC_{50x,m}$: concentration of compound x necessary to inhibit 50% of viral replication of mutant m
- $IC_{50x,wt}$: concentration of compound x necessary to inhibit 50% of viral replication of wild-type pNL-Bal Resistance factors were calculated for all compounds and reported as "IC50-fold increase" in table II:

TABLE II

Resistance factor values calculated for each compound on each mutant.

| Cpds | Resistance factor ($IC_{50mut}/IC_{50wt}$) $IC_{50}$ fold increase | | | |
|---|---|---|---|---|
| mutant | T5379534 | T0520-5895 | T20 | EFV |
| "G-I-A" | 1 | 0.5 | 13 | 0.3 |
| "D-I-A" | 1 | >40 | 227 | 0.5 |

REFERENCES OF EXAMPLE 2

Adachi A, et al. (1986) Production of acquired immunodeficiency syndrome-associated retrovirus in human and nonhuman cells transfected with an infectious molecular clone. *J. Virol.* 59(2): 284-291.

Donaldson Y K, et al. (1994) In vivo distribution and cytophatology of variants of human immunodeficiency virus type 1 showing restricted sequence variability in the V3 loop. *J. Virol.* 68(9): 5991-6005.

Theodore T S, et al. (1996) Construction and characterization of a stable full-length macrophage-tropic HIV type 1 molecular clone that directs the production of high titers of progeny virions. *AIDS Res Hum Retroviruses.* 12(3): 191-194.

Wei X., et al. (2002) Emergence of resistant human immunodeficiency virus type 1 in patients receiving fusion inhibitor (T-20) monotherapy. *Antimicrob Agents Chemother.,* 46 (6), 1896-1905.

EXAMPLE 3: GP120 BINDING TO A4B7

Studies were conducted to study the binding of gp120 to the integrin α4β7 (or a4b7; alpha4 beta7 as used herein above) and to develop a high-throughput assay to screen for compounds that interfere with the binding of HIV associated glycoprotein gp120 and the integrin α4β7.

A. Materials.

General methods were used to obtain the necessary cells, proteins, antibodies and reagents. When possible, commercial materials were used and the vendor and product number are designated.

Antibodies.

A goat HIV1 anti-gp120 polyclonal antibody (ab21179) was obtained from Abcam. Mouse anti-gp120 monoclonal antibodies (mAbs) were obtained from Abcam [HIV1 gp120] (ab13411) and Prospec [HIV-1 gp120] (ANT-151). Mouse mAbs were used in the ELISA assay and the goat polyclonal antibody was used for protein production. A rat mAb against integrin α4β7 [DATK32] (ab25329) was obtained from Abcam Inc. In addition, mouse antibodies against the human integrin α4 [44H6] (ab220) and human integrin β7 [8G2] (mca5238Z) were obtained from Abcam Inc. and AbD Serotec Inc., respectively, and used for protein purification. The integrin α4β7 mAb was also labeled with biotin using EZ-Link Sulfo-NHS biotinylation kit (21425) from ThermoScientific using the procedures described in the manufacturers protocol.

Gp120 Protein.

HIV-1 gp120 plasmid was also obtained containing the gp120 gene from an M cell-tropic HIV-1 ADA strain. The recombinant envelope gp120 glycoprotein was also previously produced in the Baculovirus Expression System (Invitrogen) on a hollow-fiber filter cell device (Filter Cell Systems Inc) in Sf9 cells (Orbigen Inc.). Crude recombinant envelope gp120 glycoprotein was purified by prep-fast protein liquid chromatography (FPLC). This method was used to prepare the gp120 protein for prior studies. Reapplication of the method delivered 4.2 mg of gp120 protein with a purity of over 95% purity by SDS PAGE analysis using a SilverQuest kit (Invitrogen) for detection.

Alpha4 Beta7 (α4β7) or LPAM-1 Protein.

Recombinant human α4β7 integrin was purchased from R&D Systems (Catalog Number: 5397-A3). Larger quantities of the α4β7 integrin were by in house. Recombinant expression of both subunits α4 and β7 was accomplished by preparation plasmids containing the α4 (protein accession # P13612) and β7 (protein accession # P26010) both containing a C-terminal 6×His tag (SEQ ID NO: 25). Both proteins were expressed in CHO cells using conventional methods and were purified to ≥98% purity (SDS PAGE analysis) by sequential His-tag purification on NTA-agarose followed by repetitive size exclusion purification using a Sephadex G-200 column. The 6×His tags (SEQ ID NO: 25) were removed prior to size exclusion purification. The purity of each subunit was evaluated by SDS-PAGE analysis and both subunits were purified to over 98% purity using a SilverQuest kit (Invitrogen) for detection. The α4β7 integrin was reconstituted was prepared by incubation of a 1:1 mixture of the α4 and β7 subunits followed by size exclusion purification by three passes on a Sephadex G-200 column. An anti-α4β7 mAb was used to identify the fractions containing the α4β7 integrin. This method was used to provide 12.5 mg of the α4β7 integrin with greater than 96% purity. The activity of the α4β7 integrin was determined by using the methods established by R&D Systems Inc., as given by measuring the ability of the immobilized α4β7 integrin to support the adhesion of VCAM-1 transfected Chinese hamster ovary (CHO) cells. When $5\times10^4$ cells per well are added to rhIntegrin α4β7 coated plates (10 μg/mL, 100 μL/well), between 60-80% will adhered in 1 h at 37° C. This procedure is described in the product catalog for the α4β7 integrin (R&D Systems Inc.). All assays were conducted with protein produced in our laboratories and was checked once in triplicate against the commercial protein.

Reagents.

HRP-NeutrAvidin (21124) from ThermoScientific and QuantaBlu Fluorogenic Peroxidase Substrate (15169) from ThermoScientific were used to develop the ELISA assays. All compounds were provided and stocked at 10 mg/mL in DMSO and stored at −80° C. until used. Buffers were all prepared as sterile media and were stored for less than 24 h. All other reagents, plates, or devices are noted as used.

C. ELISA Analysis.

It was previously demonstrated that co-immunoprecipitation analyses as analyzed via western blots were a viable means to evaluate the binding of gp120 to α4β7 in human cell lysates. This method was advanced into an ELISA format and applied to screen the number of compounds provided within the research period.

It was determined that the direction of the assay was not critical and antibodies can be used against both gp120 and the α4β7 integrins in any order. Based on these studies, an optimized ELISA assay as outlined in FIG. 36 was designed.

C.1. Assay Development.

The studies began by screening for the optimal protein concentrations for the method. The studies were conducted in goat anti-mouse IgG coated black React-Bind 96 welled-plates (R&D Biosystems), referred to herein as the anti-mouse IgG plate. We prepared twelve stock solutions containing a 1:1 stoichiometric mixture of gp120 and α4β7 integrin in PBS at pH 7.2 as given by 0 μM or control, 0.001 μM, 0.01 μM, 0.01 μM, 0.05 μM, 0.1 μM, 0.5 μM, 1 μM, 2.5 μM, 5 μM, 10 μM and 25 μM in protein (step 1, FIG. 36). A 200 μL aliquot of each stock solutions was then loaded across a 96 welled plate and treated either with 20 μL of PBS pH 7.2 (control) or 20 μL of a 100 μM stock solution of repandusinic acid in PBS pH 7.2 containing 1% DMSO. Three repetitions were run for both the control and positive or repandusinic acid treated experiments. The final concentration of repandusinic acid in each positive well was 10 μM. The plate was incubated for 4 h at 4° C. on a plate mixer at a speed that created a vortex in each well.
During this time, repandusinic binds to blocks the formation of the α4β7.gp120 complex (step 2, FIG. 36). This process provided a plate containing the antigens, or so called antigen plate.

In parallel, the anti-mouse IgG plate was washed 3 times with 200 μL of wash buffer (PBS pH 7.2. containing 0.05% Tween 20) and treated with 100 μL of a 0.5 μg/mL stock of the mouse anti-gp120 mAb in PBS pH 7.2. Two mAbs were tested (see Materials Section above). Data was reported using a combination from three repetitions from each mAb, affording an average over six experiments, as indicated by step 3 (FIG. 36). This process delivered the binding plate.

After incubating the plate for 1 h at 23° C. on a plate mixer at a speed that created a vortex in each well, each well drained by aspiration and washed three times with 200 μL of wash buffer. The contents of the antigen plate (above) were transferred to the complementary well son the binding plate. The binding plate was shaken for 1 h at 23° C. on a plate mixer at a speed that created a vortex in each well, as indicated by step 4 (FIG. 36).

Each well of the binding plate was aspirated and rinsed three times with 200 μL of wash buffer. The wells were charged with 100 μL of a 0.1 μg/mL of the rat anti α4β7 mAb and the plate was shaken for 1 h at 37° C. (step 5, FIG. 1). This process was then repeated using 100 μL of 0.2 μg/mL solution of the HRP-conjugated strepavidin (step 6, FIG. 36). The HRP activity was developed using QuantaBlu fluorogenic peroxidise substrate (ThermoScientific) and evaluated on a HTS7000 plate reader (Perkin Elmer). Using this method it was determined that the ideal concentration of gp120 and α4β7 was 0.5-1.0 μM.

C.2. Optimization.

Then the assay was exhaustively tested by screening the inhibition of the binding of gp120 and α4β7 by repandusinic acid. Stock solutions of repandusinic acid (10× stock solutions) were prepared at 0 μM or control, 0.01 μM, 0.1 μM, 0.1 μM, 0.5 μM, 1 μM, 5 μM, 10 μM, 25 μM, 50 μM, 100 μM and 250 μM). Using this gradient, we were able to identify the following optimized protocol.

Step 1: Prepare the Antigen Plate a. Prepare a PBS stock solution containing 1 μμM gp120 and 1 μM α4β7 b. Add a 200 μL aliquot to each well of the antigen plate.

Step 2: Add the Inhibitor.

a. Add 20 μL of a 10× stock of the inhibitor in PBS pH 7.2 containing 1% DMSO b. Incubate at 4° C. for 6 h with shaking. This delivers the antigen plate.

Step 3: Prepare the Binding Plate.

a. Aspirate each well of the binding plate b. Wash three times with 200 μL of wash buffer (PBS pH 7.2. containing 0.05% Tween 20).

c. Add 100 μL of a 0.5 μg/mL stock of the mouse anti-gp120 mAb in PBS pH 7.2 d. Shake for 1 h at 23° C.

Step 4: Sequester the Gp120.α4β7 Complex.

a. Aspirate each well of the binding plate.

b. Wash three times with 200 μL of wash buffer.

c. Transfer the contents of the antigen plate to the corresponding wells in the binding plate.

d. Shake for 1 h at 23° C.

Step 5: Develop the Binding Plate.

a. Aspirate each well of the binding plate.

b. Wash three times with 200 μL of wash buffer.

c. Add 100 μL of a 0.1 μg/mL of the rat anti-α4β7 mAb.

d. Shake for 1 h at 37° C.

e. Aspirate each well of the binding plate.

f. Wash three times with 200 μL of wash buffer.

g. Add 100 μL of 0.2 μg/mL solution of the HRP-conjugated strepavidin h. Shake for 1 h at 37° C.

i. Aspirate each well of the binding plate.

j. Wash three times with 200 μL of wash buffer.

k. Develop using QuantaBlu fluorogenic peroxidase substrate (ThermoScientific)

l. Evaluate the Fluorescence Output on a HTS7000 Plate Reader (Perkin Elmer).

Outcome: Repandusinic acid A inhibited the binding of gp120 to α4β7 with an activity of 1.2±0.1 μM using the described an ELISA assay. This proved better than that obtained from use of the cell extracts 9.08 μM as determined in previous studies. The inhibition of the binding of gp120 and α4β7 can be serialized and conducted in a 96 welled plate format.

Application of the Gp120 and Integrin α4β7 Association Assay

The ELISA assay was applied to screen the panel of compounds to further characterize their activity against the binding of HIV associated glycoprotein gp120 and the integrin α4β7.

D. Implementation.

The five-step assay developed was applied to screen the panel of compounds provided. These materials were stored at −80° C. over the research period and were shown to be stable and retain purity by LC/MS analysis prior to use. The experiments were run in triplicate using two antibodies against gp120. The data was compiled and plotted (FIG. 37*a*) and compared against the results with less accuracy obtained in our prior studies (FIG. 37*b*). Only modest changes were observed between the in vitro studies conducted herein (FIG. 37*a*) and those conducted on cell lysates (FIG. 37*b*). Results obtained are described in detail in the figure legend to FIG. 37A and FIG. 37B herein above.

EXAMPLE 4: PROFILING OF COMPOUNDS INTERACTING WITH THE TUNNEL IN THREE HIV STRAINS

Preparation of Compounds 4 compounds namely, A03, G03, H04 and C05 identified as interacting with amino acid residues comprised in 6 motifs forming a tunnel within gp/20 of HIV in a previous screen were tested against 3 HIV viruses expressing different envelopes.

Compounds stocks were prepared as 20 mM solutions in 100% DMSO and stored light protected at −20° C. Because of solubility issues, an intermediate dilution to 5 mM in 100% DMSO was carried out for compound A03 and to 2 mM for compounds G03, H04 and C05. Working solutions were made just prior to use by serial dilutions in Phosphate-Buffered Saline (PBS)/DMSO (90/10) and added directly to the cell cultures (200 µL final culture volume) to yield final concentrations of 25,000, 11,604, 5,386, 2,500, 1,160, 539, 250, 116, 54 and 25 for compound A03 and 10,000, 4,642, 2,155, 1,000, 464, 215, 100, 46 and 22 nM for the three other compounds under investigation.

The fusion inhibitor T20 (Fuzeon, Roche & Trimeris), was used as positive control.

Viruses

The antiviral activity of the test substances was profiled on three viruses that were selected according to their envelope sequence. The characteristics of these viruses are summarised in Table III.

TABLE III

Characteristics of viruses selected for the study

| Virus | NL4-3 | Clone 896 | Clone 94UG114 |
|---|---|---|---|
| Origin | USA | USA | Uganda |
| Subtype | B | B | D |
| Co-receptor Tropism | CXCR4 | CXCR4 | CXCR4 |

The proviral DNA pNL4-3 was obtained from the AIDS reagent centre (Genbank accession number #AF324493). After transfection, pNL4-3 produces a full-length infectious virus, NL4-3, often used as reference for CXCR4-tropic B-Subtype strain (Adachi et al., 1986).

The proviral DNA p896 was obtained from the AIDS reagent centre (Genbank accession number #U39362). After transfection of the proviral plasmid, a full-length infectious B-Subtype virus is produced (Collman et al., 1992).

The proviral DNA p94UG114 was obtained from the AIDS reagent centre (Genbank accession number #U88824). After transfection of the proviral plasmid p94UG114, a full-length infectious D-Subtype virus is produced (Gao et al., 1998).

Infection Experiment

Antiviral activity was determined according to the deCIPhR™ test described herein above (cf. FIG. 7).

Data Processing for Activity Determination

A range of nine concentrations of each test substance provided by KFLP Biotech was tested in triplicate in the deCIPhR assay described above. The colorimetric readout obtained at the end of the experiments (optical density at 405 nm) was translated into percent viral inhibition. To this end, each plate included control wells for 100% readout (diluent only, mock treated) and 0% readout i.e., wells containing 300 nM of Efavirenz, a reference inhibitor, which reflects a concentration known to completely inhibit viral replication in vitro. The readout of each well was then transformed to % viral inhibition using the formula:

$$\%\ \text{viral inhibition}\ X=100-(((\text{readout}\ X-\text{readout}\ 0\%)/(\text{readout}\ 100\%-\text{readout}\ 0\%))\times 100)$$

Where:

readout X=OD405 nm of well containing 'X' readout 100%=average of $OD_{405}$ nm of "100% readout" wells readout 0%=average of $OD_{405}$ nm of "0% readout" wells Using these transformed data, curve fitting was then performed with the help of XLfit software (version 4.3.2, IDbusiness solutions, Guilford, UK) yielding the selection of a best-modelled curve according to the following equation (equation 205: one-site pharmacological dose-response):

$$y_1 = \int_B^A A + \frac{B-A}{1+\left(\frac{C_1}{x_1}\right)^{D_1}}$$

Where:

y1 is the modelled effect (% viral inhibition) of drug 1 at concentration x1 x1 is the concentration of drug 1 yielding the modelled effect y1

A is a constant fixed to 0

B is a constant fixed to 100

C1 is the concentration required to obtain 50% of the modelled effect ($EC_{50}$) for drug 1

D1 is the slope of the modelled curve (Hill's coefficient) for drug 1.

This algorithm uses integral calculations to model inhibition curves for each compound, taking into account values of the triplicates and the observed standard deviations and allows to directly extract $EC_{50}$ and $EC_{90}$ values.

Results

In the below Table IV there is a summary of deCIPhR™ assay results displayed as effective concentration of the tested compounds inhibiting NL4-3, 896 and 94UG114 replication to 50% and 90% ($EC_{50}$ and $EC_{90}$). Due to the interaction with highly conserved amino acid residues forming a highly conserved structure within gp120, i.e. the tunnel described herein, all tested compounds exhibit antiviral activity in the different HIV strains.

TABLE IV

| | | EC50 (µM) | EC90(µM) |
|---|---|---|---|
| A03 | NL4-3 | 8.1 | 29.2 * |
| | 896 | 9.1 | 34.3 * |
| | 94UG114 | 9.7 | 145.4 * |
| G03 | NL4-3 | 3 | 8.6 |
| | 896 | 4.6 | 10.5 |
| | 94UG114 | 2.5 | 8.4 |

TABLE IV-continued

| | | EC50 (μM) | EC90(μM) |
|---|---|---|---|
| H04 | NL4-3 | 2.7 | 13.3 * |
| | 896 | 4.6 | 11.2 * |
| | 94UG114 | 4 | 4.4 |
| C05 | NL4-3 | 10.2 | 55.7 * |
| | 896 | 10.2 | 63.7 * |
| | 94UG114 | 3.8 | 5.1 |

* extrapolated values

REFERENCES OF EXAMPLE 4

Adachi A, et al. (1986) Production of acquired immunodeficiency syndrome-associated retrovirus in human and nonhuman cells transfected with an infectious molecular clone. J. Virol. 59(2): 284-291.

Collman R, et al. (1992) An infectious molecular clone of an unusual macrophage-tropic and highly cytophatic strain of human immunodeficiency virus type 1. J. Virol. 66(12): 7517-7521.

Gao F, et al. (1998) A comprehensive panel of near-full-length clones and reference sequences for non-subtype B isolates of human immunodeficiency virus type 1. J. Virol. 72(7): 5680-5698.

The invention claimed is:

1. A method of generating a medicament for the treatment of HIV, comprising confirming that a known compound is an inhibitor of the binding of HIV (human immunodeficiency virus) glycoprotein (gp)120 to a CD4-receptor comprising the method of (a) bringing into contact a HIV gp120 or a peptidomimetic reflecting the three-dimensional structure of said gp120 and the known compound;

(b) determining whether said known compound interacts with at least two amino acid residues found independently in each of three of six motifs, said three of six motifs selected from the group consisting of motif 1, motif 2 and motif 3, within the 3-dimensional structure of said gp120 or within a peptidomimetic reflecting the 3-dimensional structure of said gp120, wherein a first motif of said six motifs comprises the amino acid sequence DIISLWDQSLKPCVKLT (SEQ ID NOS 3 (HIV-1) or 9 (HIV-2); motif 1);

wherein a second motif of said six motifs comprises the amino acid sequence NVSTVQCTHGIRPV-VSTQLLLNGSLAE (SEQ ID NOS 4 (HIV-1) or 10 (HIV-2); motif 2) and wherein the interaction with any amino acid residue of said second motif is with any one or more of residues 14-18 of SEQ ID NOS 4 (HIV-1) or 10 (HIV-2);

wherein a third motif of said six motifs comprises the amino acid sequence SGGDPEIVMHSF-NCGGEFFYCN (SEQ ID NOS 5 (HIV-1) or 11 (HIV-2); motif 3);

wherein a fourth motif of said six motifs comprises the amino acid sequence CPKISFEP (SEQ ID NOS 6 (HIV-1) or 14 (HIV-2));

wherein a fifth motif of said six motifs comprises the amino acid sequence FRPGGGDMRDNWRSE-LYKYKVV (SEQ ID NO: 7 (HIV-1)); and wherein a sixth motif of said six motifs comprises the amino acid sequence CSS, said gp120 of HIV comprising or consisting of:

(i) the sequence of SEQ ID NO: 2;

(ii) the sequence encoded by the sequence of SEQ ID NO: 1;

(iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, and (c) identifying as inhibitors those known compounds which interact with at least two amino acid residues found independently in each of three of six motifs selected from the group consisting of motif 1, motif 2 and motif 3 in said six motifs within the 3-dimensional structure of said gp120 in (b), followed by screening the inhibitor in a biological assay.

2. A method of generating a medicament for the treatment of HIV, comprising confirming that a known compound is an inhibitor of the binding of HIV (human immunodeficiency virus) glycoprotein (gp)120 to a CD4-receptor comprising (a) bringing into contact a HIV gp120 or a peptidomimetic reflecting the three-dimensional structure of said gp120 and the known compound;

(b) determining whether said known compound interacts with at least two amino acid residues found independently in each of three of six motifs, said three of six motifs selected from the group consisting of motif 1, motif 2 and motif 5, within the 3-dimensional structure of said gp120 or within a peptidomimetic reflecting the 3-dimensional structure of said gp120, wherein a first motif of said six motifs comprises the amino acid sequence DIISLWDQSLKPCVKLT (SEQ ID NOS 3 (HIV-1) or 9 (HIV-2); motif 1);

wherein a second motif of said six motifs comprises the amino acid sequence NVSTVQCTHGIRPV-VSTQLLLNGSLAE (SEQ ID NOS 4 (HIV-1) or 10 (HIV-2); motif 2) and wherein the interaction with any amino acid residue of said second motif is with any one or more of residues 14-18 of SEQ ID NOS 4 (HIV-1) or 10 (HIV-2);

wherein a third motif of said six motifs comprises the amino acid sequence SGGDPEIVMHSF-NCGGEFFYCN (SEQ ID NOS 5 (HIV-1) or 11 (HIV-2));

wherein a fourth motif of said six motifs comprises the amino acid sequence CPKISFEP (SEQ ID NOS 6 (HIV-1) or 14 (HIV-2));

wherein a fifth motif of said six motifs comprises the amino acid sequence FRPGGGDMRDNWRSE-LYKYKVV (SEQ ID NO: 7 (HIV-1); motif 5); and wherein a sixth motif of said six motifs comprises the amino acid sequence CSS, said gp120 of HIV comprising or consisting of:

(i) the sequence of SEQ ID NO: 2;

(ii) the sequence encoded by the sequence of SEQ ID NO: 1;

(iii) a sequence being at least 50% identical to the sequence of SEQ ID NO: 2 or to the sequence encoded by the sequence of SEQ ID NO: 1; or (iv) a sequence encoded by a sequence being at least 50% identical to the sequence of SEQ ID NO: 1, and (c) identifying as inhibitors those known compounds which interact with at least two amino acid residues found independently in each of three of six motifs selected from the group consisting of motif 1, motif 2 and motif 5 in said six motifs within the 3-dimensional structure of said gp120 in (b), followed by screening the inhibitor in a biological assay.

3. The method of claim 1 or 2 wherein the confirmation step is performed in silico.

* * * * *

SEQUENCE LISTING

```
<160> NUMBER OF SEQ ID NOS: 47

<210> SEQ ID NO 1
<211> LENGTH: 1017
<212> TYPE: DNA
<213> ORGANISM: Human immunodeficiency virus 1
<220> FEATURE:
<223> OTHER INFORMATION: gp120 sequence, backtranslated from protein
      sequence (SEQ ID NO:2)

<400> SEQUENCE: 1

gtggtgctgg aaaacgtgac cgaacatttt aacatgtgga aaaacgatat ggtggaacag      60

atgcaggaag atattattag cctgtgggat cagagcctga aaccgtgcgt gaaactgacc     120

ccgctgtgcg tgggcgcggg cagctgcgat accagcgtga ttacccaggc gtgcccgaaa     180

attagctttg aaccgattcc gattcattat tgcgcgccgg cgggctttgc gattctgaaa     240

tgcaacgata aaacctttaa cggcaaaggc ccgtgcaaaa acgtgagcac cgtgcagtgc     300

acccatggca ttcgcccggt ggtgagcacc cagctgctgc tgaacggcag cctggcggaa     360

gaagaagtgg tgattcgcag cgataacttt accaacaacg cgaaaaccat tattgtgcag     420

ctgaaagaaa gcgtggaaat taactgcacc cgcccgaacc agaacacccg caaaagcatt     480

catattggcc cgggccgcgc gttttatacc accggcgaaa ttattggcga tattcgccag     540

gcgcattgca acattagccg cgcgaaatgg aacgataccc tgaaacagat tgtgattaaa     600

ctgcgcgaac agtttgaaaa caaaaaccatt gtgtttaacc atagcagcgg cggcgatccg    660

gaaattgtga tgcatagctt taactgcggc ggcgaatttt tttattgcaa cagcgcgcag     720

ctgtttaaca gcacctggaa caacaacacc gaaggcagca acaacaccga aggcaacacc     780

attaccctgc cgtgccgcat taaacagatt attaacatgt ggcaggaagt gggcaaagcg     840

atgtatgcgc cgccgattcg cggccagatt cgctgcagca gcaacattac cggcctgctg     900

ctgacccgcg atggcggcat taacgaaaac ggcaccgaaa tttttcgccc gggcggcggc     960

gatatgcgcg ataactggcg cagcgaactg tataaatata aagtggtgaa aattgaa       1017


<210> SEQ ID NO 2
<211> LENGTH: 344
<212> TYPE: PRT
<213> ORGANISM: Human immunodeficiency virus 1
<220> FEATURE:
<223> OTHER INFORMATION: Protein databank accession number 2B4C_G

<400> SEQUENCE: 2

Gly Ala Arg Ser Glu Val Val Leu Glu Asn Val Thr Glu His Phe Asn
1               5                   10                  15

Met Trp Lys Asn Asp Met Val Glu Gln Met Gln Glu Asp Ile Ile Ser
```

```
            20                  25                  30

Leu Trp Asp Gln Ser Leu Lys Pro Cys Val Lys Leu Thr Pro Leu Cys
        35                  40                  45

Val Gly Ala Gly Ser Cys Asp Thr Ser Val Ile Thr Gln Ala Cys Pro
    50                  55                  60

Lys Ile Ser Phe Glu Pro Ile Pro Ile His Tyr Cys Ala Pro Ala Gly
65                  70                  75                  80

Phe Ala Ile Leu Lys Cys Asn Asp Lys Thr Phe Asn Gly Lys Gly Pro
                85                  90                  95

Cys Lys Asn Val Ser Thr Val Gln Cys Thr His Gly Ile Arg Pro Val
            100                 105                 110

Val Ser Thr Gln Leu Leu Leu Asn Gly Ser Leu Ala Glu Glu Glu Val
        115                 120                 125

Val Ile Arg Ser Asp Asn Phe Thr Asn Asn Ala Lys Thr Ile Ile Val
    130                 135                 140

Gln Leu Lys Glu Ser Val Glu Ile Asn Cys Thr Arg Pro Asn Gln Asn
145                 150                 155                 160

Thr Arg Lys Ser Ile His Ile Gly Pro Gly Arg Ala Phe Tyr Thr Thr
                165                 170                 175

Gly Glu Ile Ile Gly Asp Ile Arg Gln Ala His Cys Asn Ile Ser Arg
            180                 185                 190

Ala Lys Trp Asn Asp Thr Leu Lys Gln Ile Val Ile Lys Leu Arg Glu
        195                 200                 205

Gln Phe Glu Asn Lys Thr Ile Val Phe Asn His Ser Ser Gly Gly Asp
    210                 215                 220

Pro Glu Ile Val Met His Ser Phe Asn Cys Gly Gly Glu Phe Phe Tyr
225                 230                 235                 240

Cys Asn Ser Ala Gln Leu Phe Asn Ser Thr Trp Asn Asn Asn Thr Glu
                245                 250                 255

Gly Ser Asn Asn Thr Glu Gly Asn Thr Ile Thr Leu Pro Cys Arg Ile
            260                 265                 270

Lys Gln Ile Ile Asn Met Trp Gln Glu Val Gly Lys Ala Met Tyr Ala
        275                 280                 285

Pro Pro Ile Arg Gly Gln Ile Arg Cys Ser Ser Asn Ile Thr Gly Leu
    290                 295                 300

Leu Leu Thr Arg Asp Gly Gly Ile Asn Glu Asn Gly Thr Glu Ile Phe
305                 310                 315                 320

Arg Pro Gly Gly Gly Asp Met Arg Asp Asn Trp Arg Ser Glu Leu Tyr
                325                 330                 335

Lys Tyr Lys Val Val Lys Ile Glu
            340
```

<210> SEQ ID NO 3
<211> LENGTH: 17
<212> TYPE: PRT
<213> ORGANISM: Human immunodeficiency virus 1

<400> SEQUENCE: 3

```
Asp Ile Ile Ser Leu Trp Asp Gln Ser Leu Lys Pro Cys Val Lys Leu
1               5                   10                  15

Thr
```

<210> SEQ ID NO 4
<211> LENGTH: 27
<212> TYPE: PRT

<213> ORGANISM: Human immunodeficiency virus 1

<400> SEQUENCE: 4

```
Asn Val Ser Thr Val Gln Cys Thr His Gly Ile Arg Pro Val Val Ser
1               5                   10                  15

Thr Gln Leu Leu Leu Asn Gly Ser Leu Ala Glu
            20                  25
```

<210> SEQ ID NO 5
<211> LENGTH: 22
<212> TYPE: PRT
<213> ORGANISM: Human immunodeficiency virus 1

<400> SEQUENCE: 5

```
Ser Gly Gly Asp Pro Glu Ile Val Met His Ser Phe Asn Cys Gly Gly
1               5                   10                  15

Glu Phe Phe Tyr Cys Asn
            20
```

<210> SEQ ID NO 6
<211> LENGTH: 8
<212> TYPE: PRT
<213> ORGANISM: Human immunodeficiency virus 1

<400> SEQUENCE: 6

```
Cys Pro Lys Ile Ser Phe Glu Pro
1               5
```

<210> SEQ ID NO 7
<211> LENGTH: 22
<212> TYPE: PRT
<213> ORGANISM: Human immunodeficiency virus 1

<400> SEQUENCE: 7

```
Phe Arg Pro Gly Gly Gly Asp Met Arg Asp Asn Trp Arg Ser Glu Leu
1               5                   10                  15

Tyr Lys Tyr Lys Val Val
            20
```

<210> SEQ ID NO 8
<211> LENGTH: 22
<212> TYPE: PRT
<213> ORGANISM: Human immunodeficiency virus 1

<400> SEQUENCE: 8

```
Cys Arg Ile Lys Gln Ile Ile Asn Met Trp Gln Glu Val Gly Lys Ala
1               5                   10                  15

Met Tyr Ala Pro Pro Ile
            20
```

<210> SEQ ID NO 9
<211> LENGTH: 17
<212> TYPE: PRT
<213> ORGANISM: Human immunodeficiency virus 2

<400> SEQUENCE: 9

```
Asp Ile Ile Ser Leu Trp Asp Gln Ser Leu Lys Pro Cys Val Lys Leu
1               5                   10                  15

Thr
```

<210> SEQ ID NO 10
<211> LENGTH: 27

<212> TYPE: PRT
<213> ORGANISM: Human immunodeficiency virus 2

<400> SEQUENCE: 10

Asn Val Ser Thr Val Gln Cys Thr His Gly Ile Arg Pro Val Val Ser
1               5                   10                  15

Thr Gln Leu Leu Leu Asn Gly Ser Leu Ala Glu
            20                  25

<210> SEQ ID NO 11
<211> LENGTH: 22
<212> TYPE: PRT
<213> ORGANISM: Human immunodeficiency virus 2

<400> SEQUENCE: 11

Ser Gly Gly Asp Pro Glu Ile Val Met His Ser Phe Asn Cys Gly Gly
1               5                   10                  15

Glu Phe Phe Tyr Cys Asn
            20

<210> SEQ ID NO 12
<211> LENGTH: 21
<212> TYPE: PRT
<213> ORGANISM: Human immunodeficiency virus 2

<400> SEQUENCE: 12

Arg Pro Gly Gly Gly Asp Met Arg Asp Asn Trp Arg Ser Glu Leu Tyr
1               5                   10                  15

Lys Tyr Lys Val Val
            20

<210> SEQ ID NO 13
<211> LENGTH: 22
<212> TYPE: PRT
<213> ORGANISM: Human immunodeficiency virus 2

<400> SEQUENCE: 13

Cys Arg Ile Lys Gln Ile Ile Asn Met Trp Gln Glu Val Gly Lys Ala
1               5                   10                  15

Met Tyr Ala Pro Pro Ile
            20

<210> SEQ ID NO 14
<211> LENGTH: 8
<212> TYPE: PRT
<213> ORGANISM: Human immunodeficiency virus 2

<400> SEQUENCE: 14

Cys Pro Lys Ile Ser Phe Glu Pro
1               5

<210> SEQ ID NO 15
<211> LENGTH: 17
<212> TYPE: PRT
<213> ORGANISM: Human immunodeficiency virus 1
<220> FEATURE:
<223> OTHER INFORMATION: first motif
<220> FEATURE:
<221> NAME/KEY: MOD_RES
<222> LOCATION: (1)..(1)
<223> OTHER INFORMATION: Glu, Thr, Ala, Gln, Asn, Val, Lys, Ser, Gly or
      Leu
<220> FEATURE:
<221> NAME/KEY: MOD_RES
<222> LOCATION: (2)..(2)

```
<223> OTHER INFORMATION: Tyr, Val, Leu, His, Ser, Thr, Asn, Lys, Ala,
      Met or Asp
<220> FEATURE:
<221> NAME/KEY: MOD_RES
<222> LOCATION: (3)..(3)
<223> OTHER INFORMATION: Ala, Val, Thr, Lys, Leu, Ser, Asn, Gln, Arg,
      Tyr or Glu
<220> FEATURE:
<221> NAME/KEY: MOD_RES
<222> LOCATION: (4)..(4)
<223> OTHER INFORMATION: Leu, Pro, Thr, Ala, Gln, Asn, Phe, Ile, Glu,
      Gly, Arg, Lys or Asp
<220> FEATURE:
<221> NAME/KEY: MOD_RES
<222> LOCATION: (5)..(5)
<223> OTHER INFORMATION: Phe, Ile, Val, Met, Ser, Gly, Arg, Thr, Cys,
      Pro, Lys, Tyr or Asp
<220> FEATURE:
<221> NAME/KEY: MOD_RES
<222> LOCATION: (6)..(6)
<223> OTHER INFORMATION: Tyr, Asp, Thr, Lys, Glu, Asn, Arg, Gln, Gly,
      His, Ser, Met, Phe or Leu
<220> FEATURE:
<221> NAME/KEY: MOD_RES
<222> LOCATION: (7)..(7)
<223> OTHER INFORMATION: Lys, Asn, Glu, Ser, Arg, Gly, Thr, Ala, Gln,
      Phe or Tyr
<220> FEATURE:
<221> NAME/KEY: MOD_RES
<222> LOCATION: (8)..(8)
<223> OTHER INFORMATION: Leu, Glu, Asn, Lys, Ser, Thr, Asp, Ala, Arg,
      Gly, Pro, His, Tyr, Ile, Met or Phe
<220> FEATURE:
<221> NAME/KEY: MOD_RES
<222> LOCATION: (9)..(9)
<223> OTHER INFORMATION: Asp, Glu, Lys, Asn, Gly, Thr, Ala, Met, Leu,
      Arg, Gln, Phe, Val or His
<220> FEATURE:
<221> NAME/KEY: MOD_RES
<222> LOCATION: (10)..(10)
<223> OTHER INFORMATION: Val, Ser, Asn, Ile, Met, Thr, Asp, His, Gln,
      Tyr, Pro, Arg, Glu, Gly, Ala, Phe or Lys
<220> FEATURE:
<221> NAME/KEY: MOD_RES
<222> LOCATION: (11)..(11)
<223> OTHER INFORMATION: Val, Glu, Ser, Thr, Asn, Gln, Ala, Ile, Arg,
      Phe, Gly, Tyr, Met, Leu, Pro or Asp
<220> FEATURE:
<221> NAME/KEY: MOD_RES
<222> LOCATION: (12)..(12)
<223> OTHER INFORMATION: Ser, Asn, Thr, Glu, Gly, Tyr, Lys, Arg, Gln,
      Asp, Leu, Ala or Val
<220> FEATURE:
<221> NAME/KEY: MOD_RES
<222> LOCATION: (13)..(13)
<223> OTHER INFORMATION: Ile, Thr, Glu, Met, Ser, Leu, Tyr, Ala, Lys,
      Asn, Arg, Phe, Asp, Gly, His, Val, Trp or Gln
<220> FEATURE:
<221> NAME/KEY: MOD_RES
<222> LOCATION: (14)..(14)
<223> OTHER INFORMATION: Tyr, Asp, Ile, Leu, Ser, Thr, Glu, Ala, Gly,
      Asn, Arg, Lys, His, Cys, Met, Phe or Gln
<220> FEATURE:
<221> NAME/KEY: MOD_RES
<222> LOCATION: (15)..(15)
<223> OTHER INFORMATION: Arg, Asn, Glu, Thr, Asp, Gln, Gly, Leu, Ser,
      Ile, Pro, Tyr, Ala or Val
<220> FEATURE:
<221> NAME/KEY: MOD_RES
<222> LOCATION: (16)..(16)
<223> OTHER INFORMATION: Asn, Thr, Asp, Ile, Glu, Ser, Ala, Tyr, Lys,
      Gly, Val, Arg, Met, Phe, Gln or His
<220> FEATURE:
<221> NAME/KEY: MOD_RES
<222> LOCATION: (17)..(17)
<223> OTHER INFORMATION: Ile, Asp, Val, Asn, Ser, Arg, Tyr, Lys, Glu,
      Met, His, Gly, Ala, Leu or Cys

<400> SEQUENCE: 15
```

-continued

Xaa Xaa Xaa Xaa Xaa Xaa Xaa Xaa Xaa Xaa Xaa Xaa Xaa Xaa Xaa Xaa
1 5 10 15

Xaa

<210> SEQ ID NO 16
<211> LENGTH: 27
<212> TYPE: PRT
<213> ORGANISM: Human immunodeficiency virus 1
<220> FEATURE:
<223> OTHER INFORMATION: second motif
<220> FEATURE:
<221> NAME/KEY: MOD_RES
<222> LOCATION: (1)..(1)
<223> OTHER INFORMATION: Lys, Asp, Ser, Pro, Glu, Arg, Thr, Gln, His, Gly, Ile, Met, Phe, Tyr or Val
<220> FEATURE:
<221> NAME/KEY: MOD_RES
<222> LOCATION: (2)..(2)
<223> OTHER INFORMATION: Ile, Ala, Gly, Ser, Phe, Thr, Leu, Cys, Lys, Tyr, Gln or Glu
<220> FEATURE:
<221> NAME/KEY: MOD_RES
<222> LOCATION: (3)..(3)
<223> OTHER INFORMATION: Thr, Gly, Asn, Arg, Cys, Ala, Val, Ile, Leu, Phe or Lys
<220> FEATURE:
<221> NAME/KEY: MOD_RES
<222> LOCATION: (4)..(4)
<223> OTHER INFORMATION: Ser, Val, Ile, Ala, Pro, His, Gln, Leu, Gly, Met, Lys or Arg
<220> FEATURE:
<221> NAME/KEY: MOD_RES
<222> LOCATION: (5)..(5)
<223> OTHER INFORMATION: Ile, Ala, Leu, Gly, Tyr, Glu, Arg, Ser, Thr or Phe
<220> FEATURE:
<221> NAME/KEY: MOD_RES
<222> LOCATION: (6)..(6)
<223> OTHER INFORMATION: Thr, Leu, His, Arg, Pro, Ala, Val, Ile, Lys, Ser, Asn or Glu
<220> FEATURE:
<221> NAME/KEY: MOD_RES
<222> LOCATION: (7)..(7)
<223> OTHER INFORMATION: Arg, Tyr, Trp, Gly, Phe, Ser, Met, Ala, Val, Ile, Pro or Lys
<220> FEATURE:
<221> NAME/KEY: MOD_RES
<222> LOCATION: (8)..(8)
<223> OTHER INFORMATION: Ala, Pro, Ser, Gln, Ile, Arg, Tyr, Val, Gly or His
<220> FEATURE:
<221> NAME/KEY: MOD_RES
<222> LOCATION: (9)..(9)
<223> OTHER INFORMATION: Gln, Arg, Tyr, Pro, Asn, Leu, Asp, Thr, Gly, Met, Val, Trp, Ser or Glu
<220> FEATURE:
<221> NAME/KEY: MOD_RES
<222> LOCATION: (10)..(10)
<223> OTHER INFORMATION: Arg, Glu, Ser, Trp, Ala, Val, Pro or Asn
<220> FEATURE:
<221> NAME/KEY: MOD_RES
<222> LOCATION: (11)..(11)
<223> OTHER INFORMATION: Val, Thr, Leu, Asn, Phe, Met, Ser, Gly, Ala, Arg or Asp
<220> FEATURE:
<221> NAME/KEY: MOD_RES
<222> LOCATION: (12)..(12)
<223> OTHER INFORMATION: Lys, Met, Ser, Gln, Thr, Asn, Gly, Glu, Leu, Ala, Trp, Ile, Pro or His
<220> FEATURE:
<221> NAME/KEY: MOD_RES
<222> LOCATION: (13)..(13)
<223> OTHER INFORMATION: Ala, Ser, Leu, Gln, Thr, Arg, His or Glu
<220> FEATURE:
<221> NAME/KEY: MOD_RES
<222> LOCATION: (14)..(14)

-continued

<223> OTHER INFORMATION: Thr, Ala, Ile, Met, Leu, Gly, Glu, Ser, Pro,
      Gln, Cys, Trp, His or Arg
<220> FEATURE:
<221> NAME/KEY: MOD_RES
<222> LOCATION: (15)..(15)
<223> OTHER INFORMATION: Ile, Ala, Leu, Met, Gly, Thr, Glu, Ser, Pro,
      Phe, Cys, Trp, Arg, Tyr or Asn
<220> FEATURE:
<221> NAME/KEY: MOD_RES
<222> LOCATION: (16)..(16)
<223> OTHER INFORMATION: Thr, Pro, Leu, Ala, Val, Gln, Ile, Phe, Asn,
      His, Lys or Tyr
<220> FEATURE:
<221> NAME/KEY: MOD_RES
<222> LOCATION: (17)..(17)
<223> OTHER INFORMATION: Ser, Ala, Ile, Asn, Pro, Leu, His, Gly, Val,
      Arg or Gln
<220> FEATURE:
<221> NAME/KEY: MOD_RES
<222> LOCATION: (18)..(18)
<223> OTHER INFORMATION: His, Arg, Ser, Pro, Lys, Ala, Glu, Leu, Thr,
      Asn or Met
<220> FEATURE:
<221> NAME/KEY: MOD_RES
<222> LOCATION: (19)..(19)
<223> OTHER INFORMATION: Phe, Pro, Val, Met, Ser, Ile, Thr, Ala, Cys,
      Gln, Arg, Tyr, Trp or His
<220> FEATURE:
<221> NAME/KEY: MOD_RES
<222> LOCATION: (20)..(20)
<223> OTHER INFORMATION: Ile, Pro, Val, Ala, Thr, Met, Ser, Gln, Arg,
      Cys, Phe, Tyr, Gly, Asn, Trp or Lys
<220> FEATURE:
<221> NAME/KEY: MOD_RES
<222> LOCATION: (21)..(21)
<223> OTHER INFORMATION: Val, Phe, Ile, Ser, Met, Pro, Trp, Tyr, Gly,
      Thr, Gln, Cys or Glu
<220> FEATURE:
<221> NAME/KEY: MOD_RES
<222> LOCATION: (22)..(22)
<223> OTHER INFORMATION: Asp, Ser, Lys, Pro, Tyr, His, Thr, Ile, Met,
      Phe, Ala, Gly, Leu, Trp or Glu
<220> FEATURE:
<221> NAME/KEY: MOD_RES
<222> LOCATION: (23)..(23)
<223> OTHER INFORMATION: Pro, Ser, Ala, Asp, Cys, Val, Trp, Arg, Asn,
      Phe or Glu
<220> FEATURE:
<221> NAME/KEY: MOD_RES
<222> LOCATION: (24)..(24)
<223> OTHER INFORMATION: Thr, Gly, Arg, Asn, Cys, Ile, Ala, Val, Gln,
      Leu, Pro, Lys, Met or Asp
<220> FEATURE:
<221> NAME/KEY: MOD_RES
<222> LOCATION: (25)..(25)
<223> OTHER INFORMATION: Ile, Val, Thr, Arg, Pro, Gln, Ser, Phe, Ala,
      Tyr, Met, Gly, Lys or Gln
<220> FEATURE:
<221> NAME/KEY: MOD_RES
<222> LOCATION: (26)..(26)
<223> OTHER INFORMATION: Ser, Thr, Val, Pro, Glu, Gly, Asp, Gln, Leu,
      Arg, Lys, Tyr, Asn, Cys, Met or Phe
<220> FEATURE:
<221> NAME/KEY: MOD_RES
<222> LOCATION: (27)..(27)
<223> OTHER INFORMATION: Lys, Gly, Ala, Arg, Asp, Thr, Gln, Val, Asn,
      Ser, Leu, Ile, His or Tyr

<400> SEQUENCE: 16

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25
```

<210> SEQ ID NO 17
<211> LENGTH: 22

<212> TYPE: PRT
<213> ORGANISM: Human immunodeficiency virus 1
<220> FEATURE:
<223> OTHER INFORMATION: third motif
<220> FEATURE:
<221> NAME/KEY: MOD_RES
<222> LOCATION: (1)..(1)
<223> OTHER INFORMATION: Ala, Thr, Pro, Val, Leu, Ile, Gln, Arg, Lys, Asn, Gly, Glu, His, Tyr, Phe, Met, Trp, Asp or Cys
<220> FEATURE:
<221> NAME/KEY: MOD_RES
<222> LOCATION: (2)..(2)
<223> OTHER INFORMATION: Glu, Arg, Asp, Ser, Pro, Ala, Lys, Leu, Gln, Asn, Val, Trp, Ile, His or Thr
<220> FEATURE:
<221> NAME/KEY: MOD_RES
<222> LOCATION: (3)..(3)
<223> OTHER INFORMATION: Glu, Arg, Lys, Ser, Trp, Val, Leu, Ala, Asn, Thr, Ile, Phe, Asp or Gln
<220> FEATURE:
<221> NAME/KEY: MOD_RES
<222> LOCATION: (4)..(4)
<223> OTHER INFORMATION: Gly, Thr, Met, Ala, Glu, His, Val, Ile, Ser, Arg, Tyr, Pro, Phe, Gln, Leu, Lys or Met
<220> FEATURE:
<221> NAME/KEY: MOD_RES
<222> LOCATION: (5)..(5)
<223> OTHER INFORMATION: Leu, Ile, Val, Ser, Gln, Ala, Met, Thr, Arg, Glu, Asp, Phe, His, Tyr, Lys, Trp, Asn, Cys or Gly
<220> FEATURE:
<221> NAME/KEY: MOD_RES
<222> LOCATION: (6)..(6)
<223> OTHER INFORMATION: Lys, Gln, Gly, Asp, Arg, Val, Asn, Ala, Pro, Ser, Leu, Ile, His, Thr or Tyr
<220> FEATURE:
<221> NAME/KEY: MOD_RES
<222> LOCATION: (7)..(7)
<223> OTHER INFORMATION: Val, Leu, Thr, Phe, Asn, Met, Ser, Ala, Tyr, Gly, Pro, Lys, Asp, Cys, His or Arg
<220> FEATURE:
<221> NAME/KEY: MOD_RES
<222> LOCATION: (8)..(8)
<223> OTHER INFORMATION: Thr, Ile, Glu, Ala, Met, Lys, Ser, Leu, Arg, Gln, Pro, Tyr, Cys, Gly, Asn, His, Phe or Asp
<220> FEATURE:
<221> NAME/KEY: MOD_RES
<222> LOCATION: (9)..(9)
<223> OTHER INFORMATION: Thr, Leu, Arg, Lys, Ser, Ala, His, Gln, Val, Ile, Phe, Asn, Pro, Tyr, Glu, Cys, Gly, Asp or Trp
<220> FEATURE:
<221> NAME/KEY: MOD_RES
<222> LOCATION: (10)..(10)
<223> OTHER INFORMATION: Leu, Tyr, Phe, Arg, Ile, Pro, Thr, Ser, Asn, Gln, Val, Asp, Ala, Gly, Met, Cys, Trp or Glu
<220> FEATURE:
<221> NAME/KEY: MOD_RES
<222> LOCATION: (11)..(11)
<223> OTHER INFORMATION: Thr, His, Asn, Ile, Met, Arg, Gly, Phe, Tyr, Leu, Ala, Gln, Lys, Cys, Val, Pro, Asp, Trp or Glu
<220> FEATURE:
<221> NAME/KEY: MOD_RES
<222> LOCATION: (12)..(12)
<223> OTHER INFORMATION: Val, Leu, Ser, Ile, Cys, Tyr, His, Thr, Arg, Trp, Gly or Asn
<220> FEATURE:
<221> NAME/KEY: MOD_RES
<222> LOCATION: (13)..(13)
<223> OTHER INFORMATION: Thr, Ile, Ser, Cys, Asp, Tyr, Val, His, Lys, Phe, Leu, Met, Pro, Arg, Gly, Gln, Glu or Ala
<220> FEATURE:
<221> NAME/KEY: MOD_RES
<222> LOCATION: (14)..(14)
<223> OTHER INFORMATION: Arg, Trp, Tyr, Ser, Val, Gly, Leu, Phe, Ile, His, Ala, Asn or Gln
<220> FEATURE:
<221> NAME/KEY: MOD_RES
<222> LOCATION: (15)..(15)
<223> OTHER INFORMATION: Arg, Ala, Lys, Gln, His, Glu, Met, Asn, Val, Ser, Thr, Trp, Tyr, Cys, Ile, Asp, Lys or Phe
<220> FEATURE:
<221> NAME/KEY: MOD_RES
<222> LOCATION: (16)..(16)
<223> OTHER INFORMATION: Glu, Arg, Lys, Trp, Val, Ser, Ala, Leu, Asn, Asp, Ile, Phe or Tyr
<220> FEATURE:
<221> NAME/KEY: MOD_RES
<222> LOCATION: (17)..(17)
<223> OTHER INFORMATION: Gly, Lys, Asp, Asn, Arg, Val, Ala, Leu, Phe, Ser, Gln, Trp, His, Tyr, Cys, Met or Thr
<220> FEATURE:
<221> NAME/KEY: MOD_RES
<222> LOCATION: (18)..(18)
<223> OTHER INFORMATION: Leu, Ser, Ile, Tyr, Val, Cys, Asn, Gly, Met, Trp or Gln
<220> FEATURE:
<221> NAME/KEY: MOD_RES
<222> LOCATION: (19)..(19)
<223> OTHER INFORMATION: Leu, Ser, Tyr, Val, Pro, Ile, Cys, Asp, Ala, Met or Asn
<220> FEATURE:
<221> NAME/KEY: MOD_RES
<222> LOCATION: (20)..(20)
<223> OTHER INFORMATION: Phe, Asn, Cys, His, Ser, Leu, Val, Ile, Thr, Pro, Gly, Met, Trp, Lys, Asp or Glu
<220> FEATURE:
<221> NAME/KEY: MOD_RES
<222> LOCATION: (21)..(21)
<223> OTHER INFORMATION: Arg, Tyr, Leu, Ser, Trp, Gly, Ala, Phe, Val, Ile, Met, Thr, Pro or Lys
<220> FEATURE:
<221> NAME/KEY: MOD_RES
<222> LOCATION: (22)..(22)
<223> OTHER INFORMATION: Asp, Ser, Lys, Tyr, Thr, Glu, Ile, His, Gly, Cys, Gln, Arg, Ala, Val, Pro, Met or Phe

<400> SEQUENCE: 17

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20
```

<210> SEQ ID NO 18
<211> LENGTH: 22
<212> TYPE: PRT
<213> ORGANISM: Human immunodeficiency virus 1
<220> FEATURE:
<223> OTHER INFORMATION: fifth motif
<220> FEATURE:
<221> NAME/KEY: MOD_RES
<222> LOCATION: (1)..(1)
<223> OTHER INFORMATION: Leu, Val, Ile, Ser, Thr, Tyr, Cys, Met, Ala, Pro, Asn, Trp, His, Arg or Asp
<220> FEATURE:
<221> NAME/KEY: MOD_RES
<222> LOCATION: (2)..(2)
<223> OTHER INFORMATION: Gly, Lys, Thr, Ser, Ile, Tyr, Gln, Leu, Glu, Pro, Val, Cys, Trp, Asp, Met, Phe or Asn
<220> FEATURE:
<221> NAME/KEY: MOD_RES
<222> LOCATION: (3)..(3)
<223> OTHER INFORMATION: Leu, Ser, Ala, Asp, Arg, His, Thr, Gln, Asn, Gly or Glu
<220> FEATURE:
<221> NAME/KEY: MOD_RES
<222> LOCATION: (4)..(4)
<223> OTHER INFORMATION: Ala, Glu, Ile, Val, Thr, Gln, Leu, Arg, Ser, Trp, Met, Pro, Lys or Asn
<220> FEATURE:
<221> NAME/KEY: MOD_RES
<222> LOCATION: (5)..(5)
<223> OTHER INFORMATION: Arg, Glu, Ser, Ala, Leu, Lys, Cys, Pro, Asn or Gln
<220> FEATURE:
<221> NAME/KEY: MOD_RES
<222> LOCATION: (6)..(6)

```
<223> OTHER INFORMATION: Glu, Arg, Lys, Ser, Ala, Asp, Cys or Asn
<220> FEATURE:
<221> NAME/KEY: MOD_RES
<222> LOCATION: (7)..(7)
<223> OTHER INFORMATION: Asn, Glu, Gly, Tyr, Ser, Ile, His, Arg, Ala,
      Val, Gln, Thr or Lys
<220> FEATURE:
<221> NAME/KEY: MOD_RES
<222> LOCATION: (8)..(8)
<223> OTHER INFORMATION: Ile, Thr, Val, Leu, Arg, Tyr, Lys, Phe, Gly or
      Ser
<220> FEATURE:
<221> NAME/KEY: MOD_RES
<222> LOCATION: (9)..(9)
<223> OTHER INFORMATION: Lys, Met, Gln, Gly, Glu, Val, Thr, Asn, Trp,
      Ile, Phe or Ser
<220> FEATURE:
<221> NAME/KEY: MOD_RES
<222> LOCATION: (10)..(10)
<223> OTHER INFORMATION: Asn, Glu, Gly, Val, His, Ala, Leu, Cys, Trp,
      Arg, Lys, Ser, Thr or Tyr
<220> FEATURE:
<221> NAME/KEY: MOD_RES
<222> LOCATION: (11)..(11)
<223> OTHER INFORMATION: Ile, Ser, Asp, Lys, Leu, His, Tyr, Thr, Gln,
      Gly, Arg, Ala, Cys or Met
<220> FEATURE:
<221> NAME/KEY: MOD_RES
<222> LOCATION: (12)..(12)
<223> OTHER INFORMATION: Ser, Arg, Gly, Asn, Cys, Leu, Phe, Pro or Lys
<220> FEATURE:
<221> NAME/KEY: MOD_RES
<222> LOCATION: (13)..(13)
<223> OTHER INFORMATION: Lys, Gly, Ala, Ser, Glu, Thr, Leu or Ile
<220> FEATURE:
<221> NAME/KEY: MOD_RES
<222> LOCATION: (14)..(14)
<223> OTHER INFORMATION: Asn, Thr, Gly, Arg, Gln, Met, Asp, Ile, Cys,
      Lys, Tyr, Ala, Val or His
<220> FEATURE:
<221> NAME/KEY: MOD_RES
<222> LOCATION: (15)..(15)
<223> OTHER INFORMATION: Lys, Glu, Gly, Asp, Arg, Ala, Val, Asn, His or
      Met
<220> FEATURE:
<221> NAME/KEY: MOD_RES
<222> LOCATION: (16)..(16)
<223> OTHER INFORMATION: Ile, Phe, Ser, Val, Met, Pro, Lys, Asn, Gln or
      Glu
<220> FEATURE:
<221> NAME/KEY: MOD_RES
<222> LOCATION: (17)..(17)
<223> OTHER INFORMATION: Phe, Leu, His, Cys, Ser, Asp, Ile, Ala, Val,
      Asn or Glu
<220> FEATURE:
<221> NAME/KEY: MOD_RES
<222> LOCATION: (18)..(18)
<223> OTHER INFORMATION: Arg, Asn, Gln, Glu, Thr, Tyr, Pro, Gly, Val,
      Leu, Ile, Met, Ser or Asp
<220> FEATURE:
<221> NAME/KEY: MOD_RES
<222> LOCATION: (19)..(19)
<223> OTHER INFORMATION: His, Cys, Asn, Phe, Ser, Ile or Glu
<220> FEATURE:
<221> NAME/KEY: MOD_RES
<222> LOCATION: (20)..(20)
<223> OTHER INFORMATION: Arg, Glu, Asn, Thr, Gln, Gly, Ile or Pro
<220> FEATURE:
<221> NAME/KEY: MOD_RES
<222> LOCATION: (21)..(21)
<223> OTHER INFORMATION: Ile, Thr, Ala, Leu, Gly, Met, Ser or Asp
<220> FEATURE:
<221> NAME/KEY: MOD_RES
<222> LOCATION: (22)..(22)
<223> OTHER INFORMATION: Ile, Ala, Leu, Glu, Gly, Ser, Met or Lys

<400> SEQUENCE: 18

Xaa Xaa Xaa Xaa Xaa Xaa Xaa Xaa Xaa Xaa Xaa Xaa Xaa Xaa Xaa Xaa
```

```
1               5                   10                  15

Xaa Xaa Xaa Xaa Xaa Xaa
            20


<210> SEQ ID NO 19
<211> LENGTH: 17
<212> TYPE: PRT
<213> ORGANISM: Human immunodeficiency virus 2
<220> FEATURE:
<223> OTHER INFORMATION: first motif
<220> FEATURE:
<221> NAME/KEY: MOD_RES
<222> LOCATION: (1)..(1)
<223> OTHER INFORMATION: Arg, Ser or Thr
<220> FEATURE:
<221> NAME/KEY: MOD_RES
<222> LOCATION: (2)..(2)
<223> OTHER INFORMATION: Tyr, Val or Trp
<220> FEATURE:
<221> NAME/KEY: MOD_RES
<222> LOCATION: (3)..(3)
<223> OTHER INFORMATION: Asn, Trp or Tyr
<220> FEATURE:
<221> NAME/KEY: MOD_RES
<222> LOCATION: (4)..(4)
<223> OTHER INFORMATION: Glu or Asn
<220> FEATURE:
<221> NAME/KEY: MOD_RES
<222> LOCATION: (5)..(5)
<223> OTHER INFORMATION: Thr, Leu or Lys
<220> FEATURE:
<221> NAME/KEY: MOD_RES
<222> LOCATION: (7)..(7)
<223> OTHER INFORMATION: Tyr or Glu
<220> FEATURE:
<221> NAME/KEY: MOD_RES
<222> LOCATION: (8)..(8)
<223> OTHER INFORMATION: Ser, Thr or Val
<220> FEATURE:
<221> NAME/KEY: MOD_RES
<222> LOCATION: (9)..(9)
<223> OTHER INFORMATION: Val or Thr
<220> FEATURE:
<221> NAME/KEY: MOD_RES
<222> LOCATION: (10)..(10)
<223> OTHER INFORMATION: Asp, Ile or Cys
<220> FEATURE:
<221> NAME/KEY: MOD_RES
<222> LOCATION: (11)..(11)
<223> OTHER INFORMATION: Val or Glu
<220> FEATURE:
<221> NAME/KEY: MOD_RES
<222> LOCATION: (12)..(12)
<223> OTHER INFORMATION: Val or Thr
<220> FEATURE:
<221> NAME/KEY: MOD_RES
<222> LOCATION: (14)..(14)
<223> OTHER INFORMATION: Asp, Glu or Arg
<220> FEATURE:
<221> NAME/KEY: MOD_RES
<222> LOCATION: (15)..(15)
<223> OTHER INFORMATION: Asn or Glu
<220> FEATURE:
<221> NAME/KEY: MOD_RES
<222> LOCATION: (16)..(16)
<223> OTHER INFORMATION: Asn or Ser
<220> FEATURE:
<221> NAME/KEY: MOD_RES
<222> LOCATION: (17)..(17)
<223> OTHER INFORMATION: Ser or Gln

<400> SEQUENCE: 19

Xaa Xaa Xaa Xaa Xaa Phe Xaa Xaa Xaa Xaa Xaa Xaa Thr Xaa Xaa Xaa
1               5                   10                  15

Xaa
```

<210> SEQ ID NO 20
<211> LENGTH: 27
<212> TYPE: PRT
<213> ORGANISM: Human immunodeficiency virus 2
<220> FEATURE:
<223> OTHER INFORMATION: second motif
<220> FEATURE:
<221> NAME/KEY: MOD_RES
<222> LOCATION: (1)..(1)
<223> OTHER INFORMATION: Lys, Arg or Ser
<220> FEATURE:
<221> NAME/KEY: MOD_RES
<222> LOCATION: (2)..(2)
<223> OTHER INFORMATION: Ile or Lys
<220> FEATURE:
<221> NAME/KEY: MOD_RES
<222> LOCATION: (3)..(3)
<223> OTHER INFORMATION: Val, Ile or Phe
<220> FEATURE:
<221> NAME/KEY: MOD_RES
<222> LOCATION: (4)..(4)
<223> OTHER INFORMATION: Ala, Val or Ser
<220> FEATURE:
<221> NAME/KEY: MOD_RES
<222> LOCATION: (5)..(5)
<223> OTHER INFORMATION: Ala, Ser, Thr or Gly
<220> FEATURE:
<221> NAME/KEY: MOD_RES
<222> LOCATION: (6)..(6)
<223> OTHER INFORMATION: Thr, Ser or Ala
<220> FEATURE:
<221> NAME/KEY: MOD_RES
<222> LOCATION: (7)..(7)
<223> OTHER INFORMATION: Arg or Leu
<220> FEATURE:
<221> NAME/KEY: MOD_RES
<222> LOCATION: (8)..(8)
<223> OTHER INFORMATION: Ala or Tyr
<220> FEATURE:
<221> NAME/KEY: MOD_RES
<222> LOCATION: (9)..(9)
<223> OTHER INFORMATION: Arg or Gly
<220> FEATURE:
<221> NAME/KEY: MOD_RES
<222> LOCATION: (10)..(10)
<223> OTHER INFORMATION: Met, Val, Glu, Leu, Ile or Gln
<220> FEATURE:
<221> NAME/KEY: MOD_RES
<222> LOCATION: (11)..(11)
<223> OTHER INFORMATION: Met, Arg, Lys or Thr
<220> FEATURE:
<221> NAME/KEY: MOD_RES
<222> LOCATION: (12)..(12)
<223> OTHER INFORMATION: Glu, Lys or Gly
<220> FEATURE:
<221> NAME/KEY: MOD_RES
<222> LOCATION: (13)..(13)
<223> OTHER INFORMATION: Thr, Ser, Ala or Met
<220> FEATURE:
<221> NAME/KEY: MOD_RES
<222> LOCATION: (15)..(15)
<223> OTHER INFORMATION: Thr, Ser, Ala or Pro
<220> FEATURE:
<221> NAME/KEY: MOD_RES
<222> LOCATION: (17)..(17)
<223> OTHER INFORMATION: Ala, Met or Ser
<220> FEATURE:
<221> NAME/KEY: MOD_RES
<222> LOCATION: (19)..(19)
<223> OTHER INFORMATION: Phe or Ser
<220> FEATURE:
<221> NAME/KEY: MOD_RES
<222> LOCATION: (20)..(20)
<223> OTHER INFORMATION: Gly or Ala
<220> FEATURE:
<221> NAME/KEY: MOD_RES
<222> LOCATION: (22)..(22)

```
<223> OTHER INFORMATION: Cys or Ser
<220> FEATURE:
<221> NAME/KEY: MOD_RES
<222> LOCATION: (23)..(23)
<223> OTHER INFORMATION: Ser or Pro
<220> FEATURE:
<221> NAME/KEY: MOD_RES
<222> LOCATION: (24)..(24)
<223> OTHER INFORMATION: Thr, Ala or Ile
<220> FEATURE:
<221> NAME/KEY: MOD_RES
<222> LOCATION: (25)..(25)
<223> OTHER INFORMATION: Arg or Lys
<220> FEATURE:
<221> NAME/KEY: MOD_RES
<222> LOCATION: (27)..(27)
<223> OTHER INFORMATION: Gly, Lys, Val or Asp

<400> SEQUENCE: 20

Xaa Xaa Xaa Xaa Xaa Xaa Xaa Xaa Xaa Xaa Xaa Xaa Xaa Gln Xaa Ser
1               5                   10                  15

Xaa Trp Xaa Xaa Phe Xaa Xaa Xaa Xaa Ser Xaa
            20                  25


<210> SEQ ID NO 21
<211> LENGTH: 22
<212> TYPE: PRT
<213> ORGANISM: Human immunodeficiency virus 2
<220> FEATURE:
<223> OTHER INFORMATION: third motif
<220> FEATURE:
<221> NAME/KEY: MOD_RES
<222> LOCATION: (1)..(1)
<223> OTHER INFORMATION: Ala, Lys, Arg, Glu, Gly, Thr, Gln, Val, Asp,
      Pro or Asn
<220> FEATURE:
<221> NAME/KEY: MOD_RES
<222> LOCATION: (2)..(2)
<223> OTHER INFORMATION: Pro, Ser, Asp, Asn or Lys
<220> FEATURE:
<221> NAME/KEY: MOD_RES
<222> LOCATION: (3)..(3)
<223> OTHER INFORMATION: Ser, Ala, Pro or Arg
<220> FEATURE:
<221> NAME/KEY: MOD_RES
<222> LOCATION: (4)..(4)
<223> OTHER INFORMATION: Asn, Gly or Ser
<220> FEATURE:
<221> NAME/KEY: MOD_RES
<222> LOCATION: (5)..(5)
<223> OTHER INFORMATION: Ala, Gly or Ser
<220> FEATURE:
<221> NAME/KEY: MOD_RES
<222> LOCATION: (6)..(6)
<223> OTHER INFORMATION: Asp, Pro, Lys or Gln
<220> FEATURE:
<221> NAME/KEY: MOD_RES
<222> LOCATION: (7)..(7)
<223> OTHER INFORMATION: Val, Ala, Thr or Glu
<220> FEATURE:
<221> NAME/KEY: MOD_RES
<222> LOCATION: (8)..(8)
<223> OTHER INFORMATION: Ala, Thr, Arg, Glu, Met, Lys or Ser
<220> FEATURE:
<221> NAME/KEY: MOD_RES
<222> LOCATION: (9)..(9)
<223> OTHER INFORMATION: Tyr, Phe or His
<220> FEATURE:
<221> NAME/KEY: MOD_RES
<222> LOCATION: (10)..(10)
<223> OTHER INFORMATION: Met, Leu or Thr
<220> FEATURE:
<221> NAME/KEY: MOD_RES
<222> LOCATION: (11)..(11)
<223> OTHER INFORMATION: Trp or Arg
<220> FEATURE:
```

<221> NAME/KEY: MOD_RES
<222> LOCATION: (12)..(12)
<223> OTHER INFORMATION: Thr, Ser or Ile
<220> FEATURE:
<221> NAME/KEY: MOD_RES
<222> LOCATION: (15)..(15)
<223> OTHER INFORMATION: Arg, Met, Lys or Gln
<220> FEATURE:
<221> NAME/KEY: MOD_RES
<222> LOCATION: (17)..(17)
<223> OTHER INFORMATION: Lys or Asp
<220> FEATURE:
<221> NAME/KEY: MOD_RES
<222> LOCATION: (18)..(18)
<223> OTHER INFORMATION: Leu or Ser
<220> FEATURE:
<221> NAME/KEY: MOD_RES
<222> LOCATION: (19)..(19)
<223> OTHER INFORMATION: Leu, Pro, Ser or Tyr
<220> FEATURE:
<221> NAME/KEY: MOD_RES
<222> LOCATION: (20)..(20)
<223> OTHER INFORMATION: His or Cys
<220> FEATURE:
<221> NAME/KEY: MOD_RES
<222> LOCATION: (22)..(22)
<223> OTHER INFORMATION: Asp, Ser or Lys

<400> SEQUENCE: 21

```
Xaa Xaa Xaa Xaa Xaa Xaa Xaa Xaa Xaa Xaa Xaa Xaa Asp Cys Xaa Arg
1               5                   10                  15

Xaa Xaa Xaa Xaa Cys Xaa
            20
```

<210> SEQ ID NO 22
<211> LENGTH: 22
<212> TYPE: PRT
<213> ORGANISM: Human immunodeficiency virus 2
<220> FEATURE:
<223> OTHER INFORMATION: fifth motif
<220> FEATURE:
<221> NAME/KEY: MOD_RES
<222> LOCATION: (1)..(1)
<223> OTHER INFORMATION: Asn, Ser, Ile, Tyr, Val, Arg or Asp
<220> FEATURE:
<221> NAME/KEY: MOD_RES
<222> LOCATION: (2)..(2)
<223> OTHER INFORMATION: Ile, Ser, Met or Thr
<220> FEATURE:
<221> NAME/KEY: MOD_RES
<222> LOCATION: (3)..(3)
<223> OTHER INFORMATION: Thr, Ala, Leu or Ser
<220> FEATURE:
<221> NAME/KEY: MOD_RES
<222> LOCATION: (4)..(4)
<223> OTHER INFORMATION: Phe, Met, Val, Glu, Pro or Ser
<220> FEATURE:
<221> NAME/KEY: MOD_RES
<222> LOCATION: (5)..(5)
<223> OTHER INFORMATION: Ser, Val, Ala, Leu, Ile or Asn
<220> FEATURE:
<221> NAME/KEY: MOD_RES
<222> LOCATION: (8)..(8)
<223> OTHER INFORMATION: Val, Leu, Tyr or Glu
<220> FEATURE:
<221> NAME/KEY: MOD_RES
<222> LOCATION: (9)..(9)
<223> OTHER INFORMATION: Ala, Ser, Gly or Lys
<220> FEATURE:
<221> NAME/KEY: MOD_RES
<222> LOCATION: (10)..(10)
<223> OTHER INFORMATION: Glu, Lys or Asn
<220> FEATURE:
<221> NAME/KEY: MOD_RES
<222> LOCATION: (11)..(11)
<223> OTHER INFORMATION: Leu, Met or Lys
<220> FEATURE:
<221> NAME/KEY: MOD_RES
<222> LOCATION: (12)..(12)
<223> OTHER INFORMATION: Tyr, Phe or Asn
<220> FEATURE:
<221> NAME/KEY: MOD_RES
<222> LOCATION: (14)..(14)
<223> OTHER INFORMATION: Leu or Val
<220> FEATURE:
<221> NAME/KEY: MOD_RES
<222> LOCATION: (16)..(16)
<223> OTHER INFORMATION: Pro or Ser
<220> FEATURE:
<221> NAME/KEY: MOD_RES
<222> LOCATION: (20)..(20)
<223> OTHER INFORMATION: Thr or Asn
<220> FEATURE:
<221> NAME/KEY: MOD_RES
<222> LOCATION: (21)..(21)
<223> OTHER INFORMATION: Leu or Ser

<400> SEQUENCE: 22

```
Xaa Xaa Xaa Xaa Xaa Ala Glu Xaa Xaa Xaa Xaa Xaa Lys Xaa Lys Gly
1               5                   10                  15

Xaa Asp Tyr Xaa Xaa Ile
            20
```

<210> SEQ ID NO 23
<211> LENGTH: 22
<212> TYPE: PRT
<213> ORGANISM: Human immunodeficiency virus 1
<220> FEATURE:
<223> OTHER INFORMATION: external motif
<220> FEATURE:
<221> NAME/KEY: MOD_RES
<222> LOCATION: (1)..(1)
<223> OTHER INFORMATION: Arg, Ser, Tyr, Met, Phe, Gly, Ala, Leu, Ile, Val, Trp, Pro, Thr, His or Asn
<220> FEATURE:
<221> NAME/KEY: MOD_RES
<222> LOCATION: (2)..(2)
<223> OTHER INFORMATION: Lys, Gly, Ser, Asn, Gln, Ile, Thr, Glu, Pro, His, Met, Trp, Leu, Cys, Tyr, Val or Asp
<220> FEATURE:
<221> NAME/KEY: MOD_RES
<222> LOCATION: (3)..(3)
<223> OTHER INFORMATION: Leu, Met, Val, Thr, Asn, Arg, Lys, Tyr, Cys, Ser, Pro, Phe, His, Asp or Glu
<220> FEATURE:
<221> NAME/KEY: MOD_RES
<222> LOCATION: (4)..(4)
<223> OTHER INFORMATION: Arg, Asn, Glu, Ile, Thr, Gln, Ser, Gly, Pro, Met, Tyr, Leu, His, Ala or Asp
<220> FEATURE:
<221> NAME/KEY: MOD_RES
<222> LOCATION: (5)..(5)
<223> OTHER INFORMATION: Leu, His, Arg, Pro, Lys, Ala, Asn, Glu, Gly, Thr, Met, Val or Ser
<220> FEATURE:
<221> NAME/KEY: MOD_RES
<222> LOCATION: (6)..(6)
<223> OTHER INFORMATION: Phe, Val, Leu, Met, Thr, Tyr, Asn, Ser, Lys, Ala, Pro, Arg or Asp
<220> FEATURE:
<221> NAME/KEY: MOD_RES
<222> LOCATION: (7)..(7)
<223> OTHER INFORMATION: Val, Met, Thr, Leu, Ala, Tyr, Lys, Gly, Glu, Cys, Arg, Ser or Gln
<220> FEATURE:
<221> NAME/KEY: MOD_RES
<222> LOCATION: (8)..(8)
<223> OTHER INFORMATION: Arg, His, Lys, Ser, Asp, Ile, Thr, Tyr, Gly, Gln, Leu, Cys, Met, Val, Glu, Pro or Phe
<220> FEATURE:
<221> NAME/KEY: MOD_RES
<222> LOCATION: (9)..(9)

<223> OTHER INFORMATION: Arg, Leu, Lys, Thr, Ser, Val, Ile, Pro, Gly, Tyr, His, Gln, Asn, Ala, Cys, Trp or Asp
<220> FEATURE:
<221> NAME/KEY: MOD_RES
<222> LOCATION: (10)..(10)
<223> OTHER INFORMATION: Arg, Cys, Gly, Val, Leu, Met, Ser, Ala, Pro, His, Lys, Tyr, Asn or Gln
<220> FEATURE:
<221> NAME/KEY: MOD_RES
<222> LOCATION: (11)..(11)
<223> OTHER INFORMATION: Arg, Ile, Met, Leu, His, Lys, Ala, Glu, Pro, Thr, Gly, Tyr, Val, Trp or Ser
<220> FEATURE:
<221> NAME/KEY: MOD_RES
<222> LOCATION: (12)..(12)
<223> OTHER INFORMATION: Arg, Gly, Lys, Gln, Thr, Ser, Ala, Ile, Val, Asp, Leu, Pro, His, Asn, Cys, Met, Trp or Tyr
<220> FEATURE:
<221> NAME/KEY: MOD_RES
<222> LOCATION: (13)..(13)
<223> OTHER INFORMATION: Ala, Thr, Ile, Gly, Leu, Ser, Glu, Pro, Lys, Arg, Asn, Gln, Trp or Asp
<220> FEATURE:
<221> NAME/KEY: MOD_RES
<222> LOCATION: (14)..(14)
<223> OTHER INFORMATION: Arg, Glu, Ala, Val, Lys, Gln, Thr, Asn, Asp, Pro, Trp or Ser
<220> FEATURE:
<221> NAME/KEY: MOD_RES
<222> LOCATION: (15)..(15)
<223> OTHER INFORMATION: Gln, Arg, Ser, Thr, Glu, Leu, Pro, Asn, Ile, His, Gly, Ala, Val, Tyr, Cys, Met, Trp or Asp
<220> FEATURE:
<221> NAME/KEY: MOD_RES
<222> LOCATION: (16)..(16)
<223> OTHER INFORMATION: Val, Gly, Thr, Ser, Pro, Gln, Glu, Cys, Trp, Arg, Lys, Tyr or Asp
<220> FEATURE:
<221> NAME/KEY: MOD_RES
<222> LOCATION: (17)..(17)
<223> OTHER INFORMATION: Ile, Thr, Val, Leu, Lys, Asn, Ala, Phe, Arg, Cys, Ser, Pro, Gln, His, Tyr or Glu
<220> FEATURE:
<221> NAME/KEY: MOD_RES
<222> LOCATION: (18)..(18)
<223> OTHER INFORMATION: His, Phe, Cys, Ser, Val, Asp, Asn, Met, Ala, Pro, Leu, Glu, Lys, Tyr or Gly
<220> FEATURE:
<221> NAME/KEY: MOD_RES
<222> LOCATION: (19)..(19)
<223> OTHER INFORMATION: Pro, Thr, Ser, Asn, Val, Cys, Gly, Asp, Leu, Ile, Met or His
<220> FEATURE:
<221> NAME/KEY: MOD_RES
<222> LOCATION: (20)..(20)
<223> OTHER INFORMATION: Ser, Ala, Asn, Leu, Thr, His, Arg, Val, Lys, Asp or Gln
<220> FEATURE:
<221> NAME/KEY: MOD_RES
<222> LOCATION: (21)..(21)
<223> OTHER INFORMATION: Ser, Leu, Ala, Thr, Phe, Arg, His, Gly, Tyr, Asn or Gln
<220> FEATURE:
<221> NAME/KEY: MOD_RES
<222> LOCATION: (22)..(22)
<223> OTHER INFORMATION: Val, Ser, Thr, Arg, Leu, Phe, Met, Asn, Pro, His, Ala, Lys, Gly, Trp, Tyr or Asp

<400> SEQUENCE: 23

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20
```

<210> SEQ ID NO 24
<211> LENGTH: 22

<212> TYPE: PRT
<213> ORGANISM: Human immunodeficiency virus 2
<220> FEATURE:
<223> OTHER INFORMATION: external motif
<220> FEATURE:
<221> NAME/KEY: MOD_RES
<222> LOCATION: (1)..(1)
<223> OTHER INFORMATION: Arg or Tyr
<220> FEATURE:
<221> NAME/KEY: MOD_RES
<222> LOCATION: (2)..(2)
<223> OTHER INFORMATION: His or Gln
<220> FEATURE:
<221> NAME/KEY: MOD_RES
<222> LOCATION: (4)..(4)
<223> OTHER INFORMATION: Arg, Pro or Glu
<220> FEATURE:
<221> NAME/KEY: MOD_RES
<222> LOCATION: (6)..(6)
<223> OTHER INFORMATION: Val or Lys
<220> FEATURE:
<221> NAME/KEY: MOD_RES
<222> LOCATION: (9)..(9)
<223> OTHER INFORMATION: Thr, Ala or Ile
<220> FEATURE:
<221> NAME/KEY: MOD_RES
<222> LOCATION: (11)..(11)
<223> OTHER INFORMATION: His or Arg
<220> FEATURE:
<221> NAME/KEY: MOD_RES
<222> LOCATION: (12)..(12)
<223> OTHER INFORMATION: Lys, Arg or Asn
<220> FEATURE:
<221> NAME/KEY: MOD_RES
<222> LOCATION: (13)..(13)
<223> OTHER INFORMATION: Ala, Ile or Ser
<220> FEATURE:
<221> NAME/KEY: MOD_RES
<222> LOCATION: (14)..(14)
<223> OTHER INFORMATION: Trp, Arg or Glu
<220> FEATURE:
<221> NAME/KEY: MOD_RES
<222> LOCATION: (15)..(15)
<223> OTHER INFORMATION: Gln, Arg, Ile, Val, Asn, Thr, Leu or Glu
<220> FEATURE:
<221> NAME/KEY: MOD_RES
<222> LOCATION: (16)..(16)
<223> OTHER INFORMATION: Asn, His, Tyr, Arg or Lys
<220> FEATURE:
<221> NAME/KEY: MOD_RES
<222> LOCATION: (17)..(17)
<223> OTHER INFORMATION: Val, Ile, Ala, Leu or Tyr
<220> FEATURE:
<221> NAME/KEY: MOD_RES
<222> LOCATION: (19)..(19)
<223> OTHER INFORMATION: Leu or Phe
<220> FEATURE:
<221> NAME/KEY: MOD_RES
<222> LOCATION: (20)..(20)
<223> OTHER INFORMATION: Ala or Leu
<220> FEATURE:
<221> NAME/KEY: MOD_RES
<222> LOCATION: (22)..(22)
<223> OTHER INFORMATION: Arg or Lys

<400> SEQUENCE: 24

```
Xaa Xaa Ile Xaa Gln Xaa Val Ser Xaa Arg Xaa Xaa Xaa Xaa Xaa Xaa
1               5                   10                  15

Xaa Ile Xaa Xaa Pro Xaa
            20
```

<210> SEQ ID NO 25
<211> LENGTH: 6
<212> TYPE: PRT
<213> ORGANISM: Artificial Sequence
<220> FEATURE:

```
<223> OTHER INFORMATION: Description of Artificial Sequence: Synthetic
      6xHis tag

<400> SEQUENCE: 25

His His His His His His
1               5


<210> SEQ ID NO 26
<211> LENGTH: 54
<212> TYPE: PRT
<213> ORGANISM: Human immunodeficiency virus 2

<400> SEQUENCE: 26

Val Val Leu Glu Asn Val Thr Glu His Phe Asn Met Trp Lys Asn Asp
1               5                   10                  15

Met Val Glu Gln Met Gln Glu Asp Ile Ile Ser Leu Trp Asp Gln Ser
            20                  25                  30

Leu Lys Pro Cys Val Lys Leu Thr Pro Leu Cys Val Gly Ala Gly Ser
        35                  40                  45

Cys Asp Thr Ser Val Ile
    50


<210> SEQ ID NO 27
<211> LENGTH: 41
<212> TYPE: PRT
<213> ORGANISM: Human immunodeficiency virus 2

<400> SEQUENCE: 27

Gly Lys Gly Pro Cys Lys Asn Val Ser Thr Val Gln Cys Thr His Gly
1               5                   10                  15

Ile Arg Pro Val Val Ser Thr Gln Leu Leu Leu Asn Gly Ser Leu Ala
            20                  25                  30

Glu Glu Glu Val Val Ile Arg Ser Asp
        35                  40


<210> SEQ ID NO 28
<211> LENGTH: 51
<212> TYPE: PRT
<213> ORGANISM: Human immunodeficiency virus 2

<400> SEQUENCE: 28

Arg Glu Gln Phe Glu Asn Lys Thr Ile Val Phe Asn His Ser Ser Gly
1               5                   10                  15

Gly Asp Pro Glu Ile Val Met His Ser Phe Asn Cys Gly Gly Glu Phe
            20                  25                  30

Phe Tyr Cys Asn Ser Ala Gln Leu Phe Asn Ser Thr Trp Asn Asn Asn
        35                  40                  45

Thr Glu Gly
    50


<210> SEQ ID NO 29
<211> LENGTH: 48
<212> TYPE: PRT
<213> ORGANISM: Human immunodeficiency virus 2

<400> SEQUENCE: 29

Gly Ser Asn Asn Thr Glu Gly Asn Thr Ile Thr Leu Pro Cys Arg Ile
1               5                   10                  15

Lys Gln Ile Ile Asn Met Trp Gln Glu Val Gly Lys Ala Met Tyr Ala
            20                  25                  30
```

```
Pro Pro Ile Arg Gly Gln Ile Arg Cys Ser Ser Asn Ile Thr Gly Leu
        35                  40                  45


<210> SEQ ID NO 30
<211> LENGTH: 39
<212> TYPE: PRT
<213> ORGANISM: Human immunodeficiency virus 2

<400> SEQUENCE: 30

Leu Thr Arg Asp Gly Gly Ile Asn Glu Asn Gly Thr Glu Ile Phe Arg
1               5                   10                  15

Pro Gly Gly Gly Asp Met Arg Asp Asn Trp Arg Ser Glu Leu Tyr Lys
            20                  25                  30

Tyr Lys Val Val Lys Ile Glu
        35


<210> SEQ ID NO 31
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Val, Ile, Met, Leu or Ala
<220> FEATURE:
<221> NAME/KEY: MOD_RES
<222> LOCATION: (2)..(2)
<223> OTHER INFORMATION: Val, Glu, Ile, Phe, Leu, Lys, Tyr, Arg, Pro,
      Asp, Met, Ala, Thr, Asn, Ser, Trp, Gly, His or Gln
<220> FEATURE:
<221> NAME/KEY: MOD_RES
<222> LOCATION: (3)..(3)
<223> OTHER INFORMATION: Leu, Met, Val, Ile, Phe, Ser, Trp or Lys
<220> FEATURE:
<221> NAME/KEY: MOD_RES
<222> LOCATION: (4)..(4)
<223> OTHER INFORMATION: Glu, Gly, Lys, Thr, Val, Ala, Asp, Leu, Ile,
      Gln, Tyr, His, Pro or Trp
<220> FEATURE:
<221> NAME/KEY: MOD_RES
<222> LOCATION: (5)..(5)
<223> OTHER INFORMATION: Asn, Ser, Thr, Lys or Asp
<220> FEATURE:
<221> NAME/KEY: MOD_RES
<222> LOCATION: (6)..(6)
<223> OTHER INFORMATION: Val, Thr, Ile, Met, Gly, Cys or Ser
<220> FEATURE:
<221> NAME/KEY: MOD_RES
<222> LOCATION: (7)..(7)
<223> OTHER INFORMATION: Thr, Lys, Ile, Ser, Ala or Arg
<220> FEATURE:
<221> NAME/KEY: MOD_RES
<222> LOCATION: (8)..(8)
<223> OTHER INFORMATION: Glu, Thr, Asp, Gly, Phe or Gln
<220> FEATURE:
<221> NAME/KEY: MOD_RES
<222> LOCATION: (9)..(9)
<223> OTHER INFORMATION: Asn, Glu, Asp, Leu, Ile, Lys, Ser, Pro, Tyr,
      His, Met, Thr, Phe, Val, Trp, Arg or Gln
<220> FEATURE:
<221> NAME/KEY: MOD_RES
<222> LOCATION: (10)..(10)
<223> OTHER INFORMATION: Phe, Arg, Leu, Ile, Lys, Ala, Tyr or Gly
<220> FEATURE:
<221> NAME/KEY: MOD_RES
<222> LOCATION: (11)..(11)
<223> OTHER INFORMATION: Asn, Asp, Lys, Leu, Thr, Ser, Gly, Ala, His,
      Arg or Glu
<220> FEATURE:
<221> NAME/KEY: MOD_RES
<222> LOCATION: (12)..(12)
```

<223> OTHER INFORMATION: Met, Ile, Lys, Ala, Val, Asp, Thr, Cys, Asn, Phe, Leu or Arg
<220> FEATURE:
<221> NAME/KEY: MOD_RES
<222> LOCATION: (13)..(13)
<223> OTHER INFORMATION: Trp, Thr, Lys, Gly, Arg, Ser, Tyr, Cys, Ala, Val, Gln or Phe
<220> FEATURE:
<221> NAME/KEY: MOD_RES
<222> LOCATION: (14)..(14)
<223> OTHER INFORMATION: Lys, Thr, Glu, Arg, Asn, Gln, Gly, Ser, Phe, Asp, Met or Tyr
<220> FEATURE:
<221> NAME/KEY: MOD_RES
<222> LOCATION: (15)..(15)
<223> OTHER INFORMATION: Asn, Thr, His, Gln, Ser, Lys, Phe, Arg, Gly, Leu, Ile, Val, Asp or Glu
<220> FEATURE:
<221> NAME/KEY: MOD_RES
<222> LOCATION: (16)..(16)
<223> OTHER INFORMATION: Asn, Asp, Glu, Lys, Ser, His, Gly, Tyr, Thr, Val, Pro, Ala, Leu, Ile or Arg
<220> FEATURE:
<221> NAME/KEY: MOD_RES
<222> LOCATION: (17)..(17)
<223> OTHER INFORMATION: Met, Tyr, Ile, Leu, Val, Arg, Thr, His, Lys, Ser, Ala or Asp
<220> FEATURE:
<221> NAME/KEY: MOD_RES
<222> LOCATION: (18)..(18)
<223> OTHER INFORMATION: Val, Arg, Ala, Lys, Gln, Met, Thr, Tyr, Ile, Ser, Leu, Gly, Asn, Asp or Glu
<220> FEATURE:
<221> NAME/KEY: MOD_RES
<222> LOCATION: (19)..(19)
<223> OTHER INFORMATION: Glu, Asp, Leu, Asn, Ala, Lys, Gly, Thr, Pro, Gln, Ile, Val, Phe, Arg, Ser or Tyr
<220> FEATURE:
<221> NAME/KEY: MOD_RES
<222> LOCATION: (20)..(20)
<223> OTHER INFORMATION: Gln, Lys, Phe, Arg, Leu, Glu, Ser, Ile, Ala, Val, Cys, Met, His, Thr, Asn or Asp
<220> FEATURE:
<221> NAME/KEY: MOD_RES
<222> LOCATION: (21)..(21)
<223> OTHER INFORMATION: Met, Tyr, Val, Ile, Arg, Phe, Leu, Lys, Gln, Gly, Ser, Asn, Asp or Glu
<220> FEATURE:
<221> NAME/KEY: MOD_RES
<222> LOCATION: (22)..(22)
<223> OTHER INFORMATION: His, Gln, Lys, Arg, Tyr, Asn, Ser, Leu, Pro, Glu, Asp, Gly, Phe or Thr
<220> FEATURE:
<221> NAME/KEY: MOD_RES
<222> LOCATION: (23)..(23)
<223> OTHER INFORMATION: Glu, Lys, Thr, Leu, Arg, Gln, Ile, Asp, Gly, Ser, Ala, Val, Asn, Pro, Tyr or Met
<220> FEATURE:
<221> NAME/KEY: MOD_RES
<222> LOCATION: (24)..(24)
<223> OTHER INFORMATION: Asp, Glu, Thr, Ala, Gln, Asn, Val, Lys, Ser, Gly or Leu
<220> FEATURE:
<221> NAME/KEY: MOD_RES
<222> LOCATION: (25)..(25)
<223> OTHER INFORMATION: Ile, Tyr, Val, Leu, His, Ser, Thr, Asn, Lys, Ala, Met or Asp
<220> FEATURE:
<221> NAME/KEY: MOD_RES
<222> LOCATION: (26)..(26)
<223> OTHER INFORMATION: Ile, Ala, Val, Thr, Lys, Leu, Ser, Gln, Arg, Tyr or Glu
<220> FEATURE:
<221> NAME/KEY: MOD_RES
<222> LOCATION: (27)..(27)
<223> OTHER INFORMATION: Ser, Leu, Pro, Thr, Ala, Gln, Asn, Phe, Ile, Glu, Gly, Arg, Lys or Asp
<220> FEATURE:
<221> NAME/KEY: MOD_RES

<222> LOCATION: (28)..(28)
<223> OTHER INFORMATION: Leu, Phe, Ile, Val, Met, Ser, Gly, Arg, Thr,
      Cys, Pro, Lys, Tyr or Asp
<220> FEATURE:
<221> NAME/KEY: MOD_RES
<222> LOCATION: (29)..(29)
<223> OTHER INFORMATION: Trp, Tyr, Asp, Thr, Lys, Glu, Asn, Arg, Gln,
      Gly, His, Ser, Met, Phe or Leu
<220> FEATURE:
<221> NAME/KEY: MOD_RES
<222> LOCATION: (30)..(30)
<223> OTHER INFORMATION: Asp, Lys, Asn, Glu, Ser, Arg, Gly, Thr, Ala,
      Gln, Phe or Tyr
<220> FEATURE:
<221> NAME/KEY: MOD_RES
<222> LOCATION: (31)..(31)
<223> OTHER INFORMATION: Gln, Leu, Glu, Asn, Lys, Ser, Thr, Asp, Ala,
      Arg, Gly, Pro, His, Tyr, Ile, Met or Phe
<220> FEATURE:
<221> NAME/KEY: MOD_RES
<222> LOCATION: (32)..(32)
<223> OTHER INFORMATION: Ser, Asp, Glu, Lys, Asn, Gly, Thr, Ala, Met,
      Leu, Arg, Gln, Phe, Val or His
<220> FEATURE:
<221> NAME/KEY: MOD_RES
<222> LOCATION: (33)..(33)
<223> OTHER INFORMATION: Leu, Val, Ser, Asn, Ile, Met, Thr, Asp, His,
      Gln, Tyr, Pro, Arg, Glu, Gly, Ala, Phe or Lys
<220> FEATURE:
<221> NAME/KEY: MOD_RES
<222> LOCATION: (34)..(34)
<223> OTHER INFORMATION: Lys, Val, Glu, Ser, Thr, Asn, Gln, Ala, Ile,
      Arg, Phe, Gly, Tyr, Met, Leu, Pro or Asp
<220> FEATURE:
<221> NAME/KEY: MOD_RES
<222> LOCATION: (35)..(35)
<223> OTHER INFORMATION: Pro, Ser, Asn, Thr, Glu, Gly, Tyr, Lys, Arg,
      Gln, Asp, Leu, Ala or Val
<220> FEATURE:
<221> NAME/KEY: MOD_RES
<222> LOCATION: (36)..(36)
<223> OTHER INFORMATION: Cys, Ile, Thr, Glu, Met, Ser, Leu, Tyr, Ala,
      Lys, Asn, Arg, Phe, Asp, Gly, His, Val, Trp or Gln
<220> FEATURE:
<221> NAME/KEY: MOD_RES
<222> LOCATION: (37)..(37)
<223> OTHER INFORMATION: Val, Tyr, Asp, Ile, Leu, Ser, Thr, Glu, Ala,
      Gly, Asn, Arg, Lys, His, Cys, Met, Phe or Gln
<220> FEATURE:
<221> NAME/KEY: MOD_RES
<222> LOCATION: (38)..(38)
<223> OTHER INFORMATION: Lys, Arg, Asn, Glu, Thr, Asp, Gln, Gly, Leu,
      Ser, Ile, Pro, Tyr, Ala or Val
<220> FEATURE:
<221> NAME/KEY: MOD_RES
<222> LOCATION: (39)..(39)
<223> OTHER INFORMATION: Leu, Asn, Thr, Ile, Glu, Ser, Ala, Asp, Tyr,
      Lys, Gly, Val, Arg, Met, Phe, Gln or His
<220> FEATURE:
<221> NAME/KEY: MOD_RES
<222> LOCATION: (40)..(40)
<223> OTHER INFORMATION: Thr, Ile, Asp, Val, Asn, Ser, Arg, Tyr, Lys,
      Glu, Met, His, Gly, Ala, Leu or Cys
<220> FEATURE:
<221> NAME/KEY: MOD_RES
<222> LOCATION: (41)..(41)
<223> OTHER INFORMATION: Pro, Asn, Thr, Val, Ser, Tyr, Lys, Asp, Leu,
      Arg, Cys, Ile, Ala, Glu or Phe
<220> FEATURE:
<221> NAME/KEY: MOD_RES
<222> LOCATION: (42)..(42)
<223> OTHER INFORMATION: Leu, Thr, Ile, Ser, Val, Arg, Phe, Asn, Ala,
      Met, Pro, Asp, Tyr or Lys
<220> FEATURE:
<221> NAME/KEY: MOD_RES
<222> LOCATION: (43)..(43)
<223> OTHER INFORMATION: Cys, Ser, Asn, Thr, Asp, Leu, Pro, Gln, Ile,
      Glu, Arg, Lys, Ala, Gly, Tyr, Val or His
<220> FEATURE:

```
<221> NAME/KEY: MOD_RES
<222> LOCATION: (44)..(44)
<223> OTHER INFORMATION: Val, Tyr, Ile, Glu, Thr, Asn, Lys, Gly, Ser,
      Phe, Met, Leu, Asp, Ala or Arg
<220> FEATURE:
<221> NAME/KEY: MOD_RES
<222> LOCATION: (45)..(45)
<223> OTHER INFORMATION: Gly, Thr, Arg, Asn, Ser, Lys, Asp, Glu, Ala,
      Ile, Met, Pro, Tyr, Leu or Val
<220> FEATURE:
<221> NAME/KEY: MOD_RES
<222> LOCATION: (46)..(46)
<223> OTHER INFORMATION: Leu, Met, Ala, Ser, Asn, Ile, Val, Glu, Asp,
      Thr, Gly, Lys, Arg, Gln, Tyr, Cys, Pro, Phe or His
<220> FEATURE:
<221> NAME/KEY: MOD_RES
<222> LOCATION: (47)..(47)
<223> OTHER INFORMATION: Ile, Asn, Gly, Lys, Arg, Thr, Ala, Ser, Asp,
      Gln, Met, Glu, Val, His, Leu, Phe or Tyr
<220> FEATURE:
<221> NAME/KEY: MOD_RES
<222> LOCATION: (48)..(48)
<223> OTHER INFORMATION: Ser, Asn, Cys, Thr, His, Lys, Asp, Gly, Ala,
      Glu, Leu, Ile or Pro
<220> FEATURE:
<221> NAME/KEY: MOD_RES
<222> LOCATION: (49)..(49)
<223> OTHER INFORMATION: Cys, Thr, Ser, Asn, Gly, Trp, Tyr, Arg, Ala,
      Ile, Val, Leu, Asp, Met or Phe
<220> FEATURE:
<221> NAME/KEY: MOD_RES
<222> LOCATION: (50)..(50)
<223> OTHER INFORMATION: Asn, Asp, Ser, Lys, Arg, Thr, Glu, Tyr, His,
      Gly, Ile, Pro, Cys or Phe
<220> FEATURE:
<221> NAME/KEY: MOD_RES
<222> LOCATION: (51)..(51)
<223> OTHER INFORMATION: Thr, Ser, Val, Phe, Ala, Asn, Ile, Tyr, Pro,
      Leu, Met, Lys, Arg, Asp, His or Gly
<220> FEATURE:
<221> NAME/KEY: MOD_RES
<222> LOCATION: (52)..(52)
<223> OTHER INFORMATION: Ser, Thr, Asn, Pro, Lys, Leu, Arg, Ala, Asp,
      Glu, His, Gln, Gly, Tyr, Val or Cys
<220> FEATURE:
<221> NAME/KEY: MOD_RES
<222> LOCATION: (53)..(53)
<223> OTHER INFORMATION: Val, Ala, Thr, Ile, Lys, Arg, Ser, Glu, Gly,
      Met, Asn, Leu, Pro, Tyr, Asp or Gln

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa
    50


<210> SEQ ID NO 32
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, Arg, Gln, Glu, Met, Asn, Thr, Ser, Leu,
      Ile, Phe or Cys
<220> FEATURE:
<221> NAME/KEY: MOD_RES
```

```
<222> LOCATION: (2)..(2)
<223> OTHER INFORMATION: Cys, Arg, Tyr, Gly, Ser, Trp, Val, Phe, Leu,
      Ile or Lys
<220> FEATURE:
<221> NAME/KEY: MOD_RES
<222> LOCATION: (3)..(3)
<223> OTHER INFORMATION: Asn, Lys, Arg, Thr, Gly, Phe, Ser, Asp, Leu,
      Ile, His, Met, Gln, Glu, Tyr, Pro or Val
<220> FEATURE:
<221> NAME/KEY: MOD_RES
<222> LOCATION: (4)..(4)
<223> OTHER INFORMATION: Asp, Asn, Glu, Ser, Gln, Gly, Ala, Val, Thr,
      Lys, His, Tyr, Ile, Arg, Met or Pro
<220> FEATURE:
<221> NAME/KEY: MOD_RES
<222> LOCATION: (5)..(5)
<223> OTHER INFORMATION: Lys, Glu, Thr, Asn, Ala, Arg, Pro, Ile, Val,
      Gln, Ser, Asp, Met, Gly, Leu or His
<220> FEATURE:
<221> NAME/KEY: MOD_RES
<222> LOCATION: (6)..(6)
<223> OTHER INFORMATION: Lys, Thr, Asn, Glu, Gln, Arg, Gly, Met, Asp,
      Ala, Ser, Ile, Val, Leu, His, Pro, Trp, Phe or Tyr
<220> FEATURE:
<221> NAME/KEY: MOD_RES
<222> LOCATION: (7)..(7)
<223> OTHER INFORMATION: Phe, Tyr, Ser, Leu, Cys, Val, Ile, Met, Pro,
      Lys or Asn
<220> FEATURE:
<221> NAME/KEY: MOD_RES
<222> LOCATION: (8)..(8)
<223> OTHER INFORMATION: Asn, Ser, Thr, Asp, Lys, Ile, Glu, Gln, Arg,
      Gly, His, Met, Ala, Tyr, Val, Cys, Pro or Leu
<220> FEATURE:
<221> NAME/KEY: MOD_RES
<222> LOCATION: (9)..(9)
<223> OTHER INFORMATION: Gly, Arg, Glu, Lys, Trp or Thr
<220> FEATURE:
<221> NAME/KEY: MOD_RES
<222> LOCATION: (10)..(10)
<223> OTHER INFORMATION: Thr, Lys, Ser, Ile, Ala, Leu, Arg, Gln, Met,
      Asn, Glu, Tyr, Pro, Val, Gly or Asp
<220> FEATURE:
<221> NAME/KEY: MOD_RES
<222> LOCATION: (11)..(11)
<223> OTHER INFORMATION: Gly, Glu, Arg, Ala, Asp, Ser, Lys or Val
<220> FEATURE:
<221> NAME/KEY: MOD_RES
<222> LOCATION: (12)..(12)
<223> OTHER INFORMATION: Pro, Leu, Thr, Gln, Ser, Lys, Glu, Ala, Ile,
      Arg, Asn, Asp, Met, Val, His, Gly or Phe
<220> FEATURE:
<221> NAME/KEY: MOD_RES
<222> LOCATION: (13)..(13)
<223> OTHER INFORMATION: Cys, Arg, Tyr, Ser, Gly, Ala, Val, Trp or Phe
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Asn, Lys, Asp, Ser, Pro, Glu, Arg, Thr, Gln,
      His, Gly, Ile, Met, Phe, Tyr or Val
<220> FEATURE:
<221> NAME/KEY: MOD_RES
<222> LOCATION: (16)..(16)
<223> OTHER INFORMATION: Val, Ile, Ala, Gly, Ser, Phe, Thr, Leu, Cys,
      Lys, Tyr, Gln or Glu
<220> FEATURE:
<221> NAME/KEY: MOD_RES
<222> LOCATION: (17)..(17)
<223> OTHER INFORMATION: Ser, Thr, Gly, Asn, Arg, Cys, Ala, Val, Ile,
      Leu, Phe or Lys
<220> FEATURE:
<221> NAME/KEY: MOD_RES
<222> LOCATION: (18)..(18)
<223> OTHER INFORMATION: Thr, Ser, Val, Ile, Ala, Pro, His, Gln, Leu,
      Gly, Met, Lys or Arg
```

```
<220> FEATURE:
<221> NAME/KEY: MOD_RES
<222> LOCATION: (19)..(19)
<223> OTHER INFORMATION: Val, Ile, Ala, Leu, Gly, Tyr, Glu, Arg, Ser,
      Thr or Phe
<220> FEATURE:
<221> NAME/KEY: MOD_RES
<222> LOCATION: (20)..(20)
<223> OTHER INFORMATION: Gln, Thr, Leu, His, Arg, Pro, Ala, Val, Ile,
      Lys, Ser, Asn or Glu
<220> FEATURE:
<221> NAME/KEY: MOD_RES
<222> LOCATION: (21)..(21)
<223> OTHER INFORMATION: Cys, Arg, Tyr, Trp, Gly, Phe, Ser, Met, Ala,
      Val, Ile, Pro or Lys
<220> FEATURE:
<221> NAME/KEY: MOD_RES
<222> LOCATION: (22)..(22)
<223> OTHER INFORMATION: Thr, Ala, Pro, Ser, Gln, Ile, Arg, Tyr, Val,
      Gly or His
<220> FEATURE:
<221> NAME/KEY: MOD_RES
<222> LOCATION: (23)..(23)
<223> OTHER INFORMATION: His, Gln, Arg, Tyr, Pro, Asn, Leu, Asp, Thr,
      Gly, Met, Val, Trp, Ser or Glu
<220> FEATURE:
<221> NAME/KEY: MOD_RES
<222> LOCATION: (24)..(24)
<223> OTHER INFORMATION: Gly, Arg, Glu, Ser, Trp, Ala, Val, Pro or Asn
<220> FEATURE:
<221> NAME/KEY: MOD_RES
<222> LOCATION: (25)..(25)
<223> OTHER INFORMATION: Ile, Val, Thr, Leu, Asn, Phe, Met, Ser, Gly,
      Ala, Arg or Asp
<220> FEATURE:
<221> NAME/KEY: MOD_RES
<222> LOCATION: (26)..(26)
<223> OTHER INFORMATION: Arg, Lys, Met, Ser, Gln, Thr, Asn, Gly, Glu,
      Leu, Ala, Trp, Ile, Pro or His
<220> FEATURE:
<221> NAME/KEY: MOD_RES
<222> LOCATION: (27)..(27)
<223> OTHER INFORMATION: Pro, Ala, Ser, Leu, Gln, Thr, Arg, His or Glu
<220> FEATURE:
<221> NAME/KEY: MOD_RES
<222> LOCATION: (28)..(28)
<223> OTHER INFORMATION: Val, Thr, Ala, Ile, Met, Leu, Gly, Glu, Ser,
      Pro, Gln, Cys, Trp, His or Arg
<220> FEATURE:
<221> NAME/KEY: MOD_RES
<222> LOCATION: (29)..(29)
<223> OTHER INFORMATION: Val, Ile, Ala, Leu, Met, Gly, Thr, Glu, Ser,
      Pro, Phe, Cys, Trp, Arg, Tyr or Asn
<220> FEATURE:
<221> NAME/KEY: MOD_RES
<222> LOCATION: (30)..(30)
<223> OTHER INFORMATION: Ser, Thr, Pro, Leu, Ala, Val, Gln, Ile, Phe,
      Asn, His, Lys or Tyr
<220> FEATURE:
<221> NAME/KEY: MOD_RES
<222> LOCATION: (31)..(31)
<223> OTHER INFORMATION: Thr, Ser, Ala, Ile, Asn, Pro, Leu, His, Gly,
      Val, Arg or Gln
<220> FEATURE:
<221> NAME/KEY: MOD_RES
<222> LOCATION: (32)..(32)
<223> OTHER INFORMATION: Gln, His, Arg, Ser, Pro, Lys, Ala, Glu, Leu,
       Thr, Asn or Met
<220> FEATURE:
<221> NAME/KEY: MOD_RES
<222> LOCATION: (33)..(33)
<223> OTHER INFORMATION: Leu, Phe, Pro, Val, Met, Ser, Ile, Thr, Ala,
      Cys, Gln, Arg, Tyr, Trp or His
<220> FEATURE:
<221> NAME/KEY: MOD_RES
<222> LOCATION: (34)..(34)
<223> OTHER INFORMATION: Leu, Ile, Pro, Val, Ala, Thr, Met, Ser, Gln,
      Arg, Cys, Phe, Tyr, Gly, Asn, Trp or Lys
<220> FEATURE:
```

```
<221> NAME/KEY: MOD_RES
<222> LOCATION: (35)..(35)
<223> OTHER INFORMATION: Leu, Val, Phe, Ile, Ser, Met, Pro, Trp, Tyr,
      Gly, Thr, Gln, Cys or Glu
<220> FEATURE:
<221> NAME/KEY: MOD_RES
<222> LOCATION: (36)..(36)
<223> OTHER INFORMATION: Asn, Asp, Ser, Lys, Pro, Tyr, His, Thr, Ile,
      Met, Phe, Ala, Gly, Leu, Trp or Glu
<220> FEATURE:
<221> NAME/KEY: MOD_RES
<222> LOCATION: (37)..(37)
<223> OTHER INFORMATION: Gly, Pro, Ser, Ala, Asp, Cys, Val, Trp, Arg,
      Asn, Phe or Glu
<220> FEATURE:
<221> NAME/KEY: MOD_RES
<222> LOCATION: (38)..(38)
<223> OTHER INFORMATION: Ser, Thr, Gly, Arg, Asn, Cys, Ile, Ala, Val,
      Gln, Leu, Pro, Lys, Met or Asp
<220> FEATURE:
<221> NAME/KEY: MOD_RES
<222> LOCATION: (39)..(39)
<223> OTHER INFORMATION: Leu, Ile, Val, Thr, Arg, Pro, Gln, Ser, Phe,
      Ala, Tyr, Met, Gly, Lys or Glu
<220> FEATURE:
<221> NAME/KEY: MOD_RES
<222> LOCATION: (40)..(40)
<223> OTHER INFORMATION: Ala, Ser, Thr, Val, Pro, Glu, Gly, Asp, Gln,
      Leu, Arg, Lys, Tyr, Asn, Cys, Met or Phe
<220> FEATURE:
<221> NAME/KEY: MOD_RES
<222> LOCATION: (41)..(41)
<223> OTHER INFORMATION: Glu, Lys, Gly, Ala, Arg, Asp, Thr, Gln, Val,
      Asn, Ser, Leu, Ile, His or Tyr
<220> FEATURE:
<221> NAME/KEY: MOD_RES
<222> LOCATION: (42)..(42)
<223> OTHER INFORMATION: Glu, Gly, Lys, Asp, Arg, Gln, Asn, Thr, Ser,
      Ala, Pro, Val, Ile, His or Trp
<220> FEATURE:
<221> NAME/KEY: MOD_RES
<222> LOCATION: (43)..(43)
<223> OTHER INFORMATION: Glu, Asp, Gly, Lys, Asn, Gln, Ser, Arg, Val,
      Ala, Thr, His, Met, Leu, Ile, Tyr or Pro
<220> FEATURE:
<221> NAME/KEY: MOD_RES
<222> LOCATION: (44)..(44)
<223> OTHER INFORMATION: Val, Ile, Thr, Ala, Leu, Glu, Met, Asp, Gly,
      Pro, Ser, Arg, Lys, Tyr, Asn, Phe, Cys or Gln
<220> FEATURE:
<221> NAME/KEY: MOD_RES
<222> LOCATION: (45)..(45)
<223> OTHER INFORMATION: Val, Ile, Met, Arg, Lys, Ala, Thr, Gln, Glu,
      Leu, Ser, Gly, Tyr, Asn, Pro, Cys, Asp or Phe
<220> FEATURE:
<221> NAME/KEY: MOD_RES
<222> LOCATION: (46)..(46)
<223> OTHER INFORMATION: Ile, Val, Leu, Thr, Phe, Ser, Met, Asn, Arg,
      Pro, Ala, Asp, Gly, Cys, Trp, Glu, Lys or Tyr
<220> FEATURE:
<221> NAME/KEY: MOD_RES
<222> LOCATION: (47)..(47)
<223> OTHER INFORMATION: Arg, Lys, Ser, Met, Gly, Ile, Thr, Leu, Gln,
      Asn, Asp, Ala, Val, Pro, Phe, Trp, Tyr, Glu or Cys
<220> FEATURE:
<221> NAME/KEY: MOD_RES
<222> LOCATION: (48)..(48)
<223> OTHER INFORMATION: Ser, Thr, Phe, Gly, Ala, Pro, Val, Cys, Tyr,
      Ile, Asn, Leu, Glu, Asp, Arg, Trp or Lys
<220> FEATURE:
<221> NAME/KEY: MOD_RES
<222> LOCATION: (49)..(49)
<223> OTHER INFORMATION: Glu, Ala, Asp, Lys, Gln, Ser, Val, Asn, Gly,
      Arg, Thr, Tyr, Pro, Cys, His, Ile, Leu or Trp
<220> FEATURE:
<221> NAME/KEY: MOD_RES
<222> LOCATION: (50)..(50)
<223> OTHER INFORMATION: Asn, Asp, Ser, Lys, Glu, Ile, Thr, Tyr, His,
      Arg, Gln, Gly, Ala, Leu, Pro, Phe, Val or Met
```

<220> FEATURE:
<221> NAME/KEY: MOD_RES
<222> LOCATION: (51)..(51)
<223> OTHER INFORMATION: Phe, Leu, Ile, Met, Val, Ser, Lys, Thr, Pro,
Tyr, Trp, Arg, His, Gln, Cys, Ala, Asn, Gly or Asp
<220> FEATURE:
<221> NAME/KEY: MOD_RES
<222> LOCATION: (52)..(52)
<223> OTHER INFORMATION: Any amino acid
<220> FEATURE:
<221> NAME/KEY: MOD_RES
<222> LOCATION: (53)..(53)
<223> OTHER INFORMATION: Asn, Asp, Glu, Lys, Ser, Gln, Ala, His, Gly,
Arg, Thr, Tyr, Val, Ile, Pro, Leu, Cys, Met or Phe
<220> FEATURE:
<221> NAME/KEY: MOD_RES
<222> LOCATION: (54)..(54)
<223> OTHER INFORMATION: Asn, Ser, Thr, Asp, Ala, His, Lys, Pro, Tyr,
Ile, Gln, Gly, Met, Arg, Leu or Glu
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (56)..(56)
<223> OTHER INFORMATION: Lys, Arg, Asn, Glu, Asp, Gln, Gly, Tyr, Ala,
Thr, Ile, His, Val, Pro, Ser, Met, Leu or Trp
<220> FEATURE:
<221> NAME/KEY: MOD_RES
<222> LOCATION: (57)..(57)
<223> OTHER INFORMATION: Thr, Ile, Asn, Val, Ser, Pro, Ala, Asp, Leu,
Met, Lys, Tyr, Gly, Phe, Gln, His, Arg or Glu
<220> FEATURE:
<221> NAME/KEY: MOD_RES
<222> LOCATION: (58)..(58)
<223> OTHER INFORMATION: Ile, Leu, Met, Val, Thr, Arg, Lys, Tyr, Ala,
Ser, Phe, Asn, His, Gly, Cys or Pro
<220> FEATURE:
<221> NAME/KEY: MOD_RES
<222> LOCATION: (59)..(59)
<223> OTHER INFORMATION: Ile, Leu, Met, Thr, Val, Arg, Ser, Asn, Pro,
Phe, Cys, Ala or Tyr

<400> SEQUENCE: 32

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55
```

<210> SEQ ID NO 33
<211> LENGTH: 58
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Lys, Gln, Glu, Arg, Thr, Ala, Asn, His, Ile,
Leu, Ser, Pro, Val, Gly, Tyr, Asp, Met or Phe
<220> FEATURE:
<221> NAME/KEY: MOD_RES
<222> LOCATION: (2)..(2)
<223> OTHER INFORMATION: Leu, Tyr, Phe, Ile, Ser, Val, Lys, Thr, Arg,
Gln, Asn, Trp, Cys, Pro, Gly, Met or Ala
<220> FEATURE:
<221> NAME/KEY: MOD_RES
<222> LOCATION: (3)..(5)

<223> OTHER INFORMATION: Any amino acid
<220> FEATURE:
<221> NAME/KEY: MOD_RES
<222> LOCATION: (6)..(6)
<223> OTHER INFORMATION: Phe, Tyr, Leu, Trp, Val, Ile, Thr, Ser, His, Cys, Met, Gly, Pro, Asn, Lys, Asp, Glu, Arg or Ala
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Asn, Lys, Thr, Asp, Gly, Ser, Gln, His, Ala, Arg, Ile, Glu, Val, Leu, Tyr, Met, Pro, Phe or Cys
<220> FEATURE:
<221> NAME/KEY: MOD_RES
<222> LOCATION: (9)..(9)
<223> OTHER INFORMATION: Lys, Thr, Arg, Asn, Ser, Ala, Glu, Gly, Gln, Asp, Val, Ile, Met, Pro, His, Tyr, Leu or Phe
<220> FEATURE:
<221> NAME/KEY: MOD_RES
<222> LOCATION: (10)..(10)
<223> OTHER INFORMATION: Thr, Asn, Lys, Ile, Ser, Ala, Pro, Glu, Arg, Gln, Asp, Gly, Val, Leu, His, Met, Tyr, Cys or Phe
<220> FEATURE:
<221> NAME/KEY: MOD_RES
<222> LOCATION: (11)..(11)
<223> OTHER INFORMATION: Ile, Thr, Val, Met, Leu, Ala, Tyr, Lys, Phe, Ser, Asn, Arg, Pro, His, Glu, Gly, Gln or Asp
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(13)
<223> OTHER INFORMATION: Phe, Leu, Tyr, Ile, Ser, Gln, Val, Ala, Trp, Cys, Pro, Thr, Asn, Met, Lys, Asp, Arg or His
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (15)..(15)
<223> OTHER INFORMATION: Gln, Pro, Ser, His, Asn, Arg, Lys, Glu, Thr, Ala, Gly, Asp, Leu, Tyr, Ile, Val, Phe, Cys or Trp
<220> FEATURE:
<221> NAME/KEY: MOD_RES
<222> LOCATION: (16)..(16)
<223> OTHER INFORMATION: Ser, Pro, His, Ala, Thr, Asn, Gln, Phe, Leu, Arg, Ile, Tyr, Lys, Gly, Val, Cys, Asp or Trp
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: Gly, Glu, Arg, Asp, Ser, Pro, Ala, Lys, Leu, Gln, Asn, Val, Trp, Ile, His or Thr
<220> FEATURE:
<221> NAME/KEY: MOD_RES
<222> LOCATION: (19)..(19)
<223> OTHER INFORMATION: Gly, Glu, Arg, Lys, Ser, Trp, Val, Leu, Ala, Asn, Thr, Ile, Phe, Asp or Gln
<220> FEATURE:
<221> NAME/KEY: MOD_RES
<222> LOCATION: (20)..(20)
<223> OTHER INFORMATION: Asp, Gly, Thr, Asn, Ala, Glu, His, Val, Ile, Ser, Arg, Tyr, Pro, Phe, Gln, Leu, Lys or Met
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (22)..(22)

<223> OTHER INFORMATION: Glu, Lys, Gln, Gly, Asp, Arg, Val, Asn, Ala, Pro, Ser, Leu, Ile, His, Thr or Tyr
<220> FEATURE:
<221> NAME/KEY: MOD_RES
<222> LOCATION: (23)..(23)
<223> OTHER INFORMATION: Ile, Val, Leu, Thr, Phe, Asn, Met, Ser, Ala, Tyr, Gly, Pro, Lys, Asp, Cys, His or Arg
<220> FEATURE:
<221> NAME/KEY: MOD_RES
<222> LOCATION: (24)..(24)
<223> OTHER INFORMATION: Val, Thr, Ile, Glu, Ala, Met, Lys, Ser, Leu, Arg, Gln, Pro, Tyr, Cys, Gly, Asn, His, Phe or Asp
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (26)..(26)
<223> OTHER INFORMATION: His, Leu, Tyr, Phe, Arg, Ile, Pro, Thr, Ser, Asn, Gln, Val, Asp, Ala, Gly, Met, Cys, Trp or Glu
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (28)..(28)
<223> OTHER INFORMATION: Phe, Val, Leu, Ser, Ile, Cys, Tyr, His, Thr, Arg, Trp, Gly or Asn
<220> FEATURE:
<221> NAME/KEY: MOD_RES
<222> LOCATION: (29)..(29)
<223> OTHER INFORMATION: Asn, Thr, Ile, Ser, Cys, Asp, Tyr, Val, His, Lys, Phe, Leu, Met, Pro, Arg, Gly, Gln, Glu or Ala
<220> FEATURE:
<221> NAME/KEY: MOD_RES
<222> LOCATION: (30)..(30)
<223> OTHER INFORMATION: Cys, Arg, Trp, Tyr, Ser, Val, Gly, Leu, Phe, Ile, His, Ala, Asn or Gln
<220> FEATURE:
<221> NAME/KEY: MOD_RES
<222> LOCATION: (31)..(31)
<223> OTHER INFORMATION: Gly, Arg, Ala, Lys, Gln, His, Glu, Met, Asn, Val, Ser, Thr, Trp, Tyr, Cys, Ile, Asp, Leu or Phe
<220> FEATURE:
<221> NAME/KEY: MOD_RES
<222> LOCATION: (32)..(32)
<223> OTHER INFORMATION: Gly, Glu, Arg, Lys, Trp, Val, Ser, Ala, Leu, Asn, Asp, Ile, Phe or Tyr
<220> FEATURE:
<221> NAME/KEY: MOD_RES
<222> LOCATION: (33)..(33)
<223> OTHER INFORMATION: Glu, Gly, Lys, Asp, Asn, Arg, Val, Ala, Leu, Phe, Ser, Gln, Trp, His, Tyr, Cys, Met or Thr
<220> FEATURE:
<221> NAME/KEY: MOD_RES
<222> LOCATION: (34)..(34)
<223> OTHER INFORMATION: Phe, Leu, Ser, Ile, Tyr, Val, Cys, Asn, Gly, Met, Trp or Gln
<220> FEATURE:
<221> NAME/KEY: MOD_RES
<222> LOCATION: (35)..(35)
<223> OTHER INFORMATION: Phe, Leu, Ser, Tyr, Val, Pro, Ile, Cys, Asp, Ala, Met or Asn
<220> FEATURE:
<221> NAME/KEY: MOD_RES
<222> LOCATION: (36)..(36)
<223> OTHER INFORMATION: Tyr, Phe, Asn, Cys, His, Ser, Leu, Val, Ile, Thr, Pro, Gly, Met, Trp, Lys, Asp or Glu
<220> FEATURE:
<221> NAME/KEY: MOD_RES
<222> LOCATION: (37)..(37)
<223> OTHER INFORMATION: Cys, Arg, Tyr, Leu, Ser, Trp, Gly, Ala, Phe, Val, Ile, Met, Thr, Pro or Lys
<220> FEATURE:
<221> NAME/KEY: MOD_RES
<222> LOCATION: (38)..(38)
<223> OTHER INFORMATION: Asn, Asp, Ser, Lys, Tyr, Thr, Glu, Ile, His,

```
      Gly, Cys, Gln, Arg, Ala, Val, Pro, Met or Phe
<220> FEATURE:
<221> NAME/KEY: MOD_RES
<222> LOCATION: (39)..(39)
<223> OTHER INFORMATION: Thr, Ser, Ala, Leu, Ile, Pro, Val, His, Arg,
      Tyr, Lys, Asn, Gln, Met, Glu or Gly
<220> FEATURE:
<221> NAME/KEY: MOD_RES
<222> LOCATION: (40)..(40)
<223> OTHER INFORMATION: Thr, Ser, Ala, Lys, Pro, Glu, Ile, Leu, Val,
      Asp, Asn, Gly, Arg, Gln, His, Tyr, Phe, Cys or Met
<220> FEATURE:
<221> NAME/KEY: MOD_RES
<222> LOCATION: (41)..(41)
<223> OTHER INFORMATION: Gln, Lys, Gly, Pro, Arg, Glu, Asn, Asp, Ser,
      Ala, His, Leu, Thr, Ile, Val, Trp, Tyr, Met or Cys
<220> FEATURE:
<221> NAME/KEY: MOD_RES
<222> LOCATION: (42)..(42)
<223> OTHER INFORMATION: Leu, Met, Ile, Pro, Phe, Val, Arg, Gln, Cys,
      Trp, Thr, Ser, Tyr, Gly, Ala, Lys or Asn
<220> FEATURE:
<221> NAME/KEY: MOD_RES
<222> LOCATION: (43)..(43)
<223> OTHER INFORMATION: Phe, Leu, Trp, Ser, Tyr, Val, Ile, Cys, Pro,
      Asn, Ala, Met, Lys or Thr
<220> FEATURE:
<221> NAME/KEY: MOD_RES
<222> LOCATION: (44)..(44)
<223> OTHER INFORMATION: Asn, Ser, Asp, Thr, Lys, His, Tyr, Gly, Arg,
      Gln, Ile, Glu, Phe, Ala, Leu, Pro, Trp, Met or Val
<220> FEATURE:
<221> NAME/KEY: MOD_RES
<222> LOCATION: (45)..(58)
<223> OTHER INFORMATION: Any amino acid

<400> SEQUENCE: 33

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa
    50                  55


<210> SEQ ID NO 34
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(12)
<223> OTHER INFORMATION: Any amino acid
<220> FEATURE:
<221> NAME/KEY: MOD_RES
<222> LOCATION: (13)..(13)
<223> OTHER INFORMATION: Asn, Asp, Ser, Glu, Gly, Thr, Lys, Ala, Arg,
      His, Ile, Val, Pro, Gln, Leu, Tyr, Cys, Met or Phe
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (17)..(17)
<223> OTHER INFORMATION: Leu, Ile, Pro, Phe, Thr, Val, His, Ser, Arg,
      Ala, Asn, Met, Tyr, Gly or Cys
<220> FEATURE:
<221> NAME/KEY: MOD_RES
<222> LOCATION: (18)..(18)
```

```
<223> OTHER INFORMATION: Pro, Gln, Ser, Thr, Leu, Lys, His, Arg, Asn,
      Tyr, Ile, Ala, Met, Gly, Asp, Val, Cys, Phe or Glu
<220> FEATURE:
<221> NAME/KEY: MOD_RES
<222> LOCATION: (19)..(19)
<223> OTHER INFORMATION: Cys, Arg, Ser, Tyr, Met, Phe, Gly, Ala, Leu,
      Ile, Val, Trp, Pro, Thr, His or Asn
<220> FEATURE:
<221> NAME/KEY: MOD_RES
<222> LOCATION: (20)..(20)
<223> OTHER INFORMATION: Arg, Lys, Gly, Ser, Asn, Gln, Ile, Thr, Glu,
      Pro, His, Met, Trp, Leu, Cys, Tyr, Val or Asp
<220> FEATURE:
<221> NAME/KEY: MOD_RES
<222> LOCATION: (21)..(21)
<223> OTHER INFORMATION: Ile, Leu, Met, Val, Thr, Asn, Arg, Lys, Tyr,
      Cys, Ser, Pro, Phe, His, Asp or Glu
<220> FEATURE:
<221> NAME/KEY: MOD_RES
<222> LOCATION: (22)..(22)
<223> OTHER INFORMATION: Lys, Arg, Asn, Glu, Ile, Thr, Gln, Ser, Gly,
      Pro, Met, Tyr, Leu, His, Ala or Asp
<220> FEATURE:
<221> NAME/KEY: MOD_RES
<222> LOCATION: (23)..(23)
<223> OTHER INFORMATION: Gln, Leu, His, Arg, Pro, Lys, Ala, Asn, Glu,
      Gly, Thr, Met, Val or Ser
<220> FEATURE:
<221> NAME/KEY: MOD_RES
<222> LOCATION: (24)..(24)
<223> OTHER INFORMATION: Ile, Phe, Val, Leu, Met, Thr, Tyr, Asn, Ser,
      Lys, Ala, Pro, Arg or Asp
<220> FEATURE:
<221> NAME/KEY: MOD_RES
<222> LOCATION: (25)..(25)
<223> OTHER INFORMATION: Ile, Val, Met, Thr, Leu, Ala, Tyr, Lys, Gly,
      Glu, Cys, Arg, Ser or Gln
<220> FEATURE:
<221> NAME/KEY: MOD_RES
<222> LOCATION: (26)..(26)
<223> OTHER INFORMATION: Asn, Arg, His, Lys, Ser, Asp, Ile, Thr, Tyr,
      Gly, Gln, Leu, Cys, Met, Val, Glu, Pro or Phe
<220> FEATURE:
<221> NAME/KEY: MOD_RES
<222> LOCATION: (27)..(27)
<223> OTHER INFORMATION: Met, Arg, Leu, Lys, Thr, Ser, Val, Ile, Pro,
      Gly, Tyr, His, Gln, Asn, Ala, Cys, Trp or Asp
<220> FEATURE:
<221> NAME/KEY: MOD_RES
<222> LOCATION: (28)..(28)
<223> OTHER INFORMATION: Trp, Arg, Cys, Gly, Val, Leu, Met, Ser, Ala,
      Pro, His, Lys, Tyr, Asn or Gln
<220> FEATURE:
<221> NAME/KEY: MOD_RES
<222> LOCATION: (29)..(29)
<223> OTHER INFORMATION: Gln, Arg, Ile, Met, Leu, His, Lys, Ala, Glu,
      Pro, Thr, Gly, Tyr, Val, Trp or Ser
<220> FEATURE:
<221> NAME/KEY: MOD_RES
<222> LOCATION: (30)..(30)
<223> OTHER INFORMATION: Glu, Arg, Gly, Lys, Gln, Thr, Ser, Ala, Ile,
      Val, Asp, Leu, Pro, His, Asn, Cys, Met, Trp or Tyr
<220> FEATURE:
<221> NAME/KEY: MOD_RES
<222> LOCATION: (31)..(31)
<223> OTHER INFORMATION: Val, Ala, Thr, Ile, Gly, Leu, Ser, Glu, Pro,
      Lys, Arg, Asn, Gln, Trp or Asp
<220> FEATURE:
<221> NAME/KEY: MOD_RES
<222> LOCATION: (32)..(32)
<223> OTHER INFORMATION: Gly, Arg, Glu, Ala, Val, Lys, Gln, Thr, Asn,
      Asp, Pro, Trp or Ser
<220> FEATURE:
<221> NAME/KEY: MOD_RES
<222> LOCATION: (33)..(33)
<223> OTHER INFORMATION: Lys, Gln, Arg, Ser, Thr, Glu, Leu, Pro, Asn,
      Ile, His, Gly, Ala, Val, Tyr, Cys, Met, Trp or Asp
<220> FEATURE:
<221> NAME/KEY: MOD_RES
```

-continued

<222> LOCATION: (34)..(34)
<223> OTHER INFORMATION: Ala, Val, Gly, Thr, Ser, Pro, Gln, Glu, Cys,
Trp, Arg, Lys, Tyr or Asp
<220> FEATURE:
<221> NAME/KEY: MOD_RES
<222> LOCATION: (35)..(35)
<223> OTHER INFORMATION: Met, Ile, Thr, Val, Leu, Lys, Asn, Ala, Phe,
Arg, Cys, Ser, Pro, Gln, His, Tyr or Glu
<220> FEATURE:
<221> NAME/KEY: MOD_RES
<222> LOCATION: (36)..(36)
<223> OTHER INFORMATION: Tyr, His, Phe, Cys, Ser, Val, Asp, Asn, Met,
Ala, Pro, Leu, Glu, Lys, Thr or Gly
<220> FEATURE:
<221> NAME/KEY: MOD_RES
<222> LOCATION: (37)..(37)
<223> OTHER INFORMATION: Ala, Pro, Thr, Ser, Asn, Val, Cys, Gly, Asp,
Leu, Ile, Met or His
<220> FEATURE:
<221> NAME/KEY: MOD_RES
<222> LOCATION: (38)..(38)
<223> OTHER INFORMATION: Pro, Ser, Ala, Asn, Leu, Thr, His, Arg, Val,
Lys, Asp or Gln
<220> FEATURE:
<221> NAME/KEY: MOD_RES
<222> LOCATION: (39)..(39)
<223> OTHER INFORMATION: Pro, Ser, Leu, Ala, Thr, Phe, Arg, His, Gly,
Tyr, Asn or Gln
<220> FEATURE:
<221> NAME/KEY: MOD_RES
<222> LOCATION: (40)..(40)
<223> OTHER INFORMATION: Ile, Val, Ser, Thr, Arg, Leu, Phe, Met, Asn,
Pro, His, Ala, Lys, Gly, Trp, Tyr or Asp
<220> FEATURE:
<221> NAME/KEY: MOD_RES
<222> LOCATION: (41)..(41)
<223> OTHER INFORMATION: Arg, Lys, Ala, Ser, Glu, Gln, Pro, Gly, Asn,
Asp, Thr, Ile, Met, Val, Leu or His
<220> FEATURE:
<221> NAME/KEY: MOD_RES
<222> LOCATION: (42)..(42)
<223> OTHER INFORMATION: Gly, Glu, Arg, Ala, Ser, Asp, Val, Lys, Ile,
Cys, Pro, Thr, Asn or Gln
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (44)..(44)
<223> OTHER INFORMATION: Ile, Leu, Val, Thr, Met, Ser, Asn, Phe, Arg,
Ala, Cys, Asp or Gln
<220> FEATURE:
<221> NAME/KEY: MOD_RES
<222> LOCATION: (45)..(45)
<223> OTHER INFORMATION: Arg, Thr, Asn, Lys, Ser, Gln, Ile, Glu, Met,
Gly, Ala, Tyr, Val, Trp, Asp, His, Leu, Pro or Cys
<220> FEATURE:
<221> NAME/KEY: MOD_RES
<222> LOCATION: (46)..(46)
<223> OTHER INFORMATION: Cys, Arg, Tyr, Ser, Trp, Gly, Val, Phe, Ala,
Leu, Ile, Met, Lys, Thr, Gln or Glu
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (48)..(48)
<223> OTHER INFORMATION: Ser, Thr, Pro, Leu, Ala, Gln, Ile, Val, Phe,
Cys, Trp, Lys, Tyr, Asn or Glu
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (50)..(50)
<223> OTHER INFORMATION: Ile, Val, Thr, Leu, Ser, Met, Phe, Asn, Tyr, Gly, Arg or Ala
<220> FEATURE:
<221> NAME/KEY: MOD_RES
<222> LOCATION: (51)..(51)
<223> OTHER INFORMATION: Thr, Ala, Ile, Ser, Gln, Leu, Pro, Arg, Tyr, Gly, Val or Asn
<220> FEATURE:
<221> NAME/KEY: MOD_RES
<222> LOCATION: (52)..(52)
<223> OTHER INFORMATION: Gly, Arg, Glu, Ala, Leu, Val, Asp, Trp, Ser, Lys, Gln, Ile or Thr
<220> FEATURE:
<221> NAME/KEY: MOD_RES
<222> LOCATION: (53)..(53)
<223> OTHER INFORMATION: Leu, Ile, Met, Val, Pro, Thr, Ser, Phe, Tyr, Gly, Arg, Gln, His, Ala or Asn
<220> FEATURE:
<221> NAME/KEY: MOD_RES
<222> LOCATION: (54)..(54)
<223> OTHER INFORMATION: Leu, Ile, Met, Phe, Val, Pro, Thr, Ser, Gln, Arg, Gly, Ala, Tyr, Asp, Lys or Asn
<220> FEATURE:
<221> NAME/KEY: MOD_RES
<222> LOCATION: (55)..(55)
<223> OTHER INFORMATION: Leu, Ile, Val, Ser, Phe, Trp, Met, Pro, Thr, Lys, Asn, Gly, Arg, Gln, Ala, Tyr, Asp or Glu
<220> FEATURE:
<221> NAME/KEY: MOD_RES
<222> LOCATION: (56)..(56)
<223> OTHER INFORMATION: Thr, Val, Ile, Leu, Ser, Ala, Glu, Gln, Met, Pro, Asn, Gly, Arg, Lys, Asp, His or Tyr
<220> FEATURE:
<221> NAME/KEY: MOD_RES
<222> LOCATION: (57)..(57)
<223> OTHER INFORMATION: Any amino acid
<220> FEATURE:
<221> NAME/KEY: MOD_RES
<222> LOCATION: (58)..(58)
<223> OTHER INFORMATION: Asp, Gly, Asn, Glu, Thr, Ser, Val, Ala, Arg, Lys, His, Ile, Tyr, Met, Pro or Gln
<220> FEATURE:
<221> NAME/KEY: MOD_RES
<222> LOCATION: (59)..(61)
<223> OTHER INFORMATION: Any amino acid

<400> SEQUENCE: 34

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60
```

<210> SEQ ID NO 35
<211> LENGTH: 49
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Arg, Thr, Asn, Lys, Ser, Gln, Ile, Glu, Met, Gly, Ala, Tyr, Val, Trp, Asp, His, Leu, Pro or Cys
<220> FEATURE:
<221> NAME/KEY: MOD_RES
<222> LOCATION: (2)..(2)
<223> OTHER INFORMATION: Cys, Arg, Tyr, Ser, Trp, Gly, Val, Phe, Ala, Leu, Ile, Met, Lys, Thr, Gln or Glu
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Ser, Thr, Pro, Leu, Ala, Gln, Ile, Val, Phe, Cys, Trp, Lys, Tyr, Asn or Glu
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Ile, Val, Thr, Leu, Ser, Met, Phe, Asn, Tyr, Gly, Arg or Ala
<220> FEATURE:
<221> NAME/KEY: MOD_RES
<222> LOCATION: (7)..(7)
<223> OTHER INFORMATION: Thr, Ala, Ile, Ser, Gln, Leu, Pro, Arg, Tyr, Gly, Val or Asn
<220> FEATURE:
<221> NAME/KEY: MOD_RES
<222> LOCATION: (8)..(8)
<223> OTHER INFORMATION: Gly, Arg, Glu, Ala, Leu, Val, Asp, Trp, Ser, Lys, Gln, Ile or Thr
<220> FEATURE:
<221> NAME/KEY: MOD_RES
<222> LOCATION: (9)..(9)
<223> OTHER INFORMATION: Leu, Ile, Met, Val, Pro, Thr, Ser, Phe, Tyr, Gly, Arg, Gln, His, Ala or Asn
<220> FEATURE:
<221> NAME/KEY: MOD_RES
<222> LOCATION: (10)..(10)
<223> OTHER INFORMATION: Leu, Ile, Met, Phe, Val, Pro, Thr, Ser, Gln, Arg, Gly, Ala, Tyr, Asp, Lys or Asn
<220> FEATURE:
<221> NAME/KEY: MOD_RES
<222> LOCATION: (11)..(11)
<223> OTHER INFORMATION: Leu, Ile, Val, Ser, Phe, Trp, Met, Pro, Thr, Lys, Asn, Gly, Arg, Gln, Ala, Tyr, Asp or Glu
<220> FEATURE:
<221> NAME/KEY: MOD_RES
<222> LOCATION: (12)..(12)
<223> OTHER INFORMATION: Thr, Val, Ile, Leu, Ser, Ala, Glu, Gln, Met, Pro, Asn, Gly, Arg, Lys, Asp, His or Tyr
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Asp, Gly, Asn, Glu, Thr, Ser, Val, Ala, Arg, Lys, His, Ile, Tyr, Met, Pro or Gln
<220> FEATURE:
<221> NAME/KEY: MOD_RES
<222> LOCATION: (15)..(22)
<223> OTHER INFORMATION: Any amino acid
<220> FEATURE:
<221> NAME/KEY: MOD_RES
<222> LOCATION: (23)..(23)
<223> OTHER INFORMATION: Glu, Asp, Lys, Leu, Ala, Gln, Asn, Val, Gly, Thr, Arg, Ile, His, Ser, Met, Phe, Pro, Tyr or Trp
<220> FEATURE:
<221> NAME/KEY: MOD_RES
<222> LOCATION: (24)..(24)
<223> OTHER INFORMATION: Thr, Ile, Val, Ala, Lys, Ser, Leu, Arg, Phe, Met, Pro, Asn, Asp, Gly, Tyr, Glu, Gln or Cys
<220> FEATURE:
<221> NAME/KEY: MOD_RES
<222> LOCATION: (25)..(25)
<223> OTHER INFORMATION: Phe, Leu, Val, Ile, Ser, Thr, Tyr, Cys, Met, Ala, Pro, Asn, Trp, His, Arg or Asp
<220> FEATURE:
<221> NAME/KEY: MOD_RES
<222> LOCATION: (26)..(26)
<223> OTHER INFORMATION: Arg, Gly, Lys, Thr, Ser, Ile, Tyr, Gln, Leu, Glu, Pro, Val, Cys, Trp, Asp, Met, Phe or Asn

```
<220> FEATURE:
<221> NAME/KEY: MOD_RES
<222> LOCATION: (27)..(27)
<223> OTHER INFORMATION: Pro, Leu, Ser, Ala, Asp, Arg, His, Thr, Gln,
      Asn, Gly or Glu
<220> FEATURE:
<221> NAME/KEY: MOD_RES
<222> LOCATION: (28)..(28)
<223> OTHER INFORMATION: Gly, Ala, Glu, Ile, Val, Thr, Gln, Leu, Arg,
      Ser, Trp, Met, Pro, Lys or Asn
<220> FEATURE:
<221> NAME/KEY: MOD_RES
<222> LOCATION: (29)..(29)
<223> OTHER INFORMATION: Gly, Arg, Glu, Ser, Ala, Leu, Lys, Cys, Pro,
      Asn or Gln
<220> FEATURE:
<221> NAME/KEY: MOD_RES
<222> LOCATION: (30)..(30)
<223> OTHER INFORMATION: Gly, Glu, Arg, Lys, Ser, Ala, Asp, Cys or Asn
<220> FEATURE:
<221> NAME/KEY: MOD_RES
<222> LOCATION: (31)..(31)
<223> OTHER INFORMATION: Asp, Asn, Glu, Gly, Tyr, Ser, Ile, His, Arg,
      Ala, Val, Gln, Thr or Lys
<220> FEATURE:
<221> NAME/KEY: MOD_RES
<222> LOCATION: (32)..(32)
<223> OTHER INFORMATION: Met, Ile, Thr, Val, Leu, Arg, Tyr, Lys, Phe,
      Gly or Ser
<220> FEATURE:
<221> NAME/KEY: MOD_RES
<222> LOCATION: (33)..(33)
<223> OTHER INFORMATION: Arg, Lys, Met, Gln, Gly, Glu, Val, Thr, Asn,
      Trp, Ile, Phe or Ser
<220> FEATURE:
<221> NAME/KEY: MOD_RES
<222> LOCATION: (34)..(34)
<223> OTHER INFORMATION: Asp, Asn, Glu, Gly, Val, His, Ala, Leu, Cys,
      Trp, Arg, Lys, Ser, Thr or Tyr
<220> FEATURE:
<221> NAME/KEY: MOD_RES
<222> LOCATION: (35)..(35)
<223> OTHER INFORMATION: Asn, Ile, Ser, Asp, Lys, Leu, His, Tyr, Thr,
      Gln, Gly, Arg, Ala, Cys or Met
<220> FEATURE:
<221> NAME/KEY: MOD_RES
<222> LOCATION: (36)..(36)
<223> OTHER INFORMATION: Trp, Ser, Arg, Gly, Asn, Cys, Leu, Phe, Pro or
      Lys
<220> FEATURE:
<221> NAME/KEY: MOD_RES
<222> LOCATION: (37)..(37)
<223> OTHER INFORMATION: Arg, Lys, Gly, Ala, Ser, Glu, Thr, Leu or Ile
<220> FEATURE:
<221> NAME/KEY: MOD_RES
<222> LOCATION: (38)..(38)
<223> OTHER INFORMATION: Ser, Asn, Thr, Gly, Arg, Gln, Met, Asp, Ile,
      Cys, Lys, Tyr, Ala, Val or His
<220> FEATURE:
<221> NAME/KEY: MOD_RES
<222> LOCATION: (39)..(39)
<223> OTHER INFORMATION: Glu, Lys, Gln, Gly, Asp, Arg, Ala, Val, Asn,
      His or Met
<220> FEATURE:
<221> NAME/KEY: MOD_RES
<222> LOCATION: (40)..(40)
<223> OTHER INFORMATION: Leu, Ile, Phe, Ser, Val, Met, Pro, Lys, Asn,
      Gln or Glu
<220> FEATURE:
<221> NAME/KEY: MOD_RES
<222> LOCATION: (41)..(41)
<223> OTHER INFORMATION: Tyr, Phe, Leu, His, Cys, Ser, Asp, Ile, Ala,
      Val, Asn or Glu
<220> FEATURE:
<221> NAME/KEY: MOD_RES
<222> LOCATION: (42)..(42)
<223> OTHER INFORMATION: Lys, Arg, Asn, Gln, Glu, Thr, Tyr, Pro, Gly,
      Val, Leu, Ile, Met, Ser or Asp
<220> FEATURE:
```

<221> NAME/KEY: MOD_RES
<222> LOCATION: (43)..(43)
<223> OTHER INFORMATION: Tyr, His, Cys, Asn, Phe, Ser, Ile or Glu
<220> FEATURE:
<221> NAME/KEY: MOD_RES
<222> LOCATION: (44)..(44)
<223> OTHER INFORMATION: Lys, Arg, Glu, Asn, Thr, Gln, Gly, Ile or Pro
<220> FEATURE:
<221> NAME/KEY: MOD_RES
<222> LOCATION: (45)..(45)
<223> OTHER INFORMATION: Val, Ile, Thr, Ala, Leu, Gly, Met, Ser or Asp
<220> FEATURE:
<221> NAME/KEY: MOD_RES
<222> LOCATION: (46)..(46)
<223> OTHER INFORMATION: Val, Ile, Ala, Leu, Glu, Gly, Ser, Met or Lys
<220> FEATURE:
<221> NAME/KEY: MOD_RES
<222> LOCATION: (47)..(47)
<223> OTHER INFORMATION: Lys, Glu, Arg, Gln, Ala, Thr, Ser, Gly, Val, Asn or Ile
<220> FEATURE:
<221> NAME/KEY: MOD_RES
<222> LOCATION: (48)..(48)
<223> OTHER INFORMATION: Ile, Val, Leu, Met, Thr, Ser, Asn, Phe or Pro
<220> FEATURE:
<221> NAME/KEY: MOD_RES
<222> LOCATION: (49)..(49)
<223> OTHER INFORMATION: Glu, Lys, Gln, Arg, Asp or Ser

<400> SEQUENCE: 35

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa
```

<210> SEQ ID NO 36
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Ile, Asn or Met
<220> FEATURE:
<221> NAME/KEY: MOD_RES
<222> LOCATION: (4)..(4)
<223> OTHER INFORMATION: Glu, Thr or Asp
<220> FEATURE:
<221> NAME/KEY: MOD_RES
<222> LOCATION: (5)..(5)
<223> OTHER INFORMATION: Cys or Glu
<220> FEATURE:
<221> NAME/KEY: MOD_RES
<222> LOCATION: (6)..(6)
<223> OTHER INFORMATION: His, Ala or Gln
<220> FEATURE:
<221> NAME/KEY: MOD_RES
<222> LOCATION: (8)..(8)
<223> OTHER INFORMATION: Asn or Asp
<220> FEATURE:
<221> NAME/KEY: MOD_RES
<222> LOCATION: (9)..(9)
<223> OTHER INFORMATION: Met or Ala
<220> FEATURE:
<221> NAME/KEY: MOD_RES
<222> LOCATION: (10)..(10)
<223> OTHER INFORMATION: Trp or Leu
<220> FEATURE:

<221> NAME/KEY: MOD_RES
<222> LOCATION: (11)..(11)
<223> OTHER INFORMATION: Asn or Glu
<220> FEATURE:
<221> NAME/KEY: MOD_RES
<222> LOCATION: (12)..(12)
<223> OTHER INFORMATION: Thr, Asn or Arg
<220> FEATURE:
<221> NAME/KEY: MOD_RES
<222> LOCATION: (13)..(13)
<223> OTHER INFORMATION: Gly, Thr or Asp
<220> FEATURE:
<221> NAME/KEY: MOD_RES
<222> LOCATION: (14)..(14)
<223> OTHER INFORMATION: Leu, Val or Lys
<220> FEATURE:
<221> NAME/KEY: MOD_RES
<222> LOCATION: (15)..(15)
<223> OTHER INFORMATION: Thr, Ala or Val
<220> FEATURE:
<221> NAME/KEY: MOD_RES
<222> LOCATION: (16)..(16)
<223> OTHER INFORMATION: Arg, Glu, Leu or Lys
<220> FEATURE:
<221> NAME/KEY: MOD_RES
<222> LOCATION: (17)..(17)
<223> OTHER INFORMATION: Asp or Gln
<220> FEATURE:
<221> NAME/KEY: MOD_RES
<222> LOCATION: (18)..(18)
<223> OTHER INFORMATION: Lys, Ala or Tyr
<220> FEATURE:
<221> NAME/KEY: MOD_RES
<222> LOCATION: (19)..(19)
<223> OTHER INFORMATION: Phe, Val, Ile or Asn
<220> FEATURE:
<221> NAME/KEY: MOD_RES
<222> LOCATION: (20)..(20)
<223> OTHER INFORMATION: Lys or Glu
<220> FEATURE:
<221> NAME/KEY: MOD_RES
<222> LOCATION: (21)..(21)
<223> OTHER INFORMATION: Arg, Asp, Ser or Thr
<220> FEATURE:
<221> NAME/KEY: MOD_RES
<222> LOCATION: (22)..(22)
<223> OTHER INFORMATION: Tyr, Val or Trp
<220> FEATURE:
<221> NAME/KEY: MOD_RES
<222> LOCATION: (23)..(23)
<223> OTHER INFORMATION: Asn, Trp or Tyr
<220> FEATURE:
<221> NAME/KEY: MOD_RES
<222> LOCATION: (24)..(24)
<223> OTHER INFORMATION: Glu, Ser or Asn
<220> FEATURE:
<221> NAME/KEY: MOD_RES
<222> LOCATION: (25)..(25)
<223> OTHER INFORMATION: Thr, Leu or Lys
<220> FEATURE:
<221> NAME/KEY: MOD_RES
<222> LOCATION: (26)..(26)
<223> OTHER INFORMATION: Trp or Phe
<220> FEATURE:
<221> NAME/KEY: MOD_RES
<222> LOCATION: (27)..(27)
<223> OTHER INFORMATION: Tyr, Glu or Asp
<220> FEATURE:
<221> NAME/KEY: MOD_RES
<222> LOCATION: (28)..(28)
<223> OTHER INFORMATION: Ser, Thr or Val
<220> FEATURE:
<221> NAME/KEY: MOD_RES
<222> LOCATION: (29)..(29)
<223> OTHER INFORMATION: Ser, Val or Thr
<220> FEATURE:
<221> NAME/KEY: MOD_RES
<222> LOCATION: (30)..(30)
<223> OTHER INFORMATION: Asp, Ile or Cys

<220> FEATURE:
<221> NAME/KEY: MOD_RES
<222> LOCATION: (31)..(31)
<223> OTHER INFORMATION: Val, Lys or Glu
<220> FEATURE:
<221> NAME/KEY: MOD_RES
<222> LOCATION: (32)..(32)
<223> OTHER INFORMATION: Val, Pro or Thr
<220> FEATURE:
<221> NAME/KEY: MOD_RES
<222> LOCATION: (33)..(33)
<223> OTHER INFORMATION: Cys or Thr
<220> FEATURE:
<221> NAME/KEY: MOD_RES
<222> LOCATION: (34)..(34)
<223> OTHER INFORMATION: Asp, Val, Glu or Arg
<220> FEATURE:
<221> NAME/KEY: MOD_RES
<222> LOCATION: (35)..(35)
<223> OTHER INFORMATION: Lys, Asn or Glu
<220> FEATURE:
<221> NAME/KEY: MOD_RES
<222> LOCATION: (36)..(36)
<223> OTHER INFORMATION: Asn, Leu or Ser
<220> FEATURE:
<221> NAME/KEY: MOD_RES
<222> LOCATION: (37)..(37)
<223> OTHER INFORMATION: Ser, Thr or Gln
<220> FEATURE:
<221> NAME/KEY: MOD_RES
<222> LOCATION: (38)..(38)
<223> OTHER INFORMATION: Ser, Pro, Thr or Asn
<220> FEATURE:
<221> NAME/KEY: MOD_RES
<222> LOCATION: (39)..(39)
<223> OTHER INFORMATION: Arg, Leu or Gln
<220> FEATURE:
<221> NAME/KEY: MOD_RES
<222> LOCATION: (40)..(40)
<223> OTHER INFORMATION: Cys or Thr
<220> FEATURE:
<221> NAME/KEY: MOD_RES
<222> LOCATION: (41)..(41)
<223> OTHER INFORMATION: Tyr, Val or Cys
<220> FEATURE:
<221> NAME/KEY: MOD_RES
<222> LOCATION: (42)..(42)
<223> OTHER INFORMATION: Gly, Ala or Tyr
<220> FEATURE:
<221> NAME/KEY: MOD_RES
<222> LOCATION: (43)..(43)
<223> OTHER INFORMATION: Met or Ala
<220> FEATURE:
<221> NAME/KEY: MOD_RES
<222> LOCATION: (44)..(44)
<223> OTHER INFORMATION: Asn, Gly, Lys or Thr
<220> FEATURE:
<221> NAME/KEY: MOD_RES
<222> LOCATION: (45)..(45)
<223> OTHER INFORMATION: Thr, His or Cys
<220> FEATURE:
<221> NAME/KEY: MOD_RES
<222> LOCATION: (46)..(46)
<223> OTHER INFORMATION: Cys or His
<220> FEATURE:
<221> NAME/KEY: MOD_RES
<222> LOCATION: (47)..(47)
<223> OTHER INFORMATION: Asn or Asp
<220> FEATURE:
<221> NAME/KEY: MOD_RES
<222> LOCATION: (48)..(48)
<223> OTHER INFORMATION: Thr or Ala
<220> FEATURE:
<221> NAME/KEY: MOD_RES
<222> LOCATION: (49)..(49)
<223> OTHER INFORMATION: Ser, Thr, Leu or Trp
<220> FEATURE:
<221> NAME/KEY: MOD_RES
<222> LOCATION: (50)..(50)

<223> OTHER INFORMATION: Val, Ile or Tyr
<220> FEATURE:
<221> NAME/KEY: MOD_RES
<222> LOCATION: (51)..(51)
<223> OTHER INFORMATION: Ile, Val or Met

<400> SEQUENCE: 36

```
Glu Xaa Val Xaa Xaa Xaa Phe Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa
    50
```

<210> SEQ ID NO 37
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Phe, Met or Ser
<220> FEATURE:
<221> NAME/KEY: MOD_RES
<222> LOCATION: (3)..(3)
<223> OTHER INFORMATION: Glu, Ala, Met, Lys, Ser, Gln, His, Gly or Asp
<220> FEATURE:
<221> NAME/KEY: MOD_RES
<222> LOCATION: (4)..(4)
<223> OTHER INFORMATION: Pro or Asn
<220> FEATURE:
<221> NAME/KEY: MOD_RES
<222> LOCATION: (5)..(5)
<223> OTHER INFORMATION: Cys or Asn
<220> FEATURE:
<221> NAME/KEY: MOD_RES
<222> LOCATION: (6)..(6)
<223> OTHER INFORMATION: Ser, Thr, Pro or Cys
<220> FEATURE:
<221> NAME/KEY: MOD_RES
<222> LOCATION: (7)..(7)
<223> OTHER INFORMATION: Lys, Asn, Arg or Ser
<220> FEATURE:
<221> NAME/KEY: MOD_RES
<222> LOCATION: (8)..(8)
<223> OTHER INFORMATION: Val, Ile or Lys
<220> FEATURE:
<221> NAME/KEY: MOD_RES
<222> LOCATION: (9)..(9)
<223> OTHER INFORMATION: Val, Ile or Phe
<220> FEATURE:
<221> NAME/KEY: MOD_RES
<222> LOCATION: (10)..(10)
<223> OTHER INFORMATION: Ala, Val or Ser
<220> FEATURE:
<221> NAME/KEY: MOD_RES
<222> LOCATION: (11)..(11)
<223> OTHER INFORMATION: Ala, Ser, Thr, Gly or Val
<220> FEATURE:
<221> NAME/KEY: MOD_RES
<222> LOCATION: (12)..(12)
<223> OTHER INFORMATION: Thr, Ser or Ala
<220> FEATURE:
<221> NAME/KEY: MOD_RES
<222> LOCATION: (13)..(13)
<223> OTHER INFORMATION: Cys, Arg or Leu
<220> FEATURE:
<221> NAME/KEY: MOD_RES
<222> LOCATION: (14)..(14)

<223> OTHER INFORMATION: Thr, Ala or Tyr
<220> FEATURE:
<221> NAME/KEY: MOD_RES
<222> LOCATION: (15)..(15)
<223> OTHER INFORMATION: Arg or Gly
<220> FEATURE:
<221> NAME/KEY: MOD_RES
<222> LOCATION: (16)..(16)
<223> OTHER INFORMATION: Met, Val, Glu, Leu, Ile or Gln
<220> FEATURE:
<221> NAME/KEY: MOD_RES
<222> LOCATION: (17)..(17)
<223> OTHER INFORMATION: Met, Ile, Arg, Lys or Thr
<220> FEATURE:
<221> NAME/KEY: MOD_RES
<222> LOCATION: (18)..(18)
<223> OTHER INFORMATION: Glu, Lys or Gly
<220> FEATURE:
<221> NAME/KEY: MOD_RES
<222> LOCATION: (19)..(19)
<223> OTHER INFORMATION: Thr, Ser, Ala or Met
<220> FEATURE:
<221> NAME/KEY: MOD_RES
<222> LOCATION: (21)..(21)
<223> OTHER INFORMATION: Thr, Ser, Ala or Pro
<220> FEATURE:
<221> NAME/KEY: MOD_RES
<222> LOCATION: (23)..(23)
<223> OTHER INFORMATION: Thr, Ala, Met or Ser
<220> FEATURE:
<221> NAME/KEY: MOD_RES
<222> LOCATION: (25)..(25)
<223> OTHER INFORMATION: Phe, Leu or Ser
<220> FEATURE:
<221> NAME/KEY: MOD_RES
<222> LOCATION: (26)..(26)
<223> OTHER INFORMATION: Gly or Ala
<220> FEATURE:
<221> NAME/KEY: MOD_RES
<222> LOCATION: (27)..(27)
<223> OTHER INFORMATION: Phe or Leu
<220> FEATURE:
<221> NAME/KEY: MOD_RES
<222> LOCATION: (28)..(28)
<223> OTHER INFORMATION: Asn, Cys or Ser
<220> FEATURE:
<221> NAME/KEY: MOD_RES
<222> LOCATION: (29)..(29)
<223> OTHER INFORMATION: Gly, Ser or Pro
<220> FEATURE:
<221> NAME/KEY: MOD_RES
<222> LOCATION: (30)..(30)
<223> OTHER INFORMATION: Thr, Ser, Ala or Ile
<220> FEATURE:
<221> NAME/KEY: MOD_RES
<222> LOCATION: (31)..(31)
<223> OTHER INFORMATION: Arg or Lys
<220> FEATURE:
<221> NAME/KEY: MOD_RES
<222> LOCATION: (32)..(32)
<223> OTHER INFORMATION: Ala, Ser or Thr
<220> FEATURE:
<221> NAME/KEY: MOD_RES
<222> LOCATION: (33)..(33)
<223> OTHER INFORMATION: Glu, Gly, Lys, Val or Asp
<220> FEATURE:
<221> NAME/KEY: MOD_RES
<222> LOCATION: (34)..(34)
<223> OTHER INFORMATION: Asn, Asp or Lys
<220> FEATURE:
<221> NAME/KEY: MOD_RES
<222> LOCATION: (35)..(35)
<223> OTHER INFORMATION: Arg, Lys, Gly or Thr
<220> FEATURE:
<221> NAME/KEY: MOD_RES
<222> LOCATION: (37)..(37)
<223> OTHER INFORMATION: Tyr, Phe or Cys
<220> FEATURE:
<221> NAME/KEY: MOD_RES

<222> LOCATION: (38)..(38)
<223> OTHER INFORMATION: Ile, Met, Val or Leu
<220> FEATURE:
<221> NAME/KEY: MOD_RES
<222> LOCATION: (39)..(39)
<223> OTHER INFORMATION: Tyr or Phe
<220> FEATURE:
<221> NAME/KEY: MOD_RES
<222> LOCATION: (40)..(40)
<223> OTHER INFORMATION: Trp, Cys or Leu
<220> FEATURE:
<221> NAME/KEY: MOD_RES
<222> LOCATION: (41)..(41)
<223> OTHER INFORMATION: His, Phe, Tyr or Ser

<400> SEQUENCE: 37

```
Gly Xaa Xaa Xaa Xaa Xaa Xaa Xaa Xaa Xaa Xaa Xaa Xaa Xaa Xaa Xaa
1               5                   10                  15

Xaa Xaa Xaa Gln Xaa Ser Xaa Trp Xaa Xaa Xaa Xaa Xaa Xaa Xaa Xaa
            20                  25                  30

Xaa Xaa Xaa Thr Xaa Xaa Xaa Xaa Xaa
        35                  40
```

<210> SEQ ID NO 38
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Arg, Ala, Val, Pro, Lys, His, Thr, Leu, Gln, Ile or Tyr
<220> FEATURE:
<221> NAME/KEY: MOD_RES
<222> LOCATION: (2)..(2)
<223> OTHER INFORMATION: Tyr, Lys, Arg, Glu, Gly, Pro, Asp, Asn, Ser or His
<220> FEATURE:
<221> NAME/KEY: MOD_RES
<222> LOCATION: (3)..(3)
<223> OTHER INFORMATION: Lys, His, Thr, Arg, Tyr, Phe, Gly, Pro, Ser, Asn, Ala, Asp or Glu
<220> FEATURE:
<221> NAME/KEY: MOD_RES
<222> LOCATION: (4)..(4)
<223> OTHER INFORMATION: Gly, Pro, Lys, Asn, Tyr, Thr, Ile, Met, Arg, Asp, Leu, Phe, Trp or His
<220> FEATURE:
<221> NAME/KEY: MOD_RES
<222> LOCATION: (5)..(5)
<223> OTHER INFORMATION: Thr, Arg, Asp, Gly, Glu, Lys, Ala, Ile, Pro, Ser, Tyr or Asn
<220> FEATURE:
<221> NAME/KEY: MOD_RES
<222> LOCATION: (6)..(6)
<223> OTHER INFORMATION: Asn, Thr, Tyr, Gly, His, Lys, Ser, Asp, Ile, Cys, Pro, Gln or Glu
<220> FEATURE:
<221> NAME/KEY: MOD_RES
<222> LOCATION: (7)..(7)
<223> OTHER INFORMATION: Lys, Asp, Asn, Arg, Glu, Ser, Thr, Gly, Gln, Ala, Ile, Val or His
<220> FEATURE:
<221> NAME/KEY: MOD_RES
<222> LOCATION: (8)..(8)
<223> OTHER INFORMATION: Thr, Asn, Gln, Lys, Ile, Asp, Arg, Ser, Glu, Met, Gly or His
<220> FEATURE:
<221> NAME/KEY: MOD_RES
<222> LOCATION: (9)..(9)
<223> OTHER INFORMATION: Ile, Val, Glu, Lys, Arg, Gly, Asn, Ser, Gln, Thr, Asp, Leu or Ala
<220> FEATURE:
<221> NAME/KEY: MOD_RES
<222> LOCATION: (10)..(10)
<223> OTHER INFORMATION: Lys, Asn, Thr, His, Ser, Gln, Arg, Asp, Phe, Leu, Tyr, Ile, Ala, Val or Pro
<220> FEATURE:
<221> NAME/KEY: MOD_RES
<222> LOCATION: (11)..(11)
<223> OTHER INFORMATION: Ile, Phe, Thr, Val, Ala, Asp, Ser, Lys, Leu, Met or Asn
<220> FEATURE:
<221> NAME/KEY: MOD_RES
<222> LOCATION: (12)..(12)
<223> OTHER INFORMATION: Asn, Lys, Thr, Ala, Ser, Glu, Arg, Val, Gly, His, Pro, Met, Asp or Gln
<220> FEATURE:
<221> NAME/KEY: MOD_RES
<222> LOCATION: (13)..(13)
<223> OTHER INFORMATION: Phe, Ala, Glu, Pro, His, Leu, Lys, Ser, Thr, Gly, Ile or Gln
<220> FEATURE:
<221> NAME/KEY: MOD_RES
<222> LOCATION: (14)..(14)
<223> OTHER INFORMATION: Gly, Thr, Ala, Ser, Pro, Lys, Glu, Val, Ile, Arg or Leu
<220> FEATURE:
<221> NAME/KEY: MOD_RES
<222> LOCATION: (15)..(15)
<223> OTHER INFORMATION: Ala, Lys, Arg, Glu, Gly, Thr, Ser, Gln, Val, Asp, Pro or Asn
<220> FEATURE:
<221> NAME/KEY: MOD_RES
<222> LOCATION: (16)..(16)
<223> OTHER INFORMATION: Gly, Pro, Ser, Asp, Asn or Lys
<220> FEATURE:
<221> NAME/KEY: MOD_RES
<222> LOCATION: (17)..(17)
<223> OTHER INFORMATION: Ser, Gly, Ala, Pro or Arg
<220> FEATURE:
<221> NAME/KEY: MOD_RES
<222> LOCATION: (18)..(18)
<223> OTHER INFORMATION: Asp, Asn, Gly or Ser
<220> FEATURE:
<221> NAME/KEY: MOD_RES
<222> LOCATION: (19)..(19)
<223> OTHER INFORMATION: Pro, Ala, Gly or Ser
<220> FEATURE:
<221> NAME/KEY: MOD_RES
<222> LOCATION: (20)..(20)
<223> OTHER INFORMATION: Glu, Asp, Pro, Lys or Gln
<220> FEATURE:
<221> NAME/KEY: MOD_RES
<222> LOCATION: (21)..(21)
<223> OTHER INFORMATION: Val, Ala, Ile, Thr or Glu
<220> FEATURE:
<221> NAME/KEY: MOD_RES
<222> LOCATION: (22)..(22)
<223> OTHER INFORMATION: Ala, Thr, Val, Arg, Glu, Met, Lys or Ser
<220> FEATURE:
<221> NAME/KEY: MOD_RES
<222> LOCATION: (23)..(23)
<223> OTHER INFORMATION: Tyr, Phe or His
<220> FEATURE:
<221> NAME/KEY: MOD_RES
<222> LOCATION: (24)..(24)
<223> OTHER INFORMATION: Met, Leu or Thr
<220> FEATURE:
<221> NAME/KEY: MOD_RES
<222> LOCATION: (25)..(25)
<223> OTHER INFORMATION: Trp or Arg
<220> FEATURE:
<221> NAME/KEY: MOD_RES
<222> LOCATION: (26)..(26)
<223> OTHER INFORMATION: Thr, Ser or Ile
<220> FEATURE:
<221> NAME/KEY: MOD_RES
<222> LOCATION: (27)..(27)
<223> OTHER INFORMATION: Asn or Asp
<220> FEATURE:

-continued

<221> NAME/KEY: MOD_RES
<222> LOCATION: (29)..(29)
<223> OTHER INFORMATION: Arg, Met, Lys or Gln
<220> FEATURE:
<221> NAME/KEY: MOD_RES
<222> LOCATION: (30)..(30)
<223> OTHER INFORMATION: Gly or Arg
<220> FEATURE:
<221> NAME/KEY: MOD_RES
<222> LOCATION: (31)..(31)
<223> OTHER INFORMATION: Glu, Lys or Asp
<220> FEATURE:
<221> NAME/KEY: MOD_RES
<222> LOCATION: (32)..(32)
<223> OTHER INFORMATION: Phe, Leu or Ser
<220> FEATURE:
<221> NAME/KEY: MOD_RES
<222> LOCATION: (33)..(33)
<223> OTHER INFORMATION: Leu, Phe, Pro, Ser or Tyr
<220> FEATURE:
<221> NAME/KEY: MOD_RES
<222> LOCATION: (34)..(34)
<223> OTHER INFORMATION: Tyr, His or Cys
<220> FEATURE:
<221> NAME/KEY: MOD_RES
<222> LOCATION: (36)..(36)
<223> OTHER INFORMATION: Asn, Asp, Ser or Lys
<220> FEATURE:
<221> NAME/KEY: MOD_RES
<222> LOCATION: (37)..(37)
<223> OTHER INFORMATION: Met, Val or Thr
<220> FEATURE:
<221> NAME/KEY: MOD_RES
<222> LOCATION: (38)..(38)
<223> OTHER INFORMATION: Thr, Ala, Lys, Asp, Glu, Ile or Asn
<220> FEATURE:
<221> NAME/KEY: MOD_RES
<222> LOCATION: (39)..(39)
<223> OTHER INFORMATION: Trp, Lys, Phe or Arg
<220> FEATURE:
<221> NAME/KEY: MOD_RES
<222> LOCATION: (40)..(40)
<223> OTHER INFORMATION: Phe or Leu
<220> FEATURE:
<221> NAME/KEY: MOD_RES
<222> LOCATION: (41)..(41)
<223> OTHER INFORMATION: Leu or Phe
<220> FEATURE:
<221> NAME/KEY: MOD_RES
<222> LOCATION: (42)..(42)
<223> OTHER INFORMATION: Asn, His, Asp or Glu
<220> FEATURE:
<221> NAME/KEY: MOD_RES
<222> LOCATION: (43)..(43)
<223> OTHER INFORMATION: Trp or Arg
<220> FEATURE:
<221> NAME/KEY: MOD_RES
<222> LOCATION: (44)..(44)
<223> OTHER INFORMATION: Val, Ile or Thr
<220> FEATURE:
<221> NAME/KEY: MOD_RES
<222> LOCATION: (45)..(45)
<223> OTHER INFORMATION: Trp, Glu, Tyr or Asp
<220> FEATURE:
<221> NAME/KEY: MOD_RES
<222> LOCATION: (46)..(46)
<223> OTHER INFORMATION: Ile, Val, Asn, Asp, Phe, Glu or Lys
<220> FEATURE:
<221> NAME/KEY: MOD_RES
<222> LOCATION: (47)..(47)
<223> OTHER INFORMATION: Glu, Arg, Lys, Asn, Leu or Gln
<220> FEATURE:
<221> NAME/KEY: MOD_RES
<222> LOCATION: (48)..(48)
<223> OTHER INFORMATION: Asn, Thr, Arg, Ala, Pro, Lys, Ser, Tyr or Asp
<220> FEATURE:
<221> NAME/KEY: MOD_RES
<222> LOCATION: (49)..(49)
<223> OTHER INFORMATION: Arg, Lys, Thr, Val, Asn, Glu, Asp, Gly, Ser,

```
      Ile, Met, Trp or Gln
<220> FEATURE:
<221> NAME/KEY: MOD_RES
<222> LOCATION: (50)..(50)
<223> OTHER INFORMATION: Thr, Glu, Pro, Gln, Lys, Arg, Ser, Asp, Ile,
      Ala or Val
<220> FEATURE:
<221> NAME/KEY: MOD_RES
<222> LOCATION: (51)..(51)
<223> OTHER INFORMATION: Gly, Thr, Lys, Gln, Arg, His, Glu, Asp, Ala,
      Asn, Ile, Ser, Leu, Pro or Tyr

<400> SEQUENCE: 38

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Cys Xaa Xaa Xaa Xaa
            20                  25                  30

Xaa Xaa Cys Xaa Xaa Xaa Xaa Xaa Xaa Xaa Xaa Xaa Xaa Xaa Xaa Xaa
        35                  40                  45

Xaa Xaa Xaa
    50


<210> SEQ ID NO 39
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Thr, Lys, Gln, Arg, His, Glu, Asp, Ala,
      Asn, Ile, Ser, Leu, Pro or Tyr
<220> FEATURE:
<221> NAME/KEY: MOD_RES
<222> LOCATION: (2)..(2)
<223> OTHER INFORMATION: Thr, Pro, Arg, Gln, Lys, Glu, Trp, Ala, Gly,
      Ile, Val, Leu, His, Ser, Asn or Met
<220> FEATURE:
<221> NAME/KEY: MOD_RES
<222> LOCATION: (3)..(3)
<223> OTHER INFORMATION: Asn, Lys, Gln, Asp, Arg, His, Thr, Gly, Ser,
      Leu, Pro or Trp
<220> FEATURE:
<221> NAME/KEY: MOD_RES
<222> LOCATION: (4)..(4)
<223> OTHER INFORMATION: Gln, Arg, His, Asn, Thr, Gly, Lys, Glu, Tyr,
      Asp, Ala, Pro, Trp or Ser
<220> FEATURE:
<221> NAME/KEY: MOD_RES
<222> LOCATION: (5)..(5)
<223> OTHER INFORMATION: Thr, Asn, Tyr, Ile, Pro, Arg, Ala, Lys, Gln,
      Ser or Asp
<220> FEATURE:
<221> NAME/KEY: MOD_RES
<222> LOCATION: (6)..(6)
<223> OTHER INFORMATION: Gln, Trp, Lys, Ala, Tyr, Arg, Asn, Glu, Asp,
      His or Thr
<220> FEATURE:
<221> NAME/KEY: MOD_RES
<222> LOCATION: (7)..(7)
<223> OTHER INFORMATION: His, Arg, Ala, Pro, Lys, Leu, Gly, Val, Ile or
      Thr
<220> FEATURE:
<221> NAME/KEY: MOD_RES
<222> LOCATION: (8)..(8)
<223> OTHER INFORMATION: Asn, Gln, Lys, Arg, Pro, His or Ser
<220> FEATURE:
<221> NAME/KEY: MOD_RES
<222> LOCATION: (9)..(9)
<223> OTHER INFORMATION: Tyr, Arg, His, Asn or Lys
<220> FEATURE:
<221> NAME/KEY: MOD_RES
```

<222> LOCATION: (10)..(10)
<223> OTHER INFORMATION: Val, Ala, Asn, Arg or Tyr
<220> FEATURE:
<221> NAME/KEY: MOD_RES
<222> LOCATION: (11)..(11)
<223> OTHER INFORMATION: Tyr, Ala, Asn or Thr
<220> FEATURE:
<221> NAME/KEY: MOD_RES
<222> LOCATION: (12)..(12)
<223> OTHER INFORMATION: Val or Ala
<220> FEATURE:
<221> NAME/KEY: MOD_RES
<222> LOCATION: (13)..(13)
<223> OTHER INFORMATION: Pro or Thr
<220> FEATURE:
<221> NAME/KEY: MOD_RES
<222> LOCATION: (14)..(14)
<223> OTHER INFORMATION: Cys, Arg or Tyr
<220> FEATURE:
<221> NAME/KEY: MOD_RES
<222> LOCATION: (15)..(15)
<223> OTHER INFORMATION: His, Arg or Gln
<220> FEATURE:
<221> NAME/KEY: MOD_RES
<222> LOCATION: (17)..(17)
<223> OTHER INFORMATION: Lys, Arg, Pro or Glu
<220> FEATURE:
<221> NAME/KEY: MOD_RES
<222> LOCATION: (19)..(19)
<223> OTHER INFORMATION: Ile, Val or Lys
<220> FEATURE:
<221> NAME/KEY: MOD_RES
<222> LOCATION: (20)..(20)
<223> OTHER INFORMATION: Ile or Val
<220> FEATURE:
<221> NAME/KEY: MOD_RES
<222> LOCATION: (21)..(21)
<223> OTHER INFORMATION: Asn or Ser
<220> FEATURE:
<221> NAME/KEY: MOD_RES
<222> LOCATION: (22)..(22)
<223> OTHER INFORMATION: Thr, Ala or Ile
<220> FEATURE:
<221> NAME/KEY: MOD_RES
<222> LOCATION: (23)..(23)
<223> OTHER INFORMATION: Trp or Arg
<220> FEATURE:
<221> NAME/KEY: MOD_RES
<222> LOCATION: (24)..(24)
<223> OTHER INFORMATION: His or Arg
<220> FEATURE:
<221> NAME/KEY: MOD_RES
<222> LOCATION: (25)..(25)
<223> OTHER INFORMATION: Lys, Arg or Asn
<220> FEATURE:
<221> NAME/KEY: MOD_RES
<222> LOCATION: (26)..(26)
<223> OTHER INFORMATION: Val, Ala, Ile or Ser
<220> FEATURE:
<221> NAME/KEY: MOD_RES
<222> LOCATION: (27)..(27)
<223> OTHER INFORMATION: Gly, Trp, Arg or Glu
<220> FEATURE:
<221> NAME/KEY: MOD_RES
<222> LOCATION: (28)..(28)
<223> OTHER INFORMATION: Lys, Gln, Arg, Ile, Val, Asn, Thr, Leu or Glu
<220> FEATURE:
<221> NAME/KEY: MOD_RES
<222> LOCATION: (29)..(29)
<223> OTHER INFORMATION: Asn, His, Tyr, Arg or Lys
<220> FEATURE:
<221> NAME/KEY: MOD_RES
<222> LOCATION: (30)..(30)
<223> OTHER INFORMATION: Val, Ile, Ala, Leu or Tyr
<220> FEATURE:
<221> NAME/KEY: MOD_RES
<222> LOCATION: (31)..(31)
<223> OTHER INFORMATION: Tyr or Ile
<220> FEATURE:

<221> NAME/KEY: MOD_RES
<222> LOCATION: (32)..(32)
<223> OTHER INFORMATION: Leu or Phe
<220> FEATURE:
<221> NAME/KEY: MOD_RES
<222> LOCATION: (33)..(33)
<223> OTHER INFORMATION: Pro, Ala or Leu
<220> FEATURE:
<221> NAME/KEY: MOD_RES
<222> LOCATION: (35)..(35)
<223> OTHER INFORMATION: Arg or Lys
<220> FEATURE:
<221> NAME/KEY: MOD_RES
<222> LOCATION: (36)..(36)
<223> OTHER INFORMATION: Glu, Gly, Ala or Lys
<220> FEATURE:
<221> NAME/KEY: MOD_RES
<222> LOCATION: (37)..(37)
<223> OTHER INFORMATION: Gly or Arg
<220> FEATURE:
<221> NAME/KEY: MOD_RES
<222> LOCATION: (38)..(38)
<223> OTHER INFORMATION: Glu, Gln, Leu, Lys, Asp, Val, Thr, Gly, Asn or
His
<220> FEATURE:
<221> NAME/KEY: MOD_RES
<222> LOCATION: (39)..(39)
<223> OTHER INFORMATION: Leu or Phe
<220> FEATURE:
<221> NAME/KEY: MOD_RES
<222> LOCATION: (40)..(40)
<223> OTHER INFORMATION: Thr, Ser, Val, Ile, Asn or Ala
<220> FEATURE:
<221> NAME/KEY: MOD_RES
<222> LOCATION: (41)..(41)
<223> OTHER INFORMATION: Cys or Arg
<220> FEATURE:
<221> NAME/KEY: MOD_RES
<222> LOCATION: (42)..(42)
<223> OTHER INFORMATION: Asn, Thr, Ile, Lys, Asp, Glu or Val
<220> FEATURE:
<221> NAME/KEY: MOD_RES
<222> LOCATION: (43)..(43)
<223> OTHER INFORMATION: Ser or Thr
<220> FEATURE:
<221> NAME/KEY: MOD_RES
<222> LOCATION: (44)..(44)
<223> OTHER INFORMATION: Thr, Ser, Asn, Ala or Asp
<220> FEATURE:
<221> NAME/KEY: MOD_RES
<222> LOCATION: (46)..(46)
<223> OTHER INFORMATION: Thr or Ser
<220> FEATURE:
<221> NAME/KEY: MOD_RES
<222> LOCATION: (47)..(47)
<223> OTHER INFORMATION: Ser or Gly
<220> FEATURE:
<221> NAME/KEY: MOD_RES
<222> LOCATION: (48)..(48)
<223> OTHER INFORMATION: Ile, Leu, Met, Val or Phe

<400> SEQUENCE: 39

```
Xaa Xaa Xaa Xaa Xaa Xaa Xaa Xaa Xaa Xaa Xaa Xaa Xaa Xaa Xaa Ile
1               5                   10                  15

Xaa Gln Xaa Xaa Xaa Xaa Xaa Xaa Xaa Xaa Xaa Xaa Xaa Xaa Xaa Xaa
            20                  25                  30

Xaa Pro Xaa Xaa Xaa Xaa Xaa Xaa Xaa Xaa Xaa Xaa Val Xaa Xaa Xaa
        35                  40                  45
```

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Ala, Ile, Thr or Leu
<220> FEATURE:
<221> NAME/KEY: MOD_RES
<222> LOCATION: (2)..(2)
<223> OTHER INFORMATION: Asn, Thr, Asp or Val
<220> FEATURE:
<221> NAME/KEY: MOD_RES
<222> LOCATION: (3)..(3)
<223> OTHER INFORMATION: Ile, Arg, Gln, Val, Met, Trp, Tyr or Asn
<220> FEATURE:
<221> NAME/KEY: MOD_RES
<222> LOCATION: (4)..(4)
<223> OTHER INFORMATION: Asp, Glu, Asn, Tyr or Ile
<220> FEATURE:
<221> NAME/KEY: MOD_RES
<222> LOCATION: (5)..(5)
<223> OTHER INFORMATION: Ala, Thr, Gly, Val, Trp, Asp, Ser, Tyr, Ile,
Glu, Met or Lys
<220> FEATURE:
<221> NAME/KEY: MOD_RES
<222> LOCATION: (6)..(6)
<223> OTHER INFORMATION: Gln, Asn, Gly, Arg, Asp, Ser, Trp, Glu, Ala,
Thr, Tyr, Ile, Phe or Lys
<220> FEATURE:
<221> NAME/KEY: MOD_RES
<222> LOCATION: (7)..(7)
<223> OTHER INFORMATION: Ile, Glu, Val, Asn, Asp, Thr, Met, Lys, Ser,
Ala, Gly, Leu, Arg, Tyr, Gln, Pro or His
<220> FEATURE:
<221> NAME/KEY: MOD_RES
<222> LOCATION: (8)..(8)
<223> OTHER INFORMATION: Asn, Asp, Gln, Glu, Arg, Lys, Thr, His, Val,
Ser, Tyr, Gly, Leu, Ala, Ile, Pro or Phe
<220> FEATURE:
<221> NAME/KEY: MOD_RES
<222> LOCATION: (9)..(9)
<223> OTHER INFORMATION: Ser, Thr, Glu, Asp, Asn, Val, Gln, Ile, Lys,
Gly, Ala, Arg, Leu or Trp
<220> FEATURE:
<221> NAME/KEY: MOD_RES
<222> LOCATION: (10)..(10)
<223> OTHER INFORMATION: Asn, Thr, Gln, Ser, Asp, Arg, Gly, Lys, Ala,
Ile or Tyr
<220> FEATURE:
<221> NAME/KEY: MOD_RES
<222> LOCATION: (11)..(11)
<223> OTHER INFORMATION: Thr, Gln, Gly, Asn, Ile, Phe, Asp, Arg, Lys,
Ser, Tyr, Glu, Ala, Val, Leu or His
<220> FEATURE:
<221> NAME/KEY: MOD_RES
<222> LOCATION: (12)..(12)
<223> OTHER INFORMATION: Thr, Asn, Ile, Ser, Asp, Tyr, Ala or Lys
<220> FEATURE:
<221> NAME/KEY: MOD_RES
<222> LOCATION: (13)..(13)
<223> OTHER INFORMATION: Asn, Ile, Gln, Thr, Ser, Asp, Lys, Arg, Glu,
His or Met
<220> FEATURE:
<221> NAME/KEY: MOD_RES
<222> LOCATION: (14)..(14)
<223> OTHER INFORMATION: Thr, Ile, Phe, Val, Ala, Leu or Asn
<220> FEATURE:
<221> NAME/KEY: MOD_RES
<222> LOCATION: (15)..(15)
<223> OTHER INFORMATION: Phe, Asn, Ser, Ile, Tyr, Val, Arg or Asp
<220> FEATURE:
<221> NAME/KEY: MOD_RES
<222> LOCATION: (16)..(16)
<223> OTHER INFORMATION: Ile, Ser, Arg, Met or Thr
<220> FEATURE:
<221> NAME/KEY: MOD_RES
<222> LOCATION: (17)..(17)
<223> OTHER INFORMATION: Thr, Ala, Leu or Ser
<220> FEATURE:
<221> NAME/KEY: MOD_RES
<222> LOCATION: (18)..(18)
<223> OTHER INFORMATION: Phe, Met, Gly, Val, Glu, Pro or Ser
<220> FEATURE:
<221> NAME/KEY: MOD_RES
<222> LOCATION: (19)..(19)
<223> OTHER INFORMATION: Ser, Val, Gly, Ala, Leu, Ile or Asn
<220> FEATURE:
<221> NAME/KEY: MOD_RES
<222> LOCATION: (20)..(20)
<223> OTHER INFORMATION: Ala or Gly
<220> FEATURE:
<221> NAME/KEY: MOD_RES
<222> LOCATION: (21)..(21)
<223> OTHER INFORMATION: Glu or Asp
<220> FEATURE:
<221> NAME/KEY: MOD_RES
<222> LOCATION: (22)..(22)
<223> OTHER INFORMATION: Val, Leu, Met, Tyr or Glu
<220> FEATURE:
<221> NAME/KEY: MOD_RES
<222> LOCATION: (23)..(23)
<223> OTHER INFORMATION: Ala, Ser, Gly or Lys
<220> FEATURE:
<221> NAME/KEY: MOD_RES
<222> LOCATION: (24)..(24)
<223> OTHER INFORMATION: Glu, Asp, Lys or Asn
<220> FEATURE:
<221> NAME/KEY: MOD_RES
<222> LOCATION: (25)..(25)
<223> OTHER INFORMATION: Leu, Met or Lys
<220> FEATURE:
<221> NAME/KEY: MOD_RES
<222> LOCATION: (26)..(26)
<223> OTHER INFORMATION: Tyr, Phe or Asn
<220> FEATURE:
<221> NAME/KEY: MOD_RES
<222> LOCATION: (27)..(27)
<223> OTHER INFORMATION: Arg or Lys
<220> FEATURE:
<221> NAME/KEY: MOD_RES
<222> LOCATION: (28)..(28)
<223> OTHER INFORMATION: Leu or Val
<220> FEATURE:
<221> NAME/KEY: MOD_RES
<222> LOCATION: (29)..(29)
<223> OTHER INFORMATION: Glu or Lys
<220> FEATURE:
<221> NAME/KEY: MOD_RES
<222> LOCATION: (30)..(30)
<223> OTHER INFORMATION: Leu, Pro or Ser
<220> FEATURE:
<221> NAME/KEY: MOD_RES
<222> LOCATION: (34)..(34)
<223> OTHER INFORMATION: Lys, Thr or Asn
<220> FEATURE:
<221> NAME/KEY: MOD_RES
<222> LOCATION: (35)..(35)
<223> OTHER INFORMATION: Leu or Ser
<220> FEATURE:
<221> NAME/KEY: MOD_RES
<222> LOCATION: (36)..(36)
<223> OTHER INFORMATION: Ile or Val
<220> FEATURE:
<221> NAME/KEY: MOD_RES
<222> LOCATION: (37)..(37)
<223> OTHER INFORMATION: Glu or Arg
<220> FEATURE:
<221> NAME/KEY: MOD_RES
<222> LOCATION: (38)..(38)
<223> OTHER INFORMATION: Ile or Val
<220> FEATURE:
<221> NAME/KEY: MOD_RES
<222> LOCATION: (39)..(39)
<223> OTHER INFORMATION: Arg or Lys

<400> SEQUENCE: 40

```
Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa Gly Asp
            20                  25                  30

Tyr Xaa Xaa Xaa Xaa Xaa Xaa
        35


<210> SEQ ID NO 41
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe, Tyr, Leu, Ser, Cys, His, Val, Lys, Ile,
      Asn, Gly or Thr
<220> FEATURE:
<221> NAME/KEY: MOD_RES
<222> LOCATION: (2)..(2)
<223> OTHER INFORMATION: Ala, Val, Thr, Gly, Glu, Ser, Cys, Pro, Arg,
      Leu, Met, Phe or Asn
<220> FEATURE:
<221> NAME/KEY: MOD_RES
<222> LOCATION: (3)..(3)
<223> OTHER INFORMATION: Ile, Leu, Met, Val, Thr, Phe, Asn, Pro, Ser,
      Asp, Gly, Tyr, His or Arg
<220> FEATURE:
<221> NAME/KEY: MOD_RES
<222> LOCATION: (4)..(4)
<223> OTHER INFORMATION: Leu, Ile, Phe, Val, Met, Pro, Ser, Tyr, Gln,
      Arg or Asn
<220> FEATURE:
<221> NAME/KEY: MOD_RES
<222> LOCATION: (5)..(5)
<223> OTHER INFORMATION: Lys, Arg, Gln, Glu, Met, Asn, Thr, Ser, Leu,
      Ile, Phe or Cys
<220> FEATURE:
<221> NAME/KEY: MOD_RES
<222> LOCATION: (6)..(6)
<223> OTHER INFORMATION: Cys, Arg, Tyr, Gly, Ser, Trp, Val, Phe, Leu,
      Ile or Lys
<220> FEATURE:
<221> NAME/KEY: MOD_RES
<222> LOCATION: (7)..(7)
<223> OTHER INFORMATION: Asn, Lys, Arg, Thr, Gly, Phe, Ser, Asp, Leu,
      Ile, His, Met, Gln, Glu, Tyr, Pro or Val
<220> FEATURE:
<221> NAME/KEY: MOD_RES
<222> LOCATION: (8)..(8)
<223> OTHER INFORMATION: Asp, Asn, Glu, Ser, Gln, Gly, Ala, Val, Thr,
      Lys, His, Tyr, Ile, Arg, Met or Pro
<220> FEATURE:
<221> NAME/KEY: MOD_RES
<222> LOCATION: (9)..(9)
<223> OTHER INFORMATION: Lys, Glu, Thr, Asn, Ala, Arg, Pro, Ile, Val,
      Gln, Ser, Asp, Met, Gly, Leu or His
<220> FEATURE:
<221> NAME/KEY: MOD_RES
<222> LOCATION: (10)..(10)
<223> OTHER INFORMATION: Lys, Thr, Asn, Glu, Gln, Arg, Gly, Met, Asp,
      Ala, Ser, Ile, Val, Leu, His, Pro, Trp, Phe or Tyr
<220> FEATURE:
<221> NAME/KEY: MOD_RES
<222> LOCATION: (11)..(11)
<223> OTHER INFORMATION: Phe, Tyr, Ser, Leu, Cys, Val, Ile, Met, Pro,
      Lys or Asn
<220> FEATURE:
<221> NAME/KEY: MOD_RES
<222> LOCATION: (12)..(12)
<223> OTHER INFORMATION: Asn, Ser, Thr, Asp, Lys, Ile, Glu, Gln, Arg,
      Gly, His, Met, Ala, Tyr, Val, Cys, Pro or Leu
<220> FEATURE:
<221> NAME/KEY: MOD_RES
<222> LOCATION: (13)..(13)
<223> OTHER INFORMATION: Gly, Arg, Glu, Lys, Trp or Thr
```

```
<220> FEATURE:
<221> NAME/KEY: MOD_RES
<222> LOCATION: (14)..(14)
<223> OTHER INFORMATION: Thr, Lys, Ser, Ile, Ala, Leu, Arg, Gln, Met,
      Asn, Glu, Tyr, Pro, Val, Gly or Asp
<220> FEATURE:
<221> NAME/KEY: MOD_RES
<222> LOCATION: (15)..(15)
<223> OTHER INFORMATION: Gly, Glu, Arg, Ala, Asp, Ser, Lys or Val
<220> FEATURE:
<221> NAME/KEY: MOD_RES
<222> LOCATION: (16)..(16)
<223> OTHER INFORMATION: Pro, Leu, Thr, Gln, Ser, Lys, Glu, Ala, Ile,
      Arg, Asn, Asp, Met, Val, His, Gly or Phe
<220> FEATURE:
<221> NAME/KEY: MOD_RES
<222> LOCATION: (17)..(17)
<223> OTHER INFORMATION: Cys, Arg, Tyr, Ser, Gly, Ala, Val, Trp or Phe
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Asn, Lys, Asp, Ser, Pro, Glu, Arg, Thr, Gln,
      His, Gly, Ile, Met, Phe, Tyr or Val
<220> FEATURE:
<221> NAME/KEY: MOD_RES
<222> LOCATION: (20)..(20)
<223> OTHER INFORMATION: Val, Ile, Ala, Gly, Ser, Phe, Thr, Leu, Cys,
      Lys, Tyr, Gln or Glu
<220> FEATURE:
<221> NAME/KEY: MOD_RES
<222> LOCATION: (21)..(21)
<223> OTHER INFORMATION: Ser, Thr, Gly, Asn, Arg, Cys, Ala, Val, Ile,
      Leu, Phe or Lys
<220> FEATURE:
<221> NAME/KEY: MOD_RES
<222> LOCATION: (22)..(22)
<223> OTHER INFORMATION: Thr, Ser, Val, Ile, Ala, Pro, His, Gln, Leu,
      Gly, Met, Lys or Arg
<220> FEATURE:
<221> NAME/KEY: MOD_RES
<222> LOCATION: (23)..(23)
<223> OTHER INFORMATION: Val, Ile, Ala, Leu, Gly, Tyr, Glu, Arg, Ser,
      Thr or Phe
<220> FEATURE:
<221> NAME/KEY: MOD_RES
<222> LOCATION: (24)..(24)
<223> OTHER INFORMATION: Gln, Thr, Leu, His, Arg, Pro, Ala, Val, Ile,
      Lys, Ser, Asn or Glu
<220> FEATURE:
<221> NAME/KEY: MOD_RES
<222> LOCATION: (25)..(25)
<223> OTHER INFORMATION: Cys, Arg, Tyr, Trp, Gly, Phe, Ser, Met, Ala,
      Val, Ile, Pro or Lys
<220> FEATURE:
<221> NAME/KEY: MOD_RES
<222> LOCATION: (26)..(26)
<223> OTHER INFORMATION: Thr, Ala, Pro, Ser, Gln, Ile, Arg, Tyr, Val,
      Gly or His
<220> FEATURE:
<221> NAME/KEY: MOD_RES
<222> LOCATION: (27)..(27)
<223> OTHER INFORMATION: His, Gln, Arg, Tyr, Pro, Asn, Leu, Asp, Thr,
      Gly, Met, Val, Trp, Ser or Glu
<220> FEATURE:
<221> NAME/KEY: MOD_RES
<222> LOCATION: (28)..(28)
<223> OTHER INFORMATION: Gly, Arg, Glu, Ser, Trp, Ala, Val, Pro or Asn
<220> FEATURE:
<221> NAME/KEY: MOD_RES
<222> LOCATION: (29)..(29)
<223> OTHER INFORMATION: Ile, Val, Thr, Leu, Asn, Phe, Met, Ser, Gly,
      Ala, Arg or Asp
<220> FEATURE:
<221> NAME/KEY: MOD_RES
<222> LOCATION: (30)..(30)
```

<223> OTHER INFORMATION: Arg, Lys, Met, Ser, Gln, Thr, Asn, Gly, Glu,
Leu, Ala, Trp, Ile, Pro or His
<220> FEATURE:
<221> NAME/KEY: MOD_RES
<222> LOCATION: (31)..(31)
<223> OTHER INFORMATION: Pro, Ala, Ser, Leu, Gln, Thr, Arg, His or Glu
<220> FEATURE:
<221> NAME/KEY: MOD_RES
<222> LOCATION: (32)..(32)
<223> OTHER INFORMATION: Val, Thr, Ala, Ile, Met, Leu, Gly, Glu, Ser,
Pro, Gln, Cys, Trp, His or Arg
<220> FEATURE:
<221> NAME/KEY: MOD_RES
<222> LOCATION: (33)..(33)
<223> OTHER INFORMATION: Val, Ile, Ala, Leu, Met, Gly, Thr, Glu, Ser,
Pro, Phe, Cys, Trp, Arg, Tyr or Asn
<220> FEATURE:
<221> NAME/KEY: MOD_RES
<222> LOCATION: (34)..(34)
<223> OTHER INFORMATION: Ser, Thr, Pro, Leu, Ala, Val, Gln, Ile, Phe,
Asn, His, Lys or Tyr
<220> FEATURE:
<221> NAME/KEY: MOD_RES
<222> LOCATION: (35)..(35)
<223> OTHER INFORMATION: Thr, Ser, Ala, Ile, Asn, Pro, Leu, His, Gly,
Val, Arg or Gln
<220> FEATURE:
<221> NAME/KEY: MOD_RES
<222> LOCATION: (36)..(36)
<223> OTHER INFORMATION: Gln, His, Arg, Ser, Pro, Lys, Ala, Glu, Leu,
Thr, Asn or Met
<220> FEATURE:
<221> NAME/KEY: MOD_RES
<222> LOCATION: (37)..(37)
<223> OTHER INFORMATION: Leu, Phe, Pro, Val, Met, Ser, Ile, Thr, Ala,
Cys, Gln, Arg, Tyr, Trp or His
<220> FEATURE:
<221> NAME/KEY: MOD_RES
<222> LOCATION: (38)..(38)
<223> OTHER INFORMATION: Leu, Ile, Pro, Val, Ala, Thr, Met, Ser, Gln,
Arg, Cys, Phe, Tyr, Gly, Asn, Trp or Lys
<220> FEATURE:
<221> NAME/KEY: MOD_RES
<222> LOCATION: (39)..(39)
<223> OTHER INFORMATION: Leu, Val, Phe, Ile, Ser, Met, Pro, Trp, Tyr,
Gly, Thr, Gln, Cys or Glu
<220> FEATURE:
<221> NAME/KEY: MOD_RES
<222> LOCATION: (40)..(40)
<223> OTHER INFORMATION: Asn, Asp, Ser, Lys, Pro, Tyr, His, Thr, Ile,
Met, Phe, Ala, Gly, Leu, Trp or Glu
<220> FEATURE:
<221> NAME/KEY: MOD_RES
<222> LOCATION: (41)..(41)
<223> OTHER INFORMATION: Gly, Pro, Ser, Ala, Asp, Cys, Val, Trp, Arg,
Asn, Phe or Glu
<220> FEATURE:
<221> NAME/KEY: MOD_RES
<222> LOCATION: (42)..(42)
<223> OTHER INFORMATION: Ser, Thr, Gly, Arg, Asn, Cys, Ile, Ala, Val,
Gln, Leu, Pro, Lys, Met or Asp
<220> FEATURE:
<221> NAME/KEY: MOD_RES
<222> LOCATION: (43)..(43)
<223> OTHER INFORMATION: Leu, Ile, Val, Thr, Arg, Pro, Gln, Ser, Phe,
Ala, Tyr, Met, Gly, Lys or Glu
<220> FEATURE:
<221> NAME/KEY: MOD_RES
<222> LOCATION: (44)..(44)
<223> OTHER INFORMATION: Ala, Ser, Thr, Val, Pro, Glu, Gly, Asp, Gln,
Leu, Arg, Lys, Tyr, Asn, Cys, Met or Phe
<220> FEATURE:
<221> NAME/KEY: MOD_RES
<222> LOCATION: (45)..(45)
<223> OTHER INFORMATION: Glu, Lys, Gly, Ala, Arg, Asp, Thr, Gln, Val,
Asn, Ser, Leu, Ile, His or Tyr
<220> FEATURE:
<221> NAME/KEY: MOD_RES
<222> LOCATION: (46)..(46)

<223> OTHER INFORMATION: Glu, Gly, Lys, Asp, Arg, Gln, Asn, Thr, Ser, Ala, Pro, Val, Ile, His or Trp
<220> FEATURE:
<221> NAME/KEY: MOD_RES
<222> LOCATION: (47)..(47)
<223> OTHER INFORMATION: Glu, Asp, Gly, Lys, Asn, Gln, Ser, Arg, Val, Ala, Thr, His, Met, Leu, Ile, Tyr or Pro
<220> FEATURE:
<221> NAME/KEY: MOD_RES
<222> LOCATION: (48)..(48)
<223> OTHER INFORMATION: Val, Ile, Thr, Ala, Leu, Glu, Met, Asp, Gly, Pro, Ser, Arg, Lys, Tyr, Asn, Phe, Cys or Gln
<220> FEATURE:
<221> NAME/KEY: MOD_RES
<222> LOCATION: (49)..(49)
<223> OTHER INFORMATION: Val, Ile, Met, Arg, Lys, Ala, Thr, Gln, Glu, Leu, Ser, Gly, Tyr, Asn, Pro, Cys, Asp or Phe
<220> FEATURE:
<221> NAME/KEY: MOD_RES
<222> LOCATION: (50)..(50)
<223> OTHER INFORMATION: Ile, Val, Leu, Thr, Phe, Ser, Met, Asn, Arg, Pro, Ala, Asp, Gly, Cys, Trp, Glu, Lys or Tyr
<220> FEATURE:
<221> NAME/KEY: MOD_RES
<222> LOCATION: (51)..(51)
<223> OTHER INFORMATION: Arg, Lys, Ser, Met, Gly, Ile, Thr, Leu, Gln, Asn, Asp, Ala, Val, Pro, Phe, Trp, Tyr, Glu or Cys
<220> FEATURE:
<221> NAME/KEY: MOD_RES
<222> LOCATION: (52)..(52)
<223> OTHER INFORMATION: Ser, Thr, Phe, Gly, ala, Pro, Val, Cys, Tyr, Ile, Asn, Leu, Glu, Asp, Arg, Trp or Lys
<220> FEATURE:
<221> NAME/KEY: MOD_RES
<222> LOCATION: (53)..(53)
<223> OTHER INFORMATION: Glu, Ala, Asp, Lys, Gln, Ser, Val, Asn, Gly, Arg, Thr, Tyr, Pro, Cys, His, Ile, Leu or Trp
<220> FEATURE:
<221> NAME/KEY: MOD_RES
<222> LOCATION: (54)..(54)
<223> OTHER INFORMATION: Asn, Asp, Ser, Lys, Glu, Ile, Thr, Tyr, His, Arg, Gln, Gly, Ala, Leu, Pro, Phe, Val or Met
<220> FEATURE:
<221> NAME/KEY: MOD_RES
<222> LOCATION: (55)..(55)
<223> OTHER INFORMATION: Phe, Leu, Ile, Met, Val, Ser, Lys, Thr, Pro, Tyr, Trp, Arg, His, Gln, Cys, Ala, Asn, Gly or Asp
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (57)..(57)
<223> OTHER INFORMATION: Asn, Asp, Glu, Lys, Ser, Gln, Ala, His, Gly, Arg, Thr, Tyr, Val, Ile, Pro, Leu, Cys, Met or Phe
<220> FEATURE:
<221> NAME/KEY: MOD_RES
<222> LOCATION: (58)..(58)
<223> OTHER INFORMATION: Asn, Ser, Thr, Asp, Ala, His, Lys, Pro, Tyr, Ile, Gln, Gly, Met, Arg, Leu or Glu
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (60)..(60)
<223> OTHER INFORMATION: Lys, Arg, Asn, Glu, Asp, Gln, Gly, Tyr, Ala, Thr, Ile, His, Val, Pro, Ser, Met, Leu or Trp
<220> FEATURE:
<221> NAME/KEY: MOD_RES
<222> LOCATION: (61)..(61)
<223> OTHER INFORMATION: Thr, Ile, Asn, Val, Ser, Pro, Ala, Asp, Leu, Met, Lys, Tyr, Gly, Phe, Gln, His, Arg or Glu
<220> FEATURE:
<221> NAME/KEY: MOD_RES
<222> LOCATION: (62)..(62)
<223> OTHER INFORMATION: Ile, Leu, Met, Val, Thr, Arg, Lys, Tyr, Ala, Ser, Phe, Asn, His, Gly, Cys or Pro

<400> SEQUENCE: 41

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Xaa
50 55 60

<210> SEQ ID NO 42
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Thr, Ala, Val, Met, Ile, Ser, Asn, Lys, Pro, Leu, Arg, His, Gly, Glu, Phe, Gln, Tyr, Asp or Cys
<220> FEATURE:
<221> NAME/KEY: MOD_RES
<222> LOCATION: (2)..(2)
<223> OTHER INFORMATION: Leu, Ile, Val, Phe, Met, Ser, Arg, Lys, Thr, Tyr, Pro, Trp, Ala, Gln, Gly, His, Asn or Asp
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Gln, Lys, Arg, Glu, Asn, Leu, Gly, His, Met, Trp, Asp, Ala, Ser, Tyr, Thr, Val, Pro or Ile
<220> FEATURE:
<221> NAME/KEY: MOD_RES
<222> LOCATION: (5)..(5)
<223> OTHER INFORMATION: Val, Ile, Thr, Leu, Met, Ala, Gly, Arg, Lys, Tyr, Asp, Glu, Ser, Pro, Asn, Cys, Trp, Phe or Gln
<220> FEATURE:
<221> NAME/KEY: MOD_RES
<222> LOCATION: (6)..(6)
<223> OTHER INFORMATION: Val, Ala, Ser, Thr, Gly, Lys, Arg, Glu, Ile, Gln, Leu, Phe, Asp, Tyr, Asn, Met, Pro, Trp or His
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Lys, Gln, Glu, Arg, Thr, Ala, Asn, His, Ile, Leu, Ser, Pro, Val, Gly, Tyr, Asp, Met or Phe
<220> FEATURE:
<221> NAME/KEY: MOD_RES
<222> LOCATION: (9)..(9)
<223> OTHER INFORMATION: Leu, Tyr, Phe, Ile, Ser, Val, Lys, Thr, Arg, Gln, Asn, Trp, Cys, Pro, Gly, Met or Ala
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (13)..(13)
<223> OTHER INFORMATION: Phe, Tyr, Leu, Trp, Val, Ile, Thr, Ser, His, Cys, Met, Gly, Pro, Asn, Lys, Asp, Glu, Arg or Ala
<220> FEATURE:
<221> NAME/KEY: MOD_RES
<222> LOCATION: (14)..(14)

```
<223> OTHER INFORMATION: Any amino acid
<220> FEATURE:
<221> NAME/KEY: MOD_RES
<222> LOCATION: (15)..(15)
<223> OTHER INFORMATION: Asn, Lys, Thr, Asp, Gly, Ser, Gln, His, Ala,
      Arg, Ile, Glu, Val, Leu, Tyr, Met, Pro, Phe or Cys
<220> FEATURE:
<221> NAME/KEY: MOD_RES
<222> LOCATION: (16)..(16)
<223> OTHER INFORMATION: Lys, Thr, Arg, Asn, Ser, Ala, Glu, Gly, Gln,
      Asp, Val, Ile, Met, Pro, His, Tyr, Leu or Phe
<220> FEATURE:
<221> NAME/KEY: MOD_RES
<222> LOCATION: (17)..(17)
<223> OTHER INFORMATION: Thr, Asn, Lys, Ile, Ser, Ala, Pro, Glu, Arg,
      Gln, Asp, Gly, Val, Leu, His, Met, Tyr, Cys or Phe
<220> FEATURE:
<221> NAME/KEY: MOD_RES
<222> LOCATION: (18)..(18)
<223> OTHER INFORMATION: Ile, Thr, Val, Met, Leu, Ala, Tyr, Lys, Phe,
      Ser, Asn, Arg, Pro, His, Glu, Gly, Gln or Asp
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Phe, Leu, Tyr, Ile, Ser, Gln, Val, Ala, Trp,
      Cys, Pro, Thr, Asn, Met, Lys, Asp, Arg or His
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (22)..(22)
<223> OTHER INFORMATION: Gln, Pro, Ser, His, Asn, Arg, Lys, Glu, Thr,
      Ala, Gly, Asp, Leu, Tyr, Ile, Val, Phe, Cys or Trp
<220> FEATURE:
<221> NAME/KEY: MOD_RES
<222> LOCATION: (23)..(23)
<223> OTHER INFORMATION: Ser, Pro, His, Ala, Thr, Asn, Gln, Phe, Leu,
      Arg, Ile, Tyr, Lys, Gly, Val, Cys, Asp or Trp
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (25)..(25)
<223> OTHER INFORMATION: Gly, Glu, Arg, Asp, Ser, Pro, Ala, Lys, Leu,
      Gln, Asn, Val, Trp, Ile, His or Thr
<220> FEATURE:
<221> NAME/KEY: MOD_RES
<222> LOCATION: (26)..(26)
<223> OTHER INFORMATION: Gly, Glu, Arg, Lys, Ser, Trp, Val, Leu, Ala,
      Asn, Thr, Ile, Phe, Asp or Gln
<220> FEATURE:
<221> NAME/KEY: MOD_RES
<222> LOCATION: (27)..(27)
<223> OTHER INFORMATION: Asp, Gly, Thr, Asn, Ala, Glu, His, Val, Ile,
      Ser, Arg, Tyr, Pro, Phe, Gln, Leu, Lys or Met
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (29)..(29)
<223> OTHER INFORMATION: Glu, Lys, Gln, Gly, Asp, Arg, Val, Asn, Ala,
      Pro, Ser, Leu, Ile, His, Thr or Tyr
<220> FEATURE:
<221> NAME/KEY: MOD_RES
<222> LOCATION: (30)..(30)
<223> OTHER INFORMATION: Ile, Val, Leu, Thr, Phe, Asn, Met, Ser, Ala,
      Tyr, Gly, Pro, Lys, Asp, Cys, His or Arg
<220> FEATURE:
<221> NAME/KEY: MOD_RES
```

<222> LOCATION: (31)..(31)
<223> OTHER INFORMATION: Val, Thr, Ile, Glu, Ala, Met, Lys, Ser, Leu,
Arg, Gln, Pro, Tyr, Cys, Gly, Asn, His, Phe or Asp
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (33)..(33)
<223> OTHER INFORMATION: His, Leu, Tyr, Phe, Arg, Ile, Pro, Thr, Ser,
Asn, Gln, Val, Asp, Ala, Gly, Met, Cys, Trp or Glu
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (35)..(35)
<223> OTHER INFORMATION: Phe, Val, Leu, Ser, Ile, Cys, Tyr, His, Thr,
Arg, Trp, Gly or Asn
<220> FEATURE:
<221> NAME/KEY: MOD_RES
<222> LOCATION: (36)..(36)
<223> OTHER INFORMATION: Asn, Thr, Ile, Ser, Cys, Asp, Tyr, Val, His,
Lys, Phe, Leu, Met, Pro, Arg, Gly, Gln, Glu or Ala
<220> FEATURE:
<221> NAME/KEY: MOD_RES
<222> LOCATION: (37)..(37)
<223> OTHER INFORMATION: Cys, Arg, Trp, Tyr, Ser, Val, Gly, Leu, Phe,
Ile, His, Ala, Asn or Gln
<220> FEATURE:
<221> NAME/KEY: MOD_RES
<222> LOCATION: (38)..(38)
<223> OTHER INFORMATION: Gly, Arg, Ala, Lys, Gln, His, Glu, Met, Asn,
Val, Ser, Thr, Trp, Tyr, Cys, Ile, Asp, Leu or Phe
<220> FEATURE:
<221> NAME/KEY: MOD_RES
<222> LOCATION: (39)..(39)
<223> OTHER INFORMATION: Gly, Glu, Arg, Lys, Trp, Val, Ser, Ala, Leu,
Asn, Asp, Ile, Phe or Tyr
<220> FEATURE:
<221> NAME/KEY: MOD_RES
<222> LOCATION: (40)..(40)
<223> OTHER INFORMATION: Glu, Gly, Lys, Asp, Asn, Arg, Val, Ala, Leu,
Phe, Ser, Gln, Trp, His, Tyr, Cys, Met or Thr
<220> FEATURE:
<221> NAME/KEY: MOD_RES
<222> LOCATION: (41)..(41)
<223> OTHER INFORMATION: Phe, Leu, Ser, Ile, Tyr, Val, Cys, Asn, Gly,
Met, Trp or Gln
<220> FEATURE:
<221> NAME/KEY: MOD_RES
<222> LOCATION: (42)..(42)
<223> OTHER INFORMATION: Phe, Leu, Ser, Tyr, Val, Pro, Ile, Cys, Asp,
Ala, Met or Asn
<220> FEATURE:
<221> NAME/KEY: MOD_RES
<222> LOCATION: (43)..(43)
<223> OTHER INFORMATION: Tyr, Phe, Asn, Cys, His, Ser, Leu, Val, Ile,
Thr, Pro, Gly, Met, Trp, Lys, Asp or Glu
<220> FEATURE:
<221> NAME/KEY: MOD_RES
<222> LOCATION: (44)..(44)
<223> OTHER INFORMATION: Cys, Arg, Tyr, Leu, Ser, Trp, Gly, Ala, Phe,
Val, Ile, Met, Thr, Pro or Lys
<220> FEATURE:
<221> NAME/KEY: MOD_RES
<222> LOCATION: (45)..(45)
<223> OTHER INFORMATION: Asn, Asp, Ser, Lys, Tyr, Thr, Glu, Ile, His,
Gly, Cys, Gln, Arg, Ala, Val, Pro, Met or Phe
<220> FEATURE:
<221> NAME/KEY: MOD_RES
<222> LOCATION: (46)..(46)
<223> OTHER INFORMATION: Thr, Ser, Ala, Leu, Ile, Pro, Val, His, Arg,
Tyr, Lys, Asn, Gln, Met, Glu or Gly
<220> FEATURE:
<221> NAME/KEY: MOD_RES
<222> LOCATION: (47)..(47)

<223> OTHER INFORMATION: Thr, Ser, Ala, Lys, Pro, Glu, Ile, Leu, Val,
      Asp, Asn, Gly, Arg, Gln, His, Tyr, Phe, Cys or Met
<220> FEATURE:
<221> NAME/KEY: MOD_RES
<222> LOCATION: (48)..(48)
<223> OTHER INFORMATION: Gln, Lys, Gly, Pro, Arg, Glu, Asn, Asp, Ser,
      Ala, His, Leu, Thr, Ile, Val, Trp, Tyr, Met or Cys
<220> FEATURE:
<221> NAME/KEY: MOD_RES
<222> LOCATION: (49)..(49)
<223> OTHER INFORMATION: Leu, Met, Ile, Pro, Phe, Val, Arg, Gln, Cys,
      Trp, Thr, Ser, Tyr, Gly, Ala, Lys or Asn
<220> FEATURE:
<221> NAME/KEY: MOD_RES
<222> LOCATION: (50)..(50)
<223> OTHER INFORMATION: Phe, Leu, Trp, Ser, Tyr, Val, Ile, Cys, Pro,
      Asn, Ala, Met, Lys or Thr
<220> FEATURE:
<221> NAME/KEY: MOD_RES
<222> LOCATION: (51)..(51)
<223> OTHER INFORMATION: Asn, Ser, Asp, Thr, Lys, His, Tyr, Gly, Arg,
      Gln, Ile, Glu, Phe, Ala, Leu, Pro, Trp, Met or Val
<220> FEATURE:
<221> NAME/KEY: MOD_RES
<222> LOCATION: (52)..(62)
<223> OTHER INFORMATION: Any amino acid

<400> SEQUENCE: 42

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60
```

<210> SEQ ID NO 43
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(12)
<223> OTHER INFORMATION: Any amino acid
<220> FEATURE:
<221> NAME/KEY: MOD_RES
<222> LOCATION: (13)..(13)
<223> OTHER INFORMATION: Asn, Asp, Ser, Glu, Gly, Thr, Lys, Ala, Arg,
      His, Ile, Val, Pro, Gln, Leu, Tyr, Cys, Met or Phe
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (17)..(17)
<223> OTHER INFORMATION: Leu, Ile, Pro, Phe, Thr, Val, His, Ser, Arg,
      Ala, Asn, Met, Tyr, Gly or Cys
<220> FEATURE:
<221> NAME/KEY: MOD_RES
<222> LOCATION: (18)..(18)
<223> OTHER INFORMATION: Pro, Gln, Ser, Thr, Leu, Lys, His, Arg, Asn,
      Tyr, Ile, Ala, Met, Gly, Asp, Val, Cys, Phe or Glu
<220> FEATURE:
<221> NAME/KEY: MOD_RES
<222> LOCATION: (19)..(19)
<223> OTHER INFORMATION: Cys, Arg, Ser, Tyr, Met, Phe, Gly, Ala, Leu,
      Ile, Val, Trp, Pro, Thr, His or Asn
<220> FEATURE:
<221> NAME/KEY: MOD_RES
<222> LOCATION: (20)..(20)
<223> OTHER INFORMATION: Arg, Lys, Gly, Ser, Asn, Gln, Ile, Thr, Glu, Pro, His, Met, Trp, Leu, Cys, Tyr, Val or Asp
<220> FEATURE:
<221> NAME/KEY: MOD_RES
<222> LOCATION: (21)..(21)
<223> OTHER INFORMATION: Ile, Leu, Met, Val, Thr, Asn, Arg, Lys, Tyr, Cys, Ser, Pro, Phe, His, Asp or Glu
<220> FEATURE:
<221> NAME/KEY: MOD_RES
<222> LOCATION: (22)..(22)
<223> OTHER INFORMATION: Lys, Arg, Asn, Glu, Ile, Thr, Gln, Ser, Gly, Pro, Met, Tyr, Leu, His, Ala or Asp
<220> FEATURE:
<221> NAME/KEY: MOD_RES
<222> LOCATION: (23)..(23)
<223> OTHER INFORMATION: Gln, Leu, His, Arg, Pro, Lys, Ala, Asn, Glu, Gly, Thr, Met, Val or Ser
<220> FEATURE:
<221> NAME/KEY: MOD_RES
<222> LOCATION: (24)..(24)
<223> OTHER INFORMATION: Ile, Phe, Val, Leu, Met, Thr, Tyr, Asn, Ser, Lys, Ala, Pro, Arg or Asp
<220> FEATURE:
<221> NAME/KEY: MOD_RES
<222> LOCATION: (25)..(25)
<223> OTHER INFORMATION: Ile, Val, Met, Thr, Leu, Ala, Tyr, Lys, Gly, Glu, Cys, Arg, Ser or Gln
<220> FEATURE:
<221> NAME/KEY: MOD_RES
<222> LOCATION: (26)..(26)
<223> OTHER INFORMATION: Asn, Arg, His, Lys, Ser, Asp, Ile, Thr, Tyr, Gly, Gln, Leu, Cys, Met, Val, Glu, Pro or Phe
<220> FEATURE:
<221> NAME/KEY: MOD_RES
<222> LOCATION: (27)..(27)
<223> OTHER INFORMATION: Met, Arg, Leu, Lys, Thr, Ser, Val, Ile, Pro, Gly, Tyr, His, Gln, Asn, Ala, Cys, Trp or Asp
<220> FEATURE:
<221> NAME/KEY: MOD_RES
<222> LOCATION: (28)..(28)
<223> OTHER INFORMATION: Trp, Arg, Cys, Gly, Val, Leu, Met, Ser, Ala, Pro, His, Lys, Tyr, Asn or Gln
<220> FEATURE:
<221> NAME/KEY: MOD_RES
<222> LOCATION: (29)..(29)
<223> OTHER INFORMATION: Gln, Arg, Ile, Met, Leu, His, Lys, Ala, Glu, Pro, Thr, Gly, Tyr, Val, Trp or Ser
<220> FEATURE:
<221> NAME/KEY: MOD_RES
<222> LOCATION: (30)..(30)
<223> OTHER INFORMATION: Glu, Arg, Gly, Lys, Gln, Thr, Ser, Ala, Ile, Val, Asp, Leu, Pro, His, Asn, Cys, Met, Trp or Tyr
<220> FEATURE:
<221> NAME/KEY: MOD_RES
<222> LOCATION: (31)..(31)
<223> OTHER INFORMATION: Val, Ala, Thr, Ile, Gly, Leu, Ser, Glu, Pro, Lys, Arg, Asn, Gln, Trp or Asp
<220> FEATURE:
<221> NAME/KEY: MOD_RES
<222> LOCATION: (32)..(32)
<223> OTHER INFORMATION: Gly, Arg, Glu, Ala, Val, Lys, Gln, Thr, Asn, Asp, Pro, Trp or Ser
<220> FEATURE:
<221> NAME/KEY: MOD_RES
<222> LOCATION: (33)..(33)
<223> OTHER INFORMATION: Lys, Gln, Arg, Ser, Thr, Glu, Leu, Pro, Asn, Ile, His, Gly, Ala, Val, Tyr, Cys, Met, Trp or Asp
<220> FEATURE:
<221> NAME/KEY: MOD_RES
<222> LOCATION: (34)..(34)
<223> OTHER INFORMATION: Ala, Val, Gly, Thr, Ser, Pro, Gln, Glu, Cys, Trp, Arg, Lys, Tyr or Asp
<220> FEATURE:
<221> NAME/KEY: MOD_RES
<222> LOCATION: (35)..(35)
<223> OTHER INFORMATION: Met, Ile, Thr, Val, Leu, Lys, Asn, Ala, Phe, Arg, Cys, Ser, Pro, Gln, His, Tyr or Glu
<220> FEATURE:

<221> NAME/KEY: MOD_RES
<222> LOCATION: (36)..(36)
<223> OTHER INFORMATION: Tyr, His, Phe, Cys, Ser, Val, Asp, Asn, Met,
Ala, Pro, Leu, Glu, Lys, Thr or Gly
<220> FEATURE:
<221> NAME/KEY: MOD_RES
<222> LOCATION: (37)..(37)
<223> OTHER INFORMATION: Ala, Pro, Thr, Ser, Asn, Val, Cys, Gly, Asp,
Leu, Ile, Met or His
<220> FEATURE:
<221> NAME/KEY: MOD_RES
<222> LOCATION: (38)..(38)
<223> OTHER INFORMATION: Pro, Ser, Ala, Asn, Leu, Thr, His, Arg, Val,
Lys, Asp or Gln
<220> FEATURE:
<221> NAME/KEY: MOD_RES
<222> LOCATION: (39)..(39)
<223> OTHER INFORMATION: Pro, Ser, Leu, Ala, Thr, Phe, Arg, His, Gly,
Tyr, Asn or Gln
<220> FEATURE:
<221> NAME/KEY: MOD_RES
<222> LOCATION: (40)..(40)
<223> OTHER INFORMATION: Ile, Val, Ser, Thr, Arg, Leu, Phe, Met, Asn,
Pro, His, Ala, Lys, Gly, Trp, Tyr or Asp
<220> FEATURE:
<221> NAME/KEY: MOD_RES
<222> LOCATION: (41)..(41)
<223> OTHER INFORMATION: Arg, Lys, Ala, Ser, Glu, Gln, Pro, Gly, Asn,
Asp, Thr, Ile, Met, Val, Leu or His
<220> FEATURE:
<221> NAME/KEY: MOD_RES
<222> LOCATION: (42)..(42)
<223> OTHER INFORMATION: Gly, Glu, Arg, Ala, Ser, Asp, Val, Lys, Ile,
Cys, Pro, Thr, Asn or Gln
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (44)..(44)
<223> OTHER INFORMATION: Ile, Leu, Val, Thr, Met, Ser, Asn, Phe, Arg,
Ala, Cys, Asp or Gln
<220> FEATURE:
<221> NAME/KEY: MOD_RES
<222> LOCATION: (45)..(45)
<223> OTHER INFORMATION: Arg, Thr, Asn, Lys, Ser, Gln, Ile, Glu, Met,
Gly, Ala, Tyr, Val, Trp, Asp, His, Leu, Pro or Cys
<220> FEATURE:
<221> NAME/KEY: MOD_RES
<222> LOCATION: (46)..(46)
<223> OTHER INFORMATION: Cys, Arg, Tyr, Ser, Trp, Gly, Val, Phe, Ala,
Leu, Ile, Met, Lys, Thr, Gln or Glu
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (48)..(48)
<223> OTHER INFORMATION: Ser, Thr, Pro, Leu, Ala, Gln, Ile, Val, Phe,
Cys, Trp, Lys, Tyr, Asn or Glu
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (50)..(50)
<223> OTHER INFORMATION: Ile, Val, Thr, Leu, Ser, Met, Phe, Asn, Tyr,
Gly, Arg or Ala
<220> FEATURE:
<221> NAME/KEY: MOD_RES
<222> LOCATION: (51)..(51)
<223> OTHER INFORMATION: Thr, Ala, Ile, Ser, Gln, Leu, Pro, Arg, Tyr,
Gly, Val or Asn
<220> FEATURE:
<221> NAME/KEY: MOD_RES
<222> LOCATION: (52)..(52)

<223> OTHER INFORMATION: Gly, Arg, Glu, Ala, Leu, Val, Asp, Trp, Ser, Lys, Gln, Ile or Thr
<220> FEATURE:
<221> NAME/KEY: MOD_RES
<222> LOCATION: (53)..(53)
<223> OTHER INFORMATION: Leu, Ile, Met, Val, Pro, Thr, Ser, Phe, Tyr, Gly, Arg, Gln, His, Ala or Asn
<220> FEATURE:
<221> NAME/KEY: MOD_RES
<222> LOCATION: (54)..(54)
<223> OTHER INFORMATION: Leu, Ile, Met, Phe, Val, Pro, Thr, Ser, Gln, Arg, Gly, Ala, Tyr, Asp, Lys or Asn
<220> FEATURE:
<221> NAME/KEY: MOD_RES
<222> LOCATION: (55)..(55)
<223> OTHER INFORMATION: Leu, Ile, Val, Ser, Phe, Trp, Met, Pro, Thr, Lys, Asn, Gly, Arg, Gln, Ala, Tyr, Asp or Glu
<220> FEATURE:
<221> NAME/KEY: MOD_RES
<222> LOCATION: (56)..(56)
<223> OTHER INFORMATION: Thr, Val, Ile, Leu, Ser, Ala, Glu, Gln, Met, Pro, Asn, Gly, Arg, Lys, Asp, His or Tyr

<400> SEQUENCE: 43

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa
    50                  55
```

<210> SEQ ID NO 44
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(8)
<223> OTHER INFORMATION: Any amino acid
<220> FEATURE:
<221> NAME/KEY: MOD_RES
<222> LOCATION: (9)..(9)
<223> OTHER INFORMATION: Glu, Asp, Lys, Leu, Ala, Gln, Asn, Val, Gly, Thr, Arg, Ile, His, Ser, Met, Phe, Pro, Tyr or Trp
<220> FEATURE:
<221> NAME/KEY: MOD_RES
<222> LOCATION: (10)..(10)
<223> OTHER INFORMATION: Thr, Ile, Val, Ala, Lys, Ser, Leu, Arg, Phe, Met, Pro, Asn, Asp, Gly, Tyr, Glu, Gln or Cys
<220> FEATURE:
<221> NAME/KEY: MOD_RES
<222> LOCATION: (11)..(11)
<223> OTHER INFORMATION: Phe, Leu, Val, Ile, Ser, Thr, Tyr, Cys, Met, Ala, Pro, Asn, Trp, His, Arg or Asp
<220> FEATURE:
<221> NAME/KEY: MOD_RES
<222> LOCATION: (12)..(12)
<223> OTHER INFORMATION: Arg, Gly, Lys, Thr, Ser, Ile, Tyr, Gln, Leu, Glu, Pro, Val, Cys, Trp, Asp, Met, Phe or Asn
<220> FEATURE:
<221> NAME/KEY: MOD_RES
<222> LOCATION: (13)..(13)
<223> OTHER INFORMATION: Pro, Leu, Ser, Ala, Asp, Arg, His, Thr, Gln, Asn, Gly or Glu
<220> FEATURE:
<221> NAME/KEY: MOD_RES
<222> LOCATION: (14)..(14)
<223> OTHER INFORMATION: Gly, Ala, Glu, Ile, Val, Thr, Gln, Leu, Arg, Ser, Trp, Met, Pro, Lys or Asn
<220> FEATURE:
<221> NAME/KEY: MOD_RES
<222> LOCATION: (15)..(15)
<223> OTHER INFORMATION: Gly, Arg, Glu, Ser, Ala, Leu, Lys, Cys, Pro,
      Asn or Gln
<220> FEATURE:
<221> NAME/KEY: MOD_RES
<222> LOCATION: (16)..(16)
<223> OTHER INFORMATION: Gly, Glu, Arg, Lys, Ser, Ala, Asp, Cys or Asn
<220> FEATURE:
<221> NAME/KEY: MOD_RES
<222> LOCATION: (17)..(17)
<223> OTHER INFORMATION: Asp, Asn, Glu, Gly, Tyr, Ser, Ile, His, Arg,
      Ala, Val, Gln, Thr or Lys
<220> FEATURE:
<221> NAME/KEY: MOD_RES
<222> LOCATION: (18)..(18)
<223> OTHER INFORMATION: Met, Ile, Thr, Val, Leu, Arg, Tyr, Lys, Phe,
      Gly or Ser
<220> FEATURE:
<221> NAME/KEY: MOD_RES
<222> LOCATION: (19)..(19)
<223> OTHER INFORMATION: Arg, Lys, Met, Gln, Gly, Glu, Val, Thr, Asn,
      Trp, Ile, Phe or Ser
<220> FEATURE:
<221> NAME/KEY: MOD_RES
<222> LOCATION: (20)..(20)
<223> OTHER INFORMATION: Asp, Asn, Glu, Gly, Val, His, Ala, Leu, Cys,
      Trp, Arg, Lys, Ser, Thr or Tyr
<220> FEATURE:
<221> NAME/KEY: MOD_RES
<222> LOCATION: (21)..(21)
<223> OTHER INFORMATION: Asn, Ile, Ser, Asp, Lys, Leu, His, Tyr, Thr,
      Gln, Gly, Arg, Ala, Cys or Met
<220> FEATURE:
<221> NAME/KEY: MOD_RES
<222> LOCATION: (22)..(22)
<223> OTHER INFORMATION: Trp, Ser, Arg, Gly, Asn, Cys, Leu, Phe, Pro or
      Lys
<220> FEATURE:
<221> NAME/KEY: MOD_RES
<222> LOCATION: (23)..(23)
<223> OTHER INFORMATION: Arg, Lys, Gly, Ala, Ser, Glu, Thr, Leu or Ile
<220> FEATURE:
<221> NAME/KEY: MOD_RES
<222> LOCATION: (24)..(24)
<223> OTHER INFORMATION: Ser, Asn, Thr, Gly, Arg, Gln, Met, Asp, Ile,
      Cys, Lys, Tyr, Ala, Val or His
<220> FEATURE:
<221> NAME/KEY: MOD_RES
<222> LOCATION: (25)..(25)
<223> OTHER INFORMATION: Glu, Lys, Gln, Gly, Asp, Arg, Ala, Val, Asn,
      His or Met
<220> FEATURE:
<221> NAME/KEY: MOD_RES
<222> LOCATION: (26)..(26)
<223> OTHER INFORMATION: Leu, Ile, Phe, Ser, Val, Met, Pro, Lys, Asn,
      Gln or Glu
<220> FEATURE:
<221> NAME/KEY: MOD_RES
<222> LOCATION: (27)..(27)
<223> OTHER INFORMATION: Tyr, Phe, Leu, His, Cys, Ser, Asp, Ile, Ala,
      Val, Asn or Glu
<220> FEATURE:
<221> NAME/KEY: MOD_RES
<222> LOCATION: (28)..(28)
<223> OTHER INFORMATION: Lys, Arg, Asn, Gln, Glu, Thr, Tyr, Pro, Gly,
      Val, Leu, Ile, Met, Ser or Asp
<220> FEATURE:
<221> NAME/KEY: MOD_RES
<222> LOCATION: (29)..(29)
<223> OTHER INFORMATION: Tyr, His, Cys, Asn, Phe, Ser, Ile or Glu
<220> FEATURE:
<221> NAME/KEY: MOD_RES
<222> LOCATION: (30)..(30)
<223> OTHER INFORMATION: Lys, Arg, Glu, Asn, Thr, Gln, Gly, Ile or Pro
<220> FEATURE:
<221> NAME/KEY: MOD_RES
<222> LOCATION: (31)..(31)

-continued

<223> OTHER INFORMATION: Val, Ile, Thr, Ala, Leu, Gly, Met, Ser or Asp
<220> FEATURE:
<221> NAME/KEY: MOD_RES
<222> LOCATION: (32)..(32)
<223> OTHER INFORMATION: Val, Ile, Ala, Leu, Glu, Gly, Ser, Met or Lys
<220> FEATURE:
<221> NAME/KEY: MOD_RES
<222> LOCATION: (33)..(33)
<223> OTHER INFORMATION: Lys, Glu, Arg, Gln, Ala, Thr, Ser, Gly, Val, Asn or Ile
<220> FEATURE:
<221> NAME/KEY: MOD_RES
<222> LOCATION: (34)..(34)
<223> OTHER INFORMATION: Ile, Val, Leu, Met, Thr, Ser, Asn, Phe or Pro
<220> FEATURE:
<221> NAME/KEY: MOD_RES
<222> LOCATION: (35)..(35)
<223> OTHER INFORMATION: Glu, Lys, Gln, Arg, Asp or Ser

<400> SEQUENCE: 44

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa
        35
```

<210> SEQ ID NO 45
<211> LENGTH: 69
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Val, Ile, Met, Leu or Ala
<220> FEATURE:
<221> NAME/KEY: MOD_RES
<222> LOCATION: (2)..(2)
<223> OTHER INFORMATION: Val, Glu, Ile, Phe, Leu, Lys, Tyr, Arg, Pro, Asp, Met, Ala, Thr, Asn, Ser, Trp, Gly, His or Gln
<220> FEATURE:
<221> NAME/KEY: MOD_RES
<222> LOCATION: (3)..(3)
<223> OTHER INFORMATION: Leu, Met, Val, Ile, Phe, Ser, Trp or Lys
<220> FEATURE:
<221> NAME/KEY: MOD_RES
<222> LOCATION: (4)..(4)
<223> OTHER INFORMATION: Glu, Gly, Lys, Thr, Val, Ala, Asp, Leu, Ile, Gln, Tyr, His, Pro or Trp
<220> FEATURE:
<221> NAME/KEY: MOD_RES
<222> LOCATION: (5)..(5)
<223> OTHER INFORMATION: Asn, Ser, Thr, Lys or Asp
<220> FEATURE:
<221> NAME/KEY: MOD_RES
<222> LOCATION: (6)..(6)
<223> OTHER INFORMATION: Val, Thr, Ile, Met, Gly, Cys or Ser
<220> FEATURE:
<221> NAME/KEY: MOD_RES
<222> LOCATION: (7)..(7)
<223> OTHER INFORMATION: Thr, Lys, Ile, Ser, Ala or Arg
<220> FEATURE:
<221> NAME/KEY: MOD_RES
<222> LOCATION: (8)..(8)
<223> OTHER INFORMATION: Glu, Thr, Asp, Gly, Phe or Gln
<220> FEATURE:
<221> NAME/KEY: MOD_RES
<222> LOCATION: (9)..(9)
<223> OTHER INFORMATION: Asn, Glu, Asp, Leu, Ile, Lys, Ser, Pro, Tyr, His, Met, Thr, Phe, Val, Trp, Arg or Gln
<220> FEATURE:
<221> NAME/KEY: MOD_RES
<222> LOCATION: (10)..(10)
<223> OTHER INFORMATION: Phe, Arg, Leu, Ile, Lys, Ala, Tyr or Gly
<220> FEATURE:
<221> NAME/KEY: MOD_RES
<222> LOCATION: (11)..(11)
<223> OTHER INFORMATION: Asn, Asp, Lys, Leu, Thr, Ser, Gly, Ala, His,
Arg or Glu
<220> FEATURE:
<221> NAME/KEY: MOD_RES
<222> LOCATION: (12)..(12)
<223> OTHER INFORMATION: Met, Ile, Lys, Ala, Val, Asp, Thr, Cys, Asn,
Phe, Leu or Arg
<220> FEATURE:
<221> NAME/KEY: MOD_RES
<222> LOCATION: (13)..(13)
<223> OTHER INFORMATION: Trp, Thr, Lys, Gly, Arg, Ser, Tyr, Cys, Ala,
Val, Gln or Phe
<220> FEATURE:
<221> NAME/KEY: MOD_RES
<222> LOCATION: (14)..(14)
<223> OTHER INFORMATION: Lys, Thr, Glu, Arg, Asn, Gln, Gly, Ser, Phe,
Asp, Met or Tyr
<220> FEATURE:
<221> NAME/KEY: MOD_RES
<222> LOCATION: (15)..(15)
<223> OTHER INFORMATION: Asn, Thr, His, Gln, Ser, Lys, Phe, Arg, Gly,
Leu, Ile, Val, Asp or Glu
<220> FEATURE:
<221> NAME/KEY: MOD_RES
<222> LOCATION: (16)..(16)
<223> OTHER INFORMATION: Asn, Asp, Glu, Lys, Ser, His, Gly, Tyr, Thr,
Val, Pro, Ala, Leu, Ile or Arg
<220> FEATURE:
<221> NAME/KEY: MOD_RES
<222> LOCATION: (17)..(17)
<223> OTHER INFORMATION: Met, Tyr, Ile, Leu, Val, Arg, Thr, His, Lys,
Ser, Ala or Asp
<220> FEATURE:
<221> NAME/KEY: MOD_RES
<222> LOCATION: (18)..(18)
<223> OTHER INFORMATION: Val, Arg, Ala, Lys, Gln, Met, Thr, Tyr, Ile,
Ser, Leu, Gly, Asn, Asp or Glu
<220> FEATURE:
<221> NAME/KEY: MOD_RES
<222> LOCATION: (19)..(19)
<223> OTHER INFORMATION: Glu, Asp, Leu, Asn, Ala, Lys, Gly, Thr, Pro,
Gln, Ile, Val, Phe, Arg, Ser or Tyr
<220> FEATURE:
<221> NAME/KEY: MOD_RES
<222> LOCATION: (20)..(20)
<223> OTHER INFORMATION: Gln, Lys, Phe, Arg, Leu, Glu, Ser, Ile, Ala,
Val, Cys, Met, His, Thr, Asn or Asp
<220> FEATURE:
<221> NAME/KEY: MOD_RES
<222> LOCATION: (21)..(21)
<223> OTHER INFORMATION: Met, Tyr, Val, Ile, Arg, Phe, Leu, Lys, Gln,
Gly, Ser, Asn, Asp or Glu
<220> FEATURE:
<221> NAME/KEY: MOD_RES
<222> LOCATION: (22)..(22)
<223> OTHER INFORMATION: His, Gln, Lys, Arg, Tyr, Asn, Ser, Leu, Pro,
Glu, Asp, Gly, Phe or Thr
<220> FEATURE:
<221> NAME/KEY: MOD_RES
<222> LOCATION: (23)..(23)
<223> OTHER INFORMATION: Glu, Lys, Thr, Leu, Arg, Gln, Ile, Asp, Gly,
Ser, Ala, Val, Asn, Pro, Tyr or Met
<220> FEATURE:
<221> NAME/KEY: MOD_RES
<222> LOCATION: (24)..(24)
<223> OTHER INFORMATION: Asp, Glu, Thr, Ala, Gln, Asn, Val, Lys, Ser,
Gly or Leu
<220> FEATURE:
<221> NAME/KEY: MOD_RES
<222> LOCATION: (25)..(25)
<223> OTHER INFORMATION: Ile, Tyr, Val, Leu, His, Ser, Thr, Asn, Lys,
Ala, Met or Asp
<220> FEATURE:
<221> NAME/KEY: MOD_RES
<222> LOCATION: (26)..(26)
<223> OTHER INFORMATION: Ile, Ala, Val, Thr, Lys, Leu, Ser, Gln, Arg,
      Tyr or Glu
<220> FEATURE:
<221> NAME/KEY: MOD_RES
<222> LOCATION: (27)..(27)
<223> OTHER INFORMATION: Ser, Leu, Pro, Thr, Ala, Gln, Asn, Phe, Ile,
      Glu, Gly, Arg, Lys or Asp
<220> FEATURE:
<221> NAME/KEY: MOD_RES
<222> LOCATION: (28)..(28)
<223> OTHER INFORMATION: Leu, Phe, Ile, Val, Met, Ser, gly, Arg, Thr,
      Cys, Pro, Lys, Tyr or Asp
<220> FEATURE:
<221> NAME/KEY: MOD_RES
<222> LOCATION: (29)..(29)
<223> OTHER INFORMATION: Trp, Tyr, Asp, Thr, Lys, Glu, Asn, Arg, Gln,
      Gly, His, Ser, Met, Phe or Leu
<220> FEATURE:
<221> NAME/KEY: MOD_RES
<222> LOCATION: (30)..(30)
<223> OTHER INFORMATION: Asp, Lys, Asn, Glu, Ser, Arg, Gly, Thr, Ala,
      Gln, Phe or Tyr
<220> FEATURE:
<221> NAME/KEY: MOD_RES
<222> LOCATION: (31)..(31)
<223> OTHER INFORMATION: Gln, Leu, Glu, Asn, Lys, Ser, Thr, Asp, Ala,
      Arg, Gly, Pro, His, Tyr, Ile, Met or Phe
<220> FEATURE:
<221> NAME/KEY: MOD_RES
<222> LOCATION: (32)..(32)
<223> OTHER INFORMATION: Ser, Asp, Glu, Lys, Asn, Gly, Thr, Ala, Met,
      Leu, Arg, Gln, Phe, Val or His
<220> FEATURE:
<221> NAME/KEY: MOD_RES
<222> LOCATION: (33)..(33)
<223> OTHER INFORMATION: Leu, Val, Ser, Asn, Ile, Met, Thr, Asp, His,
      Gln, Tyr, Pro, Arg, Glu, Gly, Ala, Phe or Lys
<220> FEATURE:
<221> NAME/KEY: MOD_RES
<222> LOCATION: (34)..(34)
<223> OTHER INFORMATION: Lys, Val, Glu, Ser, Thr, Asn, Gln, Ala, Ile,
      Arg, Phe, Gly, Tyr, Met, Leu, Pro or Asp
<220> FEATURE:
<221> NAME/KEY: MOD_RES
<222> LOCATION: (35)..(35)
<223> OTHER INFORMATION: Pro, Ser, Asn, Thr, Glu, Gly, Tyr, Lys, Arg,
      Gln, Asp, Leu, Ala or Val
<220> FEATURE:
<221> NAME/KEY: MOD_RES
<222> LOCATION: (36)..(36)
<223> OTHER INFORMATION: Cys, Ile, Thr, Glu, Met, Ser, Leu, Tyr, Ala,
      Lys, Asn, Arg, Phe, Asp, Gly, His, Val, Trp or Gln
<220> FEATURE:
<221> NAME/KEY: MOD_RES
<222> LOCATION: (37)..(37)
<223> OTHER INFORMATION: Val, Tyr, Asp, Ile, Leu, Ser, Thr, Glu, Ala,
      Gly, Asn, Arg, Lys, His, Cys, Met, Phe or Gln
<220> FEATURE:
<221> NAME/KEY: MOD_RES
<222> LOCATION: (38)..(38)
<223> OTHER INFORMATION: Lys, Arg, Asn, Glu, Thr, Asp, Gln, Gly, Leu,
      Ser, Ile, Pro, Tyr, Ala or Val
<220> FEATURE:
<221> NAME/KEY: MOD_RES
<222> LOCATION: (39)..(39)
<223> OTHER INFORMATION: Leu, Asn, Thr, Ile, Glu, Ser, Ala, Asp, Tyr,
      Lys, Gly, Val, Arg, Met, Phe, Gln or His
<220> FEATURE:
<221> NAME/KEY: MOD_RES
<222> LOCATION: (40)..(40)
<223> OTHER INFORMATION: Thr, Ile, Asp, Val, Asn, Ser, Arg, Tyr, Lys,
      Glu, Met, His, Gly, Ala, Leu or Cys
<220> FEATURE:
<221> NAME/KEY: MOD_RES
<222> LOCATION: (41)..(41)
<223> OTHER INFORMATION: Pro, Asn, Thr, Val, Ser, Tyr, Lys, Asp, Leu,
      Arg, Cys, Ile, Ala, Glu or Phe
<220> FEATURE:

<221> NAME/KEY: MOD_RES
<222> LOCATION: (42)..(42)
<223> OTHER INFORMATION: Leu, Thr, Ile, Ser, Val, Arg, Phe, Asn, Ala, Met, Pro, Asp, Tyr or Lys
<220> FEATURE:
<221> NAME/KEY: MOD_RES
<222> LOCATION: (43)..(43)
<223> OTHER INFORMATION: Cys, Ser, Asn, Thr, Asp, Leu, Pro, Gln, Ile, Glu, Arg, Lys, Ala, Gly, Tyr, Val or His
<220> FEATURE:
<221> NAME/KEY: MOD_RES
<222> LOCATION: (44)..(44)
<223> OTHER INFORMATION: Val, Tyr, Ile, Glu, Thr, Asn, Lys, Gly, Ser, Phe, Met, Leu, Asp, Ala or Arg
<220> FEATURE:
<221> NAME/KEY: MOD_RES
<222> LOCATION: (45)..(45)
<223> OTHER INFORMATION: Gly, Thr, Arg, Asn, Ser, Lys, Asp, Glu, Ala, Ile, Met, Pro, Tyr, Leu or Val
<220> FEATURE:
<221> NAME/KEY: MOD_RES
<222> LOCATION: (46)..(46)
<223> OTHER INFORMATION: Leu, Met, Ala, Ser, Asn, Ile, Val, Glu, Asp, Thr, Gly, Lys, Arg, Gln, Tyr, Cys, Pro, Phe or His
<220> FEATURE:
<221> NAME/KEY: MOD_RES
<222> LOCATION: (47)..(47)
<223> OTHER INFORMATION: Ile, Asn, Gly, Lys, Arg, Thr, Ala, Ser, Asp, Gln, Met, Glu, Val, His, Leu, Phe or Tyr
<220> FEATURE:
<221> NAME/KEY: MOD_RES
<222> LOCATION: (48)..(48)
<223> OTHER INFORMATION: Ser, Asn, Cys, Thr, His, Lys, Asp, Gly, Ala, Glu, Leu, Ile or Pro
<220> FEATURE:
<221> NAME/KEY: MOD_RES
<222> LOCATION: (49)..(49)
<223> OTHER INFORMATION: Cys, Thr, Ser, Asn, Gly, Trp, Tyr, Arg, Ala, Ile, Val, Leu, Asp, Met or Phe
<220> FEATURE:
<221> NAME/KEY: MOD_RES
<222> LOCATION: (50)..(50)
<223> OTHER INFORMATION: Asn, Asp, Ser, Lys, Arg, Thr, Glu, Tyr, His, Gly, Ile, Pro, Cys or Phe
<220> FEATURE:
<221> NAME/KEY: MOD_RES
<222> LOCATION: (51)..(51)
<223> OTHER INFORMATION: Thr, Ser, Val, Phe, Ala, Asn, Ile, Tyr, Pro, Leu, Met, Lys, Arg, Asp, His or Gly
<220> FEATURE:
<221> NAME/KEY: MOD_RES
<222> LOCATION: (52)..(52)
<223> OTHER INFORMATION: Ser, Thr, Asn, Pro, Lys, Leu, Arg, Ala, Asp, Glu, His, Gln, Gly, Tyr, Val or Cys
<220> FEATURE:
<221> NAME/KEY: MOD_RES
<222> LOCATION: (53)..(53)
<223> OTHER INFORMATION: Val, Ala, Thr, Ile, Lys, Arg, Ser, Glu, Gly, Met, Asn, Leu, Pro, Tyr, Asp or Gln
<220> FEATURE:
<221> NAME/KEY: MOD_RES
<222> LOCATION: (54)..(54)
<223> OTHER INFORMATION: Ile, Val, Leu, Thr, Met, Ser, His, Ala, Arg, Glu, Gln, Asn, Phe, Gly, Lys, Tyr, Pro or Asp
<220> FEATURE:
<221> NAME/KEY: MOD_RES
<222> LOCATION: (55)..(55)
<223> OTHER INFORMATION: Thr, Lys, Ala, Arg, Ser, Val, Asn, Ile, Met, Pro, Leu, Asp, Glu, Tyr or Gln
<220> FEATURE:
<221> NAME/KEY: MOD_RES
<222> LOCATION: (56)..(56)
<223> OTHER INFORMATION: Gln, Lys, Glu, Ser, Asn, Arg, His, Gly, Pro, Asp, Leu, Ala, Val or Thr
<220> FEATURE:
<221> NAME/KEY: MOD_RES
<222> LOCATION: (57)..(57)
<223> OTHER INFORMATION: Ala, Thr, Ser, Ile, Val, Leu, Gly, Met, Glu, Lys, Asn, His, Asp, Pro, Arg, Gln, Cys or Tyr

<220> FEATURE:
<221> NAME/KEY: MOD_RES
<222> LOCATION: (58)..(58)
<223> OTHER INFORMATION: Cys, Arg, Lys, Ser, Phe, Ala, Ile, Gly, Thr, Tyr, Gln, Val, Met, Leu, Trp, Asn, Glu or Pro
<220> FEATURE:
<221> NAME/KEY: MOD_RES
<222> LOCATION: (59)..(59)
<223> OTHER INFORMATION: Pro, Asp, Ser, Tyr, Gln, Thr, Lys, Glu, Leu, Gly, Ala, Arg, Phe, His, Ile or Cys
<220> FEATURE:
<221> NAME/KEY: MOD_RES
<222> LOCATION: (60)..(60)
<223> OTHER INFORMATION: Lys, Arg, Asn, Glu, Thr, Ala, Tyr, Gln, Phe, Ile, Met, Ser, Asp, His or Leu
<220> FEATURE:
<221> NAME/KEY: MOD_RES
<222> LOCATION: (61)..(61)
<223> OTHER INFORMATION: Val, Ile, Thr, Met, Leu, Ala, Tyr, Cys, Gly, Arg, Ser, Glu, Asn, Phe, Lys or Asp
<220> FEATURE:
<221> NAME/KEY: MOD_RES
<222> LOCATION: (62)..(62)
<223> OTHER INFORMATION: Ser, Thr, Asn, Lys, Ala, Asp, Pro, Gln, Phe, Leu, Arg, Val, Tyr, Ile, Cys, Glu or Met
<220> FEATURE:
<221> NAME/KEY: MOD_RES
<222> LOCATION: (63)..(63)
<223> OTHER INFORMATION: Phe, Trp, Leu, Lys, Tyr, Val, Ile, Ser, Thr, Cys, Ala, Met, Pro or Arg
<220> FEATURE:
<221> NAME/KEY: MOD_RES
<222> LOCATION: (64)..(64)
<223> OTHER INFORMATION: Glu, Asp, Gln, Gly, Thr, Lys, Asn, Val, Arg, Ser, Ala, Tyr, His, Pro or Trp
<220> FEATURE:
<221> NAME/KEY: MOD_RES
<222> LOCATION: (65)..(65)
<223> OTHER INFORMATION: Pro, Val, Ile, Ser, Leu, Ala, Gln, Thr, Glu, Arg, Lys, Tyr or Asp
<220> FEATURE:
<221> NAME/KEY: MOD_RES
<222> LOCATION: (66)..(66)
<223> OTHER INFORMATION: Ile, Val, Thr, Leu, Phe, Met, Asn, Ala, Ser, Tyr, Gly, Cys or Asp
<220> FEATURE:
<221> NAME/KEY: MOD_RES
<222> LOCATION: (67)..(67)
<223> OTHER INFORMATION: Pro, Ser, Leu, Ala, Thr, Ile, Tyr, His, Arg, Asp, Gly, Gln or Glu
<220> FEATURE:
<221> NAME/KEY: MOD_RES
<222> LOCATION: (68)..(68)
<223> OTHER INFORMATION: Ile, Leu, Val, Thr, Tyr, Met, Phe, His, Lys, Pro, Ser or Asn
<220> FEATURE:
<221> NAME/KEY: MOD_RES
<222> LOCATION: (69)..(69)
<223> OTHER INFORMATION: His, Tyr, Gln, Asn, Arg, Ser, Ile, Leu, Pro, Thr, Glu, Asp or Lys

<400> SEQUENCE: 45

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65
```

<210> SEQ ID NO 46
<211> LENGTH: 55
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(11)
<223> OTHER INFORMATION: Any amino acid
<220> FEATURE:
<221> NAME/KEY: MOD_RES
<222> LOCATION: (12)..(12)
<223> OTHER INFORMATION: Asn, Asp, Ser, Glu, Gly, Thr, Lys, Ala, Arg,
His, Ile, Val, Pro, Gln, Leu, Tyr, Cys, Met or Phe
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (16)..(16)
<223> OTHER INFORMATION: Leu, Ile, Pro, Phe, Thr, Val, His, Ser, Arg,
Ala, Asn, Met, Tyr, Gly or Cys
<220> FEATURE:
<221> NAME/KEY: MOD_RES
<222> LOCATION: (17)..(17)
<223> OTHER INFORMATION: Pro, Gln, Ser, Thr, Leu, Lys, His, Arg, Asn,
Tyr, Ile, Ala, Met, Gly, Asp, Val, Cys, Phe or Glu
<220> FEATURE:
<221> NAME/KEY: MOD_RES
<222> LOCATION: (18)..(18)
<223> OTHER INFORMATION: Cys, Arg, Ser, Tyr, Met, Phe, Gly, Ala, Leu,
Ile, Val, Trp, Pro, Thr, His or Asn
<220> FEATURE:
<221> NAME/KEY: MOD_RES
<222> LOCATION: (19)..(19)
<223> OTHER INFORMATION: Arg, Lys, Gly, Ser, Asn, Gln, Ile, Thr, Glu,
Pro, His, Met, Trp, Leu, Cys, Tyr, Val or Asp
<220> FEATURE:
<221> NAME/KEY: MOD_RES
<222> LOCATION: (20)..(20)
<223> OTHER INFORMATION: Ile, Leu, Met, Val, Thr, Asn, Arg, Lys, Tyr,
Cys, Ser, Pro, Phe, His, Asp or Glu
<220> FEATURE:
<221> NAME/KEY: MOD_RES
<222> LOCATION: (21)..(21)
<223> OTHER INFORMATION: Lys, Arg, Asn, Glu, Ile, Thr, Gln, Ser, Gly,
Pro, Met, Tyr, Leu, His, Ala or Asp
<220> FEATURE:
<221> NAME/KEY: MOD_RES
<222> LOCATION: (22)..(22)
<223> OTHER INFORMATION: Gln, Leu, His, Arg, Pro, Lys, Ala, Asn, Glu,
Gly, Thr, Met, Val or Ser
<220> FEATURE:
<221> NAME/KEY: MOD_RES
<222> LOCATION: (23)..(23)
<223> OTHER INFORMATION: Ile, Phe, Val, Leu, Met, Thr, Tyr, Asn, Ser,
Lys, Ala, Pro, Arg or Asp
<220> FEATURE:
<221> NAME/KEY: MOD_RES
<222> LOCATION: (24)..(24)
<223> OTHER INFORMATION: Ile, Val, Met, Thr, Leu, Ala, Tyr, Lys, Gly,
Glu, Cys, Arg, Ser or Gln
<220> FEATURE:
<221> NAME/KEY: MOD_RES
<222> LOCATION: (25)..(25)
<223> OTHER INFORMATION: Asn, Arg, His, Lys, Ser, Asp, Ile, Thr, Tyr,
Gly, Gln, Leu, Cys, Met, Val, Glu, Pro or Phe
<220> FEATURE:
<221> NAME/KEY: MOD_RES
<222> LOCATION: (26)..(26)
<223> OTHER INFORMATION: Met, Arg, Leu, Lys, Thr, Ser, Val, Ile, Pro,
Gly, Tyr, His, Gln, Asn, Ala, Cys, Trp or Asp
<220> FEATURE:
<221> NAME/KEY: MOD_RES
<222> LOCATION: (27)..(27)
<223> OTHER INFORMATION: Trp, Arg, Cys, Gly, Val, Leu, Met, Ser, Ala, Pro, His, Lys, Tyr, Asn, Gln
<220> FEATURE:
<221> NAME/KEY: MOD_RES
<222> LOCATION: (28)..(28)
<223> OTHER INFORMATION: Gln, Arg, Ile, Met, Leu, His, Lys, Ala, Glu, Pro, Thr, Gly, Tyr, Val, Trp or Ser
<220> FEATURE:
<221> NAME/KEY: MOD_RES
<222> LOCATION: (29)..(29)
<223> OTHER INFORMATION: Glu, Arg, Gly, Lys, Gln, Thr, Ser, Ala, Ile, Val, Asp, Leu, Pro, His, Asn, Cys, Met, Trp or Tyr
<220> FEATURE:
<221> NAME/KEY: MOD_RES
<222> LOCATION: (30)..(30)
<223> OTHER INFORMATION: Val, Ala, Thr, Ile, Gly, Leu, Ser, Glu, Pro, Lys, Arg, Asn, Gln, Trp or Asp
<220> FEATURE:
<221> NAME/KEY: MOD_RES
<222> LOCATION: (31)..(31)
<223> OTHER INFORMATION: Gly, Arg, Glu, Ala, Val, Lys, Gln, Thr, Asn, Asp, Pro, Trp or Ser
<220> FEATURE:
<221> NAME/KEY: MOD_RES
<222> LOCATION: (32)..(32)
<223> OTHER INFORMATION: Lys, Gln, Arg, Ser, Thr, Glu, Leu, Pro, Asn, Ile, His, Gly, Ala, Val, Tyr, Cys, Met, Trp or Asp
<220> FEATURE:
<221> NAME/KEY: MOD_RES
<222> LOCATION: (33)..(33)
<223> OTHER INFORMATION: Ala, Val, Gly, Thr, Ser, Pro, Gln, Glu, Cys, Trp, Arg, Lys, Tyr or Asp
<220> FEATURE:
<221> NAME/KEY: MOD_RES
<222> LOCATION: (34)..(34)
<223> OTHER INFORMATION: Met, Ile, Thr, Val, Leu, Lys, Asn, Ala, Phe, Arg, Cys, Ser, Pro, Gln, His, Tyr or Glu
<220> FEATURE:
<221> NAME/KEY: MOD_RES
<222> LOCATION: (35)..(35)
<223> OTHER INFORMATION: Tyr, His, Phe, Cys, Ser, Val, Asp, Asn, Met, Ala, Pro, Leu, Glu, Lys, Thr or Gly
<220> FEATURE:
<221> NAME/KEY: MOD_RES
<222> LOCATION: (36)..(36)
<223> OTHER INFORMATION: Ala, Pro, Thr, Ser, Asn, Val, Cys, Gly, Asp, Leu, Ile, Met or His
<220> FEATURE:
<221> NAME/KEY: MOD_RES
<222> LOCATION: (37)..(37)
<223> OTHER INFORMATION: Pro, Ser, Ala, Asn, Leu, Thr, His, Arg, Val, Lys, Asp or Gln
<220> FEATURE:
<221> NAME/KEY: MOD_RES
<222> LOCATION: (38)..(38)
<223> OTHER INFORMATION: Pro, Ser, Leu, Ala, Thr, Phe, Arg, His, Gly, Tyr, Asn or Gln
<220> FEATURE:
<221> NAME/KEY: MOD_RES
<222> LOCATION: (39)..(39)
<223> OTHER INFORMATION: Ile, Val, Ser, Thr, Arg, Leu, Phe, Met, Asn, Pro, His, Ala, Lys, Gly, Trp, Tyr or Asp
<220> FEATURE:
<221> NAME/KEY: MOD_RES
<222> LOCATION: (40)..(40)
<223> OTHER INFORMATION: Arg, Lys, Ala, Ser, Glu, Gln, Pro, Gly, Asn, Asp, Thr, Ile, Met, Val, Leu or His
<220> FEATURE:
<221> NAME/KEY: MOD_RES
<222> LOCATION: (41)..(41)
<223> OTHER INFORMATION: Gly, Glu, Arg, Ala, Ser, Asp, Val, Lys, Ile, Cys, Pro, Thr, Asn or Gln
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (43)..(43)
<223> OTHER INFORMATION: Ile, Leu, Val, Thr, Met, Ser, Asn, Phe, Arg,

```
      Ala, Cys, Asp or Gln
<220> FEATURE:
<221> NAME/KEY: MOD_RES
<222> LOCATION: (44)..(44)
<223> OTHER INFORMATION: Arg, Thr, Asn, Lys, Ser, Gln, Ile, Glu, Met,
      Gly, Ala, Tyr, Val, Trp, Asp, His, Leu, Pro or Cys
<220> FEATURE:
<221> NAME/KEY: MOD_RES
<222> LOCATION: (45)..(45)
<223> OTHER INFORMATION: Cys, Arg, Tyr, Ser, Trp, Gly, Val, Phe, Ala,
      Leu, Ile, Met, Lys, Thr, Gln or Glu
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (47)..(47)
<223> OTHER INFORMATION: Ser, Thr, Pro, Leu, Ala, Gln, Ile, Val, Phe,
      Cys, Trp, Lys, Tyr, Asn or Glu
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (49)..(49)
<223> OTHER INFORMATION: Ile, Val, Thr, Leu, Ser, Met, Phe, Asn, Tyr,
      Gly, Arg or Ala
<220> FEATURE:
<221> NAME/KEY: MOD_RES
<222> LOCATION: (50)..(50)
<223> OTHER INFORMATION: Thr, Ala, Ile, Ser, Gln, Leu, Pro, Arg, Tyr,
      Gly, Val or Asn
<220> FEATURE:
<221> NAME/KEY: MOD_RES
<222> LOCATION: (51)..(51)
<223> OTHER INFORMATION: Gly, Arg, Glu, Ala, Leu, Val, Asp, Trp, Ser,
      Lys, Gln, Ile or Thr
<220> FEATURE:
<221> NAME/KEY: MOD_RES
<222> LOCATION: (52)..(52)
<223> OTHER INFORMATION: Leu, Ile, Met, Val, Pro, Thr, Ser, Phe, Tyr,
      Gly, Arg, Gln, His, Ala or Asn
<220> FEATURE:
<221> NAME/KEY: MOD_RES
<222> LOCATION: (53)..(53)
<223> OTHER INFORMATION: Leu, Ile, Met, Phe, Val, Pro, Thr, Ser, Gln,
      Arg, Gly, Ala, Tyr, Asp, Lys or Asn
<220> FEATURE:
<221> NAME/KEY: MOD_RES
<222> LOCATION: (54)..(54)
<223> OTHER INFORMATION: Leu, Ile, Val, Ser, Phe, Trp, Met, Pro, Thr,
      Lys, Asn, Gly, Arg, Gln, Ala, Tyr, Asp or Glu
<220> FEATURE:
<221> NAME/KEY: MOD_RES
<222> LOCATION: (55)..(55)
<223> OTHER INFORMATION: Thr, Val, Ile, Leu, Ser, Ala, Glu, Gln, Met,
      Pro, Asn, Gly, Arg, Lys, Asp, His or Tyr

<400> SEQUENCE: 46

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa
    50                  55


<210> SEQ ID NO 47
<211> LENGTH: 51
<212> TYPE: PRT
<213> ORGANISM: Artificial Sequence
```

<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Lys, Thr, Arg, Asn, Ser, Ala, Glu, Gly, Gln,
Asp, Val, Ile, Met, Pro, His, Tyr, Leu or Phe
<220> FEATURE:
<221> NAME/KEY: MOD_RES
<222> LOCATION: (2)..(2)
<223> OTHER INFORMATION: Thr, Asn, Lys, Ile, Ser, Ala, Pro, Glu, Arg,
Gln, Asp, Gly, Val, Leu, His, Met, Tyr, Cys or Phe
<220> FEATURE:
<221> NAME/KEY: MOD_RES
<222> LOCATION: (3)..(3)
<223> OTHER INFORMATION: Ile, Thr, Val, Met, Leu, Ala, Tyr, Lys, Phe,
Ser, Asn, Arg, Pro, His, Glu, Gly, Gln or Asp
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Phe, Leu, Tyr, Ile, Ser, Gln, Val, Ala, Trp,
Cys, Pro, Thr, Asn, Met, Lys, Asp, Arg or His
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Gln, Pro, Ser, His, Asn, Arg, Lys, Glu, Thr,
Ala, Gly, Asp, Leu, Tyr, Ile, Val, Phe, Cys or Trp
<220> FEATURE:
<221> NAME/KEY: MOD_RES
<222> LOCATION: (8)..(8)
<223> OTHER INFORMATION: Ser, Pro, His, Ala, Thr, Asn, Gln, Phe, Leu,
Arg, Ile, Tyr, Lys, Gly, Val, Cys, Asp or Trp
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Gly, Glu, Arg, Asp, Ser, Pro, Ala, Lys, Leu,
Gln, Asn, Val, Trp, Ile, His or Thr
<220> FEATURE:
<221> NAME/KEY: MOD_RES
<222> LOCATION: (11)..(11)
<223> OTHER INFORMATION: Gly, Glu, Arg, Lys, Ser, Trp, Val, Leu, Ala,
Asn, Thr, Ile, Phe, Asp or Gln
<220> FEATURE:
<221> NAME/KEY: MOD_RES
<222> LOCATION: (12)..(12)
<223> OTHER INFORMATION: Asp, Gly, Thr, Asn, Ala, Glu, His, Val, Ile,
Ser, Arg, Tyr, Pro, Phe, Gln, Leu, Lys or Met
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Glu, Lys, Gln, Gly, Asp, Arg, Val, Asn, Ala,
Pro, Ser, Leu, Ile, His, Thr or Tyr
<220> FEATURE:
<221> NAME/KEY: MOD_RES
<222> LOCATION: (15)..(15)
<223> OTHER INFORMATION: Ile, Val, Leu, Thr, Phe, Asn, Met, Ser, Ala,
Tyr, Gly, Pro, Lys, Asp, Cys, His or Arg
<220> FEATURE:
<221> NAME/KEY: MOD_RES
<222> LOCATION: (16)..(16)
<223> OTHER INFORMATION: Val, Thr, Ile, Glu, Ala, Met, Lys, Ser, Leu,
Arg, Gln, Pro, Tyr, Cys, Gly, Asn, His, Phe or Asp <220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (18)..(18)
<223> OTHER INFORMATION: His, Leu, Tyr, Phe, Arg, Ile, Pro, Thr, Ser, Asn, Gln, Val, Asp, Ala, Gly, Met, Cys, Trp or Glu
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Phe, Val, Leu, Ser, Ile, Cys, Tyr, His, Thr, Arg, Trp, Gly or Asn
<220> FEATURE:
<221> NAME/KEY: MOD_RES
<222> LOCATION: (21)..(21)
<223> OTHER INFORMATION: Asn, Thr, Ile, Ser, Cys, Asp, Tyr, Val, His, Lys, Phe, Leu, Met, Pro, Arg, Gly, Gln, Glu or Ala
<220> FEATURE:
<221> NAME/KEY: MOD_RES
<222> LOCATION: (22)..(22)
<223> OTHER INFORMATION: Cys, Arg, Trp, Tyr, Ser, Val, Gly, Leu, Phe, Ile, His, Ala, Asn or Gln
<220> FEATURE:
<221> NAME/KEY: MOD_RES
<222> LOCATION: (23)..(23)
<223> OTHER INFORMATION: Gly, Arg, Ala, Lys, Gln, His, Glu, Met, Asn, Val, Ser, Thr, Trp, Tyr, Cys, Ile, Asp, Leu or Phe
<220> FEATURE:
<221> NAME/KEY: MOD_RES
<222> LOCATION: (24)..(24)
<223> OTHER INFORMATION: Gly, Glu, Arg, Lys, Trp, Val, Ser, Ala, Leu, Asn, Asp, Ile, Phe or Tyr
<220> FEATURE:
<221> NAME/KEY: MOD_RES
<222> LOCATION: (25)..(25)
<223> OTHER INFORMATION: Glu, Gly, Lys, Asp, Asn, Arg, Val, Ala, Leu, Phe, Ser, Gln, Trp, His, Tyr, Cys, Met or Thr
<220> FEATURE:
<221> NAME/KEY: MOD_RES
<222> LOCATION: (26)..(26)
<223> OTHER INFORMATION: Phe, Leu, Ser, Ile, Tyr, Val, Cys, Asn, Gly, Met, Trp or Gln
<220> FEATURE:
<221> NAME/KEY: MOD_RES
<222> LOCATION: (27)..(27)
<223> OTHER INFORMATION: Phe, Leu, Ser, Tyr, Val, Pro, Ile, Cys, Asp, Ala, Met or Asn
<220> FEATURE:
<221> NAME/KEY: MOD_RES
<222> LOCATION: (28)..(28)
<223> OTHER INFORMATION: Tyr, Phe, Asn, Cys, His, Ser, Leu, Val, Ile, Thr, Pro, Gly, Met, Trp, Lys, Asp or Glu
<220> FEATURE:
<221> NAME/KEY: MOD_RES
<222> LOCATION: (29)..(29)
<223> OTHER INFORMATION: Cys, Arg, Tyr, Leu, Ser, Trp, Gly, Ala, Phe, Val, Ile, Met, Thr, Pro or Lys
<220> FEATURE:
<221> NAME/KEY: MOD_RES
<222> LOCATION: (30)..(30)
<223> OTHER INFORMATION: Asn, Asp, Ser, Lys, Tyr, Thr, Glu, Ile, His, Gly, Cys, Gln, Arg, Ala, Val, Pro, Met or Phe
<220> FEATURE:
<221> NAME/KEY: MOD_RES
<222> LOCATION: (31)..(31)
<223> OTHER INFORMATION: Thr, Ser, Ala, Leu, Ile, Pro, Val, His, Arg, Tyr, Lys, Asn, Gln, Met, Glu or Gly
<220> FEATURE:
<221> NAME/KEY: MOD_RES
<222> LOCATION: (32)..(32)
<223> OTHER INFORMATION: Thr, Ser, Ala, Lys, Pro, Glu, Ile, Leu, Val, Asp, Asn, Gly, Arg, Gln, His, Tyr, Phe, Cys or Met
<220> FEATURE:

-continued

```
<221> NAME/KEY: MOD_RES
<222> LOCATION: (33)..(33)
<223> OTHER INFORMATION: Gln, Lys, Gly, Pro, Arg, Glu, Asn, Asp, Ser,
      Ala, His, Leu, Thr, Ile, Val, Trp, Tyr, Met or Cys
<220> FEATURE:
<221> NAME/KEY: MOD_RES
<222> LOCATION: (34)..(34)
<223> OTHER INFORMATION: Leu, Met, Ile, Pro, Phe, Val, Arg, Gln, Cys,
      Trp, Thr, Ser, Tyr, Gly, Ala, Lys or Asn
<220> FEATURE:
<221> NAME/KEY: MOD_RES
<222> LOCATION: (35)..(35)
<223> OTHER INFORMATION: Phe, Leu, Trp, Ser, Tyr, Val, Ile, Cys, Pro,
      Asn, Ala, Met, Lys or Thr
<220> FEATURE:
<221> NAME/KEY: MOD_RES
<222> LOCATION: (36)..(36)
<223> OTHER INFORMATION: Asn, Ser, Asp, Thr, Lys, His, Tyr, Gly, Arg,
      Gln, Ile, Glu, Phe, Ala, Leu, Pro, Trp, Met or Val
<220> FEATURE:
<221> NAME/KEY: MOD_RES
<222> LOCATION: (37)..(51)
<223> OTHER INFORMATION: Any amino acid

<400> SEQUENCE: 47

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa
    50
```